United States Patent
Madsen et al.

(10) Patent No.: US 10,259,856 B2
(45) Date of Patent: *Apr. 16, 2019

(54) PROTEASE STABILIZED ACYLATED INSULIN ANALOGUES

(71) Applicant: Novo Nordisk A/S, Bagsvaerd (DK)

(72) Inventors: Peter Madsen, Bagsvaerd (DK); Thomas Boerglum Kjeldsen, Virum (DK); Thomas Hoeg-Jensen, Klampenborg (DK); Palle Jakobsen, Vaerloese (DK); Tina Moeller Tagmose, Ballerup (DK); Tine Glendorf, Lyngby (DK); Janos Tibor Kodra, Koebenhavn (DK); Patrick William Garibay, Holte (DK); Jacob Sten Petersen, Charlottenlund (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/686,176

(22) Filed: Apr. 14, 2015

(65) Prior Publication Data

US 2015/0210748 A1  Jul. 30, 2015

Related U.S. Application Data

(63) Continuation of application No. 14/684,863, filed on Apr. 13, 2015, now Pat. No. 9,688,737, which is a continuation of application No. 13/973,183, filed on Aug. 22, 2013, now Pat. No. 9,045,560, which is a continuation of application No. 12/922,117, filed as application No. PCT/EP2009/053017 on Mar. 13, 2009, now Pat. No. 8,691,759.

(60) Provisional application No. 61/039,120, filed on Mar. 25, 2008.

(30) Foreign Application Priority Data

Mar. 18, 2008 (EP) ..................... 08102708
Nov. 28, 2008 (EP) ..................... 08170231

(51) Int. Cl.
*A61K 38/28* (2006.01)
*C07K 14/62* (2006.01)
*A61K 38/00* (2006.01)

(52) U.S. Cl.
CPC .............. *C07K 14/62* (2013.01); *A61K 38/00* (2013.01)

(58) Field of Classification Search
CPC ..................................... A61K 38/28
See application file for complete search history.

(56) References Cited

U.S. PATENT DOCUMENTS

| | | | |
|---|---|---|---|
| 2,832,685 A | 4/1958 | Scott | |
| 3,528,960 A | 9/1970 | Haas | |
| 3,719,655 A | 3/1973 | Jackson et al. | |
| 3,869,437 A | 3/1975 | Lindsay et al. | |
| 3,950,517 A | 4/1976 | Lindsay et al. | |
| 4,033,941 A | 7/1977 | Stilz et al. | |
| 4,179,337 A | 12/1979 | Davis et al. | |
| 4,462,984 A | 7/1984 | Mizuno et al. | |
| 4,614,730 A | 9/1986 | Hansen et al. | |
| 4,839,341 A | 6/1989 | Massey et al. | |
| 4,849,227 A | 7/1989 | Cho | |
| 5,149,777 A | 9/1992 | Hansen et al. | |
| 5,179,189 A | 1/1993 | Domb et al. | |
| 5,206,219 A | 4/1993 | Desai | |
| 5,266,310 A | 11/1993 | Mundorf et al. | |
| 5,359,030 A | 10/1994 | Ekwuribe | |
| 5,446,020 A | 8/1995 | Andy et al. | |
| 5,478,575 A | 12/1995 | Miyazaki et al. | |
| 5,506,202 A | 4/1996 | Vertesy et al. | |
| 5,506,203 A | 4/1996 | Backstrom et al. | |
| 5,597,796 A | 1/1997 | Brange | |
| 5,621,073 A | 4/1997 | Dickhardt et al. | |
| 5,700,662 A | 12/1997 | Chance et al. | |
| 5,716,927 A | 2/1998 | Balschmidt et al. | |
| 5,898,067 A | 4/1999 | Balschmidt et al. | |
| 5,922,675 A | 7/1999 | Baker et al. | |
| 5,981,489 A | 11/1999 | Stevenson et al. | |
| 6,221,837 B1 | 4/2001 | Ertl et al. | |
| 6,251,856 B1 | 6/2001 | Markussen et al. | |
| 6,475,795 B1 | 11/2002 | Turley et al. | |
| 6,500,645 B1 | 12/2002 | Kjeldsen et al. | |
| 6,746,853 B1 | 6/2004 | Dahiyat et al. | |
| 6,770,625 B2 | 8/2004 | Soltero et al. | |
| 6,858,580 B2 | 2/2005 | Ekwuribe et al. | |
| 6,867,183 B2 | 3/2005 | Soltero et al. | |
| 6,869,930 B1 | 3/2005 | Havelund et al. | |
| 7,030,082 B2 | 4/2006 | Soltero et al. | |
| 7,030,083 B2 | 4/2006 | Schreiner et al. | |
| 7,060,675 B2 | 6/2006 | Ekwuribe et al. | |
| 7,317,000 B2 | 1/2008 | Hoeg-Jensen et al. | |
| 8,993,516 B2 | 3/2015 | Weiss | |
| 9,018,161 B2 | 4/2015 | Nielsen et al. | |
| 9,045,560 B2 | 6/2015 | Madsen et al. | |
| 9,150,633 B2 | 10/2015 | Madsen et al. | |
| 9,260,503 B2 | 2/2016 | Hoeg-Jensen et al. | |
| 9,481,721 B2 | 11/2016 | Naver et al. | |

(Continued)

FOREIGN PATENT DOCUMENTS

CN  1318416 A  10/2001
CN  1390854 A  1/2003

(Continued)

OTHER PUBLICATIONS

Havelund et al., "The Mechanism of Protraction of Insulin Detemir, a Long-Acting, Acylated Analog of Human Insulin," Pharmaceutical Research, 2004, vol. 21, No. 8, pp. 1498-1504.

(Continued)

*Primary Examiner* — Gyan Chandra
(74) *Attorney, Agent, or Firm* — Jianjie Hu

(57) ABSTRACT

Novel acylated insulin analogues exhibiting resistance towards proteases can, effectively, be administered pulmonary or orally. The insulin analogues contain B25H and A14E or A14H.

18 Claims, 6 Drawing Sheets

Specification includes a Sequence Listing.

(56) References Cited

U.S. PATENT DOCUMENTS

| | | |
|---|---|---|
| 2002/0045731 A1 | 4/2002 | Schaffer et al. |
| 2002/0055496 A1 | 5/2002 | McCoy et al. |
| 2002/0058614 A1 | 5/2002 | Filvaroff et al. |
| 2002/0142955 A1 | 10/2002 | Dubois et al. |
| 2002/0198140 A1 | 12/2002 | Havelund |
| 2003/0027748 A1 | 2/2003 | Ekwuribe et al. |
| 2003/0035775 A1 | 2/2003 | Klibanov |
| 2003/0050228 A1 | 3/2003 | Ekwuribe et al. |
| 2003/0083232 A1 | 5/2003 | Soltero et al. |
| 2003/0104981 A1 | 6/2003 | Mandic |
| 2003/0134294 A1 | 7/2003 | Sandford et al. |
| 2003/0166508 A1 | 9/2003 | Zhang |
| 2003/0228652 A1* | 12/2003 | Radhakrishnan ...... C07K 14/62 435/68.1 |
| 2004/0038867 A1 | 2/2004 | Still et al. |
| 2004/0097410 A1 | 5/2004 | Zheng et al. |
| 2004/0138101 A1 | 7/2004 | Filvaroff et al. |
| 2004/0198949 A1 | 10/2004 | Ekwuribe et al. |
| 2004/0242460 A1 | 12/2004 | Brader et al. |
| 2004/0254119 A1 | 12/2004 | West et al. |
| 2005/0039235 A1 | 2/2005 | Moloney et al. |
| 2005/0054818 A1 | 3/2005 | Brader et al. |
| 2005/0232981 A1 | 10/2005 | Ben-Sasson |
| 2005/0276843 A1 | 12/2005 | Quay et al. |
| 2006/0019874 A1 | 1/2006 | Radhakrishnan et al. |
| 2006/0030518 A1 | 2/2006 | Havelund et al. |
| 2006/0182714 A1* | 8/2006 | Behrens ........... A61K 47/48215 424/85.2 |
| 2006/0183668 A1 | 8/2006 | Jonassen et al. |
| 2007/0054941 A1 | 3/2007 | Biba et al. |
| 2007/0096431 A1 | 5/2007 | Mochizuki et al. |
| 2008/0076705 A1 | 3/2008 | Kodra et al. |
| 2008/0171695 A1 | 7/2008 | Garibay et al. |
| 2008/0200383 A1 | 8/2008 | Jennings et al. |
| 2009/0087484 A1 | 4/2009 | Dong et al. |
| 2010/0009898 A1 | 1/2010 | Nielsen et al. |
| 2011/0092419 A1 | 4/2011 | Nielsen et al. |
| 2011/0098440 A1 | 4/2011 | Madsen et al. |
| 2011/0105720 A1 | 5/2011 | Madsen et al. |
| 2011/0230402 A1 | 9/2011 | Johansen et al. |
| 2011/0293714 A1 | 12/2011 | Foger |
| 2011/0294729 A1 | 12/2011 | Stidsen et al. |
| 2012/0196800 A1 | 8/2012 | Naver et al. |
| 2015/0111820 A1 | 4/2015 | Pridal et al. |
| 2015/0126442 A1 | 5/2015 | Naver et al. |
| 2015/0210747 A1 | 7/2015 | Madsen et al. |
| 2015/0210748 A1 | 7/2015 | Madsen et al. |
| 2016/0058840 A1 | 3/2016 | Johansen et al. |
| 2018/0169190 A1 | 6/2018 | Norrman et al. |

FOREIGN PATENT DOCUMENTS

| | | |
|---|---|---|
| CN | 1812808 A | 8/2006 |
| CN | 1882356 A | 12/2006 |
| EP | 214826 A2 | 3/1987 |
| EP | 254516 A2 | 1/1988 |
| EP | 265213 A2 | 4/1988 |
| EP | 376156 A2 | 7/1990 |
| EP | 511600 A2 | 11/1992 |
| EP | 544466 A1 | 6/1993 |
| EP | 712861 A2 | 5/1996 |
| EP | 712862 A2 | 5/1996 |
| EP | 837072 A2 | 4/1998 |
| EP | 925792 A2 | 6/1999 |
| EP | 1121144 A1 | 4/2000 |
| EP | 1002547 A1 | 5/2000 |
| EP | 0894095 | 5/2003 |
| GB | 894095 A | 4/1962 |
| GB | 1492997 | 11/1977 |
| GB | 1492997 A | 11/1977 |
| JP | 1254699 | 5/1979 |
| JP | 57-067548 A | 4/1982 |
| JP | H01254699 A | 10/1989 |
| JP | H02121929 | 5/1990 |
| JP | H03504240 A | 9/1991 |
| JP | H03-506023 A | 12/1991 |
| JP | H06509796 | 11/1994 |
| JP | H08502490 | 3/1996 |
| JP | H08502492 | 3/1996 |
| JP | H08507066 | 7/1996 |
| JP | H08507078 | 7/1996 |
| JP | H09502867 | 3/1997 |
| JP | H09502867 A | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-516256 A | 12/2000 |
| JP | 2001-521004 A | 11/2001 |
| JP | 2001-521006 A | 11/2001 |
| JP | 2001-521904 A | 11/2001 |
| JP | 2002-308899 A | 10/2002 |
| JP | 2002-543092 A | 12/2002 |
| JP | 2003-518917 A | 6/2003 |
| JP | 2006-526579 A | 11/2006 |
| JP | 2007-511525 A | 5/2007 |
| JP | 5749155 B2 | 7/2015 |
| RU | 2146139 C1 | 3/2000 |
| RU | 2164520 C2 | 3/2001 |
| RU | 2252782 C2 | 5/2005 |
| WO | 8910937 A1 | 11/1989 |
| WO | 90/01038 A1 | 2/1990 |
| WO | 90/12814 A1 | 11/1990 |
| WO | 91/03935 A1 | 4/1991 |
| WO | 91/12817 A1 | 9/1991 |
| WO | 92/00321 A1 | 1/1992 |
| WO | 92/000322 A1 | 1/1992 |
| WO | 92/01476 A1 | 2/1992 |
| WO | 92/04893 A1 | 4/1992 |
| WO | 92/012999 A1 | 8/1992 |
| WO | 92/12999 A1 | 8/1992 |
| WO | 94/08599 A1 | 4/1994 |
| WO | 94/19020 A1 | 9/1994 |
| WO | 95/07931 A1 | 3/1995 |
| WO | 95/13795 A1 | 6/1995 |
| WO | 95/24183 A1 | 9/1995 |
| WO | 96/15803 A1 | 5/1996 |
| WO | 96/29344 | 9/1996 |
| WO | 96/29344 A1 | 9/1996 |
| WO | 96/37215 A1 | 11/1996 |
| WO | 9702043 A1 | 1/1997 |
| WO | 97/31022 A1 | 8/1997 |
| WO | 98/01473 A1 | 1/1998 |
| WO | 98/02460 A1 | 1/1998 |
| WO | 98/05361 A2 | 2/1998 |
| WO | 9856406 | 12/1998 |
| WO | 99/21573 | 5/1999 |
| WO | 99/21888 A1 | 5/1999 |
| WO | 99/24071 A1 | 5/1999 |
| WO | 99/32116 A1 | 7/1999 |
| WO | 99/65941 A1 | 12/1999 |
| WO | 00/00176 A1 | 1/2000 |
| WO | 00/10541 A1 | 3/2000 |
| WO | 00/23098 A1 | 4/2000 |
| WO | 00/43034 A2 | 7/2000 |
| WO | 0042993 A2 | 7/2000 |
| WO | 00/61178 A1 | 10/2000 |
| WO | 00/64940 A1 | 11/2000 |
| WO | 00/69901 A2 | 11/2000 |
| WO | 00/78302 A1 | 12/2000 |
| WO | 01/01960 A1 | 1/2001 |
| WO | 0100674 A1 | 1/2001 |
| WO | 0143762 | 6/2001 |
| WO | 0152937 | 7/2001 |
| WO | 01/92334 A1 | 12/2001 |
| WO | 02064415 | 8/2002 |
| WO | 020677969 | 9/2002 |
| WO | 02/094200 | 11/2002 |
| WO | 02/094200 A2 | 11/2002 |
| WO | 02098232 | 12/2002 |
| WO | 02098446 A1 | 12/2002 |
| WO | 03/013573 | 2/2003 |
| WO | 03/022208 A2 | 3/2003 |

(56) References Cited

FOREIGN PATENT DOCUMENTS

| | | |
|---|---|---|
| WO | 03/022996 A2 | 3/2003 |
| WO | 03/047493 A2 | 6/2003 |
| WO | 03/048195 A2 | 6/2003 |
| WO | 2003/047493 A2 | 6/2003 |
| WO | 03/053339 A2 | 7/2003 |
| WO | 03/053460 A1 | 7/2003 |
| WO | 03075950 A1 | 9/2003 |
| WO | 03/094951 A1 | 11/2003 |
| WO | 03/094956 A1 | 11/2003 |
| WO | 2003/094951 A1 | 11/2003 |
| WO | 2003/094956 A1 | 11/2003 |
| WO | 04/105790 A1 | 12/2004 |
| WO | 2004/105790 A1 | 12/2004 |
| WO | 05/005477 A2 | 1/2005 |
| WO | 05/012346 A1 | 2/2005 |
| WO | 05/012347 A2 | 2/2005 |
| WO | 05/016312 A1 | 2/2005 |
| WO | 2005/016312 A1 | 2/2005 |
| WO | 2005/027978 A2 | 3/2005 |
| WO | 05/047508 A1 | 5/2005 |
| WO | 2005/047508 A1 | 5/2005 |
| WO | 05/049061 A2 | 6/2005 |
| WO | 05/055976 A2 | 6/2005 |
| WO | 05/058961 A2 | 6/2005 |
| WO | 2005/049061 A2 | 6/2005 |
| WO | 05/092301 A1 | 10/2005 |
| WO | 2005/115441 A2 | 12/2005 |
| WO | 2006005683 A1 | 1/2006 |
| WO | 2006/020580 A2 | 2/2006 |
| WO | 06/023943 A1 | 3/2006 |
| WO | 2006/035418 | 4/2006 |
| WO | 2006060753 A2 | 6/2006 |
| WO | 06/079641 A2 | 8/2006 |
| WO | 06/082204 A1 | 8/2006 |
| WO | 06/082205 A1 | 8/2006 |
| WO | 2006/079641 A2 | 8/2006 |
| WO | 06086856 A1 | 8/2006 |
| WO | 2006082205 A1 | 8/2006 |
| WO | 2006082245 A1 | 8/2006 |
| WO | 06/097521 A1 | 9/2006 |
| WO | 2006/97521 A1 | 9/2006 |
| WO | 2006/103657 A2 | 10/2006 |
| WO | 2006/125763 | 11/2006 |
| WO | 07/006320 A1 | 1/2007 |
| WO | 2007/006320 A1 | 1/2007 |
| WO | 07/041481 A1 | 4/2007 |
| WO | 07/047948 A2 | 4/2007 |
| WO | 2007/047948 A2 | 4/2007 |
| WO | 07/074133 A2 | 7/2007 |
| WO | 07/081824 A2 | 7/2007 |
| WO | 2007/081824 A2 | 7/2007 |
| WO | 07/096332 A1 | 8/2007 |
| WO | 07/096431 A1 | 8/2007 |
| WO | 2007/096332 A1 | 8/2007 |
| WO | 2007/096431 A1 | 8/2007 |
| WO | 07/104737 A1 | 9/2007 |
| WO | 2007104738 A2 | 9/2007 |
| WO | 07/128815 A1 | 11/2007 |
| WO | 07/128817 A1 | 11/2007 |
| WO | 08/015099 A2 | 2/2008 |
| WO | 2008/015099 A2 | 2/2008 |
| WO | 08/034881 A1 | 3/2008 |
| WO | 2008/034881 A1 | 3/2008 |
| WO | 08043033 A2 | 4/2008 |
| WO | 08/132229 A2 | 11/2008 |
| WO | 2008/132224 A2 | 11/2008 |
| WO | 2008/132229 A2 | 11/2008 |
| WO | 08/145730 A1 | 12/2008 |
| WO | 2008/145728 | 12/2008 |
| WO | 2008/145730 A1 | 12/2008 |
| WO | 2008/152106 A1 | 12/2008 |
| WO | 09/010428 A1 | 1/2009 |
| WO | 2009/010428 A1 | 1/2009 |
| WO | 09/022005 A1 | 2/2009 |
| WO | 09/022006 A1 | 2/2009 |
| WO | 2009/021955 A1 | 2/2009 |
| WO | 2009/022005 A1 | 2/2009 |
| WO | 2009/063072 A2 | 5/2009 |
| WO | 2009/112583 A2 | 9/2009 |
| WO | 2009/115469 A1 | 9/2009 |
| WO | 2009152128 A1 | 12/2009 |
| WO | 2010/049488 A1 | 5/2010 |
| WO | 2010/066636 A1 | 6/2010 |
| WO | 2011051486 A2 | 5/2011 |
| WO | 2011/086093 A2 | 7/2011 |
| WO | 2011161124 A1 | 12/2011 |
| WO | 2011161125 A1 | 12/2011 |
| WO | 2012049307 A2 | 4/2012 |
| WO | 12080320 A1 | 6/2012 |
| WO | 2013153000 A2 | 10/2013 |
| WO | 2015052088 A1 | 4/2015 |
| WO | 2015071368 A1 | 5/2015 |
| WO | 2015131902 A1 | 9/2015 |
| WO | 2015171484 A1 | 11/2015 |
| WO | 2016100042 A1 | 6/2016 |

OTHER PUBLICATIONS

Chu, Ying-Chi et al., "The A14 Position of Insuling Tolerates Considerable . . ." J. Protein Chem., vol. 11(5), pp. 571-577 (1992).

Huang Tao, "Preparation and MALDI-TOF-MS Analysis of the . . . " Chemical Research & Application, vol. 18(7), pp. 834-836 (2006).

Authier F et al. "Uptake and Metabolic Fate of [HisA8,HisB4,GluB10,HisB27]insulin in rat liver in vivo." Biochemistry Journal. 1998. vol. 332 pp. 421-430.

Yang, S.Z. et al. "Relationship between insulin A chain regions and insulin biological activities." World J Gastroentero. 2000 vol. 6(3): 371-373.

Brems, D.N. et al. "Improved insulin stability through amino acid substitution" Protein Engineering. 1992 vol. 5(6): 519-525.

Bhatnagar S et al. Molecular variants and derivatives of insulin for improved glycemic control in diabetes, "Progress in Biophysics and Molecular Biology" Year 2006, vol. 91, No. 3, pp. 199-228, XP027932180.

David R.Owens New Horizons—Alternative Routes for Insulin Therapy, "Nature Reviews Drug Discovery" year 2002, vol. 1, No. 7, pp. 529-540, XP002682141.

R. Murray et al., Human Biochemistry in 2 Volumes, vol. 1, Moscow, "Mir", 1993, p. 384.

Chang-Cheng You et al., "Contrasting Effects of Exterior and Interior Hydrophobic Moieties in the Complexation of Amino Acid Functionalized Gold Clusters with Alpha-Chymotrypsin," Organic Letters, 2005, vol. 7, No. 25, pp. 5685-5688.

Hinds D K et al. PEGylated insulin in PLGA microparticles. In vivo and in vitro analysis, "Journal of Controlled Release" Year 2005, vol. 104, pp. 447-460.

Poulsen et al., Pharmaceutical Research, "Effect of Ethylenediamine on Chemical Degradation of Insulin Aspart in Pharmaceutical Solutions", 2008, vol. 25, No. 11, pp. 2534-2544.

Prasad et al., Journal of Steroid Biochemistry, "Solid-Phase Reagents for the Isolation and Protection of Carbonyl Compounds", 1983, vol. 18, No. 3, pp. 257-261.

Toorisaka, Eiichi et al, Membrane. "Emulsion-Based Drug Delivery Systems", 2004, vol. 29, No. 2, pp. 98-104.

Bekerman, Tania et al, Journal of Pharmaceutical Sciences, "Cyclosporin Nanoparticulate Liposheres for Oral Administration", 2004, vol. 93, No. 5, pp. 1264-1270.

Klibanov et al,"Biotechnology and Bioengineering on Protein Solubility in Organic Solvents" 1994 vol. 44 pp. 140-145.

Toorisaka et al., "Emulsion Based Drug Delivery Systems," Membrane, 2004, vol. 29, No. 2, pp. 98-104.

Aminlari et al., 1977, "Protein Dispersibility of Spray-Dried Whole Soybean Milk Base: Effect of Processing Variables," Journal of Food Science 42(4):985-988.

Bennett et al., 2003, "Insulin Inhibition of the Proteasome Is Dependent on Degradation of Insulin by Insulin-Degrading Enzyme," Journal of Endocrinology 177:399-405.

(56) References Cited

OTHER PUBLICATIONS

Bhatnagar et al., 2006, "Molecular Variants and Derivatives of Insulin for Improved Glycemic Control in Diabetes," Progress in Biophysics and Molecular Biology 91(3):199-228.

Chin et al., 1994, "Communication to the Editor: On Protein Solubility in Organic Solvents," Biotechnology and Bioengineering 44:140-145.

Chu et al., 1992, "The A14 Position of Insulin Tolesrates Considerable Structural Alterations With Modest Effects on the Biological Behavior of the Hormone," Journal of Protein Chemistry 11(5):571-577.

Foster et al., 1995, "Powder Characteristics of Proteins Spray-Dried From Different Spray-Driers," Drug Development and Industrial Pharmacy 21(15):1705-1723.

Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3):175-181.

Hashimoto et al., 1989, "Synthesis of Palmitoyl Derivatives of Insulin and Their Biological Activities" Pharmaceutical Research 6(2):171-176.

Havelund et al., 2004, "The Mechanism of Protraction of Insulin Detemir, a Long-Acting, Acylated Analog of Human Insulin" Pharmaceutical Research 21(8):1498-1504.

Hinds et al., 2000, "Synthesis and Characterization of Poly(Ethylene Glycol)-Insulin Conjugates," Bioconjugate Chemistry 11(2):195-201.

Hinds et al., 2002, "Effects of Peg Conjugation on Insulin Properties," Advanced Drug Delivery Reviews 54(4):505-530.

Iwamoto, Yasuhiko, 2000, "New Insulin Formulation," Annual Review Increation and Metabolism, pp. 46-53.

Jonassen et al., 2006, "Biochemical and Physiological Properties of a Novel Series of Long-Acting Insulin Analogs Dbtained by Acylation with Cholic Acid Derivatives", Pharmaceutical Research, vol. 23, No. 1, pp. 49-55.

Kochendoerfer et al., 2003, "Design and Chemical Synthesis of a Homogenous Polymer-Modified Erythropoiesis Protein," Science 299:884-887.

Kurtz et al., 1983, "Circulating IgG Antibody to Protamine in Patients Treated with Protamine-Insulins," Diabetologia 25(4):322-324.

Markussen et al., 1987, "Soluble, Prolonged-Acting Insulin Derivatives. I. Degree of Protraction, Crystallizability of Insulins Substituted in the . . . " Protein Engineering 1(3):205-213.

Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2(2):157-166.

Muranishi et al., 1992, "Trials of Lipid Modification of Peptide Hormones for Intestinal Delivery," Journal of Controlled Release 19:179-188.

Samuel et al., 1978, "Studies on the Immunogenicity of Protamines in Humans and experimental Animals by Means of a Micro-Complement Fixation Test," Clinical Experminental Immunology 33:252-260.

Schilling et al., 1991, "Degradation of Insulin by Trypsin and Alpha Chymotrypsin," Pharmaceutical Research 8(6):721-727.

Schlichtkrull et al., 1956, "Insulin Crystals," Acta Chemica Scandinavica 10(9):1455-1458.

Seabright et al., 1996, "The Characterization of Endosomal Insulin Degradation Intermediates and Their Sequence of Production," Biochemical Journal 320(3):947-956.

Stentz et al., 1989, "Identification of Insulin Intermediates and Sites of Cleavage of Native Insulin by Insulin Protease From Human Fibroblasts," Journal of Biological Chemistry 264(34):20275-20285.

Uchio et al., 1999, "Site-Specific Insulin Conjugates With Enhanced Stability and Extended Action Profile," Advanced Drug Delivery Reviews 35:289-306.

Whittingham et al., 2004, "Crystallographic and Solution . . . " Biochemistry 43:5987-5995.

Teagarden DL, Baker DS, European Journal of Pharmaceutical Sceiences, Practical Aspects of Lyophilization using non-aqueours co-solvent systems, 2002, vol. 15, No. 2, pp. 115-133.

Level of Protein Structure, Exemplified by Insulin. http://www.biotopics.co.uk/as/insulinproteinstructure.html Nov. 1, 2005.

Ichikawa, J. Pharm Pharmacol., May 1980; vol. 32(5); pp. 314-318 (abstract only).

Brange et al (1992) "Chemical Stability of Insulin. 2. Formation of Higher Molecular Weight Transformation Products During Storage of Pharmaceutical Preparations" Pharmaceutical Research vol. 9: 727-734.

Kudvu and Basu, "Ultra-Long-Acting Insulins for a Lifestyle-Related Pandemic," Lancet, 2011, vol. 377, pp. 880-881.

American Diabetes Association, "Diagnosis and Classification of Diabetes Mellitus," Diabetes Care, 2010, vol. 33, Supp 1, pp. S62-S69.

Bethel and Feinglos (Bethel), "Basal Insulin Therapy in Type 2 Diabetes," J Am Board Fam Med, 2005, vol. 18, No. 3, pp. 199-204 (printed as pp. 1-7).

Bekerman et al., 2004, "Cyclosporin Nanoparticulate Liposphere for Oral Administration," Journal of Pharmaceutical Sciences 93(5):1264-1270.

Iwamoto, 2000, "New Insulin Formulation," Annual Review Endocrine Metabolism pp. 46-53.

Jonassen et al., 2006, "Synthesis of Palmitoyl Derivatives of Insulin and Their Biological Activities," Pharmaceutical Research 23(1):49-55.

Kurtz et al., 1983, "Circulating IgG Antibody to Protamine in Patients Treated with Protamine-Insulins," Diabetologia 25(2):322-324.

Samuel et al., 1978, "Studies on the Immunogenicity of Protamines in Humans Andexperimental Animals by Means of a Micro-Complement Fixation Test," Clinical Experminemtal Immunology 33:252-260.

Toorisaka et al., 2004, "Emulsion-Based Drug Delivery Systems," Membrane 29(2):98-104 Abstract.

L. Schaffer et al ,A novel high-affinity peptide antagonist to the insulin receptor.Journal: Biochemical and Biophysical Research Communications, Year 2008, vol. 376 , pp. 380-383.

L. Schäffer et al, Assembly of high-affinity insulin receptor agonists and antagonists from peptide building blocks, Journal :Proceedings of the National Academy of Sciences of the United States of America, Year 2003, vol. 100, pp. 4435-4439.

Riebel, U. et al,Equivalent In Vivo Biological Activity of Insulin Analogues and Human Insulin Despite Different In Vitro Potencies, Journal :Diabetes, Year 1990,vol. 39, pp. 1033-1039.

Hinds, K D et al. Advanced Drugs Delivery Reviews. "Effects of PEG Conjugation on Insulin Properties." 2002. vol. 54. pp. 505-530.

Chu Ying-Chi et al. Journal of Protein Chemistry. "The A14 Position of Insulin Tolesrates Considerable Structural Alterations With Modest Effects on the Biological Behavior of the Hormone." 1992. vol. 11(5). pp. 571-577.

Database Geneseq [Online] May 7, 1992 (May 7, 1992), "Modified human proinsulin with Gln A13 and Asp B17.", retrieved from EBI accession No. GSP:AAR20702 Database accession No. AAR20702.

Hydrophobic Amino Acids, Molecular Cell Biology 6th edition (2008, W.H. Freeman and company) http://www.bio.miami.edu/tom/courses/protected/MCB6/ch02/2-14_part_1_jpg.

The online Medical dictionary year 2005 Website:http://cancerweb.ncl.ac.uklomd/about.html, 5 pages, Jul. 7, 2005.

Joseph A. Affholter et al., "Identification of Residues in the Insulin Molecule Important for Binding to Insulin-Degrading Enzyme," Biochemistry, 1990, vol. 29, No. 33, pp. 7727-7733.

Kudvu & Basu, "Ultra-Long-Acting Insulins for a Lifestyle-Related Pandemic," Lancet, 2011, vol. 377, pp. 880-881.

Jonassen et al., "Design of the Novel Protraction Mechanism of Insulin Degludec, an Ultra-Long-Acting Basal Insulin," Pharm Res, 2012, vol. 29, pp. 2104-2114.

Amy S. Rosenberg, "Effects of Protein Aggregates: An Immunologic Perspective," AAPS J, 2006, vol. 8, pp. E501-E507.

(56) References Cited

OTHER PUBLICATIONS

Michael F. Dunn, "Zinc-ligand interactions modulate assembly and stability of the insulin hexamer—a review," Biometals, 2005, vol. 18, pp. 295-303.
Bennett, R.G., et al, "Insulin inhibition of the proteasome is dependent on degradation of insulin by insulin-degrading enzyme" Journal of Endocrinology, 2003, vol. 177, pp. 399-405.
Seabright, Paul J et al. Biochemical Journal, "The Characterization of Endosomal Insulin Degradation Intermediates and Their Sequence of Production", 1996, vol. 320, No. 3, pp. 947-956.
Brange et al. ("Design of Novel Insulins with Changed Self-Association and Ligand Binding Properties, " GBF Monographs, 1989, 12, 139-144).
Ying-Chi Chu et al. "The A14 Position of Insulin Tolerates Considerable Structural Alterations with Modest Effects on the Biological Behavior of the Hormone," Journal of Protein Chemistry, 1992, vol. 11, pp. 571-577.
Yip, C.C. et al. "Structure and function of Insulin: Preparation and Biological Activity of Guinea Pig DES-B-ASP30, DES-A-ASN21—Insulin." Canadian Journal of Biochemistry, 1976, vol. 54 pp. 866-871.
Stentz, F.13. et al., "Identification of Insulin Intermediates and Sites of Cleavage of Native Insulin by Insulin Protease from Human Fibroblasts," Journal of Biological Chemistry, 1989, vol. 264, No. 34 pp. 20275-20282.
Bajaj et al., "Coypu Insulin: Primary Structure, Conformation and Biological Properties of a Hystricomorph Rodent Insulin", Journal of Biochemistry, 1986, vol. 238, pp. 345-351.
Spoden M et al. International Journal of Peptide and Protein. "Structure-Function Relationships of DES-(B26-B30)—Insulin." 1995. vol. 46(3-4). pp. 221-227.
Chen, Y et al. Journal of Biological Chemistry. "In Vitro Refolding/Unfolding Pathways of Amphioxus Insulin-Like Peptide Implications for Folding Behavior of Insulin Family Proteins." 2004. vol. 279(53). pp. 55224-55233.
Smith, L.E, "Accession: P01337 1 [gi: 32172038] & Accession: P01337 2 [gi: 32172039], Definition: [Segment 1 of 2] Insulin-1 & [Segment 2 of 2] Insulin-1", NCBI Entrez Protein [online]; Mar. 21, 2006 uploaded, NCBI, [retrieved on Sep. 11, 2013], Retrieved from the internet:http://www.ncbi.nlm.nih.gov/protein/32172037?sat=34&satkey=10044352.
Baker et al., "The Structure of 2Zn Pig Insulin Crystals at 1.5 Å Resolution," Philosophical Transactions of the Royal Society of London, 1988, vol. 319, p. 369-456.
Ward et al., "Ligard-induced activiation of the insulin receptor: a multi-step process involving structural changes in both the ligand and the receptor," Bioessays, 2009, vol. 31, pp. 422-434.
Seino et al., "Alternative Splicing of Human Insulin Receptor Messenger RNA," Biochemical and Biophysical Research Communications, 1989, vol. 159, pp. 312-316.
Moller et al., "Tissue-Specific Expression of Two Alternatively Spliced Insulin Receptor mRNAs in Man," Molecular Endocrinology, 1989, vol. 3, No. 8, pp. 1263-1269.
Mosthaf et al., "Functionally Distinct Insulin Receptors Generated by Tissue-Specific Alternative Splicing," The EMBO Journal, 1990, vol. 9, pp. 2409-2413.
Yamaguchi et al, "Functional Properties of Two Naturally Occurring Isoforms of the Human Insulin Receptor in Chinese Hamster Ovary Cells," Endocrinology, 1991, vol. 129, No. 4, pp. 2058-2066.
Yamaguchi et al, "Ligand-Binding Properties of the Two Isoforms of the Human Insulin Receptor," Endocrinology, 1993, vol. 132, No. 3, pp. 1132-1138.
Blundell et al., "Expression on *Escherichia coli* of a chemically synthesized gene for a "mini-C" analog of human proinsulin," Advances in Protein Chemistry, 1972, vol. 26, pp. 279-402.
Pullen et al., "Receptor-binding region of insulin," Nature, 1976, vol. 259, pp. 369-373.
Nakagawa et al., "Role of the COOH-terminal B-chain Domain in Insulin-Receptor Interactions," Journal of Biological Chemistry, 1987, vol. 262, No. 25, pp. 12054-12058.

Mirmira et al., "Importance of the Character and Configuration of Residues B24, B25, and B26 in Insulin-Receptor Interactions," The Journal of Biological Chemistry, 1991, vol. 266, No. 3, pp. 1428-1436.
Xu et al., "Diabetes-Associated Mutations in Insulin: Consecutive Residues in the B Chain Contact Distinct Domains of the Insulin Receptor," Biochemistry, 2004, vol. 43, pp. 8356-8372.
De Meyts et al., "Insulin Interactions with its Receptors: Experimental Evidence for Negative Cooperativity," Biochemical and Biophysical Research Communications, 1973, vol. 55, pp. 154-161.
Kurose et al., "Cross-linking of a B25 Azidophenylalanine Insulin Derivative to the Carboxyl-terminal Region of the α-Subunit of the Insulin Receptor," Journal of Biological Chemistry, 1994, vol. 269, No. 46, pp. 29190-29197.
Shoelson et al., "BpaB25 Insulins," Journal of Biological Chemistry, 1993, vol. 268, No. 6, pp. 4085-4091.
Zakova et al., "Insulin Analogues with Modifications at Position B26. Divergence of Binding Affinity and Biological Activity," Biochemistry, 2008, vol. 47, pp. 5858-5868.
Fischer et al., "A Shortened Insulin with Full in vitro Potency," Biological Chemistry, 1985, vol. 366, pp. 521-525.
Hua et al., "Receptor binding redefined by a structural switch in a mutant human insulin," Nature, 1991, vol. 354, pp. 238-241.
Ludvigsen et al., "A Structural Switch in a Mutant Insulin Exposes Key Residues for Receptor Binding," Journal of Molecular Biology, 1998, vol. 279, pp. 1-7.
Nakagawa et al., "Importance of Aliphatic Side-Chain Structure at Positions 2 and 3 of Insulin A Chain in Insulin-Receptor Interactions," Biochemistry, 1992, vol. 31, pp. 3204-3214.
Markussen et al., "Single chain des-(B30) insulin," International Journal of Peptide and Protein Research, 1985, vol. 26, No. 1, pp. 70-77.
Shoelson et al., "Three mutant insulins in man," Nature, 1983, vol. 302, pp. 540-543.
Glendorf et al., "Importance of the Solvent-Exposed Residues of the Insulin B Chain ?-Helix for Receptor Binding," Biochemistry, 2008, vol. 47, pp. 4743-4751.
Soos et al., "Monoclonal antibodies reacting with multiple epitopes on the human insulin receptor," Biochemical Journal, 1986, vol. 235, No. 1, pp. 199-208.
Slaaby et al., "Hybrid Receptors Formed by Insulin Receptor (IR) and Insulin-like Growth Factor I Receptor (IGF-IR) Have Low Insulin and High IGF-1 Affinity Irrespective of the IR Splice Variant," Journal of Biological Chemistry, 2006, vol. 281, No. 36, pp. 25869-25874.
Volund, "Application of the Four-Parameter Logisic Model to Bioassay: Comparison with Slope Ratio and Parallel Line Models," Biometrics, 1978, vol. 34, pp. 357-365.
Kabsch, "Automatic Processing of Rotation Diffraction Data from Crystals of Initially Unknown Symmetry and Cell Constants," Journal of Applied Crystallogrpahy, 1993, vol. 26, pp. 795-800.
Vagin et al., "MOLREP: an Automated Program for Molecular Replacement," Journal of Applied Crystallography, 1997, vol. 30, pp. 1022-1025.
Murshudov, "Refinement of Macromolecular Structures by the Maximum-Likelihood Method," ACTA Crystallographica, 1997, vol. 53, pp. 240-255.
Emsley et al., "Coot: model-building tools for molecular graphics," ACTA Crystallographica, 2004, vol. 60, pp. 2126-2132.
Kjeldsen et al., "Expression of Insulin in Yeast: The Importance of Molecular Adaptation for Secretion and Conversion," Biotechnology and Genetic Engineering Reviews, 2001, vol. 18, pp. 89-121.
Schaffer, "A model for insulin binding to the insulin receptor," European Journal of Biochemistry, 1994, vol. 221, pp. 1127-1132.
Wells, "Additivity of Mutational Effects in Proteins," Biochemistry, 1990, vol. 29, vol. 37, pp. 8509-8517.
Kaarsholm et al., "Engineering Stability of the Insulin Monomer Fold with Application to Structure-Activity Relationships," Biochemistry, 1993, vol. 32, pp. 10773-10778.
Kristensen et al., "Functional Reconsitiution of Insulin Receptor Binding Site from Non-binding Receptor Fragments," Journal of Biological Chemistry, 2002, vol. 277, No. 21, pp. 18340-18345.

(56) References Cited

OTHER PUBLICATIONS

Mynarcik et al., "Alanine-scanning Mutagenesis of a C-terminal Ligand Binding Domain of the Insulin Receptor ? Subunit," Journal of Biological Chemistry, 1996, vol. 271, No. 5, pp. 2439-2442.

Whittaker, "Characterization of the Functional Insulin Binding Epitopes of the Full-length Insulin Receptor," Journal of Biological Chemistry, 2005, vol. 280, No. 22, pp. 20932-20936.

Whittaker et al., "Comparison of the Functional Insulin Binding Epitopes of the A and B Isoforms of the Insulin Receptor," Journal of Biological Chemistry, 2002, vol. 277, No. 49, pp. 47380-47384.

Frasca et al., "Insulin Receptor Isoform A, a Newly Recognized High-Affinity Insulin-Like Growth Factor II Receptor in Fetal and Cancel Cells," Molecular and Cellular Biology, 1999, vol. 19, No. 5, pp. 3278-3288.

Kjeldsen et al., "The ligand specificities of the insulin receptor and the insulin-like growth factor I receptor reside in different regions of a common binding site," Proceedings of the National Academy of Sciences of the USA, 1991, vol. 88, No. 10, pp. 4404-4408.

Definition of hydrophobic and hydrophilic, Amino Acids, NJMS Department of Biochemistry and Molecular Biology. (http://njms2.umdnj.edu/biochweb/education/bioweb/PreK/AminoAcids.htm), accessed Dec. 16, 2014.

\* cited by examiner

PROTEASE STABILIZED ACYLATED INSULIN ANALOGUES

CROSS-REFERENCE TO RELATED APPLICATIONS

This application is a continuation of U.S. application Ser. No. 14/684,863, filed Apr. 13, 2015, which is a continuation of U.S. application Ser. No. 13/973,183, filed Aug. 22, 2013, which is a continuation of U.S. application Ser. No. 12/922,117, filed Dec. 10, 2010, now U.S. Pat. No. 8,691,759, which is a 371 National Stage Filing of International Application No. PCT/EP2009/053017, filed Mar. 13, 2009, which claimed priority of European Patent Application 08102708.8, filed Mar. 18, 2008, and European Patent Application 08170231.8, filed Nov. 28, 2008; this application also claims priority under 35 U.S.C. § 119(e) of U.S. Provisional Application 61/039,120, filed Mar. 25, 2008; the contents of all above-named applications are incorporated herein by reference.

FIELD OF THIS INVENTION

The present invention relates to novel acylated insulin analogues exhibiting resistance towards proteases, a method for the preparation of such insulin analogues, insulin preparations containing the insulin analogues of the invention and a method of treating diabetes mellitus using these insulin analogues.

BACKGROUND OF THIS INVENTION

Diabetes mellitus is a metabolic disorder in which the ability to utilize glucose is partly or completely lost. About 5% of all people suffer from diabetes and the disorder approaches epidemic proportions. Since the introduction of insulin in the 1920's, continuous efforts have been made to improve the treatment of diabetes mellitus. Since people suffering from diabetes are subject to chronic treatment over several decades, there is a major need for safe, convenient and life quality improving insulin formulations.

The oral route is by far the most widely used route for drug administration and is in general very well accepted by patients, especially for chronic therapies. Administration of therapeutic peptides or proteins is however often limited to parenteral routes rather than the preferred oral administration due to several barriers such as enzymatic degradation in the gastrointestinal (GI) tract and intestinal mucosa, drug efflux pumps, insufficient and variable absorption from the intestinal mucosa, as well as first pass metabolism in the liver.

Normally, insulin formulations are administered by subcutaneous injection. However, administration by other routes, e.g., orally or pulmonary, would be advantageous due to patient compliance, safety and convenience. Some of the commercial available insulin formulations are characterized by a fast onset of action and other formulations have a relatively slow onset but show a more or less prolonged action. It is vary important for diabetic patients that there is, on the market, a big variety of insulins with different durations of actions (profiles of actions). Briefly, insulins can be classified as being short-, intermediate- or long-acting.

WO 2008/034881 relates to certain insulin analogues wherein at least two hydrophobic amino acids have been substituted with hydrophilic amino acids which insulin analogues are not acylated.

EP 2008/060733 and EP 2008/060733 relate to certain acylated insulin analogues wherein the insulin analogue comprises an elongation with an amino acid or a peptide residue connected C terminally to the A21 amino acid.

EP 2008/060734 relates to certain acylated insulins wherein an acyl moiety is attached to the parent insulin and wherein said acyl moiety comprises repeating units of alkylene glycol containing amino acids.

SEQUENCE LISTING

The instant application contains a Sequence Listing which has been submitted in ASCII format via EFS-Web and is hereby incorporated by reference in its entirety. Said ASCII copy, created on Apr. 13, 2015, is named 7777US01_Seq_ST25.txt and is 15 kilobytes in size.

BRIEF DESCRIPTION OF THE DRAWINGS

FIG. 10 is shown with the data from the first 250 minutes; FIG. 11 is shown with the full 24 hour (1440 minutes) time-course.

ASPECTS OF THIS INVENTION

Figure 1:
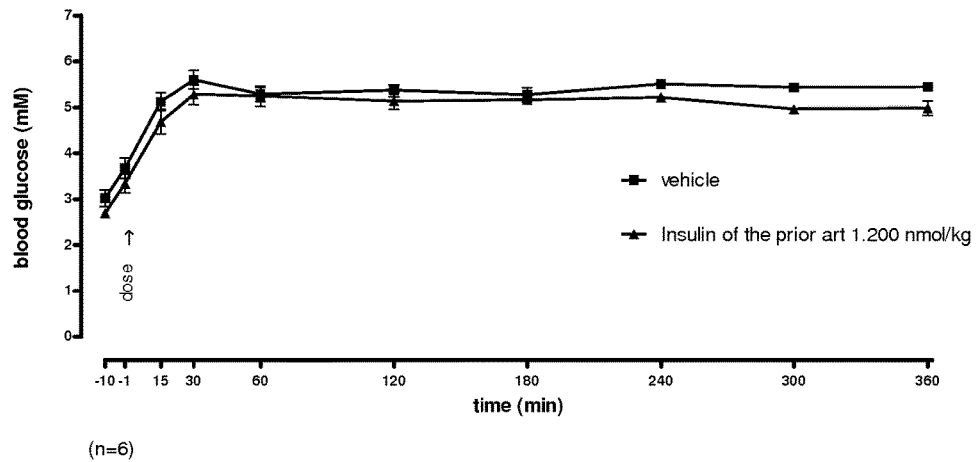
FIG. 1 shows the oral effect of the compound of Example 183 on overnight fasted male Wistar rats.

An aspect of this invention relates to the furnishing of insulin analogues which, when administered orally, can give a satisfactory control of the blood glucose level.

Another aspect of this invention relates to furnishing of insulin analogues which, when administered orally, can give a prolonged lowering of the glucose level Another aspect of this invention relates to furnishing of basal insulin analogues which, when administered orally, can give a prolonged lowering of the glucose level Another aspect of this invention relates to furnishing of basal insulin analogues which, when administered orally, can give a satisfactory control of the blood glucose level following thrice daily administration.

Another aspect of this invention relates to furnishing of basal insulin analogues which, when administered orally, can give a satisfactory control of the blood glucose level following twice daily administration.

Another aspect of this invention relates to furnishing of basal insulin analogues which, when administered orally, can give a satisfactory control of the blood glucose level following once daily administration.

Another aspect of this invention relates to furnishing of basal insulin analogues which are hydrophilic.

Another aspect of this invention relates to furnishing of basal insulin analogues which are more hydrophilic than human insulin.

Another aspect of this invention relates to furnishing of basal insulin analogues which are less hydrophobic than human insulin, as measured by the relative hydrophobicity (k'rel) as described herein.

Another aspect of this invention relates to furnishing of basal insulin analogues which are less hydrophobic than of similar non-protease stabilised parent insulins acylated with the same acyl moiety, as measured by the relative hydrophobicity (k'rel) as described herein.

K'rel of the basal insulin analogues of the invention are preferably less than 5, more preferably less than 3, more preferably less than 2, more preferably less than 1, more preferably less than 0.8, more preferably less than 0.6, more preferably less than 0.5, more preferably less than 0.4, more preferably less than 0.3, more preferably less than 0.2, more preferably less than 0.1.

Another aspect of this invention relates to furnishing of basal insulin analogues which, when administered orally, have satisfactory bioavailabilities. Compared with the bioavailabilities of similar acylated insulins without the protease stabilising mutations given in similar doses, the bioavailability of preferred compounds of this invention is at least 10% higher, preferably 20% higher, preferably 25% higher, preferably 30% higher, preferably 35% higher, preferably 40% higher, preferably 45% higher, preferably 50% higher, preferably 55% higher, preferably 60% higher, preferably 65% higher, preferably 70% higher, preferably 80% higher, preferably 90% higher, preferably 100% higher, preferably more than 100% higher than that of the non-protease stabilised comparator.

Another aspect of this invention relates to furnishing of basal insulin analogues which, when administered orally, have satisfactory bioavailabilities. Bioavailabilities of preferred compounds of this invention (relative to i.v. administration) are at least 0.3%, preferably >0.5%, preferably >1%, preferably >1.5%, preferably >2%, preferably >2.5%, preferably >3%, preferably >3.5%, preferably >4%, preferably >5%, preferably >6%, preferably >7%, preferably >8%, preferably >9%, preferably >10%.

Another aspect of this invention relates to furnishing of basal insulin analogues which, when administered by intravenous infusion, have satisfactory potencies. Compared with the potency of human insulin, potencies of preferred protease stabilised insulin analogues of the invention are preferably >5%, preferably >10%, preferably >20%, preferably >30%, preferably >40%, preferably >50%, preferably >75% and preferably >100%.

Another aspect of this invention relates to the furnishing of insulin analogues which, when administered pulmonarily, can give a satisfactory control of the blood glucose level.

Another aspect of this invention relates to the furnishing of insulin analogues which, when administered pulmonarily, can give a satisfactory control of the blood glucose level with a relatively slow onset of action and/or a more or less prolonged action.

Another aspect of this invention relates to the furnishing of insulin analogues having a satisfactory prolonged action following pulmonary administration. Compared with similar acylated insulin without protease stabilising mutations given in similar doses, the duration of action of preferred compounds of this invention is at least 10% longer, preferably 20% longer, preferably 25% longer, preferably 30% longer, preferably 35% longer, preferably 40% longer, preferably 45% longer, preferably 50% longer, preferably 55% longer, preferably 60% longer, preferably 65% longer, preferably 70% longer, preferably 80% longer, preferably 90% longer, preferably 100% longer, preferably more than 100% longer than that of the comparator. Duration of action can be measured by the time that blood glucose is suppressed, or by measuring relevant pharmacokinetic properties, for example $t_{1/2}$ or MRT (mean residence time).

Another aspect of this invention relates to the furnishing of insulin analogues having a satisfactory pulmonary bioavailability. Compared with the bioavailability of human insulin or compared with similar acylated insulin without protease stabilising mutations given in similar doses, the bioavailability of preferred compounds of this invention is at least 10% higher, preferably 20% higher, preferably 25% higher, preferably 30% higher, preferably 35% higher, preferably 40% higher, preferably 45% higher, preferably 50% higher, preferably 55% higher, preferably 60% higher, preferably 65% higher, preferably 70% higher, preferably 80% higher, preferably 90% higher, preferably 100% higher, preferably more than 100% higher than that of the comparator.

Another aspect of this invention relates to the furnishing of insulin analogues having increased apparent in vivo potency.

Another aspect of this invention relates to the furnishing of prolonged acting insulins with oral bioavailability.

Another aspect of this invention relates to the furnishing of insulin analogues having an increased proteolytical stability compared to the stability of human insulin. Compared with human insulin, the proteolytical stability of preferred compounds of this invention is at least 2 fold more stable, preferably 3 fold more stable, preferably 4 fold more stable, preferably 5 fold more stable, preferably 6 fold more stable, preferably 7 fold more stable, preferably 8 fold more stable, preferably 9 fold more stable, preferably 10 fold more stable, preferably 12 fold more stable, preferably 14 fold more stable, preferably 16 fold more stable, preferably 18 fold more stable, preferably 20 fold more stable, preferably 25 fold more stable, preferably more than 25 fold more stable than that of the comparator. Proteolytical stability can be measured by exposing the insulins to (a mixture of) proteolytic enzymes, e.g. an extract of gut enzymes as described herein.

The object of this invention is to overcome or ameliorate at least one of the disadvantages of the prior art, or to provide a useful alternative.

Definitions

Herein, the term insulin covers natural occurring insulins, e.g., human insulin, as well as insulin analogues thereof. Human insulin consists of two polypeptide chains, the so-called A and B chains which contain 21 and 30 amino acid residues, respectively, and which are interconnected by two cystine disulphide bridges.

Herein, the term amino acid residue covers an amino acid from which a hydrogen atom has been removed from an amino group and/or a hydroxy group has been removed from a carboxy group and/or a hydrogen atom has been removed from a mercapto group. Imprecise, an amino acid residue may be designated an amino acid.

Herein, hydrophobic amino acids are to be understood as the naturally occurring amino acids tryptophan (Trp, W), phenylalanine (Phe, F), valine (Val, V), isoleucine (Ile, I), leucine (Leu, L) and tyrosine (Tyr, Y) (with the three-letter and the one-letter abbreviation in brackets).

Herein, hydrophilic amino acids are to be understood as natural amino acids that are not hydrophobic amino acids according to the definition above. In one embodiment hydrophilic acids according to the invention are selected from the group consisting of: Glutamic acid (Glu, E), aspartic acid (Asp, D), histidine (His, H), glutamine (Gln, Q), asparagine (Asn, N), serine (Ser, S), threonine (Thr, T), proline (Pro, P), glycine (Gly, G), lysine (Lys, K) and arginine (Arg, R). In a further embodiment hydrophilic amino acids according to the invention are selected from the group consisting of: Glutamic acid (Glu, E), aspartic acid (Asp, D), histidine (His, H), glutamine (Gln, Q), asparagine (Asn, N), lysine (Lys, K) and arginine (Arg, R).

Herein, the term insulin analogue covers a polypeptide which has a molecular structure which formally can be derived from the structure of a naturally occurring insulin, e.g., human insulin, by deleting and/or substituting (replacing) one or more amino acid residue occurring in the natural insulin and/or by adding one or more amino acid residue. The added and/or substituted amino acid residues can either be codable amino acid residues or other naturally occurring amino acid residues or purely synthetic amino acid residues. In a preferred embodiment, the insulin analogue has two or more mutations compared to human insulin.

Herein, the term protease stabilised insulin means the insulin without an appended acyl moiety. Said protease stabilised insulins have an improved stability against degradation from proteases.

Herein, the term parent insulin means the insulin without an appended acyl moiety and without mutations to improve stability against degradation from proteases. Said parent insulins have optionally mutations relative to human insulin. Parent insulins are thus also insulin analogues as defined above.

Herein, the terms parent insulin and non-protease stabilised insulin covers the same compounds.

Herein, the term mutation covers any change in amino acid sequence (substitutions and insertions with codable amino acids as well as deletions).

Herein, the term analogues of the A chain and analogues of the B chains of human insulin covers A and B chains of human insulin, respectively, having one or more substitutions, deletions and or extensions (additions) of the A and B amino acid chains, respectively, relative to the A and B chains, respectively, of human insulin.

Herein, terms like A1, A2, A3 etc. indicate the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are AlaA21, GlyA21 and GlnA21, respectively.

Herein, the terms A(0) or B(0) indicate the positions N-terminally neighbouring the A1 or B1 positions, respectively, in the A or B chains, respectively. The terms A(−1) or B(−1) indicate the positions of the first amino acids N-terminally to A(0) or B(0), respectively. Thus A(−2) and B(−2) indicate positions N-terminally to A(−1) and B(−1), respectively, A(−3) and B(−3) indicate positions N-terminally to A(−2) and B(−2), respectively, and so forth.

Herein, terms like desB29 and desB30 indicate an insulin analogue lacking the B29 or B30 amino acid residue, respectively.

Herein, the term "fast acting insulin" covers an insulin having a faster onset of action than normal or regular human insulin.

Herein, the term "long acting insulin" or the term "basal insulin" covers an insulin having a longer duration of action than normal or regular human insulin. Preferably, the time-action is more than 5, or 8 hours, in particularly of at least 9 hours. Preferably, the basal insulin has a time-action of at least 10 hours. The basal insulin may thus have a time-action in the range from about 8 to 24 hours, preferably in the range from about 9 to about 15 hours.

The numbering of the positions in insulin analogues, insulins and A and B chains is done so that the parent compound is human insulin with the numbering used for it.

Herein, the term "acylated insulin" covers modification of insulin by attachment of one or more acyl moieties via a linker to the protease stabilised insulin.

By acylated insulin having insulin activity is meant an acylated insulin with either the ability to lower the blood glucose in mammalians as measured in a suitable animal model, which may, e.g., be a rat, rabbit, or pig model, after suitable administration, e.g., by intravenous or subcutaneous administration, or an insulin receptor binding affinity.

Herein, the term alkyl covers a saturated, branched or straight hydrocarbon group.

Herein, the term alkoxy covers the radical "alkyl-O—". Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), hexoxy (1-hexoxy and 3-hexoxy), and the like.

Herein, the term alkylene covers a saturated, branched or straight bivalent hydrocarbon group having from 1 to 12 carbon atoms. Representative examples include, but are not limited to, methylene; 1,2-ethylene; 1,3-propylene; 1,2-propylene; 1,3-butylene; 1,4-butylene; 1,4-pentylene; 1,5-pentylene; 1,5-hexylene; 1,6-hexylene; and the like.

Herein, the term "neutral linear amino acid" covers. Non limiting examples of neutral linear amino acids are.

Herein, the term "cyclic amino acid" covers. Non limiting examples of cyclic amino acids are.

Herein, the term "acidic amino acid" covers. Non limiting examples of acidic amino acids are.

Herein, the term "fatty acid" covers a linear or branched, aliphatic carboxylic acids having at least two carbon atoms and being saturated or unsaturated. Non limiting examples of fatty acids are myristic acid, palmitic acid, and stearic acid.

Herein, the term "fatty diacid" covers a linear or branched, aliphatic dicarboxylic acids having at least two carbon atoms and being saturated or unsaturated. Non limiting examples of fatty diacids are succinic acid, hexanedioic acid, octanedioic acid, decanedioic acid, dodecanedioic acid, tetradecanedioic acid, hexadecanedioic acid, heptadecanedioic acid, octadecanedioic acid, and eicosanedioic acid.

Herein, the naming of the insulins is done according to the following principles: The names are given as mutations and modifications (acylations) relative to human insulin. For the naming of the acyl moiety, the naming is done according to IUPAC nomenclature and in other cases as peptide nomenclature. For example, naming the acyl moiety:

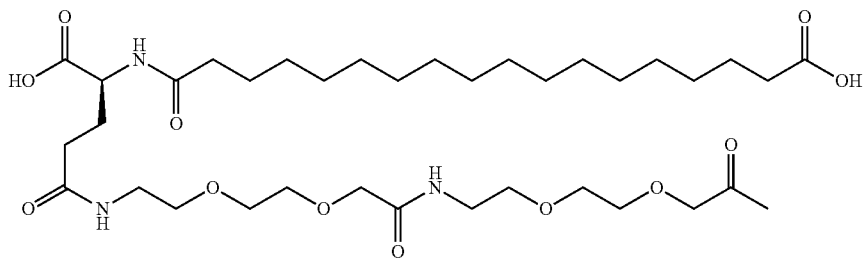 [SMILES: CC(=O)COCCOCCNC(=O)COCCOCCNC(=O)CC[C@H](NC(=O)CCCCCCCCCCCCCCCCC(=O)O)C(=O)O]

can for example be "octadecanedioyl-γGlu-OEG-OEG", or "17-carboxyheptadecanoyl-γGlu-OEG-OEG", wherein OEG is short hand notation for the amino acid $NH_2(CH_2)_2O(CH_2)_2OCH_2CO_2H$, γGlu is short hand notation for the amino acid gamma glutamic acid.

Other short hand notations for amino acids are, for example:

PEG3 is $NH_2((CH_2)_2O)_4CH_2CH_2CO_2H$
PEG7 is $NH_2((CH_2)_2O)_8CH_2CH_2CO_2H$

For example, the insulin of example 9 (with the sequence/structure given below) is named "A14E, B25H, B29K (N$^\varepsilon$Octadecanedioyl-γGlu-OEG-OEG), desB30 human insulin" to indicate that the amino acid in position A14, Y in human insulin, has been mutated to E, the amino acid in position B25, F in human insulin, has been mutated to H, the amino acid in position B29, K as in human insulin, has been modified by acylation on the epsilon nitrogen in the lysine residue of B29, denoted N$^\varepsilon$, by the residue octadecanedioyl-γGlu-OEG-OEG, and the amino acid in position B30, T in human insulin, has been deleted. Asterisks in the formula below indicate that the residue in question is different (i.e. mutated) as compared to human insulin. Throughout this application both formulas and names of preferred insulins of the invention are given Herein, the term "chemical stability" and "high chemical stability", means that chemically, the insulins of the invention are sufficiently stable in the desired formulation. That is that chemical degradation products are only formed in amounts that do not compromise shelf life of the final drug product. Chemical degradation products includes deamidation products, iso-aspartate formation, dimer formation, racemisation products, products resulting from dehydration processes etcetera. Chemical stability may be measured by HPLC analyses of aged samples or formulations.

Herein, the term "high physical stability" covers a tendency to fibrillation being less than 50% of that of human insulin. Fibrillation may be described by the lag time before fibril formation is initiated at a given conditions.

A polypeptide with insulin receptor and IGF-1 receptor affinity is a polypeptide which is capable of interacting with an insulin receptor and a human IGF-1 receptor in a suitable binding assay. Such receptor assays are well-know within the field and are further described in the examples. The present acylated insulin will not bind to the IGF-1 receptor or will have a rather low affinity to said receptor. More precisely, the acylated insulins of this invention will have an affinity towards the IGF-1 receptor of substantially the same magnitude or less as that of human insulin The term "pharmaceutically acceptable" as used herein means suited for normal pharmaceutical applications, i.e., giving rise to no serious adverse events in patients etc.

The terms treatment and treating as used herein means the management and care of a patient for the purpose of combating a disease, disorder or condition. The term is intended to include the delaying of the progression of the disease,

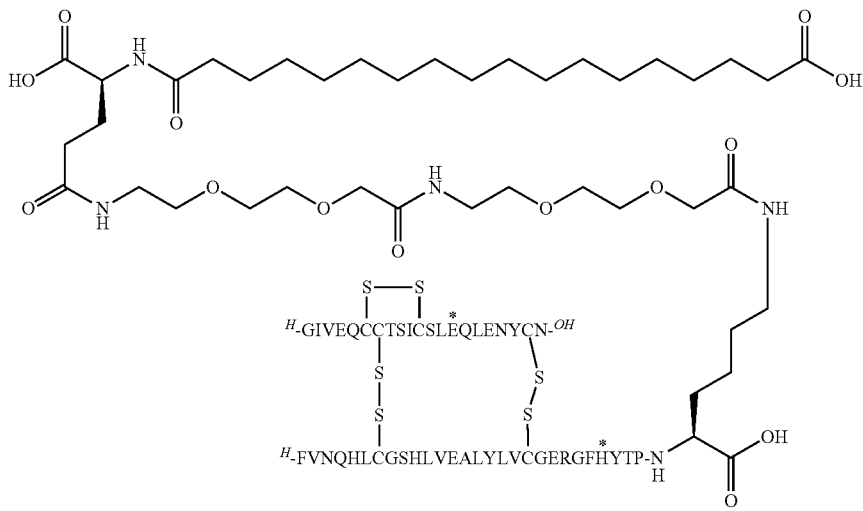

disorder or condition, the alleviation or relief of symptoms and complications, and/or the cure or elimination of the disease, disorder or condition. The patient to be treated is preferably a mammal, in particular a human being.

The term treatment of a disease as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term prevention of a disease as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term effective amount as used herein means a dosage which is sufficient in order for the treatment of the patient to be effective compared with no treatment.

POT is the *Schizosaccharomyces pombe* triose phosphate isomerase gene, and TPI1 is the *S. cerevisiae* triose phosphate isomerase gene.

By a leader is meant an amino acid sequence consisting of a pre-peptide (the signal peptide) and a pro-peptide.

The term signal peptide is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of this invention including yeast aspartic protease 3 (YAP3) signal peptide or any functional analog (Egel-Mitani et al. (1990) YEAST 6:127-137 and U.S. Pat. No. 5,726,038) and the α-factor signal of the MFα1 gene (Thorner (1981) in The Molecular Biology of the Yeast *Saccharomyces cerevisiae*, Strathern et al., eds., pp 143-180, Cold Spring Harbor Laboratory, NY and U.S. Pat. No. 4,870,00.

Herein, the term "pro-peptide" covers a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analogue thereof.

Unless indicated explicitly, the amino acids mentioned herein are L-amino acids. Further, the left and right ends of an amino acid sequence of a peptide are, respectively, the N- and C-termini, unless otherwise specified.

SUMMARY OF THE INVENTION

It has been discovered that insulins that are stabilised towards proteolytic degradation (by specific mutations) and acylated at the B29-lysine are efficacious and protracted and possess high potential as protracted insulins that can be administered pulmonary or orally. The acylation confers binding to serum albumin, and, consequently, protraction. In addition, the acylated insulins of the invention display substantial reduction of insulin receptor affinity, compared to similar acylated insulins that are not stabilised towards proteolytic degradation. This reduction in insulin receptor affinity of albumin-bound insulins of the invention contributes to the protraction of the acylated insulin in circulation, since insulin is internalised and degraded upon receptor activation. Hence, clearance of the insulins of the invention is reduced. The reduction of insulin receptor affinity does probably not cause a loss of potency, e.g., as measured in the hyperinsulinaemic euglycaemic clamp as described herein. The combination of high albumin binding affinity and low insulin receptor affinity is, thus, beneficial for obtaining long duration of action of the insulins (basal insulins). Furthermore, after oral administration, these acylated insulins have a higher degree of bioavailability than similar known acylated insulins, that are not stabilised towards proteolytic degradation. Hence, these acylated insulin analogues are valuable for oral administration. Similarly, after pulmonary administration, these acylated protease stabilised insulins displays higher apparent potency and/or bioavailability than similar known acylated insulins, that are not stabilised towards proteolytic degradation. Furthermore, these acylated protease stabilised insulins displays protracted time-action profiles when administered pulmonary to mammals. Hence, these acylated insulin analogues are valuable for pulmonary administration.

The above-mentioned insulins that are stabilised towards proteolytic degradation are herein designated protease stabilised insulins.

The protease stabilised insulin molecule has a limited number of the naturally occurring amino acid residues substituted with other amino acid residues relative to human insulin as explained in the detailed part of the specification.

In one embodiment, this invention relates to an acylated insulin, wherein the protease stabilised insulin analogue deviates from human insulin in one or more of the following deletions or substitutions: Q in position A18, A, G or Q in position A21, G or Q in position B1 or no amino acid residue in position B1, Q, S or T in position B3 or no amino acid residue in position B3, Q in position B13, no amino acid residue in position B27, D, E or R in position B28 and no amino acid in position B30.

In still a further aspect, this invention relates to pharmaceutical preparations comprising the acylated insulin of this invention and suitable adjuvants and additives such as one or more agents suitable for stabilization, preservation or iso-toni, e.g., zinc ions, phenol, cresol, a parabene, sodium chloride, glycerol or mannitol. The zinc content of the present formulations may be between 0 and about 6 zinc atoms per 6 molecules of insulin. The pH value of the pharmaceutical preparation may be between about 4 and about 8.5, between about 4 and about 5 or between about 6.5 and about 7.5.

In a further embodiment, this invention is related to the use of the acylated insulin as a pharmaceutical for the reducing of blood glucose levels in mammalians, in particularly for the treatment of diabetes.

In a further aspect, this invention is related to the use of the acylated insulin for the preparation of a pharmaceutical preparation for the reducing of blood glucose level in mammalians, in particularly for the treatment of diabetes.

In a further embodiment, this invention is related to a method of reducing the blood glucose level in mammalians by administrating a therapeutically active dose of an acylated insulin of this invention to a patient in need of such treatment.

In a further aspect of this invention, the acylated insulins are administered in combination with one or more further active substances in any suitable ratios. Such further active agents may be selected from human insulin, fast acting insulin analogues, antidiabetic agents, antihyperlipidemic agents, antiobesity agents, antihypertensive agents and agents for the treatment of complications resulting from or associated with diabetes.

In one embodiment, the two active components are administered as a mixed pharmaceutical preparation. In another embodiment, the two components are administered separately either simultaneously or sequentially.

In one embodiment, the acylated insulins of this invention may be administered together with fast acting human insulin or human insulin analogues. Such fast acting insulin analogue may be such wherein the amino acid residue in position B28 is Asp, Lys, Leu, Val, or Ala and the amino acid residue in position B29 is Lys or Pro, des(B28-B30) human insulin, des(B27) human insulin or des(B30) human insulin, and an analogue wherein the amino acid residue in position B3 is Lys and the amino acid residue in position B29 is Glu or Asp. The acylated insulin of this invention and the rapid acting human insulin or human insulin analogue can be mixed in a ratio from about 90% of the acylated insulin to about 10% of the rapid acting human insulin or human insulin analogue; preferably from about 70% of the acylated insulin to about 30% of the rapid acting human insulin or human insulin analogue, and even more preferred from about 50% of the acylated insulin to about 50% of the rapid acting human insulin or human insulin analogue (% being weight percentage).

The acylated insulins of this invention may also be used on combination treatment together with an antidiabetic agent.

Antidiabetic agents will include insulin, GLP-1(1-37) (glucagon like peptide-1) described in WO 98/08871, WO 99/43706, U.S. Pat. No. 5,424,286, WO 00/09666, WO 2006/097537, PCT/EP2008/061755 and PCT/EP2008/061830, GLP-2, exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted.

The acylated insulins of this invention may also be used on combination treatment together with an oral antidiabetic such as a thiazolidindione, metformin and other type 2 diabetic pharmaceutical preparation for oral treatment.

Furthermore, the acylated insulin of this invention may be administered in combination with one or more antiobesity agents or appetite regulating agents.

In one embodiment this invention is related to a pulmonal pharmaceutical preparation comprising the acylated insulin of this invention and suitable adjuvants and additives such as one or more agents suitable for stabilization, preservation or isotoni, e.g., zinc ions, phenol, cresol, a parabene, sodium chloride, glycerol, propyleneglycol or mannitol.

It should be understood that any suitable combination of the acylated insulins with diet and/or exercise, one or more of the above-mentioned compounds and optionally one or more other active substances are considered to be within the scope of this invention.

DESCRIPTION OF THE PREFERRED EMBODIMENTS

The stability and solubility properties of insulin are important underlying aspects for current insulin therapy. This invention is addressed to these issues by providing stable, acylated insulin analogues wherein the acylation decreases molecular flexibility and concomitantly reduce the fibrillation propensity and limit or modify the pH precipitation zone.

The acylated insulins of this invention are in particularly intended for pulmonary or oral administration due to their relatively high bioavailability compared to, e.g., human insulin and acylated human insulin. Furthermore, the acylated insulins will have a protracted insulin activity.

As mentioned above, insulins that are stabilised towards proteolytic degradation are herein designated protease stabilised insulins. The acylated insulins of this invention are said protease stabilised insulins which have been acylated as described herein.

Said protease stabilised insulins are derived from insulin compounds which herein are designated parent insulins or non-protease stabilised insulins.

In one embodiment a parent insulin is selected from the group consisting of a) human insulin; b) an insulin analogue of human insulin wherein the amino acid residue in position B28 of is Pro, Asp, Lys, Leu, Val, or Ala and the amino acid residue in position B29 is Lys or Pro and optionally the amino acid residue in position B30 is deleted; c) an insulin analogue which is des(B28-B30) human insulin, des(B27) human insulin or des(B30) human insulin; d) an insulin analogue of human insulin wherein the amino acid residue in position B3 is Lys and the amino acid residue in position B29 is Glu or Asp; e) an insulin analogue of human insulin wherein the amino acid residue in position A21 is Gly and wherein the insulin analogue is further extended in the C-terminal with two arginine residues; f) an insulin derivative wherein the amino acid residue in position B30 is substituted with a threonine methyl ester; and g) an insulin derivative wherein to the NE position of lysine in the position B29 of des(B30) human insulin a tetradecanoyl chain is attached. Each of these groups is a specific embodiment.

In another embodiment, a parent insulin is selected from the group consisting of human insulin; desB30 human insulin; AspB28 human insulin; AspB28, DesB30 human insulin; LysB3, GluB29 human insulin; LysB28, ProB29 human insulin; GlyA21, ArgB31, ArgB32 human insulin; and desB30, ArgB31, ArgB32 human insulin.

More specifically, the protease stabilised insulin is an insulin molecule having two or more mutations of the A and/or B chain relative to the parent insulin. Surprisingly, it has been found that by substituting two or more hydrophobic amino acids within or in close proximity to two or more protease sites on an insulin with hydrophilic amino acids, an insulin analogue (i.e., a protease stabilised insulin) is obtained which is proteolytically more stable compared to the parent insulin. In a broad aspect, a protease stabilised insulin is an insulin analogue wherein at least two hydrophobic amino acids have been substituted with hydrophilic amino acids relative to the parent insulin, wherein the substitutions are within or in close proximity to two or more protease cleavage sites of the parent insulin and wherein such insulin analogue optionally further comprises one or more additional mutations.

In another embodiment, a protease stabilised insulin is an insulin analogue wherein the amino acid in position A12 is Glu or Asp and/or the amino acid in position A13 is His, Asn, Glu or Asp and/or the amino acid in position A14 is Asn, Gln, Glu, Arg, Asp, Gly or His and/or the amino acid in position A15 is Glu or Asp; and the amino acid in position B24 is His and/or the amino acid in position B25 is His and/or the amino acid in position B26 is His, Gly, Asp or Thr and/or the amino acid in position B27 is His, Glu, Gly or Arg and/or the amino acid in position B28 is His, Gly or Asp; and which optionally further comprises one or more additional mutations.

In another embodiment a protease stabilised insulin is an analogue comprising the B25H or B25N mutations in combination with mutations in B27, optionally in combination with other mutations.

In another embodiment a protease stabilised insulin is an analogue comprising the B25H or B25N mutations in combination with mutations in B27, optionally in combination with other mutations. The mutations in position B27 can, for example, be Glu or Asp.

These protease stabilised acylated insulin analogues comprising both the B25 and B27 mutations have advantageous properties.

In another embodiment, a protease stabilised insulin is an insulin analogue comprising an A-chain amino acid sequence of formula 1:

```
Formula (1)
                                              (SEQ ID No: 1)
Xaa_{A(-2)}-Xaa_{A(-1)}-Xaa_{A0}-Gly-Ile-Val-Glu-Gln-Cys-Cys- Xaa_{A8}-Ser-Ile-Cys-Xaa_{A12}-Xaa_{A13}-Xaa_{A14}-Xaa_{A15}-Leu- Glu-Xaa_{A18}-Tyr-Cys-Xaa_{A21}
``` and a B-chain amino acid sequence of formula 2:

```
Formula (2)
                                              (SEQ ID No: 2)
Xaa_{B(-2)}-Xaa_{B(-1)}-Xaa_{B0}-Xaa_{B1}-Xaa_{B2}-Xaa_{B3}-Xaa_{B4}-His- Leu-Cys-Gly-Ser-Xaa_{B10}-Leu-Val-Glu-Ala-Leu- Xaa_{B16}-Leu-Val-Cys-Gly-Glu-Arg-Gly-Xaa_{B24}-Xaa_{B25}-

Xaa_{B26}-Xaa_{B27}-Xaa_{B28}-Xaa_{B29}-Xaa_{B30}-Xaa_{B31}-Xaa_{B32}
``` wherein
$Xaa_{A(-2)}$ is absent or Gly;
$Xaa_{A(-1)}$ is absent or Pro;
$Xaa_{A0}$ is absent or Pro;
$Xaa_{A8}$ is independently selected from Thr and His;
$Xaa_{A12}$ is independently selected from Ser, Asp and Glu;
$Xaa_{A13}$ is independently selected from Leu, Thr, Asn, Asp, Gln, His, Lys, Gly, Arg, Pro, Ser and Glu;
$Xaa_{A14}$ is independently selected from Tyr, Thr, Asn, Asp, Gln, His, Lys, Gly, Arg, Pro, Ser and Glu;
$Xaa_{A15}$ is independently selected from Gln, Asp and Glu;
$Xaa_{A18}$ is independently selected from Asn, Lys and Gln;
$Xaa_{A21}$ is independently selected from Asn and Gln;
$Xaa_{B(-2)}$ is absent or Gly;
$Xaa_{B(-1)}$ is absent or Pro;
$Xaa_{B0}$ is absent or Pro;
$Xaa_{B1}$ is absent or independently selected from Phe and Glu;
$Xaa_{B2}$ is absent or Val;
$Xaa_{B3}$ is absent or independently selected from Asn and Gln;
$Xaa_{B4}$ is independently selected from Gln and Glu;
$Xaa_{B10}$ is independently selected from His, Asp, Pro and Glu;
$Xaa_{B16}$ is independently selected from Tyr, Asp, Gln, His, Arg, and Glu;
$Xaa_{B24}$ is independently selected from Phe and His;
$Xaa_{B25}$ is independently selected from Asn, Phe and His;
$Xaa_{B26}$ is absent or independently selected from Tyr, His, Thr, Gly and Asp;
$Xaa_{B27}$ is absent or independently selected from Thr, Asn, Asp, Gln, His, Lys, Gly, Arg, Pro, Ser and Glu;
$Xaa_{B28}$ is absent or independently selected from Pro, His, Gly and Asp;
$Xaa_{B29}$ is absent or independently selected from Lys, Arg and Gln; and, preferably, $Xaa_{B29}$ is absent or independently selected from Lys and Gln;
$Xaa_{B30}$ is absent or Thr;
$Xaa_{B31}$ is absent or Leu;
$Xaa_{B32}$ is absent or Glu;
the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

In another embodiment, a protease stabilised insulin is an insulin analogue comprising an A-chain amino acid sequence of formula 3:

```
Formula (3)
                                              (SEQ ID No: 3)
Gly-Ile-Val-Glu-Gln-Cys-Cys-Xaa_{A8}-Ser-Ile-Cys- Xaa_{A12}-Xaa_{A13}-Xaa_{A14}-Xaa_{A15}-Leu-Glu-Xaa_{A18}-Tyr-Cys- Xaa_{A21}
``` and a B-chain amino acid sequence of formula 4:

```
Formula (4)
                                              (SEQ ID No: 4)
Xaa_{B1}-Val-Xaa_{B3}-Xaa_{B4}-His-Leu-Cys-Gly-Ser-Xaa_{B10}-

Leu-Val-Glu-Ala-Leu-Xaa_{B16}-Leu-Val-Cys-Gly-Glu-

Arg-Gly-Xaa_{B24}-His-Xaa_{B26}-Xaa_{B27}-Xaa_{B28}-Xaa_{B29}-Xaa_{B30}
``` wherein
$Xaa_{A8}$ is independently selected from Thr and His;
$Xaa_{A12}$ is independently selected from Ser, Asp and Glu;
$Xaa_{A13}$ is independently selected from Leu, Thr, Asn, Asp, Gln, His, Lys, Gly, Arg, Pro, Ser and Glu;
$Xaa_{A14}$ is independently selected from Thr, Asn, Asp, Gln, His, Lys, Gly, Arg, Pro, Ser and Glu;
$Xaa_{A15}$ is independently selected from Gln, Asp and Glu;
$Xaa_{A18}$ is independently selected from Asn, Lys and Gln;
$Xaa_{A21}$ is independently selected from Asn, and Gln;
$Xaa_{B1}$ is independently selected from Phe and Glu;
$Xaa_{B3}$ is independently selected from Asn and Gln;
$Xaa_{B4}$ is independently selected from Gln and Glu;
$Xaa_{B10}$ is independently selected from His, Asp, Pro and Glu;
$Xaa_{B16}$ is independently selected from Tyr, Asp, Gln, His, Arg, and Glu;
$Xaa_{B24}$ is independently selected from Phe and His;

$Xaa_{B26}$ is absent or independently selected from Tyr, His, Thr, Gly and Asp;
$Xaa_{B27}$ is absent or independently selected from Thr, Asn, Asp, Gln, His, Lys, Gly, Arg, Pro, Ser and Glu;
$Xaa_{B28}$ is absent or independently selected from Pro, His, Gly and Asp;
$Xaa_{B29}$ is absent or independently selected from Lys, Arg and Gln; and, preferably, $Xaa_{B29}$ is absent or independently selected from Lys and Gln;
$Xaa_{B30}$ is absent or Thr;
the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

In another embodiment, a protease stabilised insulin is an insulin analogue
wherein
$Xaa_{A8}$ is independently selected from Thr and His;
$Xaa_{A12}$ is independently selected from Ser and Glu;
$Xaa_{A13}$ is independently selected from Leu, Thr, Asn, Asp, Gln, His, Lys, Gly, Arg, Pro, Ser and Glu;
$Xaa_{A14}$ is independently selected from Asp, His, and Glu;
$Xaa_{A15}$ is independently selected from Gln and Glu;
$Xaa_{A18}$ is independently selected from Asn, Lys and Gln;
$Xaa_{A21}$ is independently selected from Asn, and Gln;
$Xaa_{B1}$ is independently selected from Phe and Glu;
$Xaa_{B3}$ is independently selected from Asn and Gln;
$Xaa_{B4}$ is independently selected from Gln and Glu;
$Xaa_{B10}$ is independently selected from His, Asp, Pro and Glu;
$Xaa_{B16}$ is independently selected from Tyr, Asp, Gln, His, Arg, and Glu;
$Xaa_{B24}$ is independently selected from Phe and His;
$Xaa_{B25}$ is independently selected from Phe, Asn and His;
$Xaa_{B26}$ is independently selected from Tyr, Thr, Gly and Asp;
$Xaa_{B27}$ is independently selected from Thr, Asn, Asp, Gln, His, Lys, Gly, Arg, and Glu;
$Xaa_{B28}$ is independently selected from Pro, Gly and Asp;
$Xaa_{B29}$ is independently selected from Lys and Gln;
$Xaa_{B30}$ is absent or Thr;
the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

Other embodiments of protease stabilised insulins are mentioned below.

A "protease" or a "protease enzyme" is a digestive enzyme which degrades proteins and peptides and which is found in various tissues of the human body such as e.g. the stomach (pepsin), the intestinal lumen (chymotrypsin, trypsin, elastase, carboxypeptidases, etc.) or mucosal surfaces of the GI tract (aminopeptidases, carboxypeptidases, enteropeptidases, dipeptidyl peptidases, endopeptidases, etc.), the liver (Insulin degrading enzyme, cathepsin D etc), and in other tissues.

A proteolytically stable insulin analogue (also designated a protease stabilised insulin) is herein to be understood as an insulin analogue, which is subjected to slower degradation by one or more proteases relative to human insulin. In one embodiment, a protease stabilised insulin is subjected to slower degradation by one or more proteases relative to the parent insulin. In a further embodiment, a protease stabilised insulin is stabilized against degradation by one or more enzymes selected from the group consisting of: pepsin (such as, e.g., the isoforms pepsin A, pepsin B, pepsin C and/or pepsin F), chymotrypsin (such as, e.g., the isoforms chymotrypsin A, chymotrypsin B and/or chymotrypsin C), trypsin, Insulin-Degrading Enzyme (IDE), elastase (such as, e.g., the isoforms pancreatic elastase I and/or II), carboxypeptidase (e.g., the isoforms carboxypeptidase A, carboxypeptidase A2 and/or carboxypeptidase B), aminopeptidase, cathepsin D and other enzymes present in intestinal extracts derived from rat, pig or human.

In one embodiment, a protease stabilised insulin is stabilized against degradation by one or more enzymes selected from the group consisting of: chymotrypsin, trypsin, Insulin-Degrading Enzyme (IDE), elastase, carboxypeptidases, aminopeptidases and cathepsin D. In a further embodiment, a protease stabilised insulin is stabilized against degradation by one or more enzymes selected from the group consisting of: chymotrypsin, carboxypeptidases and IDE. In a yet further embodiment, a protease stabilised insulin is stabilized against degradation by one or more enzymes selected from: chymotrypsin and carboxypeptidases.

T½ may be determined as described in the Examples as a measure of the proteolytical stability of a protease stabilised insulin towards protease enzymes such as chymotrypsin, pepsin and/or carboxypeptidase A. In one embodiment of the invention, T½ is increased relative to human insulin. In a further embodiment, T½ is increased relative to the parent insulin. In a yet further embodiment, T½ is increased at least 2-fold relative to the parent insulin. In a yet further embodiment, T½ is increased at least 3-fold relative to the parent insulin. In a yet further embodiment, T½ is increased at least 4-fold relative to the parent insulin. In a yet further embodiment, T½ is increased at least 5-fold relative to the parent insulin. In a yet further embodiment, T½ is increased at least 10-fold relative to the parent insulin.

An alternative way of measuring proteolytical stability is to measure the relative stability towards a comparator, e.g., human insulin. The relative stability is defines as T½/T½(comparator), where T½ and T½(comparator) are the half-lives of the analogue and the comparator, respectively, in the degradation assay. In the examples section, the relative stability of selected insulins of the invention towards an enzyme mixture extracted from duodenum from rats is given (relative to human insulin as well as relative to a protease-resistant insulin without acylation).

Protease cleavage sites (herein also mentioned as protease sites) are to be understood as amino acid residues that are recognized by proteases and/or amino acid residues whose peptide bond is cleaved by proteases. Protease cleavage sites may be determined by determining cleavage "hotspots" by HPLC, MS or LC-MS analyses and/or by prediction based on enzyme specificity of the protease enzyme for which the protease cleavage site is to be determined. A skilled person in the art will know how to determine protease cleavage sites for example based on enzyme specificities as for example described in Handbook of Proteolytical Enzymes, 2nd ed., Barrett, A. J., Rawlings, N. D., Woesner, J. F. editors, Elsevier Academic Press 2004. For example chymotrypsin is predicted to cleave peptide bonds C-terminal to aromatic residues (Trp, Tyr, Phe or Leu), that are not followed by Pro. Similarly, trypsin is predicted to cleave peptide bonds C-terminal to basic residues Lys or Arg, that are not followed by Pro, elastase is predicted to cleave residues C-terminal to Ala, Val, Gly or Ser and carboxypeptidase A will remove any C-terminal amino acid, but not Arg, Lys or Pro. Insulin-degrading enzyme (IDE) is predicted to cleave the following positions of human insulin B9-10, B10-11, B13-14, B14-15, B24-25, B25-26, A13-14 and A14-15.

The term substituting (an) amino acid "within or in close proximity" to a protease cleavage site is herein used to indicate the substitution of an amino acid within or in close proximity to a position of the parent insulin which has been determined to be a protease cleavage site. In one embodiment, two or more hydrophobic amino acids within or in close proximity to two or more protease sites on an insulin are substituted, wherein said hydrophobic amino acids are substituted with hydrophilic amino acids. In a further embodiment, two or more hydrophobic amino acids within two or more protease sites on an insulin are substituted with hydrophilic amino acids. In a yet further embodiment, two or more hydrophobic amino acids situated next to two or more protease sites on an insulin are substituted with hydrophilic amino acids. In a still further embodiment, two or more hydrophobic amino acids situated two amino acids away from to two or more protease sites on an insulin are substituted with hydrophilic amino acids. In a yet further embodiment, two or more hydrophobic amino acids situated three amino acids away from two or more protease sites on an insulin are substituted with hydrophilic amino acids. In a still further embodiment, two or more hydrophobic amino acids situated up to four amino acids away from two or more protease sites on an insulin are substituted with hydrophilic amino acids. In a yet further embodiment two or more hydrophobic amino acids situated one, two or three amino acids away from or within two or more protease sites on an insulin are substituted with hydrophilic amino acids. In a still further embodiment, two or more hydrophobic amino acids situated one or two amino acids away from or within two or more protease sites on an insulin are substituted with hydrophilic amino acids. In a yet further embodiment, two or more hydrophobic amino acids situated next to or within two or more protease sites on an insulin are substituted with hydrophilic amino acids.

A protease stabilised insulin may have a net charge which is different than the net charge of the parent insulin. In one embodiment, the net charge of a protease stabilised insulin is more positive than the net charge of the parent insulin. In one embodiment, the net charge of a protease stabilised insulin is more negative than the net charge of the parent insulin. In one embodiment, the average positive net charge of a protease stabilised insulin is between 0.5 and 5 as measured in an aqueous solution. In one embodiment, the average positive net charge of a protease stabilised insulin is between 1 and 5. In one embodiment, the average positive net charge of a protease stabilised insulin is between 1 and 4. In one embodiment, the average positive net charge of a protease stabilised insulin is between 1 and 3. In one embodiment, the average positive net charge of a protease stabilised insulin is between 2 and 3. In one embodiment, the average negative net charge of a protease stabilised insulin is between −0.5 and −5 as measured in an aqueous solution. In one embodiment, the average negative net charge of a protease stabilised insulin is between −1 and −5. In one embodiment, the average negative net charge of a protease stabilised insulin is between −1 and −4. In one embodiment, the average negative net charge of a protease stabilised insulin is between −1 and −3. In one embodiment, the average negative net charge of a protease stabilised insulin is between −2 and −3.

In one embodiment, a protease stabilised insulin may have increased solubility relative to human insulin. In a further embodiment, a protease stabilised insulin has increased solubility relative to human insulin at pH 3-9. In a yet further embodiment, a protease stabilised insulin has increased solubility relative to human insulin at pH 4-8.5. In a still further embodiment, a protease stabilised insulin has increased solubility relative to human insulin at pH 4-8. In a yet further embodiment, a protease stabilised insulin has increased solubility relative to human insulin at pH 4.5-8. In a further embodiment, a protease stabilised insulin has increased solubility relative to human insulin at pH 5-8. In a yet further embodiment, a protease stabilised insulin has increased solubility relative to human insulin at pH 5.5-8. In a further embodiment, a protease stabilised insulin has increased solubility relative to human insulin at pH 6-8.

In one embodiment, a protease stabilised insulin has increased solubility relative to human insulin at pH 2-4.

In one embodiment, a protease stabilised insulin may have increased solubility relative to the parent insulin. In a further embodiment, a protease stabilised insulin has increased solubility relative to the parent insulin at pH 3-9. In a yet further embodiment a protease stabilised insulin has increased solubility relative to parent insulin at pH 4-8.5. In a still further embodiment, a protease stabilised insulin has increased solubility relative to parent insulin at pH 4-8. In a yet further embodiment, a protease stabilised insulin has increased solubility relative to parent insulin at pH 4.5-8. In a still further embodiment, a protease stabilised insulin has increased solubility relative to parent insulin at pH 5-8. In a yet further embodiment, a protease stabilised insulin has increased solubility relative to parent insulin at pH 5.5-8. In a further embodiment, a protease stabilised insulin has increased solubility relative to parent insulin at pH 6-8.

In one embodiment, a protease stabilised insulin has increased solubility relative to parent insulin at pH 2-4.

By "increased solubility at a given pH" is meant that a larger concentration of a protease stabilised insulin dissolves in an aqueous or buffer solution at the pH of the solution relative to the parent insulin. Methods for determining whether the insulin contained in a solution is dissolved are known in the art.

In one embodiment, the solution may be subjected to centrifugation for 20 minutes at 30,000 g and then the insulin concentration in the supernatant may be determined by RP-HPLC. If this concentration is equal within experimental error to the insulin concentration originally used to make the composition, then the insulin is fully soluble in the composition of the invention. In another embodiment, the solubility of the insulin in a composition of the invention can simply be determined by examining by eye the container in which the composition is contained. The insulin is soluble if the solution is clear to the eye and no particulate matter is either suspended or precipitated on the sides/bottom of the container.

A protease stabilised insulin may have increased apparent potency and/or bioavailability relative to the parent insulin when compared upon measurement.

Standard assays for measuring insulin in vitro potency are known to the person skilled in the art and include inter alia (1) insulin radioreceptorassays, in which the relative potency of an insulin is defined as the ratio of insulin to insulin analogue required to displace 50% of $^{125}$I-insulin specifically bound to insulin receptors present on cell membranes, e.g., a rat liver plasma membrane fraction; (2) lipogenesis assays, performed, e.g., with rat adipocytes, in which relative insulin potency is defined as the ratio of insulin to insulin analogue required to achieve 50% of the maximum conversion of [3-$^3$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radioimmunoassays which can determine the immunogenicity of insulin analogues by measuring the effectiveness by which insulin or an insulin analogue competes with $^{125}$I-insulin in binding to specific anti-insulin antibodies; and (5) other assays which measure the binding of insulin or an insulin analogue to antibodies in animal blood plasma samples, such as ELISA assays possessing specific insulin antibodies.

Increased apparent in vivo potency can be estimated/visualised by comparison of blood glucose vs. time profiles of the insulin in question with a similar insulin without protease stabilising mutations given in similar doses. The insulin of the invention will have increased blood glucose lowering effect relative to the comparator.

Standard assays for measuring insulin bioavailability are known to the person skilled in the art and include inter alia measurement of the relative areas under the curve (AUC) for the concentration of the insulin in question administered pulmonary or orally and intra venously (i.v.) in the same species. Quantitation of insulin concentrations in blood (plasma) samples can be done using for example antibody assays (ELISA) or by mass spectrometry. Pulmonary administration can be performed by several means. For example, insulins can be dosed to rats by drop instillation, or to pigs by dry powder insufflation.

Protease stabilised insulin may optionally be analyzed for further protease sites which may be subject to further substitutions of one or more hydrophobic amino acids with hydrophilic amino acids. A protease stabilised insulin may be an insulin analogue which has at least two hydrophilic acids in protease sites compared to the parent insulin, the first modified insulin, and which has further at least one amino acid substitution in a new protease site of the first modified insulin wherein at least one hydrophobic amino acid has been substituted with at least one hydrophilic amino acid.

For the sake of convenience, here follows the names of codable, natural amino acids with the usual three letter codes & one letter codes in parenthesis: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the insulins of this invention are, preferably, amino acids which can be coded for by a nucleic acid. In one embodiment insulin or an insulin analogue is substituted by Gly, Glu, Asp, His, Gln, Asn, Ser, Thr, Lys, Arg and/or Pro and/or Gly, Glu, Asp, His, Gln, Asn, Ser, Thr, Lys, Arg and/or Pro is added to insulin or an insulin analogue. In one embodiment insulin or an insulin analogue is substituted by Glu, Asp, His, Gln, Asn, Lys and/or Arg and/or Glu, Asp, His, Gln, Asn, Lys and/or Arg is added to insulin or an insulin analogue.

In one embodiment, a protease stabilised insulin is selected from the group consisting of the following compounds: A14E, B25H, desB30 human insulin; A14H, B25H, desB30 human insulin; A14E, B1E, B25H, desB30 human insulin; A14E, B16E, B25H, desB30 human insulin; A14E, B25H, B28D, desB30 human insulin; A14E, B25H, B27E, desB30 human insulin; A14E, B1E, B25H, B27E, desB30 human insulin; A14E, B1E, B16E, B25H, B27E, desB30 human insulin; A8H, A14E, B25H, desB30 human insulin; A8H, A14E, B25H, B27E, desB30 human insulin; A8H, A14E, B1E, B25H, desB30 human insulin; A8H, A14E, B1E, B25H, B27E, desB30 human insulin; A8H, A14E, B1E, B16E, B25H, B27E, desB30 human insulin; A8H, A14E, B16E, B25H, desB30 human insulin; A14E, B25H, B26D, desB30 human insulin; A14E, B1E, B27E, desB30 human insulin; A14E, B27E, desB30 human insulin; A14E, B28D, desB30 human insulin; A14E, B28E, desB30 human insulin; A14E, B1E, B28E, desB30 human insulin; A14E, B1E, B27E, B28E, desB30 human insulin; A14E, B1E, B25H, B28E, desB30 human insulin; A14E, B1E, B25H, B27E, B28E, desB30 human insulin; A14D, B25H, desB30 human insulin; B25N, B27E, desB30 human insulin; A8H, B25N, B27E, desB30 human insulin; A14E, B27E, B28E, desB30 human insulin; A14E, B25H, B28E, desB30 human insulin; B25H, B27E, desB30 human insulin; B1E, B25H, B27E, desb30 human insulin; A8H, B1E, B25H, B27E, desB30 human insulin; A8H, B25H, B27E, desB30 human insulin; B25N, B27D, desB30 human insulin; A8H, B25N, B27D, desB30 human insulin; B25H, B27D, desB309 human insulin; A8H, B25H, B27D, desB30 human insulin; A(−1)P, A(0)P, A14E, B25H, desB30 human insulin; A14E, B(−1)P, B(0)P, B25H, desB30 human insulin; A(−1)P, A(0)P, A14E, B(−1)P, B(0)P, B25H, desB30 human insulin; A14E, B25H, B30T, B31L, B32E human insulin; A14E, B25H human insulin; A14E, B16H, B25H, desB30 human insulin; A14E, B10P, B25H, desB30 human insulin; A14E, B10E, B25H, desB30 human insulin; A14E, B4E, B25H, desB30 human insulin; A14H, B16H, B25H, desB30 human insulin; A14H, B10E, B25H, desB30 human insulin; A13H, A14E, B10E, B25H, desB30 human insulin; A13H, A14E, B25H, desB30 human insulin; A14E, A18Q, B3Q, B25H, desB30 human insulin; A14E, B24H, B25H, desB30 human insulin; A14E, B25H, B26G, B27G, B28G, desB30 human insulin; A14E, B25H, B26G, B27G, B28G, B29R, desB30 human insulin; A14E, A21G, B25H, B26G, B27G, B28G, desB30 human insulin; A14E, A21G, B25H, B26G, B27G, B28G, B29R, desB30 human insulin; A14E, A18Q, A21Q, B3Q, B25H, desB30 human insulin; A14E, A18Q, A21Q, B3Q, B25H, B27E, desB30 human insulin; A14E, A18Q, B3Q, B25H, desB30 human insulin; A13H, A14E, B1E, B25H, desB30 human insulin; A13N, A14E, B25H, desB30 human insulin; A13N, A14E, B1E, B25H, desB30 human insulin; A(−2)G, A(−1)P, A(0)P, A14E, B25H, desB30 human insulin; A14E, B(−2)G, B(−1)P, B(0)P, B25H, desB30 human insulin; A(−2)G, A(−1)P, A(0)P, A14E, B(−2)G, B(−1)P, B(0)P, B25H, desB30 human insulin; A14E, B27R, B28D, B29K, desB30 human insulin; A14E, B25H, B27R, B28D, B29K, desB30 human insulin; A14E, B25H, B26T, B27R, B28D, B29K, desB30 human insulin; A14E, B25H, B27R, desB30 human insulin; A14E, B25H, B27H, desB30 human insulin; A14E, A18Q, B3Q, B25H, desB30 human insulin; A13E, A14E, B25H, desB30 human insulin; A12E, A14E, B25H, desB30 human insulin; A15E, A14E, B25H, desB30 human insulin; A13E, B25H, desB30 human insulin; A12E, B25H, desB30 human insulin; A15E, B25H, desB30 human insulin; A14E, B25H, desB27, desB30 human insulin; A14E, B25H, B26D, B27E, desB30 human insulin; A14E, B25H, B27R, desB30 human insulin; A14E, B25H, B27N, desB30 human insulin; A14E, B25H, B27D, desB30 human insulin; A14E, B25H, B27Q, desB30 human insulin; A14E, B25H, B27E, desB30 human insulin; A14E, B25H, B27G, desB30 human insulin; A14E, B25H, B27H, desB30 human insulin; A14E, B25H, B27K, desB30 human insulin; A14E, B25H, B27P, desB30 human insulin; A14E, B25H, B27S, desB30 human insulin; A14E, B25H, B27T, desB30 human insulin; A13R, A14E, B25H, desB30 human insulin; A13N, A14E, B25H, desB30 human insulin; A13D, A14E, B25H, desB30 human insulin; A13Q, A14E, B25H, desB30 human insulin; A13E, A14E, B25H, desB30 human insulin; A13G, A14E, B25H, desB30 human insulin; A13H, A14E, B25H, desB30 human insulin; A13K, A14E, B25H, desB30 human insulin; A13P, A14E, B25H, desB30 human insulin; A13S, A14E, B25H, desB30 human insulin; A13T, A14E, B25H, desB30 human insulin; A14E, B16R, B25H, desB30 human insulin; A14E, B16D, B25H, desB30 human insulin; A14E, B16Q, B25H, desB30 human insulin; A14E, B16E, B25H, desB30 human insulin; A14E, B16H, B25H, desB30 human insulin; A14R, B25H, desB30 human insulin; A14N, B25H, desB30 human insulin; A14D, B25H, desB30 human insulin; A14Q, B25H, desB30 human insulin; A14E, B25H, desB30 human insulin; A14G, B25H, desB30 human insulin; A14H, B25H, desB30 human insulin; A8H, B1 OD, B25H human insulin; and A8H, A14E, B10E, B25H, desB30 human insulin and this embodiment may, optionally, comprise A14E, B25H, B29R, desB30 human insulin; B25H, desB30 human insulin; and B25N, desB30 human insulin.

In a preferred embodiment, a protease stabilised insulin is selected from the group consisting of the following compounds: A14E, B25H, desB30 human insulin; A14E, B16H, B25H, desB30 human insulin; A14E, B16E, B25H, desB30 human insulin; A14E, B25H, B29R, desB30 human insulin; A14E, B25H, B26G, B27G, B28G, desB30 human insulin; B25H, desB30 human insulin and A14E, B25H, desB27, desB30 human insulin.

In a preferred embodiment, a protease stabilised insulin is selected from any of the groups above that, in addition, are containing the desB27 mutation.

In a preferred embodiment, a protease stabilised insulin is selected from the group consisting of the following compounds: A14E, B25H, desB27, desB30 human insulin; A14E, B16H, B25H, desB27, desB30 human insulin; A14E, B16E, B25H, desB27, desB30 human insulin; A14E, B25H, desB27, B29R, desB30 human insulin and B25H, desB27, desB30 human insulin.

In one embodiment, a protease stabilised insulin is selected from any of the groups above that, in addition, are containing the following mutations in position A21 and/or B3 to improve chemical stability: A21G, desA21, B3Q, or B3G.

In a preferred embodiment, a protease stabilised insulin is selected from the following protease stabilised insulins: A14E, A21G, B25H, desB30 human insulin; A14E, A21G, B16H, B25H, desB30 human insulin; A14E, A21G, B16E, B25H, desB30 human insulin; A14E, A21G, B25H, desB27, desB30 human insulin; A14E, A21G, B25H, desB27, desB30 human insulin; A14E, A21G, B25H, B26G, B27G, B28G, desB30 human insulin; A14E, A21G, B25H, B26G, B27G, B28G, B29R, desB30 human insulin; A21G, B25H, desB30 human insulin and A21G, B25N, desB30 human insulin, and, preferably, it is selected from the following protease stabilised insulins: A14E, A21G, B25H, desB30 human insulin; A14E, A21G, B16H, B25H, desB30 human insulin; A14E, A21G, B16E, B25H, desB30 human insulin; A14E, A21G, B25H, desB27, desB30 human insulin; A14E, A21G, B25H, desB27, desB30 human insulin; A14E, A21G, B25H, desB27, desB30 human insulin; A14E, A21G, B25H, desB27, desB30 human insulin; A21G, B25H, desB30 human insulin and A21G, B25N, desB30 human insulin.

In a preferred embodiment, a protease stabilised insulin is acylated in the B29 position, at the epsilon nitrogen position of B29K.

In a preferred embodiment, a protease stabilised insulin is acylated in the A1 position, at the alpha nitrogen position of A1.

In a preferred embodiment, a protease stabilised insulin is acylated in the A1 position, at the alpha nitrogen position of A1, and the protease stabilized insulin is comprising the B29R mutation.

The protease stabilised insulins are produced by expressing a DNA sequence encoding the insulin in question in a suitable host cell by well known technique as disclosed in, e.g., U.S. Pat. No. 6,500,645. The protease stabilised insulin is either expressed directly or as a precursor molecule which has an N-terminal extension on the B-chain. This N-terminal extension may have the function of increasing the yield of the directly expressed product and may be of up to 15 amino acid residues long. The N-terminal extension is to be cleaved of in vitro after isolation from the culture broth and will therefore have a cleavage site next to B1. N-terminal extensions of the type suitable in this invention are disclosed in U.S. Pat. No. 5,395,922, and European Patent No. 765, 395A.

The polynucleotide sequence coding for the protease stabilised insulin may be prepared synthetically by established standard methods, e.g., the phosphoamidite method described by Beaucage et al. (1981) *Tetrahedron Letters* 22:1859-1869, or the method described by Matthes et al. (1984) *EMBO Journal* 3: 801-805. According to the phosphoamidite method, oligonucleotides are synthesized, e.g., in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant method will typically make use of a vector which is capable of replicating in the selected microorganism or host cell and which carries a polynucleotide sequence encoding the protease stabilised insulin. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector is capable of replicating in yeast. Examples of sequences which enable the vector to replicate in yeast are the yeast plasmid 2 μm replication genes REP 1-3 and origin of replication.

The vector may contain one or more selectable markers which permit easy selection of transformed cells. A selectable marker is a gene the product of which provides for biocide or viral resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide sequence encoding the protease stabilised insulin will also typically be operably connected to a suitable terminator. In yeast a suitable terminator is the TPI terminator (Alber et al. (1982) *J. Mol. Appl. Genet.* 1:419-434).

The procedures used to ligate the polynucleotide sequence encoding the protease stabilised insulin, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulins of this invention, and subsequently inserting this fragment into a suitable expression vector, or by sequentially inserting DNA fragments containing genetic information for the individual elements (such as the signal, pro-peptide, connecting peptide, A and B chains) followed by ligation.

The vector comprising the polynucleotide sequence encoding the protease stabilised insulin is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In one embodiment, the host cell is a yeast cell. The yeast organism may be any suitable yeast organism which, on cultivation, produces large amounts of the single chain insulin of the invention. Examples of suitable yeast organisms are strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans.*

The transformation of the yeast cells may for instance be effected by protoplast formation followed by transformation in a manner known per se. The medium used to cultivate the cells may be any conventional medium suitable for growing yeast organisms. The secreted insulin, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g., ammonium sulphate, followed by purification by a variety of chromatographic procedures, e.g., ion exchange chromatography, affinity chromatography, or the like.

Preferably, the acylated insulins of this invention are mono-substituted having only one acylation group attached to a lysine amino acid residue in the protease stabilised insulin molecule.

In one embodiment, the acyl moiety attached to the protease stabilised insulin has the general formula:

$$\text{Acy-AA1}_n\text{-AA2}_m\text{-AA3}_p\text{-} \qquad (I),$$

wherein n is 0 or an integer in the range from 1 to 3; m is 0 or an integer in the range from 1 to 10; p is 0 or an integer in the range from 1 to 10; Acy is a fatty acid or a fatty diacid comprising from about 8 to about 24 carbon atoms; AA1 is a neutral linear or cyclic amino acid residue; AA2 is an acidic amino acid residue; AA3 is a neutral, alkyleneglycol-containing amino acid residue; the order by which AA1, AA2 and AA3 appears in the formula can be interchanged independently; AA2 can occur several times along the formula (e.g., Acy-AA2-AA3$_2$-AA2-); AA2 can occur independently (=being different) several times along the formula (e.g., Acy-AA2-AA3$_2$-AA2-); the connections between Acy, AA1, AA2 and/or AA3 are amide (peptide) bonds which, formally, can be obtained by removal of a hydrogen atom or a hydroxyl group (water) from each of Acy, AA1, AA2 and AA3; and attachment to the protease stabilised insulin can be from the C-terminal end of a AA1, AA2, or AA3 residue in the acyl moiety of the formula (I) or from one of the side chain(s) of an AA2 residue present in the moiety of formula (I).

In another embodiment, the acyl moiety attached to the protease stabilised insulin has the general formula Acy-AA1$_n$-AA2$_m$-AA3$_p$- (I), wherein AA1 is selected from Gly, D- or L-Ala, βAla, 4-aminobutyric acid, 5-aminovaleric acid, 6-aminohexanoic acid, D- or L-Glu-α-amide, D- or L-Glu-γ-amide, D- or L-Asp-α-amide, D- or L-Asp-β-amide, or a group of one of the formula:

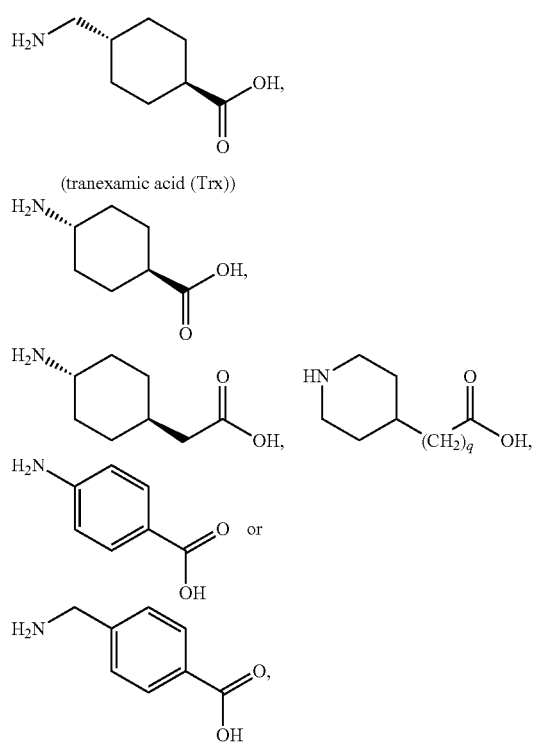

(tranexamic acid (Trx))

from which a hydrogen atom and/or a hydroxyl group has been removed and wherein q is 0, 1, 2, 3 or 4 and, in this embodiment, AA1 may, alternatively, be 7-aminoheptanoic acid or 8-aminooctanoic acid.

In another embodiment, the acyl moiety attached to the protease stabilised insulin has the general formula Acy-AA1$_n$-AA2$_m$-AA3$_p$- (I), wherein AA1 is as defined above and AA2 is selected from L- or D-Glu, L- or D-Asp, L- or D-homoGlu or any of the following:

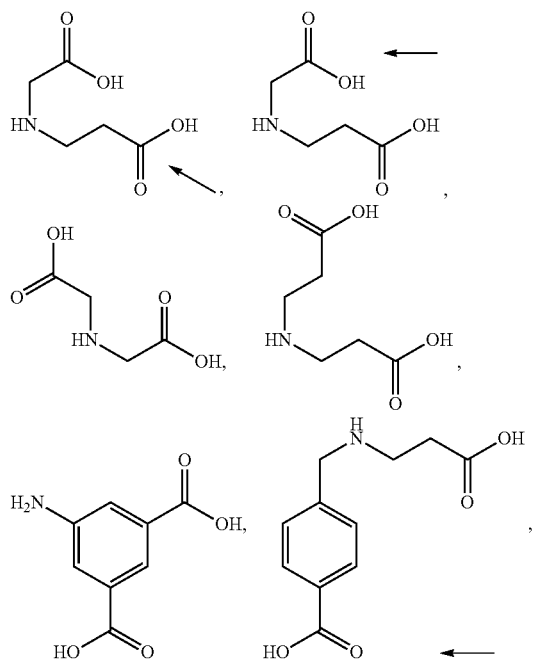

-continued from which a hydrogen atom and/or a hydroxyl group has been removed and wherein the arrows indicate the attachment point to the amino group of AA1, AA2, AA3, or to the amino group of the protease stabilised insulin.

In one aspect, the neutral cyclic amino acid residue designated AA1 is an amino acid containing a saturated 6-membered carbocyclic ring, optionally containing a nitrogen hetero atom, and preferably the ring is a cyclohexane ring or a piperidine ring. Preferably, the molecular weight of this neutral cyclic amino acid is in the range from about 100 to about 200 Da.

The acidic amino acid residue designated AA2 is an amino acid with a molecular weight of up to about 200 Da comprising two carboxylic acid groups and one primary or secondary amino group. Alternatively, acidic amino acid residue designated AA2 is an amino acid with a molecular weight of up to about 250 Da comprising one carboxylic acid group and one primary or secondary sulphonamide group.

The neutral, alkyleneglycol-containing amino acid residue designated AA3 is an alkyleneglycol moiety, optionally an oligo- or polyalkyleneglycol moiety containing a carboxylic acid functionality at one end and a amino group functionality at the other end.

Herein, the term alkyleneglycol moiety covers mono-alkyleneglycol moieties as well as oligoalkyleneglycol moieties. Mono- and oligoalkyleneglycols comprises mono- and oligoethyleneglycol based, mono- and oligopropyleneglycol based and mono- and oligobutyleneglycol based chains, i.e., chains that are based on the repeating unit —CH$_2$CH$_2$O—, —CH$_2$CH$_2$CH$_2$O— or —CH$_2$CH$_2$CH$_2$CH$_2$O—. The alkyleneglycol moiety is monodisperse (with well defined length/molecular weight). Monoalkyleneglycol moieties comprise —OCH$_2$CH$_2$O—, —OCH$_2$CH$_2$O— or —OCH$_2$CH$_2$CH$_2$CH$_2$O— containing different groups at each end.

As mentioned herein, the order by which AA1, AA2 and AA3 appears in the acyl moiety with the formula (I) (Acy-$AA1_n$-$AA2_m$-$AA3_p$-) can be interchanged independently. Consequently, the formula Acy-$AA1_n$-$AA2_m$-$AA3_p$- also covers moieties like, e.g., the formula Acy-$AA2_m$-$AA1_n$-$AA3_p$-, the formula Acy-AA2-$AA3_n$-AA2-, and the formula Acy-$AA3_p$-$AA2_m$-$AA1_n$-, wherein Acy, AA1, AA2, AA3, n, m and p are as defined herein.

As mentioned herein, the connections between the moieties Acy, AA1, AA2 and/or AA3 are formally obtained by amide bond (peptide bond) formation (—CONH—) by removal of water from the parent compounds from which they formally are build. This means that in order to get the complete formula for the acyl moiety with the formula (I) (Acy-$AA1_n$-$AA2_m$-$AA3_p$-, wherein Acy, AA1, AA2, AA3, n, m and p are as defined herein), one has, formally, to take the compounds given for the terms Acy, AA1, AA2 and AA3 and remove a hydrogen and/or hydroxyl from them and, formally, to connect the building blocks so obtained at the free ends so obtained.

Non-limiting, specific examples of the acyl moieties of the formula Acy-$AA1_n$-$AA2_m$-$AA3_p$- which may be present in the acylated insulin analogues of this invention are the following:

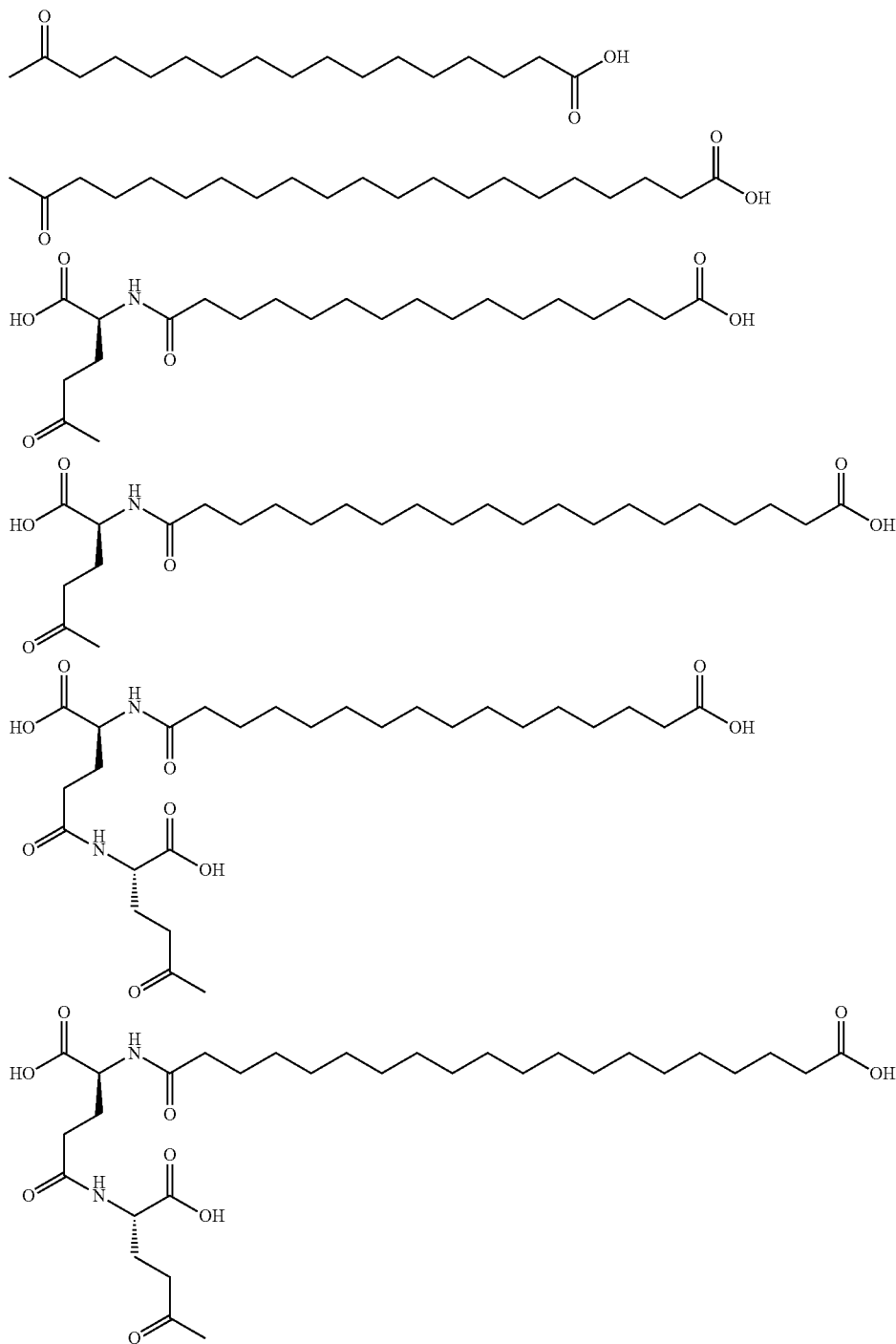

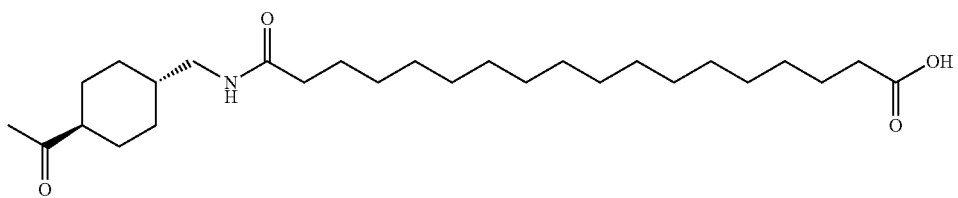
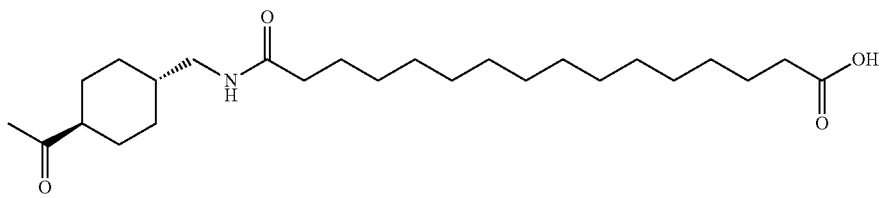
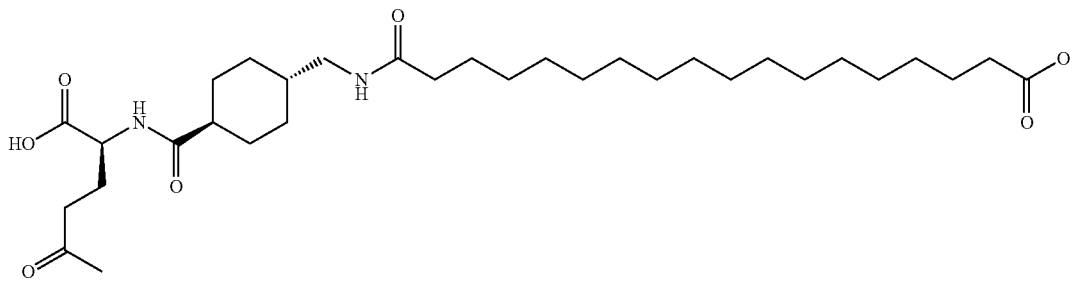
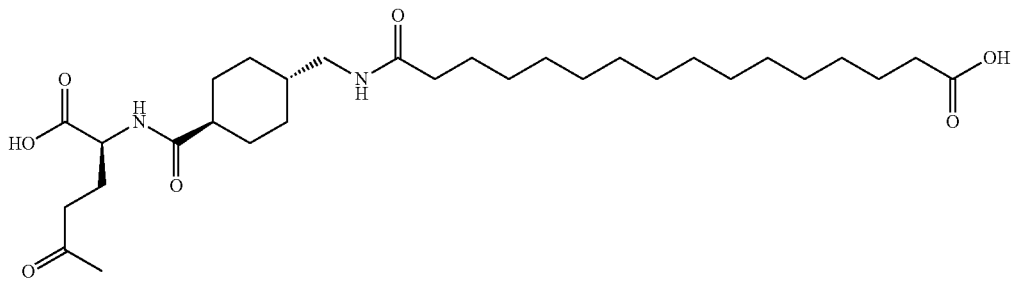
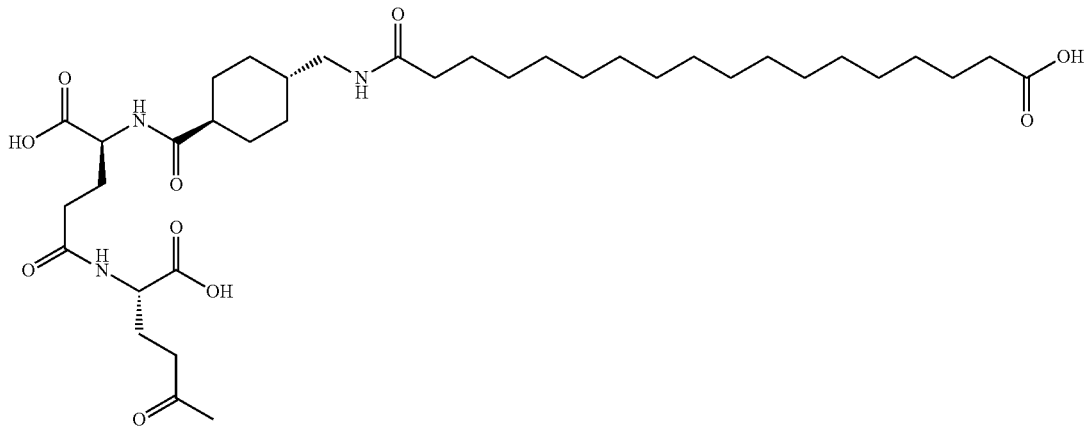

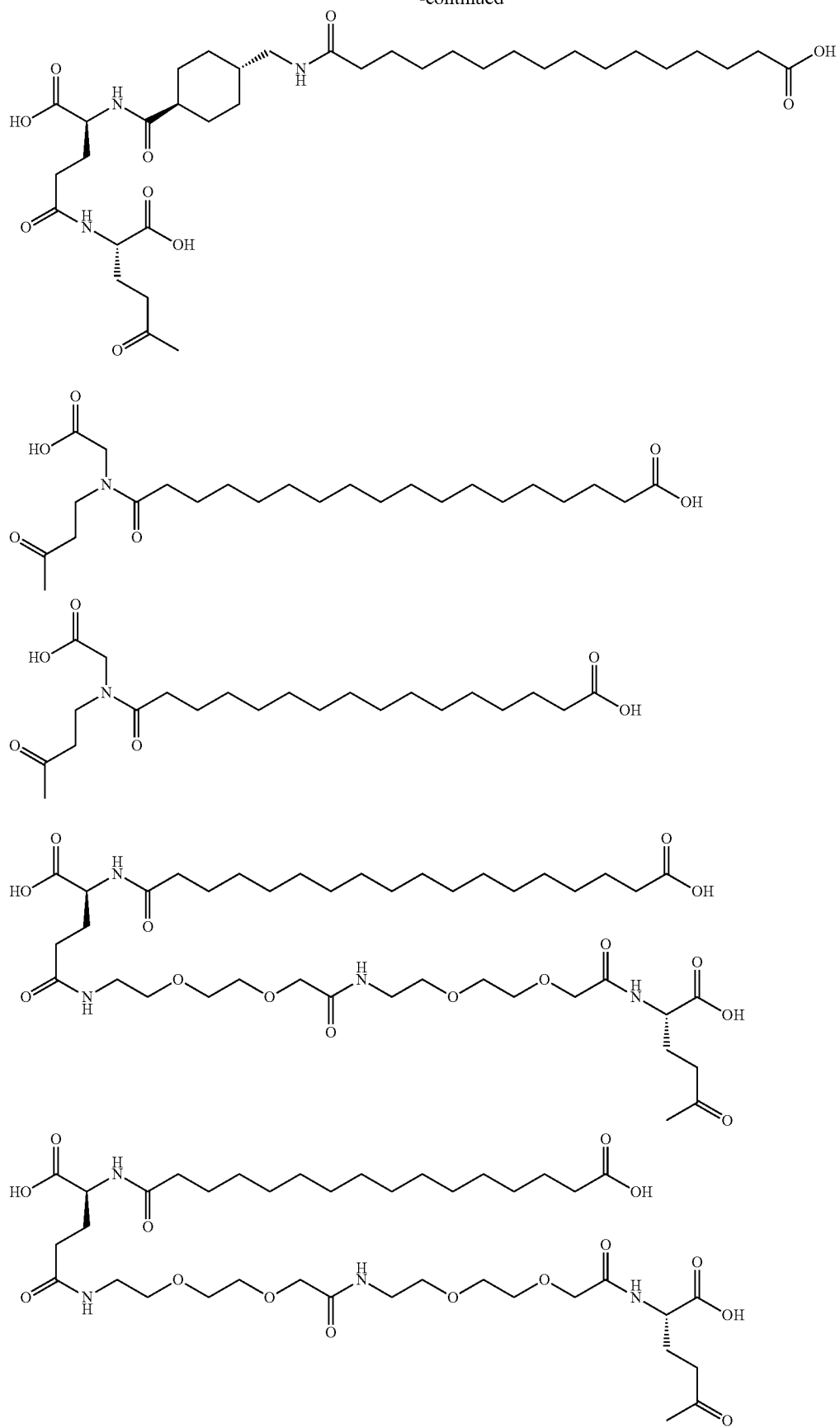

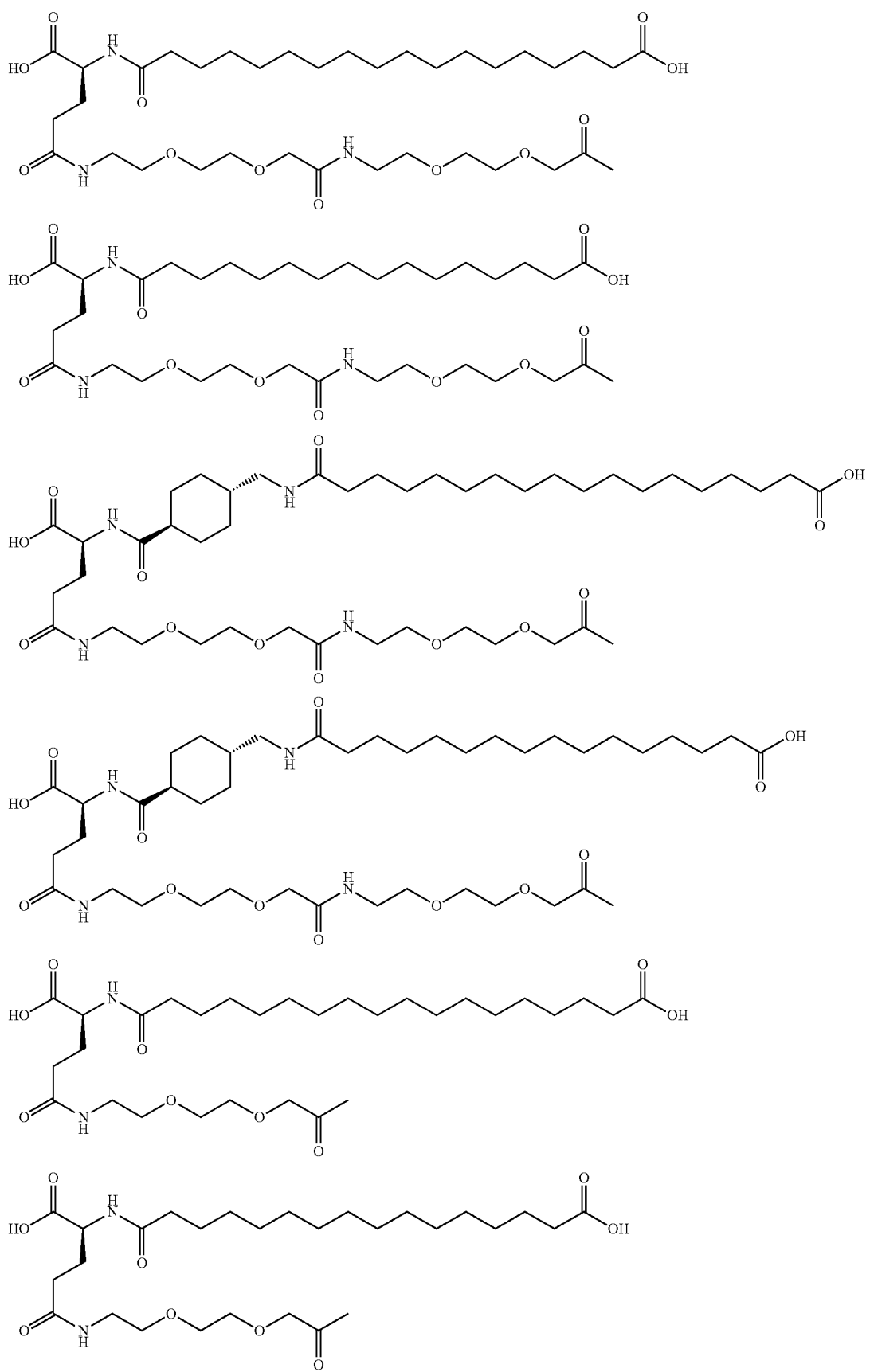

-continued
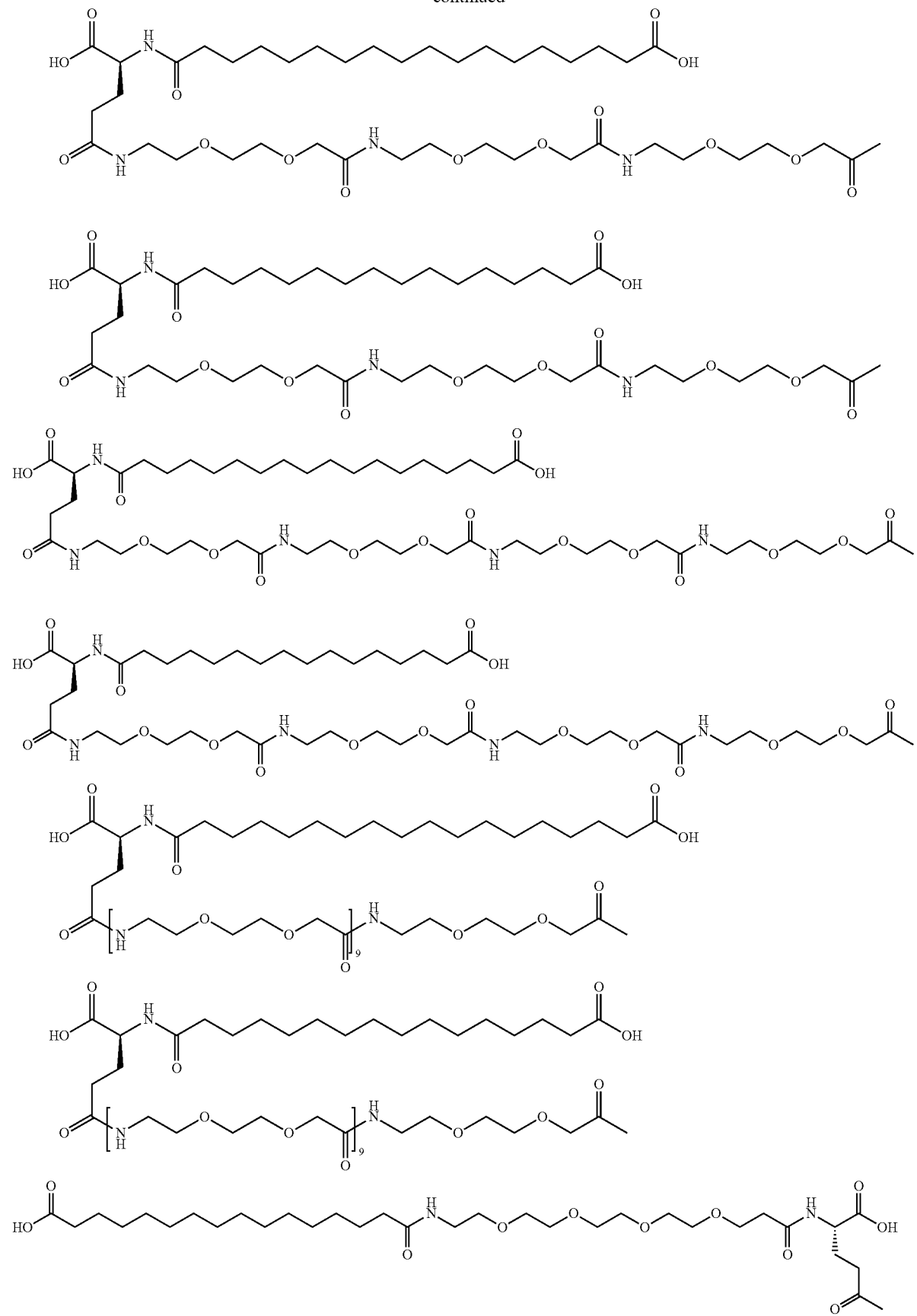

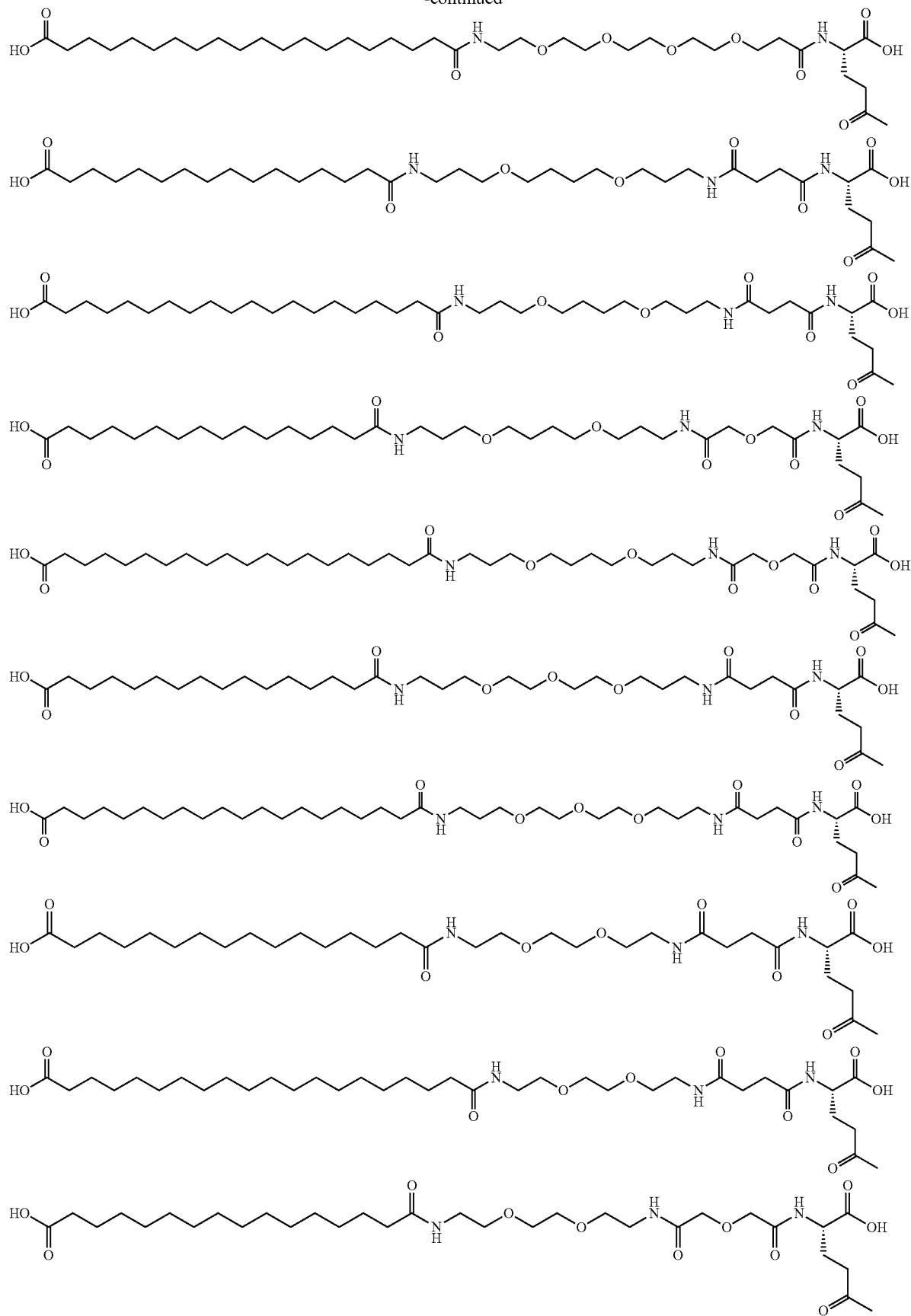

-continued
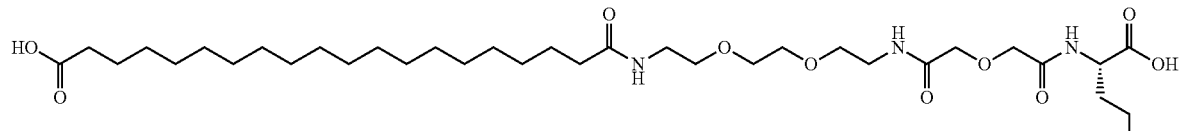
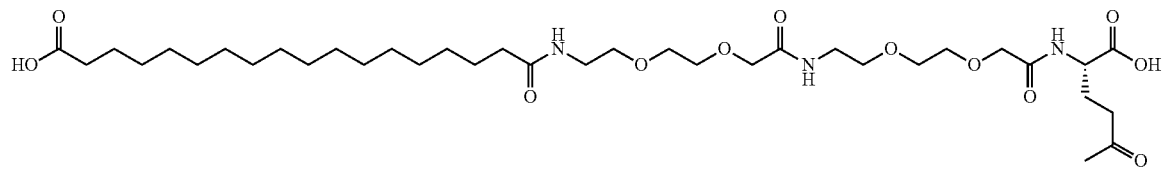
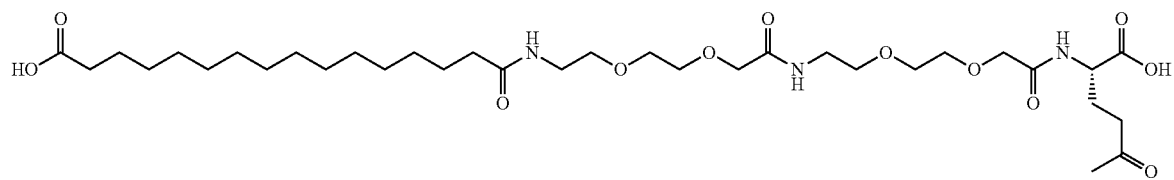
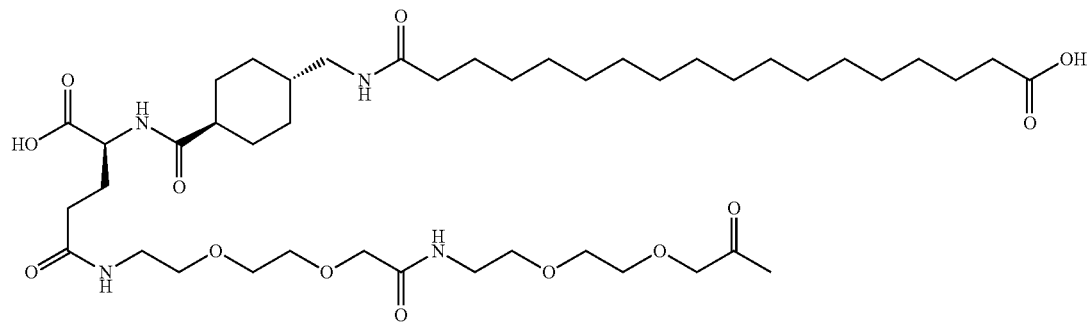
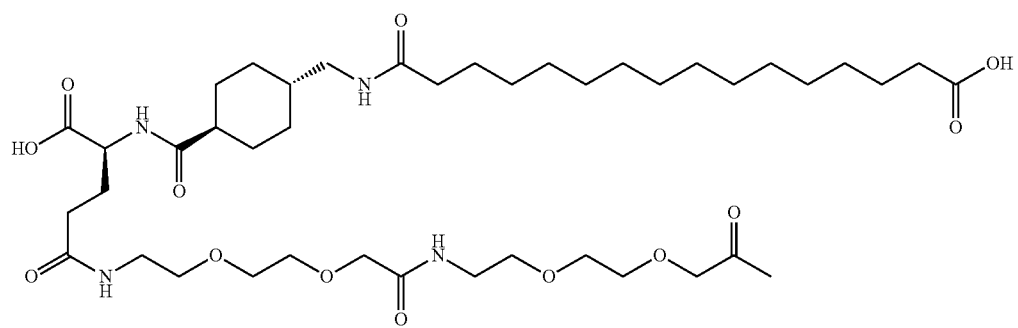
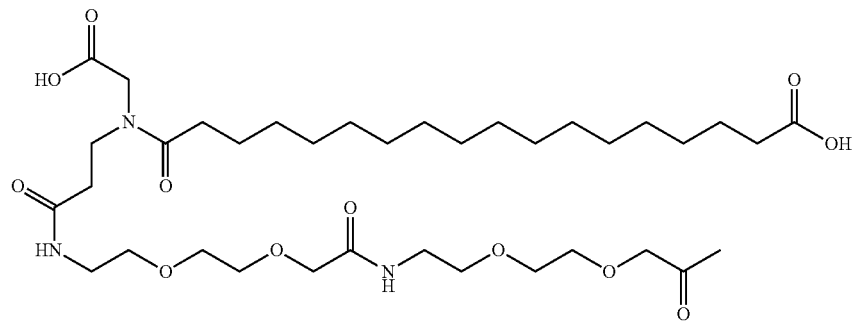

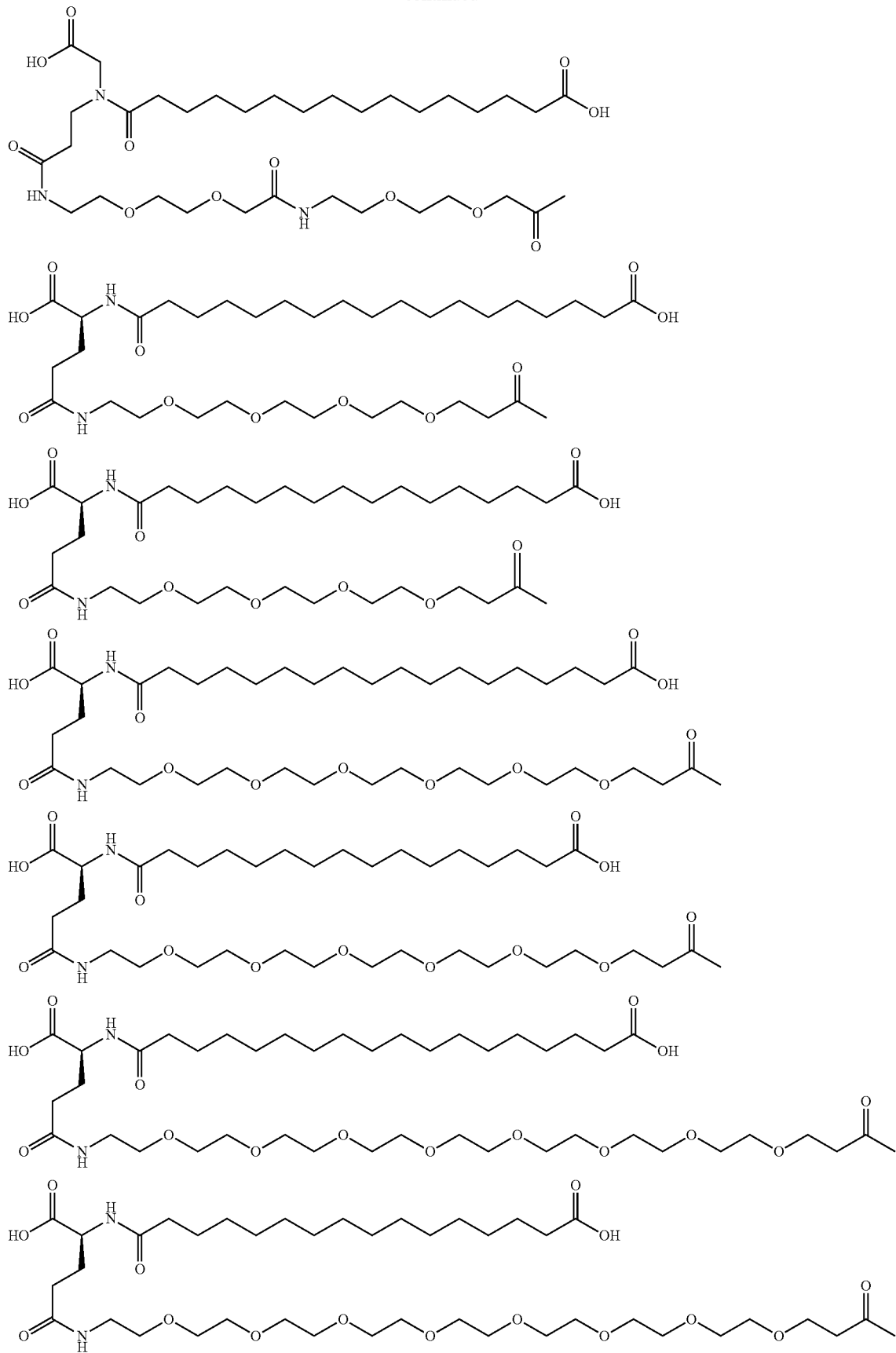

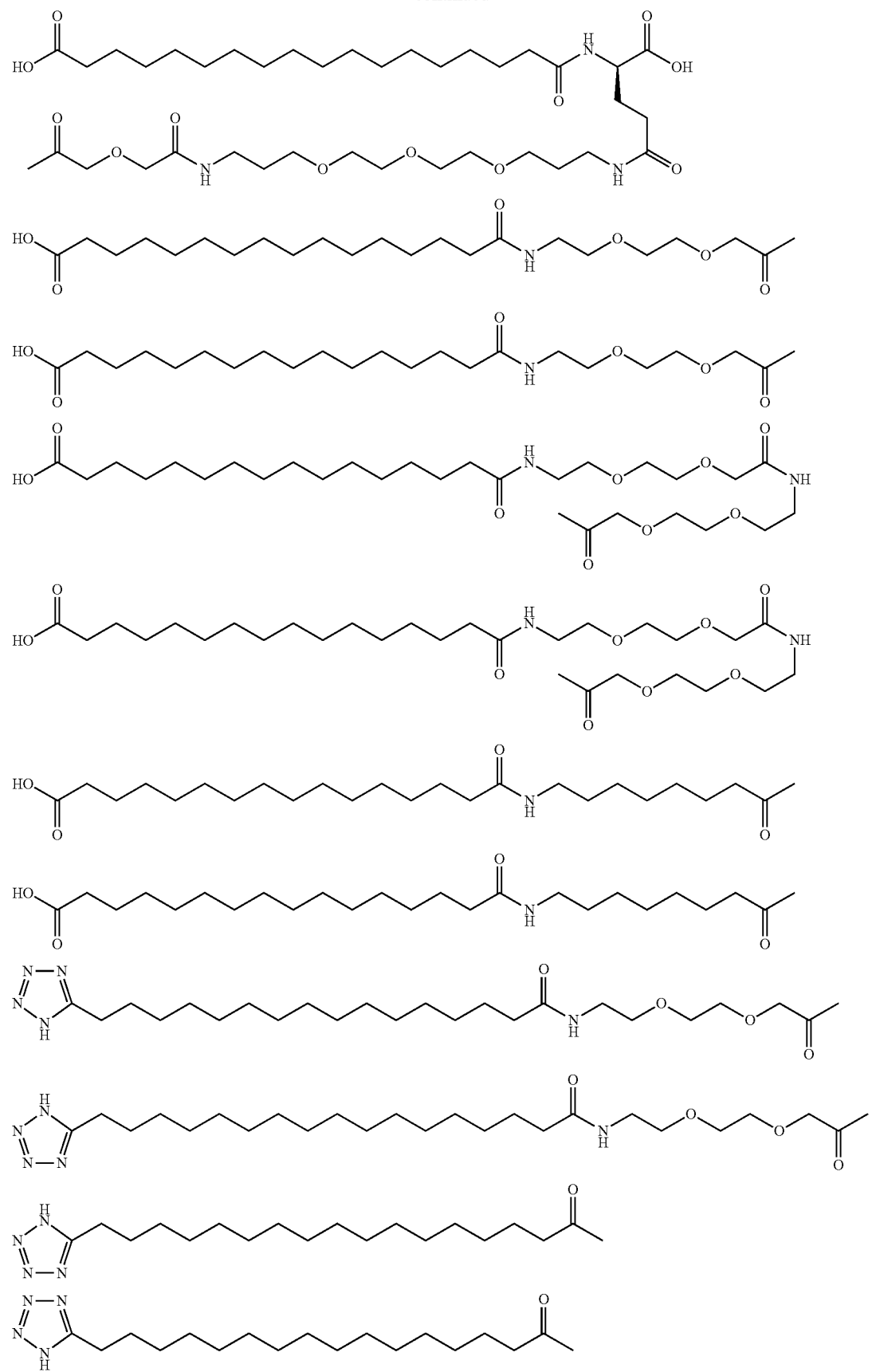

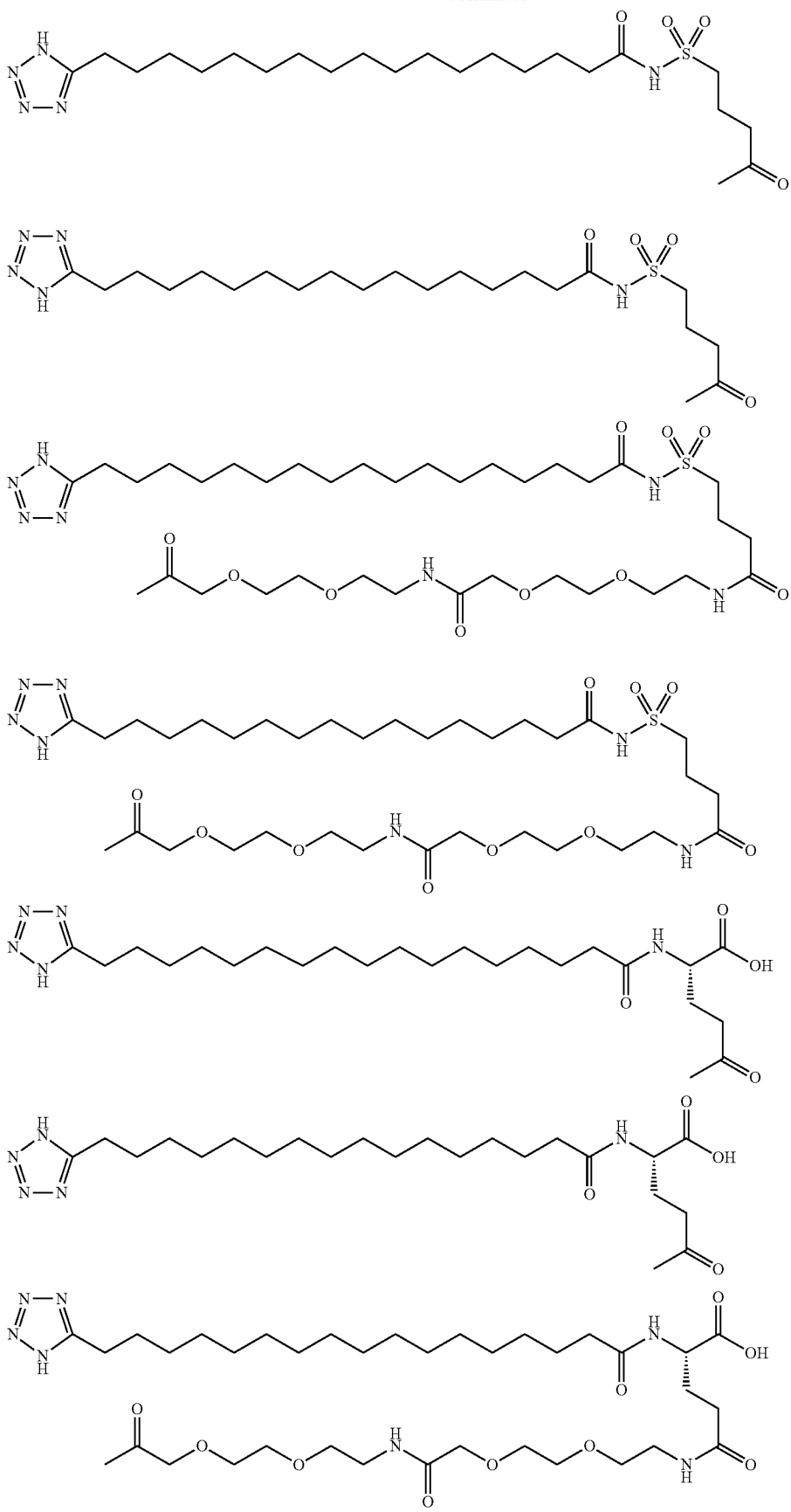

-continued
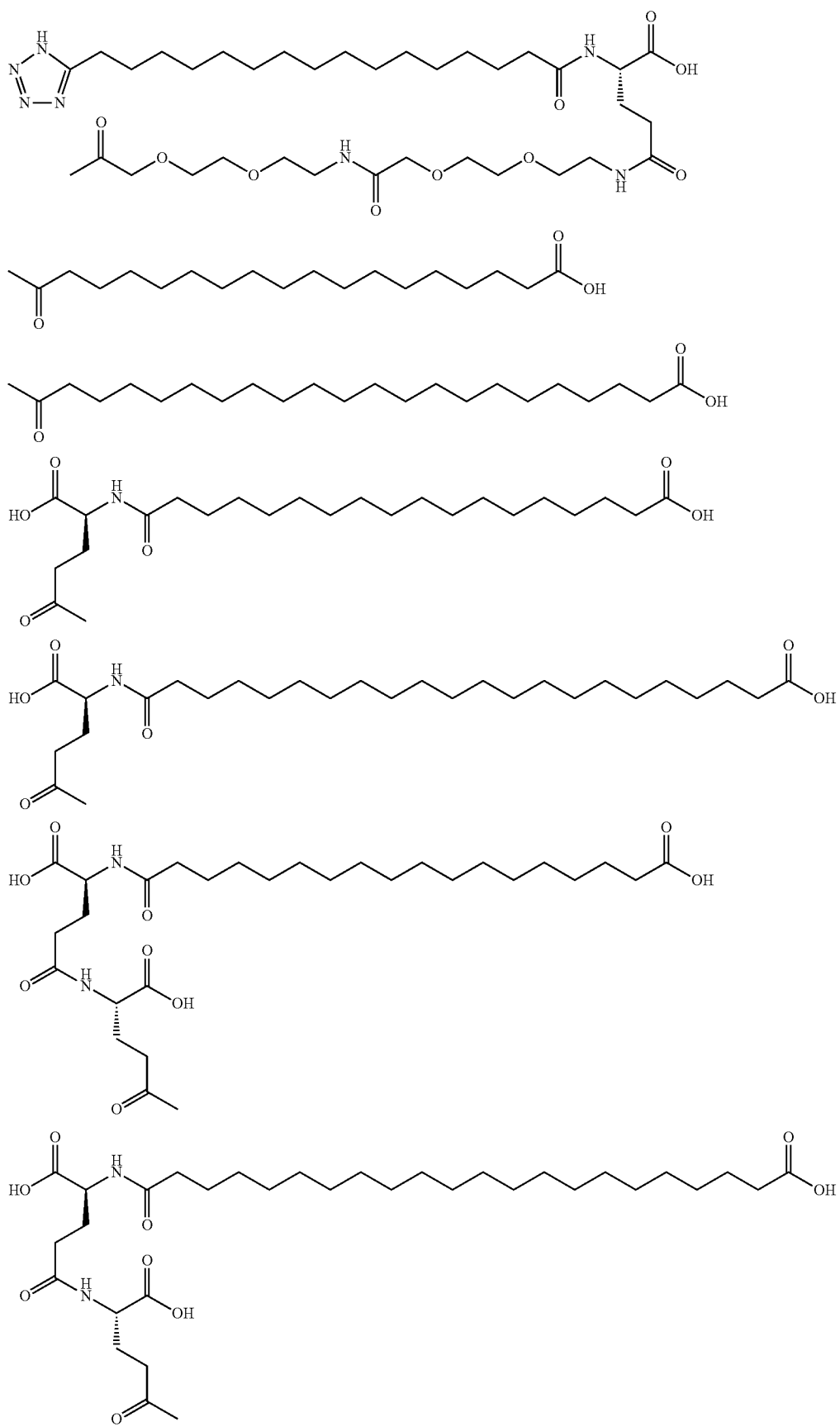

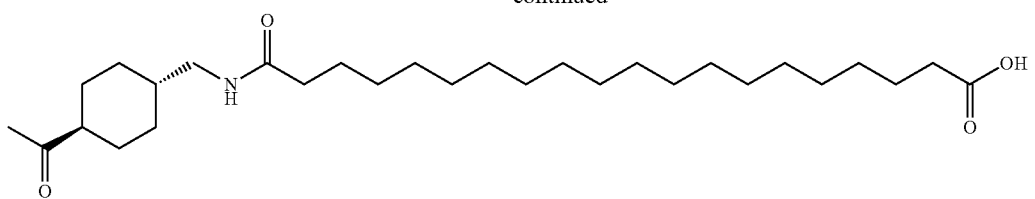
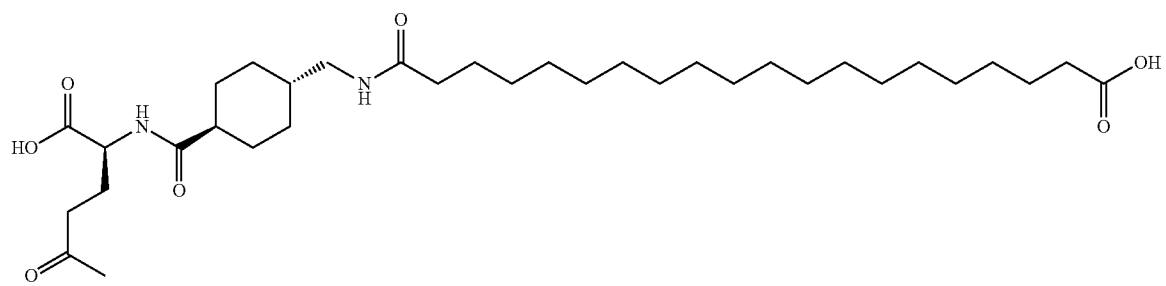
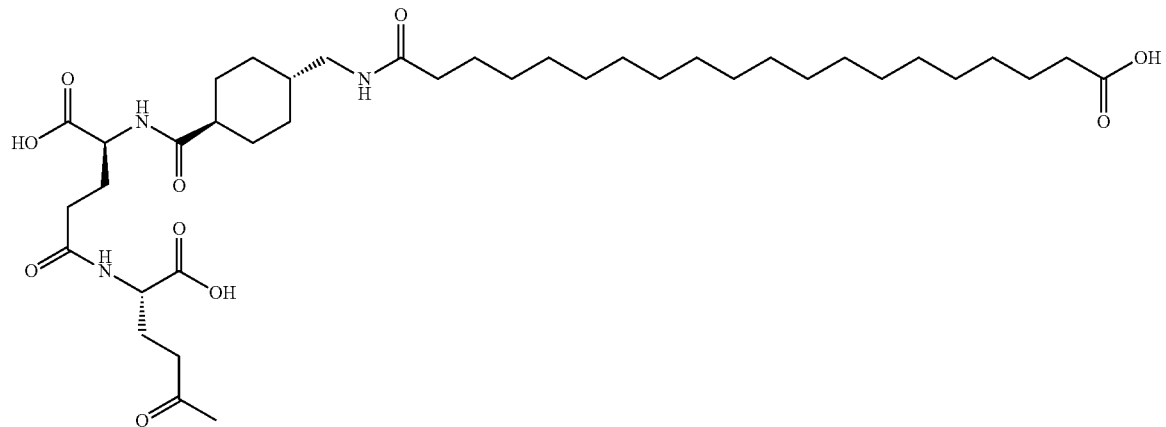
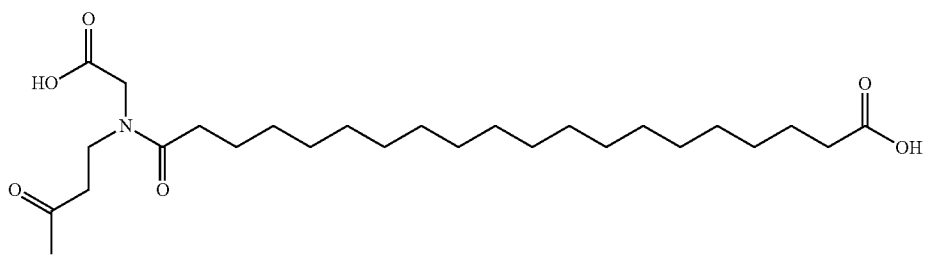
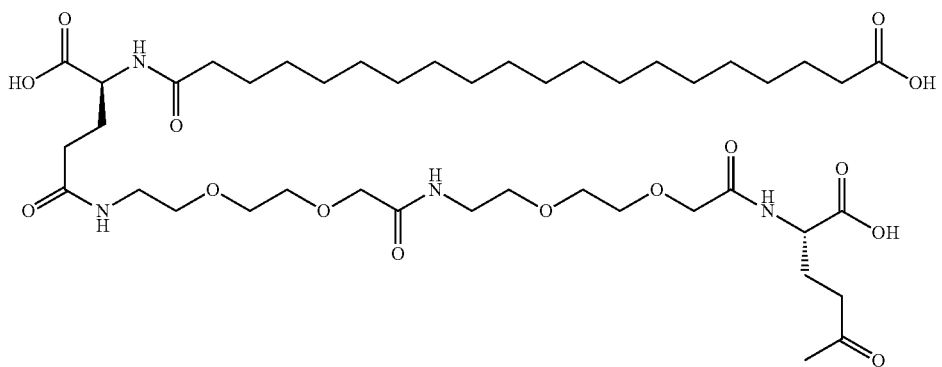

-continued
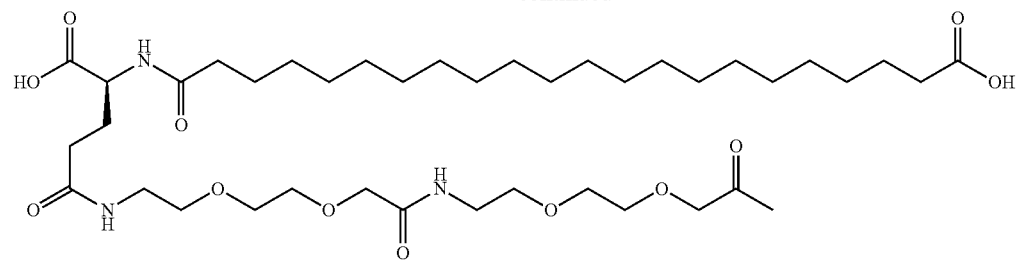
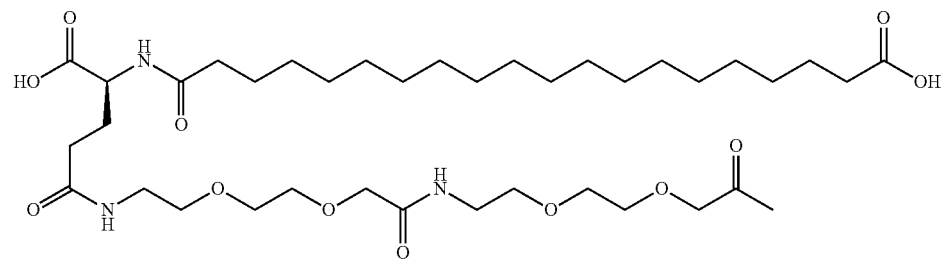
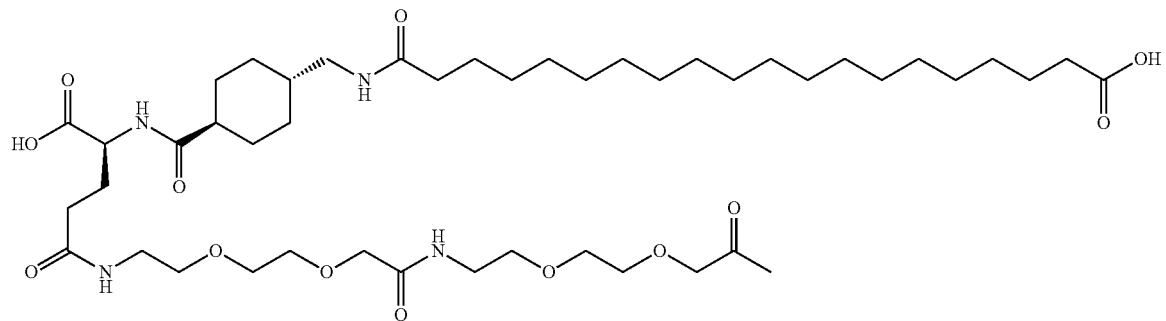
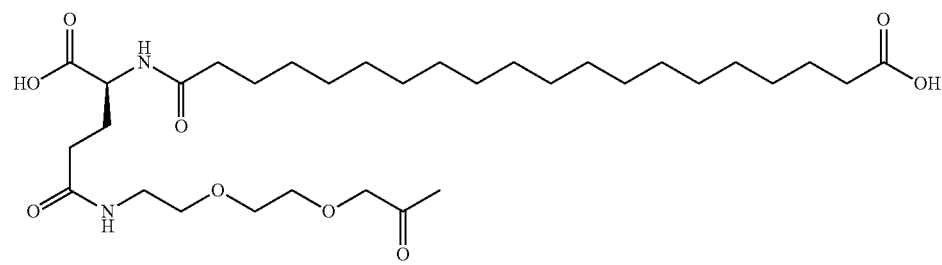
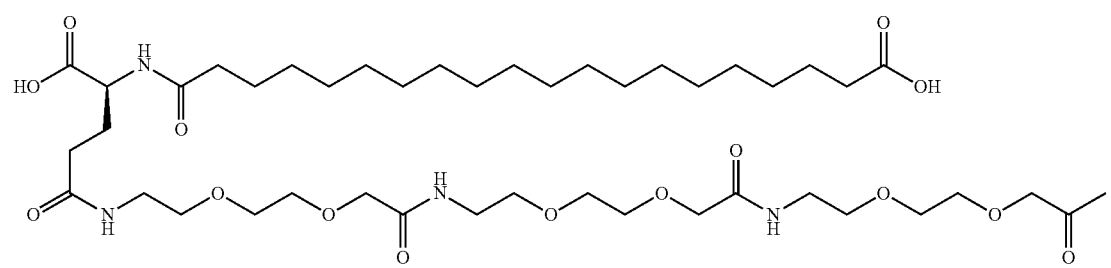
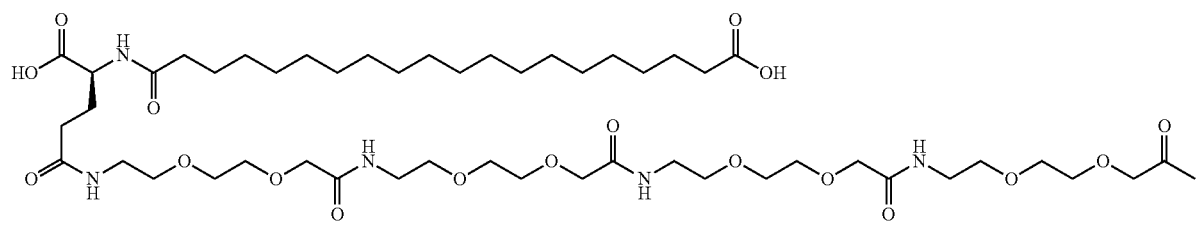

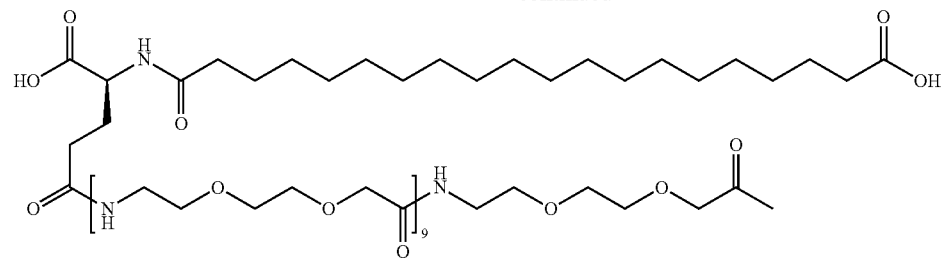
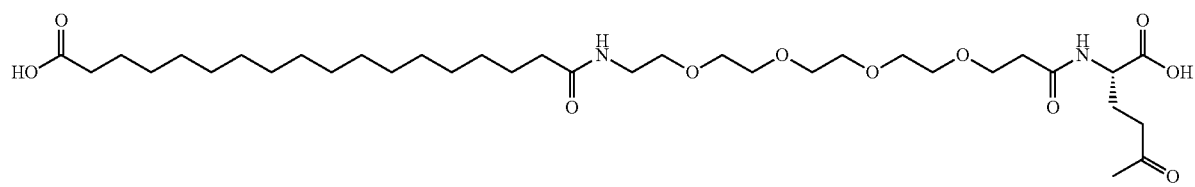
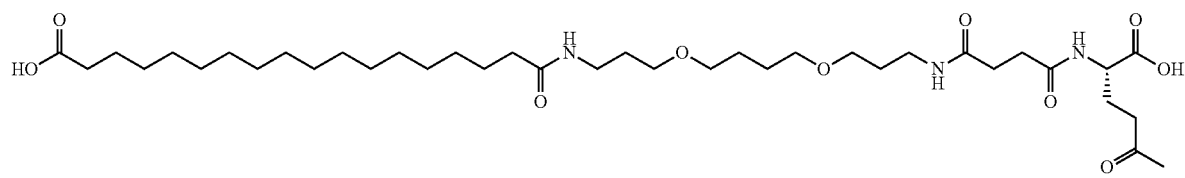
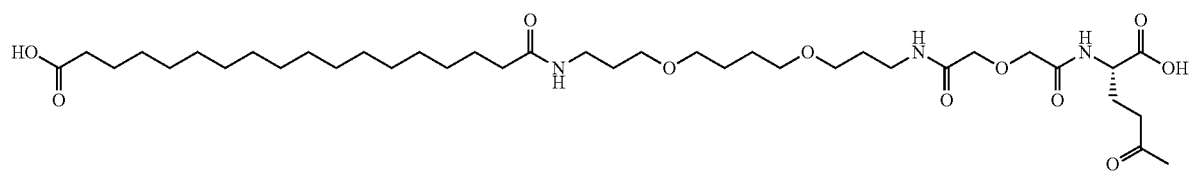
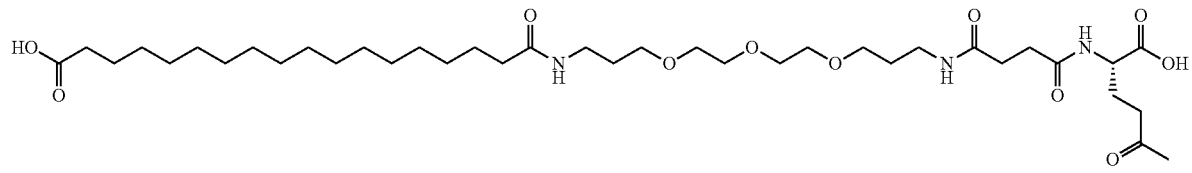
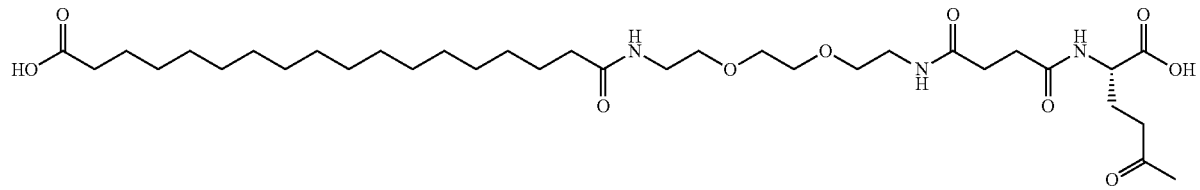
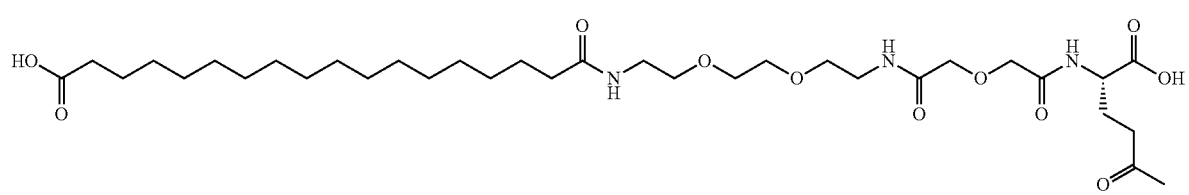
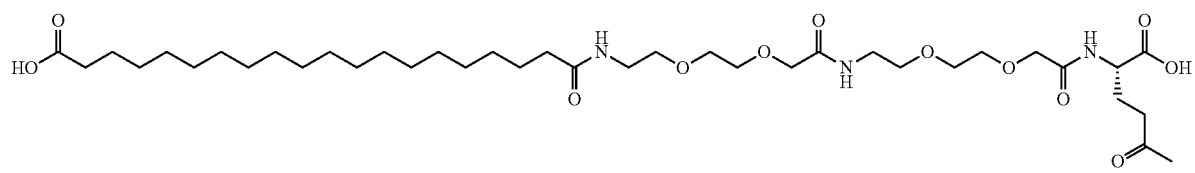

-continued
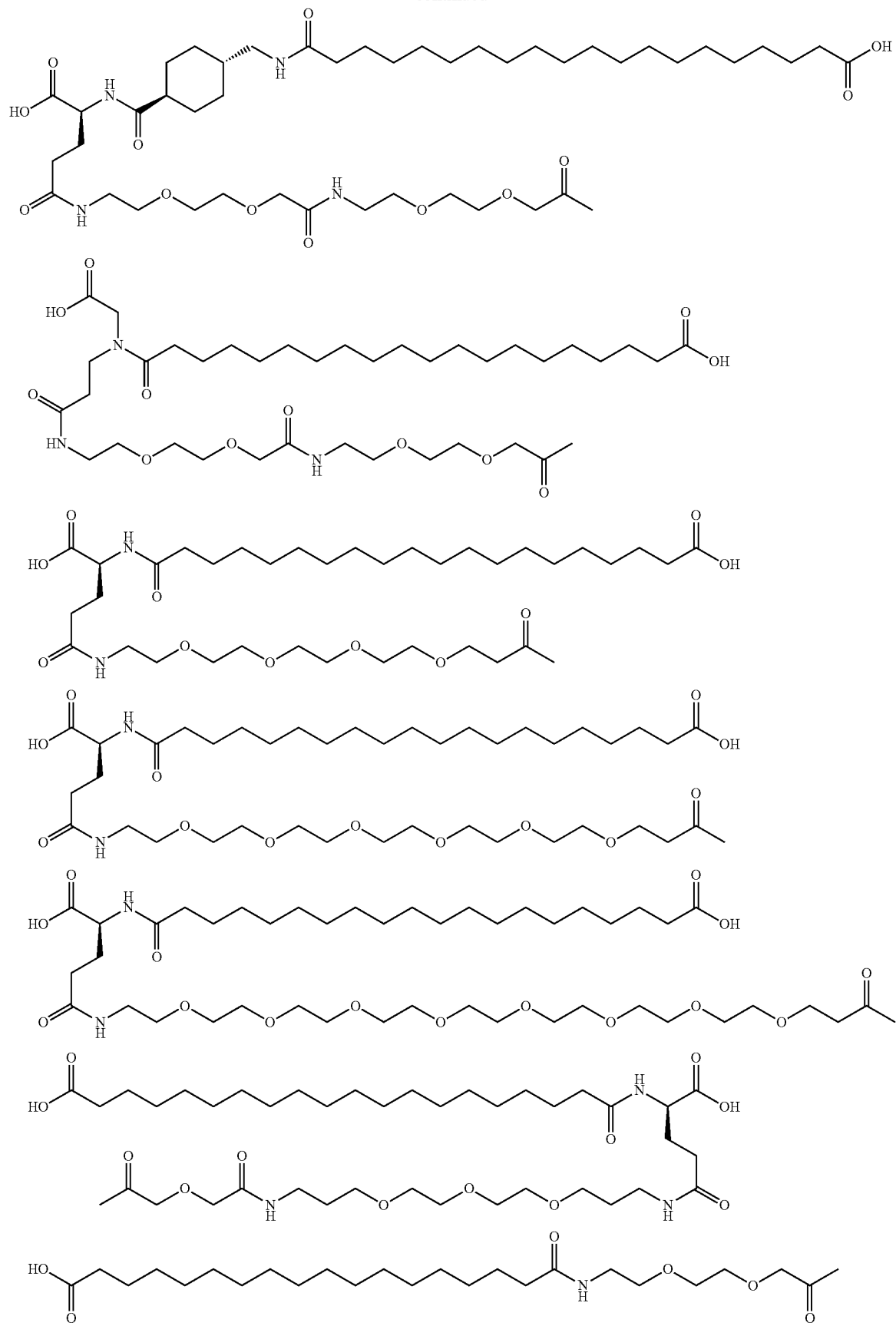

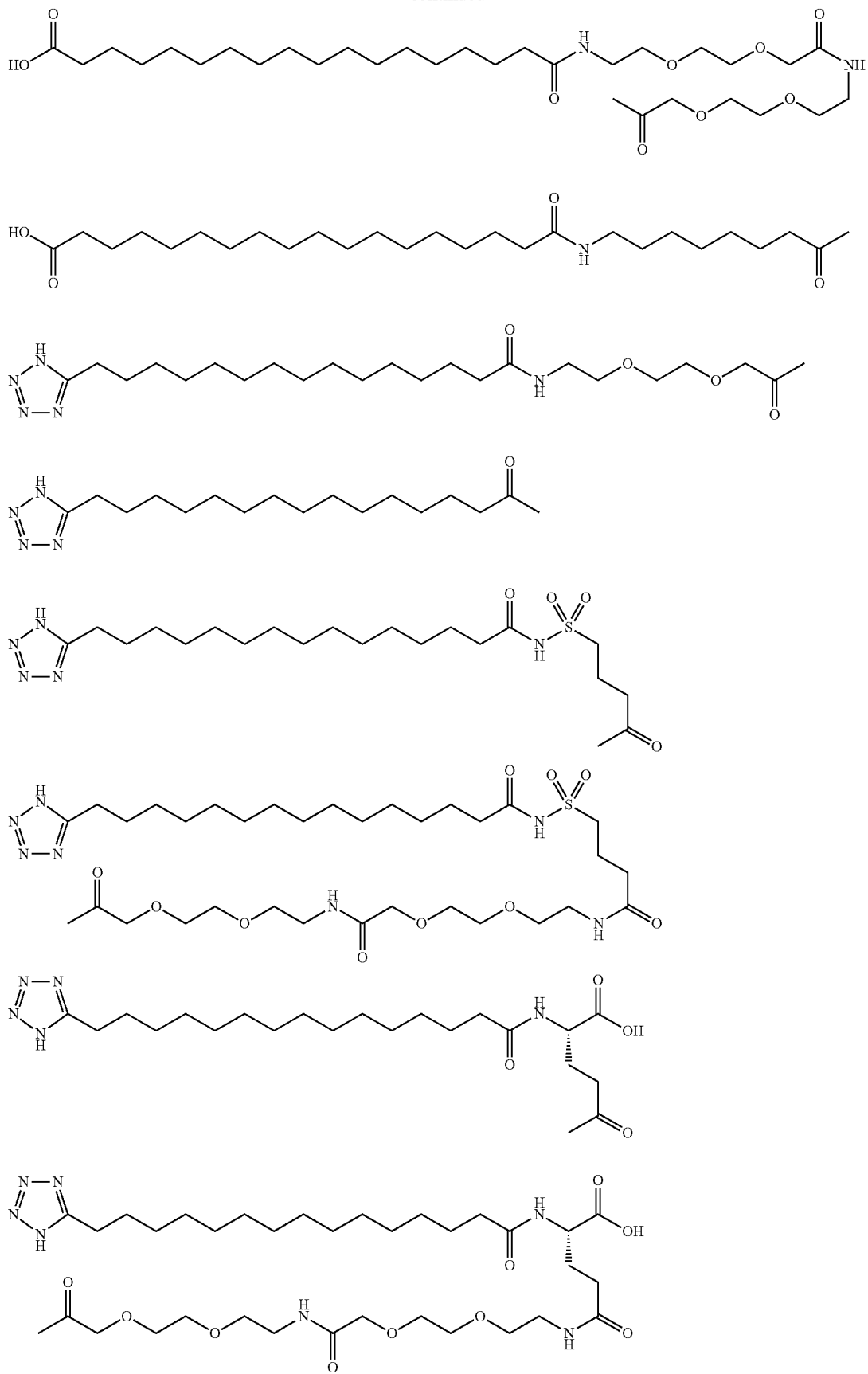

Any of the above non-limiting specific examples of acyl moieties of the formula Acy-AA1$_n$-AA2$_m$-AA3$_p$- can be attached to an epsilon amino group of a lysine residue present in any of the above non-limiting specific examples of insulin analogues thereby giving further specific examples of acylated insulin analogues of this invention.

Any of the above non-limiting specific examples of acyl moieties of the formula Acy-AA1$_n$-AA2$_m$-AA3$_p$- can be attached to an alpha amino group of a A1 residue present in any of the above non-limiting specific examples of insulin analogues thereby giving further specific examples of acylated insulin analogues of this invention.

The protease stabilized insulins can be converted into the acylated protease stabilized insulins of this invention by introducing of the desired group of the formula Acy-AA1$_n$-AA2$_m$-AA3$_p$- in the lysine residue or in a N-terminal position in the insulin analogue. The desired group of the formula Acy-AA1$_n$-AA2$_m$-AA3$_p$- can be introduced by any convenient method and many methods are disclosed in the prior art for such reactions. More details appear from the examples herein.

In an embodiment, the present invention does not relate to compounds described in EP 07114387.9, i.e., acylated insulins wherein an acyl moiety is attached to the parent insulin and wherein said acyl moiety comprises repeating units of alkylene glycol containing amino acids and wherein there is only one lysine residue (K & Lys) in the parent insulin.

Pharmaceutical Compositions

The acylated insulins of this invention may be administered subcutaneously, nasally, orally, or pulmonary.

For subcutaneous administration, the acylated insulins of this invention are formulated analogously with the formulation of known insulins. Furthermore, for subcutaneous administration, the acylated insulins of this invention are administered analogously with the administration of known insulins and, generally, the physicians are familiar with this procedure.

Acylated insulins of this invention may be administered by inhalation in a dose effective to increase circulating insulin levels and/or to lower circulating glucose levels. Such administration can be effective for treating disorders such as diabetes or hyperglycemia. Achieving effective doses of insulin requires administration of an inhaled dose of more than about 0.5 μg/kg to about 50 μg/kg of acylated insulins of this invention. A therapeutically effective amount can be determined by a knowledgeable practitioner, who will take into account factors including insulin level, blood glucose levels, the physical condition of the patient, the patient's pulmonary status, or the like.

The acylated insulins of this invention may be delivered by inhalation to achieve slow absorption and/or reduced systemical clearance thereof. Different inhalation devices typically provide similar pharmacokinetics when similar particle sizes and similar levels of lung deposition are compared.

The acylated insulins of this invention may be delivered by any of a variety of inhalation devices known in the art for administration of a therapeutic agent by inhalation. These devices include metered dose inhalers, nebulizers, dry powder generators, sprayers, and the like. Preferably, the acylated insulins of this are delivered by a dry powder inhaler or a sprayer. There are a several desirable features of an inhalation device for administering acylated insulins of this invention. For example, delivery by the inhalation device is advantageously reliable, reproducible, and accurate. The inhalation device should deliver small particles or aerosols, e.g., less than about 10 μm, for example about 1-5 μm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of acylated insulins of this invention, the quantity of the formulation delivered and the duration of administration of a single dose depend on the type of inhalation device employed. For some aerosol delivery systems, such as nebulizers, the frequency of administration and length of time for which the system is activated will depend mainly on the concentration of acylated insulins in the aerosol. For example, shorter periods of administration can be used at higher concentrations of acylated insulins in the nebulizer solution. Devices such as metered dose inhalers can produce higher aerosol concentrations, and can be operated for shorter periods to deliver the desired amount of the acylated insulins. Devices such as powder inhalers deliver active agent until a given charge of agent is expelled from the device. In this type of inhaler, the amount of insulin acylated insulins of this invention in a given quantity of the powder determines the dose delivered in a single administration.

The particle size of acylated insulins of this invention in the formulation delivered by the inhalation device is critical with respect to the ability of insulin to make it into the lungs, and preferably into the lower airways or alveoli. Preferably, the acylated insulins of this invention ion is formulated so that at least about 10% of the acylated insulins delivered is deposited in the lung, preferably about 10 to about 20%, or more. It is known that the maximum efficiency of pulmonary deposition for mouth breathing humans is obtained with particle sizes of about 2 μm to about 3 μm. When particle sizes are above about 5 μm, pulmonary deposition decreases substantially. Particle sizes below about 1 μm cause pulmonary deposition to decrease, and it becomes difficult to deliver particles with sufficient mass to be therapeutically effective. Thus, particles of the acylated insulins delivered by inhalation have a particle size preferably less than about 10 μm, more preferably in the range of about 1 μm to about 5 μm. The formulation of the acylated insulins is selected to yield the desired particle size in the chosen inhalation device.

Advantageously for administration as a dry powder an acylated insulin of this invention is prepared in a particulate form with a particle size of less than about 10 μm, preferably about 1 to about 5 μm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 μm. Such formulations can be achieved by spray drying, milling, or critical point condensation of a solution containing the acylated insulin of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of acylated insulins of this invention for administration from a dry powder inhaler typically include a finely divided dry powder containing the derivative, but the powder can also include a bulking agent, carrier, excipient, another additive, or the like. Additives can be included in a dry powder formulation of acylated insulin, e.g., to dilute the powder as required for delivery from the particular powder inhaler, to facilitate processing of the formulation, to provide advantageous powder properties to the formulation, to facilitate dispersion of the powder from the inhalation device, to stabilize the formutation (for example, antioxidants or buffers), to provide taste to the formulation, or the like. Advantageously, the additive does not adversely affect the patient's airways. The acylated insulin can be mixed with an additive at a molecular level or the solid formulation can include particles of the acylated insulin mixed with or coated on particles of the additive. Typical additives include mono-, di-, and polysaccharides; sugar alcohols and other polyols, such as, e.g., lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the acylated insulins of this invention can be produced by forcing a suspension or solution of the acylated insulin through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Advantageously, particles of insulin conjugate delivered by a sprayer have a particle size less than about 10 µm, preferably in the range of about 1 µm to about 5 µm.

Formulations of acylated insulins of this invention suitable for use with a sprayer will typically include the acylated insulins in an aqueous solution at a concentration of from about 1 mg to about 500 mg of the acylated insulin per ml of solution. Depending on the acylated insulin chosen and other factors known to the medical advisor, the upper limit may be lower, e.g., 450, 400, 350, 300, 250, 200, 150, 120, 100 or 50 mg of the acylated insulin per ml of solution. The formulation can include agents such as an excipient, a buffer, an isotonicity agent, a preservative, a surfactant, and, preferably, zinc. The formulation can also include an excipient or agent for stabilization of the acylated insulin, such as a buffer, a reducing agent, a bulk protein, or a carbohydrate. Bulk proteins useful in formulating insulin conjugates include albumin, protamine, or the like. Typical carbohydrates useful in formulating the acylated insulin include sucrose, mannitol, lactose, trehalose, glucose, or the like. The acylated insulins formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an acylated insulin of this invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the acylated insulins of this invention can be prepared using the conventional techniques of the pharmaceutical industry which involve dissolving and mixing the ingredients as appropriate to give the desired end product. Thus, according to one procedure, an acylated insulin is dissolved in an amount of water which is somewhat less than the final volume of the composition to be prepared. Zink, an isotonic agent, a preservative and/or a buffer is/are added as required and the pH value of the solution is adjusted—if necessary—using an acid, e.g., hydrochloric acid, or a base, e.g., aqueous sodium hydroxide as needed. Finally, the volume of the solution is adjusted with water to give the desired concentration of the ingredients.

In a further embodiment of this invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)aminomethan, bicine, tricine, malic acid, succinate, maleic acid, fumaric acid, tartaric acid, aspartic acid or mixtures thereof. Each one of these specific buffers constitutes an alternative embodiment of this invention.

In a further embodiment of this invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)-1,2-propanediol) or mixtures thereof. In a further embodiment of this invention the preservative is present in a concentration from about 0.1 mg/ml to 20 mg/ml. In a further embodiment of this invention the preservative is present in a concentration from about 0.1 mg/ml to 5 mg/ml. In a further embodiment of this invention the preservative is present in a concentration from about 5 mg/ml to 10 mg/ml. In a further embodiment of this invention the preservative is present in a concentration from about 10 mg/ml to 20 mg/ml. Each one of these specific preservatives constitutes an alternative embodiment of this invention. The use of a preservative in pharmaceutical compositions is well-known to the skilled person. For convenience reference is made to Remington: *The Science and Practice of Pharmacy*, 19$^{th}$ edition, 1995.

In a further embodiment of this invention, the formulation further comprises an isotonic agent which may be selected from the group consisting of a salt (e.g., sodium chloride), a sugar or sugar alcohol, an amino acid (for example, L-glycine, L-histidine, arginine, lysine, isoleucine, aspartic acid, tryptophan or threonine), an alditol (e.g. glycerol (glycerine), 1,2-propanediol (propyleneglycol), 1,3-propanediol or 1,3-butanediol), polyethyleneglycol (e.g., PEG400) or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, e.g., mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of this invention. In one embodiment, the sugar or sugar alcohol concentration is between about 1 mg/ml and about 150 mg/ml. In a further embodiment of this invention the isotonic agent is present in a concentration from about 1 mg/ml to 50 mg/ml. In a further embodiment of this invention the isotonic agent is present in a concentration from about 1 mg/ml to 7 mg/ml. In a further embodiment of this invention the isotonic agent is present in a concentration from about 8 mg/ml to 24 mg/ml. In a further embodiment of this invention the isotonic agent is present in a concentration from about 25 mg/ml to 50 mg/ml. Each one of these specific isotonic agents constitutes an alternative embodiment of this invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an acylated insulins of this invention may, e.g., be prepared as described in European Patent No. 272,097.

Oral preparations containing an acylated protease stabilised insulin of this inventions can be prepared in a manner known per se. One way of making preparations containing an acylated protease stabilised insulin of this invention which can conveniently be administered orally is by using a procedure which is analagous to the process described in WO 2008/145728.

Another way of preparing oral preparations containing an acylated protease stabilised insulin of this invention is to prepare a water-free liquid or semisolid pharmaceutical compositions comprising an acylated protease stabilised insulin of this invention (a), at least one polar organic solvent (b) for the acylated protease stabilised insulin, at least one lipophilic component (c), and optionally a surfactant (d) and/or at least one solid hydrophilic component (e). This could be in the form of an oily solution. Alternatively, the at least one solid hydrophilic component (d) is at least one solid hydrophilic polymer. Alternatively, the pharmaceutical composition comprising at least one solid hydrophilic component is free of surfactant, wherein said surfactant has an HLB value which is at least 8, i.e. there is no surfactant, which has an HLB value which is at least 8, present in the composition.

For example, a pharmaceutical composition containing an acylated protease stabilised insulin may be a water-free oily solution and/or a SEDDS or SMEDDS pharmaceutical composition.

Alternatively said pharmaceutical composition is a self emulsifying drug delivery system (herein designated SEDDS).

It is believed that the high solubility of an acylated protease stabilised insulin in the polar organic solvent of the pharmaceutical composition resulting in the relatively low total amount of polar organic solvent needed in said pharmaceutical composition may improve compatibility of the pharmaceutical composition with capsule materials.

The pharmaceutical composition may contain a carrier that comprises a lipophilic component, a surfactant and a polar organic solvent and optionally a solid hydrophilic component (e). If there is a solid hydrophilic component present, at least one of the components selected from the group consisting of a lipophilic component and a surfactant is liquid or semi-solid. If there is a liquid hydrophilic component (e) present, both the lipophilic component and the surfactant may be solid. For example, the surfactant is liquid or semisolid. In one aspect, a solid hydrophilic component is present.

As used herein, the term "carrier" refers to the pharmaceutically acceptable vehicle that transports the therapeutically active water-soluble polypeptide across the biological membrane or within a biological fluid. The carrier comprises a lipophilic component and a polar organic solvent, and optionally a solid hydrophilic component and/or a surfactant. The carrier is capable of spontaneously producing an emulsion or colloidal structures, when brought in contact, dispersed, or diluted, with an aqueous medium, e.g., water, fluids containing water, or in vivo media in mammals, such as the gastric juices of the gastrointestinal tract. The colloidal structures can be solid or liquid particles including domains, droplets, micelles, mixed micelles, vesicles and nanoparticles.

For example, when the pharmaceutical composition is brought into contact with an aqueous medium, an emulsion, such as a microemulsion, spontaneously forms. In particular, an emulsion or microemulsion forms in the digestive tract of a mammal when the delivery system is orally ingested. In addition to the aforementioned components, the spontaneously dispersible preconcentrate can also optionally contain other excipients, such as buffers, pH adjusters, stabilizers and other adjuvants recognized by one of ordinary skill in the art to be appropriate for such a pharmaceutical use.

The term "water-free" as used herein refers to a composition to which no water is added during preparation of the pharmaceutical composition. The acylated protease stabilised insulin and/or one or more of the excipients in the pharmaceutical composition may have small amounts of water bound to it before preparing a pharmaceutical composition. Fore example, a water-free pharmaceutical composition comprises less than 10% w/w water, for example, less than 5% w/w water, for example, less than 4% w/w water, for example, less than 3% w/w water, for example, less than 2% w/w water, for example, less than 1% w/w water.

As used herein, the term "microemulsion preconcentrate" means a composition, which spontaneously forms a microemulsion, e.g., an oil-in-water microemulsion, in an aqueous medium, e.g., in water or in the gastrointestinal fluids after oral application. The composition self-emulsifies upon dilution in an aqueous medium for example in a dilution of 1:5, 1:10, 1:50, 1:100 or higher.

Due to the high solubility of the acylated protease stabilised insulin, the total amount of polar organic solvent in the SEDDS can be kept low which on the one hand improves compatibility of the formulation with capsule materials and on the other hand gives more design space for the composition.

The pharmaceutical composition comprises a lipophilic component, and an organic polar component. The components of the drug delivery system can be present in any relative amounts. For example, the drug delivery system can comprises up to 40% polar organic component by weight of the composition of the carrier, e.g., less than 30%, 20%, 15% or 10%. In another aspect, the drug delivery system comprises from 5% to 40% by weight polar organic solvent of the total composition of the carrier. In yet a further aspect, the drug delivery system comprises from 10% to 30% by weight polar organic solvent of the total composition of the carrier.

The pharmaceutical composition may be in the form of a non-powder composition, i.e. in a semi-solid or liquid form.

As used herein, the term "liquid" means a component or composition that is in a liquid state at room temperature ("RT"), and having a melting point of, for example, below 20° C. As used herein room temperature (RT) means approximately 20-25° C.

As used herein, the term "semi-solid" relates to a component or composition which is not liquid at room temperature, e.g., having a melting point between room temperature and about 40° C. A semisolid can have the qualities and/or attributes of both the solid and liquid states of matter. As used-herein, the term "solidify" means to make solid or semi-solid.

Examples of semi-solid or liquid compositions are pharmaceutical compositions in the form of, e.g., oils, solutions, liquid or semisolid SMEDDS and liquid or semisolid SEDDS.

"SMEDDS" (being an abbreviation for self-micro-emulsifying drug delivery systems) are herein defined as isotropic mixtures of a hydrophilic component, a surfactant, optionally a cosurfactant and a drug that rapidly form an oil in water microemulsion when exposed to aqueous media under conditions of gentle agitation or digestive motility that would be encountered in the GI tract.

"SEDDS" (being an abbreviation for self emulsifying drug delivery systems) are herein defined as mixtures of a hydrophilic component, a surfactant, optionally a cosurfactant and a drug that forms spontaneously a fine oil in water emulsion when exposed to aqueous media under conditions of gentle agitation or digestive motility that would be encountered in the GI tract.

As used herein, the term "microemulsion" refers to a clear or translucent, slightly opaque, opalescent, non-opaque or substantially non-opaque colloidal dispersion that is formed spontaneously or substantially spontaneously when its components are brought into contact with an aqueous medium.

As used herein, the term "emulsion" refers to a slightly opaque, opalescent or opague colloidal dispersion that is formed spontaneously or substantially spontaneously when its components are brought into contact with an aqueous medium.

A microemulsion is thermodynamically stable and contains homogenously dispersed particles or domains, for example of a solid or liquid state (e.g., liquid lipid particles or droplets), of a mean diameter of less than about 500 nm, e.g., less than about 400 nm or less than 300 nm, less than 200 nm, less than 100 nm, and greater than about 2-4 nm as measured by standard light scattering techniques, e.g., using a MALVERN ZETASIZER Nano ZS. The term "domain size" as used herein refers to repetitive scattering units and can be measured by, e.g., small angle X-ray. In one aspect, the domain size is smaller than 400 nm, in another aspect, smaller than 300 nm and in yet another aspect, smaller than 200 nm.

As used herein the term "spontaneously dispersible" when referring to a pre-concentrate refers to a composition that is capable of producing colloidal structures such as microemulsions, emulsions and other colloidal systems, when diluted with an aqueous medium when the components of the composition are brought into contact with an aqueous medium, e.g., by simple shaking by hand for a short period of time, for example for ten seconds. In one aspect a spontaneously dispersible concentrate according to the invention is a SEDDS or SMEDDS.

As used herein, the term "lipophilic component" refers to a substance, material or ingredient that is more compatible with oil than with water. A material with lipophilic properties is insoluble or almost insoluble in water but is easily soluble in oil or other nonpolar solvents. The term "lipophilic component" can comprise one or more lipophilic substances. Multiple lipophilic components may constitute the lipophilic phase of the spontaneously dispersible pre-concentrate and form the oil aspect, e.g., in an oil-in-water emulsion or microemulsion. At room temperature, the lipophilic component and lipophilic phase of the spontaneously dispersible preconcentrate can be solid, semisolid or liquid. For example, a solid lipophilic component can exist as a paste, granular form, powder or flake. If more than one excipient comprises the lipophilic component, the lipophilic component can be a mixture of liquids, solids, or both.

In one aspect, the lipophilic component is present in the pharmaceutical composition in an amount of at least 20% w/w. In a further aspect, the lipophilic component is present in an amount of at least 30%, at least 50%, at least 80% or at least 90% w/w. For example, the lipophilic component may be present from about 5% to about 90% by weight of the composition, e.g., from about 15% to about 60%, e.g., from about 20% to about 40%. Examples of solid lipophilic components, i.e., lipophilic components which are solid or semisolid at room temperature, include, but are not limited to, the following:

1. mixtures of mono-, di- and triglycerides, such as hydrogenated coco-glycerides (melting point (m.p.) of about 33.5° C. to about 37° C.], commercially-available as WITEPSOL HI5 from Sasol Germany (Witten, Germany); Examples of fatty acid triglycerides e.g., C10-C22 fatty acid triglycerides include natural and hydrogenated oils, such as vegetable oils;

2. esters, such as propylene glycol (PG) stearate, commercially available as MONOSTEOL (m.p. of about 33° C. to about 36° C.) from Gattefosse Corp. (Paramus, N.J.); diethylene glycol palmito stearate, commercially available as HYDRINE (m.p. of about 44.5° C. to about 48.5° C.) from Gattefosse Corp.;

3. polyglycosylated saturated glycerides, such as hydrogenated palm/palm kernel oil PEG-6 esters (m.p. of about 30.5° C. to about 38° C.), commercially-available as LABRAFIL M2130 CS from Gattefosse Corp. or Gelucire 33/01;

4. fatty alcohols, such as myristyl alcohol (m.p. of about 39° C.), commercially available as LANETTE 14 from Cognis Corp. (Cincinnati, Ohio); esters of fatty acids with fatty alcohols, e.g., cetyl palmitate (m.p. of about 50° C.); isosorbid monolaurate, e.g., commercially available under the trade name ARLAMOL ISML from Uniqema (New Castle, Del.), e.g. having a melting point of about 43° C.;

5. PEG-fatty alcohol ether, including polyoxyethylene (2) cetyl ether, e.g. commercially available as BRIJ 52 from Uniqema, having a melting point of about 33° C., or polyoxyethylene (2) stearyl ether, e.g. commercially available as BRIJ 72 from Uniqema having a melting point of about 43° C.;

6. sorbitan esters, e.g. sorbitan fatty acid esters, e.g. sorbitan monopalmitate or sorbitan monostearate, e.g, commercially available as SPAN 40 or SPAN 60 from Uniqema and having melting points of about 43° C. to 48° C. or about 53° C. to 57° C. and 41° C. to 54° C., respectively; and 7. glyceryl mono-C6-C14-fatty acid esters. These are obtained by esterifying glycerol with vegetable oil followed by molecular distillation. Monoglycerides include, but are not limited to, both symmetric (i.e. β-monoglycerides) as well as asymmetric monoglycerides (α-monoglycerides). They also include both uniform glycerides (in which the fatty acid constituent is composed primarily of a single fatty acid) as well as mixed glycerides (i.e. in which the fatty acid constituent is composed of various fatty acids). The fatty acid constituent may include both saturated and unsaturated fatty acids having a chain length of from e.g. C8-C14. Particularly suitable are glyceryl mono laurate e.g. commercially available as IMWITOR 312 from Sasol North America (Houston, Tex.), (m.p. of about 56° C.-60° C.); glyceryl mono dicocoate, commercially available as IMWITOR 928 from Sasol (m.p. of about 33° C.-37° C.); monoglyceryl citrate, commercially available as IMWITOR 370, (m.p. of about 59 to about 63° C.); or glyceryl mono stearate, e.g., commercially available as IMWITOR 900 from Sasol (m.p. of about 56° C.-61° C.); or self-emulsifying glycerol mono stearate, e.g., commercially available as IMWITOR 960 from Sasol (m.p. of about 56° C.-61° C.).

Examples of liquid lipophilic components, i.e., lipophilic components which are liquid at room temperature include, but are not limited to, the following:

1. mixtures of mono-, di- and triglycerides, such as medium chain mono- and diglycerides, glyceryl caprylate/caprate, commercially-available as CAPMUL MCM from Abitec Corp. (Columbus, Ohio);

2. glyceryl mono- or di fatty acid ester, e.g. of C6-C18, e.g. C6-C16 e.g. C8-C10, e.g. C8, fatty acids, or acetylated derivatives thereof, e.g. MYVACET 9-45 or 9-08 from Eastman Chemicals (Kingsport, Tenn.) or IMWITOR 308 or 312 from Sasol;

3. propylene glycol mono- or di-fatty acid ester, e.g. of C8-C20, e.g. C8-C12, fatty acids, e.g. LAUROGLYCOL 90, SEFSOL 218, or CAPRYOL 90 or CAPMUL PG-8 (same as propylene glycol caprylate) from Abitec Corp.;

4. oils, such as safflower oil, sesame oil, almond oil, peanut oil, palm oil, wheat germ oil, corn oil, castor oil, coconut oil, cotton seed oil, soybean oil, olive oil and mineral oil;

5. fatty acids or alcohols, e.g. C8-C20, saturated or mono- or di-unsaturated, e.g. oleic acid, oleyl alcohol, linoleic acid, capric acid, caprylic acid, caproic acid, tetradecanol, dodecanol, decanol;

6. medium chain fatty acid triglycerides, e.g. C8-C12, e.g. MIGLYOL 812, or long chain fatty acid triglycerides, e.g. vegetable oils;

7. transesterified ethoxylated vegetable oils, e.g. commercially available as LABRAFIL M2125 CS from Gattefosse Corp;

8. esterified compounds of fatty acid and primary alcohol, e.g. C8-C20, fatty acids and C2-C3 alcohols, e.g. ethyl linoleate, e.g. commercially available as NIKKOL VF-E from Nikko Chemicals (Tokyo, Japan), ethyl butyrate, ethyl caprylate oleic acid, ethyl oleate, isopropyl myristate and ethyl caprylate;

9. essential oils, or any of a class of volatile oils that give plants their characteristic odors, such as spearmint oil, clove oil, lemon oil and peppermint oil;

10. fractions or constituents of essential oils, such as menthol, carvacrol and thymol;

11. synthetic oils, such as triacetin, tributyrin;

12. triethyl citrate, acetyl triethyl citrate, tributyl citrate, acetyl tributyl citrate;

13. polyglycerol fatty acid esters, e.g. diglyceryl monooleate, e.g. DGMO-C, DGMO-90, DGDO from Nikko Chemicals; and 14. sorbitan esters, e.g. sorbitan fatty acid esters, e.g. sorbitan monolaurate, e.g. commercially available as SPAN 20 from Uniqema.

15. Phospholipids, e.g. Alkyl-O-Phospholipids, Diacyl Phosphatidic Acids, Diacyl Phosphatidyl Cholines, Diacyl Phosphatidyl Ethanolamines, Diacyl Phosphatidyl Glycerols, Di-O-Alkyl Phosphatidic Acids, L-alpha-Lysophosphatidylcholines (LPC), L-alpha-Lysophosphatidylethanolamines (LPE), L-alpha-Lysophosphatidylglycerol (LPG), L-alpha-Lysophosphatidylinositols (LPI), L-alpha-Phosphatidic acids (PA), L-alpha-Phosphatidylcholines (PC), L-alpha-Phosphatidylethanolamines (PE), L-alpha-Phosphatidylglycerols (PG), Cardiolipin (CL), L-alpha-Phosphatidylinositols (PI), L-alpha-Phosphatidylserines (PS), Lyso-Phosphatidylcholines, Lyso-Phosphatidylglycerols, sn-Glycerophosphorylcholines commercially available from LARODAN, or soybean phospholipid (Lipoid S100) commercially available from Lipoid GmbH.

For example, the lipophilic component is one or more selected from the group consisting of mono-, di-, and triglycerides. In one aspect, the lipophilic component is one or more selected from the group consisting of mono- and diglycerides. In yet a further aspect, the lipophilic component is Capmul MCM or Capmul PG-8. In a still further aspect, the lipophilic component is Capmul PG-8.

The term "polar organic solvent" refers in one aspect herein to a "polar protic organic solvent" which is a hydrophilic, water miscible carbon-containing solvent that contains an O—H or N—H bond, or mixtures thereof. The polarity is reflected in the dielectric constant or the dipole moment of a solvent. The polarity of a solvent determines what type of compounds it is able to dissolve and with what other solvents or liquid compounds it is miscible. Typically, polar organic solvents dissolve polar compounds best and non-polar solvents dissolve non-polar compounds best: "like dissolves like". Strongly polar compounds like inorganic salts (e.g. sodium chloride) dissolve only in very polar solvents.

Polar organic solvents may be selected from solvent wherein the acylated proteases stabilised insulin show better solubility in said polar organic solvents than in other solvents.

Hence, the acylated proteases stabilised insulin can be dissolved to a high degree in a water-free pharmaceutical acceptable polar organic solvent such as propylene glycol, glycerol and PEG200. For example, at least 20% (w/w) of the acylated proteases stabilised insulin dissolve in a water-free pharmaceutical acceptable polar organic solvent, i.e. when adding 20% w/w of the acylated proteases stabilised insulin to the polar organic solvent, a clear solution is obtained. In another aspect, at least 25%, 30%, 40% or 50% (w/w) of the acylated proteases stabilised insulin dissolve in a water-free pharmaceutical acceptable polar organic solvent.

The polar organic solvent may thus refer to a hydrophilic, water miscible carbon-containing solvent that contains an O—H or N—H bond, or mixtures thereof. The polarity is reflected in the dielectric constant or the dipole moment of a solvent. The polarity of a solvent determines what type of compounds it is able to dissolve and with what other solvents or liquid compounds it is miscible. Typically, polar solvents dissolve polar compounds best and non-polar solvents dissolve non-polar compounds best: "like dissolves like". Strongly polar compounds like inorganic salts (e.g. sodium chloride) dissolve only in very polar solvents.

For example, the polar organic solvent is a solvent having a dielectric constant above 20, preferably in the range of 20-50. Examples of different polar organic solvent are listed in Table 1 together with water as a reference.

TABLE 1

Dielectric constants (static permittivity) of selected polar organic solvents and water as a reference (Handbook of Chemistry and Physics, CMC Press, dielectric constants are measured in static electric fields or at relatively low frequencies, where no relaxation occurs)

| Solvent (Temperature, Kelvin) | Dielectric constant, $\varepsilon^*$ |
| --- | --- |
| Water (293.2) | 80.1 |
| Propanetriol [Glycerol] (293.2) | 46.53 |
| Ethanediol [Ethylene Glycol] (293.2) | 41.4 |
| 1,3-propanediol (293.2) | 35.1 |
| Methanol (293.2) | 33.0 |
| 1,4-butanediol (293.2) | 31.9 |
| 1,3-butanediol (293.2) | 28.8 |
| 1,2-propanediol [propylene glycol] (303.2) | 27.5 |
| Ethanol (293.2) | 25.3 |
| Isopropanol [2-propanol, isopropyl alcohol] (293.2) | 20.18 |

In the present context, 1,2-propanediol and propylene glycol is used interchangeably. In the present context, propanetriol and glycerol is used interchangeably. In the present context, ethanediol and ethylene glycol is used interchangeably.

For example, the polar organic solvent is selected from the group consisting of polyols. The term "polyol" as used herein refers to chemical compounds containing multiple hydroxyl groups.

In one aspect, the polar organic solvent is selected from the group consisting of diols and triols. The term "diol" as used herein refers to chemical compounds containing two hydroxyl groups. The term "triol" as used herein refers to chemical compounds containing three hydroxyl groups.

For example, the polar organic solvent is selected from the group consisting of glycerol (propanetriol), ethanediol (ethylene glycol), 1,3-propanediol, methanol, 1,4-butanediol, 1,3-butanediol, propylene glycol (1,2-propanediol), ethanol and isopropanol, or mixtures thereof. In one alternative, the polar organic solvent is selected from the group consisting of propylene glycol and glycerol. Glycerol is biocompatible even at high dosages and has a high solvent capacity for the acylated proteasde stabilised insulin. Alternatively, the polar organic solvent is selected from the group consisting of propylene glycol and ethylene glycol. These polar organic solvent have a low viscosity, are biocompatible at moderate doses, and have very high polar organic solvent capacity for the acylated proteasde stabilised insulin.

The polar organic solvent should preferably be of high purity with a low content of, e.g., aldehydes, ketones and other reducing impurities in order to minimize chemical deterioration of the solubilized polypeptide due to e.g. Maillard reaction. Scavenger molecules like glycyl glycine and ethylene diamine may be added to the formulations comprising polar organic solvent (s) such as polyols to reduce deterioration of the polypeptide whereas antioxidants can be added to reduce the rate of formation of further reducing impurities.

In one aspect of the invention, the polar organic solvent is present in the pharmaceutical composition in an amount of 1-50% w/w, for example, 5-40% w/w, for example, 5-30% w/w. Alternatively, the organic polar solvent is present in an amount of 10-30% w/w, for example, 10-25% w/w, for example, in an amount of about 20% w/w or about 15% w/w.

For example, the polar organic polar solvent is propylene glycol and is present in the pharmaceutical composition in an amount of 1-50% w/w, for example, 5-40% w/w, for example, 10-30% w/w, for example, 10-25% w/w, for example, 10-20% w/w, for example, about 20% w/w or about 15% w/w.

For example, the polar organic solvent is selected from the group consisting of glycerol, propylene glycol and mixtures thereof.

A solid hydrophilic component may be added to the pharmaceutical composition in order to render or help render the pharmaceutical composition solid or semi-solid at room temperature. The hydrophilic component can comprise more than one excipient. If more than one excipient comprises the hydrophilic component, the hydrophilic component can be a mixture of liquids, solids, or both.

When a solid hydrophilic component is present, the pharmaceutical composition may comprise from about 1% to about 25% by weight of solid hydrophilic component, e.g., from about 2% to about 20%, e.g., from about 3% to about 15%, e.g. from about 4% to about 10%.

An example of a hydrophilic component is PEG which is the polymer of ethylene oxide that conforms generally to the formula $H(OCH_2CH_2)_nOH$ in which n correlates with the average molecular weight of the polymer.

The types of PEG useful in preparing pharmaceutical compositions can be categorized by its state of matter, i.e., whether the substance exists in a solid or liquid form at room temperature and pressure. As used herein, "solid PEG" refers to PEG having a molecular weight such that the substance is in a solid state at room temperature and pressure. For example, PEG having a molecular weight ranging between 1,000 and 10,000 is a solid PEG. Such PEGs include, but are not limited to PEG 1000, PEG 1550, PEG 2000, PEG 3000, PEG 3350, PEG 4000 or PEG 8000. Particularly useful solid PEGs are those having a molecular weight between 1,450 and 8,000. Especially useful as a solid PEG are PEG 1450, PEG 3350, PEG 4000, PEG 8000, derivatives thereof and mixtures thereof. PEGs of various molecular weights are commercially-available as the CARBOWAX SENTRY series from Dow Chemicals (Danbury, Conn.). Moreover, solid PEGs have a crystalline structure, or polymeric matrix, Polyethylene oxide ("PEO") which has an identical structure to PEG but for chain length and end groups are also suitable. Various grades of PEO are commercially available as POLYOX from Dow Chemicals. PEO, for example, has a molecular weight ranging from about 100,000 to 7,000,000. The hydrophilic component can comprise PEG, PEO, and any combinations of the foregoing.

The hydrophilic components can optionally include a lower alkanol, e.g., ethanol. While the use of ethanol is not essential, it can improve solubility of the polypeptide in the carrier, improve storage characteristics and/or reduce the risk of drug precipitation.

In an alternative exemplary aspect, the hydrophilic component of the carrier consists of a single hydrophilic component, e.g., a solid PEG, e.g., PEG 1450, PEG 3350, PEG 4000 and PEG 8000. In this exemplary aspect, the hydrophilic phase of the microemulsion component consists of a single hydrophilic substance. For example, if the carrier comprised PEG 3350, the carrier would contain no other hydrophilic substances, e.g., lower alkanols (lower alkyl being $C_1$-$C_4$), such as ethanol; or water.

In yet another alternative exemplary aspect, the hydrophilic component of the carrier consists of a mixture of solid PEGs. For example, the hydrophilic component comprises PEG 1450, PEG 3350, PEG 4000, PEG 8000, derivatives thereof and any combinations and mixtures thereof.

In one aspect, the carrier comprises one or more surfactants, i.e., optionally a mixture of surfactants; or surface active agents, which reduce interfacial tension. The surfactant is, e.g., nonionic, ionic or amphoteric. Surfactants can be complex mixtures containing side products or un-reacted starting products involved in the preparation thereof, e.g., surfactants made by polyoxyethylation may contain another side product, e.g., PEG. The surfactant or surfactants have a hydrophilic-lipophilic balance (HLB) value which is at least 8. For example, the surfactant may have a mean HLB value of 8-30, e.g., 12-30, 12-20 or 13-15. The surfactants can be liquid, semisolid or solid in nature.

The term "surfactant" as used herein refers to any substance, in particular a detergent that can adsorb at surfaces and interfaces, like liquid to air, liquid to liquid, liquid to container or liquid to any solid. The surfactant may be selected from a detergent, such as ethoxylated castor oil, polyglycolyzed glycerides, acetylated monoglycerides, sorbitan fatty acid esters, polysorbate, such as polysorbate-20, poloxamers, such as poloxamer 188 and poloxamer 407, polyoxyethylene sorbitan fatty acid esters, polyoxyethylene derivatives such as alkylated and alkoxylated derivatives (tweens, e.g. Tween20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, cephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-hexadecyl-N,N-dimethyl-3-ammonio-1-propanesulfonate, anionic (alkylaryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g., lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lyso-phosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quaternary ammonium bases) (e.g. cetyl-trimethylammonium bromide, cetylpyridinium chloride), non-ionic surfactants (e.g., alkyl glucosides like dodecyl β-D-glucopyranoside, dodecyl β-D-maltoside, tetradecyl β-D-glucopyranoside, decyl β-D-maltoside, dodecyl β-D-maltoside, tetradecyl β-D-maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, fatty alcohol ethoxylates (e.g., polyoxyethylene alkyl ethers like octaethylene glycol mono tridecyl ether, octaethylene glycol mono dodecyl ether, octaethylene glycol mono tetradecyl ether), block copolymers as polyethyleneoxide/polypropyleneoxide block copolymers (Pluronics/Tetronics, Triton X-100) ethoxylated sorbitan alkanoates surfactants (e.g., Tween-40, Tween-80, Brij-35), fusidic acid derivatives (e.g., sodium tauro-dihydrofusidate etc.), long-chain fatty acids and salts thereof C8-C20 (e.g., oleic acid and caprylic acid), acylcarnitines and derivatives, N-acylated derivatives of lysine, arginine or histidine, or side-chain acylated derivatives of lysine or arginine, N-acylated derivatives of dipeptides comprising any combination of lysine, arginine or histidine and a neutral or acidic amino acid, N-acylated derivative of a tripeptide comprising any combination of a neutral amino acid and two charged amino acids, or the surfactant may be selected from the group of imidazoline derivatives, or mixtures thereof.

Examples of solid surfactants include, but are not limited to, 1. reaction products of a natural or hydrogenated castor oil and ethylene oxide. The natural or hydrogenated castor oil may be reacted with ethylene oxide in a molar ratio of from about 1:35 to about 1:60, with optional removal of the PEG component from the products. Various such surfactants are commercially available, e-g., the CREMOPHOR series from BASF Corp. (Mt. Olive, N.J.), such as CREMOPHOR RH 40 which is PEG40 hydrogenated castor oil which has a saponification value of about 50- to 60, an acid value less than about one, a water content, i.e., Fischer, less than about 2%, an $n_D^{60}$ of about 1.453-1.457, and an HLB of about 14-16;

2. polyoxyethylene fatty acid esters that include polyoxyethylene stearic acid esters, such as the MYRJ series from Uniqema e.g., MYRJ 53 having a m.p. of about 47° C.

Particular compounds in the MYRJ series are, e.g., MYRJ 53 having an m.p. of about 47° C. and PEG-40-stearate available as MYRJ 52;

3. sorbitan derivatives that include the TWEEN series from Uniqema, e.g., TWEEN 60;

4. polyoxyethylene-polyoxypropylene co-polymers and block co-polymers or poloxamers, e.g., Pluronic F127, Pluronic F68 from BASF;

5. polyoxyethylene alkyl ethers, e.g., such as polyoxyethylene glycol ethers of $C_{12}$-$C_{18}$ alcohols, e.g., polyoxyl 10- or 20-cetyl ether or polyoxyl 23-lauryl ether, or 20-oleyl ether, or polyoxyl 10-, 20- or 100-stearyl ether, as known and commercially available as the BRIJ series from Uniqema. Particularly useful products from the BRIJ series are BRIJ 58; BRIJ 76; BRIJ 78; BRIJ 35, i.e., polyoxyl 23 lauryl ether; and BRIJ 98, i.e., polyoxyl 20 oleyl ether. These products have a m.p. between about 32° C. to about 43° C.;

6. water-soluble tocopheryl PEG succinic acid esters available from Eastman Chemical Co. with a m.p. of about 36° C., e.g, TPGS, e.g., vitamin E TPGS.

7. PEG sterol ethers having, e.g., from 5-35 [$CH_2$—$CH_2$—O] units, e.g., 20-30 units, e-g., SOLULAN C24 (Choleth-24 and Cetheth-24) from Chemron (Paso Robles, Calif.); similar products which may also be used are those which are known and commercially available as NIKKOL BPS-30 (polyethoxylated 30 phytosterol) and NIKKOL BPSH-25 (polyethoxylated 25 phytostanol) from Nikko Chemicals;

8. polyglycerol fatty acid esters, e.g., having a range of glycerol units from 4-10, or 4, 6 or 10 glycerol units. For example, particularly suitable are deca-/hexa-/tetraglyceryl monostearate, e.g., DECAGLYN, HEXAGLYN and TETRAGLYN from Nikko Chemicals;

9. alkylene polyol ether or ester, e.g., lauroyl macrogol-32 glycerides and/or stearoyl macrogol-32 glycerides which are GELUCIRE 44/14 and GELUCIRE 50/13 respectively;

10. polyoxyethylene mono esters of a saturated $C_{10}$ to $C_{22}$, such as $C_{18}$ substituted e.g. hydroxy fatty acid; e.g. 12 hydroxy stearic acid PEG ester, e.g. of PEG about e.g. 600-900 e.g. 660 Daltons MW, e.g. SOLUTOL HS 15 from BASF (Ludwigshafen, 20 Germany). According to a BASF technical leaflet MEF 151E (1986), SOLUTOL HS 15 comprises about 70% polyethoxylated 12-hydroxystearate by weight and about 30% by weight unesterified polyethylene glycol component. It has a hydrogenation value of 90 to 110, a saponification value of 53 to 63, an acid number of maximum 1, and a maximum water content of 0.5% by weight;

11. polyoxyethylene-polyoxypropylene-alkyl ethers, e.g. polyoxyethylene-polyoxypropylene-ethers of $C_{12}$ to $C_{18}$ alcohols, e.g. polyoxyethylene-20-polyoxypropylene-4-cetylether which is commercially available as NIKKOL PBC 34 from Nikko Chemicals;

12. polyethoxylated distearates, e.g. commercially available under the tradenames ATLAS G 1821 from Uniqema and NIKKOCDS-6000P from Nikko Chemicals; and 13. lecithins, e.g., soy bean phospholipid, e.g. commercially available as LIPOID S75 from Lipoid GmbH (Ludwigshafen, Germany) or egg phospholipid, commercially available as PHOSPHOLIPON 90 from Nattermann Phospholipid (Cologne, Germany).

Examples of liquid surfactants include, but are not limited to, sorbitan derivatives such as TWEEN 20, TWEEN 40 and TWEEN 80, SYNPERONIC L44, and polyoxyl 10-oleyl ether, all available from Uniqema, and polyoxyethylene containing surfactants e.g. PEG-8 caprylic/capric glycerides (e.g. Labrasol available from Gattefosse).

The composition of the invention may comprise from about 0% to about 95% by weight surfactant, e.g. from about 5% to about 80% by weight, e.g., about 10% to about 70% by weight, e.g., from about 20% to about 60% by weight, e.g., from about 30% to about 50%.

In one aspect, the surfactant is polyoxyethylene-polyoxypropylene co-polymers and block co-polymers or poloxamers, e.g., Pluronic F127, Pluronic F68 from BASF.

In one aspect, the surfactant is a poloxamer. In a further aspect, the surfactant is selected from the group consisting of poloxamer 188, poloxamer 407 and mixtures of poloxamer 407 and poloxamer 188.

In one aspect, the surfactant is a polyoxyethylene containing surfactants e.g., PEG-8 caprylic/capric glycerides (e.g., Labrasol available from Gattefosse).

In one aspect, the surfactant is a lauroyl polyoxylglyceride (e.g. Gelucire 44/14 available from Gattefosse).

In one aspect, the surfactant is Cremophor RH40 from BASF.

In certain aspects, the pharmaceutical composition may comprise additional excipients commonly found in pharmaceutical compositions, examples of such excipients include, but are not limited to, antioxidants, antimicrobial agents, enzyme inhibitors, stabilizers, preservatives, flavors, sweeteners and other components as described in Handbook of Pharmaceutical Excipients, Rowe et al., Eds., 4'h Edition, Pharmaceutical Press (2003), which is hereby incorporated by reference.

These additional excipients may be in an amount from about 0.05-5% by weight of the total pharmaceutical composition. Antioxidants, anti-microbial agents, enzyme inhibitors, stabilizers or preservatives typically provide up to about 0.05-1% by weight of the total pharmaceutical composition. Sweetening or flavoring agents typically provide up to about 2.5% or 5% by weight of the total pharmaceutical composition.

Examples of antioxidants include, but are not limited to, ascorbic acid and its derivatives, tocopherol and its derivatives, butyl hydroxyl anisole and butyl hydroxyl toluene.

In one aspect, the composition comprises a buffer. The term "buffer" as used herein refers to a chemical compound in a pharmaceutical composition that reduces the tendency of pH of the composition to change over time as would otherwise occur due to chemical reactions. Buffers include chemicals such as sodium phosphate, TRIS, glycine and sodium citrate.

The term "preservative" as used herein refers to a chemical compound which is added to a pharmaceutical composition to prevent or delay microbial activity (growth and metabolism). Examples of pharmaceutically acceptable preservatives are phenol, m-cresol and a mixture of phenol and m-cresol.

The term "stabilizer" as used herein refers to chemicals added to peptide containing pharmaceutical compositions in order to stabilize the peptide, i.e., to increase the shelf life and/or in-use time of such compositions. Examples of stabilizers used in pharmaceutical formulations are L-glycine, L-histidine, arginine, glycylglycine, ethylenediamine, citrate, EDTA, zinc, sodium chloride, polyethylene glycol, carboxymethylcellulose, and surfactants and antioxidants like alfa-tocopherol and I-ascorbic acid.

In a further aspect, a process for preparing a pharmaceutical composition, containing an acylated protease stabilised insulin, comprises the steps of bringing the drug and a carrier comprising a polar organic solvent, a lipophilic component, and optionally a surfactant and/or a hydrophilic component into intimate admixture. For example, the acylated protease stabilised insulin and the carrier can be liquefied, for example, by heating to about 20° C. to about 80° C., and then solidifying by cooling to room temperature.

The carrier can be prepared separately before bringing a carrier comprising a polar organic solvent, a lipophilic component, and optionally a surfactant and/or a hydrophilic component into intimate admixture with the derivatized insulin peptide. Alternatively, one, two or more of the components of the carrier can be mixed together with the polypeptide.

The acylated protease stabilised insulin can be dissolved in the polar organic solvent, and then be mixed with the lipid component and optionally with a surfactant.

Alternatively, a process for preparing a pharmaceutical composition such as SEDDS or SMEDDS (which can be filled into a capsule, e.g. enteric coated capsule, soft capsule, enteric soft capsule) containing an acylated protease stabilised insulin, comprises the following steps:

(a) dissolving the derivatized insulin peptide in the polar organic solvent and (b) mixing with the lipophilic component, surfactant and optionally hydrophilic component.

For example, a process for preparing the pharmaceutical composition is carried out at low temperature (e.g. room temperature or below room temperature).

When preparing the pharmaceutical composition, the acylated protease stabilised insulin may, e.g., be dissolved in the polar organic solvent using the following method:

a) providing an aqueous solution of the acylated protease stabilised insulin, optionally comprising excipients, b) adjusting the pH value to a target pH value which is 1 unit, alternatively 2 units and alternatively 2.5 pH units above or below the pI of the acylated protease stabilised insulin, c) removing water (dehydrating) from the acylated protease stabilised insulin by conventional drying technologies such as freeze- and spray drying, and d) mixing and dissolution of the acylated protease stabilised insulin in said polar non-aqueous solvent, e.g., by stirring, tumbling or other mixing methods, e) optionally filtration or centrifugation of the non-aqueous solution of the acylated protease stabilised insulin to remove non-dissolved inorganic salts, f) optionally removing residual amounts of waters by, e.g., adding solid dessicants or vacuum drying.

For example, the acylated protease stabilised insulin is dissolved in the polar organic solvent by the following method:

a) providing an aqueous solution of a acylated protease stabilised insulin, optionally containing stabilizers such as zinc and glycylglycine, b) adjusting the pH value to 1 unit, alternatively 2 units and alternatively 2.5 pH units above or below the pI of the polypeptide, e.g., by adding a non-volatile base or a acid, such as hydrochloric acid or sodium hydroxide, to the solution, c) removing water (dehydrating) from the acylated protease stabilised insulin by conventional drying technologies such as freeze- and spray drying, d) mixing and dissolution of the acylated protease stabilised insulin in said polar non-aqueous solvent, e.g., by stirring, tumbling or other mixing methods, e) optionally filtration or centrifugation of the non-aqueous solution of the acylated protease stabilised insulin to remove non-dissolved inorganic salts, f) optionally removing residual amounts of waters by, e.g., adding solid dessicants or vacuum drying.

By "volatile base" is meant a base, which to some extend will evaporate upon heating and/or at reduced pressure, e.g., bases which have a vapour pressure above 65 Pa at room temperature or an aqueous azeotropic mixture including a base having a vapour pressure above 65 Pa at room temperature. Examples of volatile bases are ammonium hydroxides, tetraalkylammonium hydroxides, secondary amines, tertiary amines, aryl amines, alphatic amines or ammonium bicarbonate or a combination. For example the volatile base can be bicarbonate, carbonate, ammonia, hydrazine or an organic base such as a lower aliphatic amines e.g. trimethyl amine, triethylamine, diethanolamines, triethanolamine and their salts. Furthermore, the volatile base can be ammonium hydroxide, ethyl amine or methyl amine or a combination hereof.

By "volatile acid" is meant an acid, which to some extend will evaporate upon heating and/or at reduced pressure, e.g., acids which have a vapour pressure above 65 Pa at room temperature or an aqueous azeotropic mixture including an acid having a vapour pressure above 65 Pa at room temperature. Examples of volatile acids are carbonic acid, formic acid, acetic acid, propionic acid and butyric acid.

A "non volatile base" as mentioned herein means a base, which do not evaporate or only partly evaporate upon heating, e.g., bases with a vapour pressure below 65 Pa at room temperature. The non volatile base can be selected from the group consisting of alkaline metal salts, alkaline metal hydroxides, alkaline earth metal salts, alkaline earth metal hydroxides and amino acids or a combination hereof. Examples of non-volatile bases are sodium hydroxide, potassium hydroxide, calcium hydroxide, and calcium oxide.

A "non volatile acid" as mentioned herein means an acid, which do not evaporate or only partly evaporate upon heating, e.g., bases with a vapour pressure below 65 Pa at room temperature. Examples of non-volatile acids are hydrochloric acid, phosphoric acid and sulfuric acid.

The acylated protease stabilised insulin may be present in an amount up to about 40% such as up to about 20% by weight of the composition, or from about 0.01% such as from about 0.1%, alternatively, from about 0.01% to about 20%, alternatively, from about 1% to 20% or from about 1% to 10% by weight of the composition. It is intended, however, that the choice of a particular level of polypeptide will be made in accordance with factors well-known in the pharmaceutical arts, including the solubility of the polypeptide in the polar organic solvent or optional hydrophilic component or surfactant used, or a mixture thereof, mode of administration and the size and condition of the patient.

For example, the pharmaceutical formulation comprises an acylated protease stabilised insulin in a concentration from 0.1% w/w to 30% w/w.

Each unit dosage will suitably contain from 0.1 mg to 300 mg acylated protease stabilised insulin polypeptide, e.g., about 0.1 mg, 1 mg, 5 mg, 10 mg, 15 mg, 25 mg, 50 mg, 100 mg, 200 mg, 250 mg, 300 mg, e.g., between 5 mg and 300 mg of the acylated protease stabilised insulin. For example, each unit dosage contains between 10 mg and 300 mg, for example 10 mg and 100 mg or between 20 mg and 300 mg, fore example, between 20 mg and 100 mg of the acylated protease stabilised insulin. Such unit dosage forms are suitable for administration 1-5 times daily depending upon the particular purpose of therapy.

The acylated protease stabilsed insulin is pH optimized before dissolution in the polar organic solvent to improve solubility in the polar organic solvent.

When using the term "pH optimized" it is herein meant that the acylated protease stabilsed insulin has been dehydrated at a target pH which is at least 1 pH unit from the pI of the acylated protease stabilsed insulin in aqueous solution. Thus, the target pH is more than 1 pH unit above the isoelectric point of the acylated protease stabilsed insulin. Alternatively, the target pH is more than 1 pH unit below the isoelectric point of the acylated protease stabilsed insulin. Hence, the target pH could be more than 1.5 pH units above or below the pI, for example, 2.0 pH units or more above or below the pI, for example, 2.5 pH units or more above or below the pI of the acylated protease stabilsed insulin.

The term "dehydrated" as used herein in connection with an acylated protease stabilsed insulin refers to a derivatized acylated protease stabilsed insulin which has been dried from an aqueous solution. The term "target pH" as used herein refers to the aqueous pH which will establish when the dehydrated acylated protease stabilsed insulin is rehydrated in pure water to a concentration of approximately 40 mg/ml or more. The target pH will typically be identical to the pH of the aqueous solution of the acylated protease stabilsed insulin from which the acylated protease stabilsed insulin was recovered by drying. However, the pH of the acylated protease stabilsed insulin solution will not be identical to the target pH, if the solution contains volatile acids or bases. It has been found that the pH history of the acylated protease stabilsed insulin will be determinant for the amount of the acylated protease stabilsed insulin, which can be solubilized in the polar organic solvent.

The term "the pI of the polypeptide" as used herein refers to the isoelectric point of a polypeptide.

The term "isoelectric point" as used herein means the pH value where the overall net charge of a macromolecule such as a peptide is zero. In peptides there may be several charged groups, and at the isoelectric point the sum of all these charges is zero. At a pH above the isoelectric point the overall net charge of the peptide will be negative, whereas at pH values below the isoelectric point the overall net charge of the peptide will be positive.

The pI of a protein can be determined experimentally by electrophoresis techniques such as electrofocusing:

A pH gradient is established in an anticonvective medium, such as a polyacrylamide gel. When a protein is introduced in to the system it will migrate under influence of an electric field applied across the gel. Positive charged proteins will migrate to the cathode. Eventually, the migrating protein reaches a point in the pH gradient where its net electrical charge is zero and is said to be focused. This is the isoelectric pH (pI) of the protein. The protein is then fixed on the gel and stained. The pI of the protein can then be determined by comparison of the position of the protein on the gel relative to marker molecules with known pI values.

The net charge of a protein at a given pH value can be estimated theoretically by a person skilled in the art by conventional methods. In essence, the net charge of protein is the equivalent to the sum of the fractional charges of the charged amino acids in the protein: aspartate (β-carboxyl group), glutamate (δ-carboxyl group), cysteine (thiol group), tyrosine (phenol group), histidine (imidazole side chains), lysine (ε-ammonium group) and arginine (guanidinium group). Additionally, one should also take into account charge of protein terminal groups (α-NH2 and α-COOH). The fractional charge of the ionisable groups can be calculated from the intrinsic pKa values.

The drying, i.e., dehydration of the acylated protease stabilsed insulin can be performed by any conventional drying method such, e.g., by spray-, freeze-, vacuum-, open- and contact drying. For example, the acylated protease stabilsed insulin solution is spray dried to obtain a water content below about 10%, for example, below about 8%, below about 6%, below about 5%, below about 4%, below about 3%, below about 2% or below about 1% calculated on/measured by loss on drying test (gravimetric) as stated in the experimental part.

For example, the acylated protease stabilised insulin is spray dried or freeze-dried.

Compositions containing acylated protease stabilised insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the acylated insulin of this invention be determined for each individual patient by those skilled in the art in a similar way as for known insulin compositions.

PREFERRED FEATURES OF THIS INVENTION

The features of this invention are as follows:
1. An acylated protease stabilised insulin wherein the protease stabilised insulin, formally, consists of a non-protease stabilised insulin (parent insulin) wherein at least one hydrophobic amino acid has been substituted with hydrophilic amino acids, and wherein said substitution is within or in close proximity to one or more protease cleavage sites of the non-protease stabilised insulin (parent insulin) and wherein such protease stabilised insulin optionally further comprises one or more additional mutations with the proviso that there is only one lysine residue in the stabilized insulin, and wherein the acyl moiety is attached to the lysine residue or to a N-terminal position in the protease stabilized insulin.
2. An acylated protease stabilised insulin wherein the protease stabilised insulin, formally, consists of a non-protease stabilised insulin (parent insulin) wherein at least two hydrophobic amino acids have been substituted with hydrophilic amino acids, and wherein said substitutions are within or in close proximity to two or more protease cleavage sites of the non-protease stabilised insulin (parent insulin) and wherein such protease stabilised insulin optionally further comprises one or more additional mutations with the proviso that there is only one lysine residue in the stabilized insulin, and wherein the acyl moiety is attached to the lysine residue in the protease stabilized insulin.
3. An acylated protease stabilised insulin wherein the protease stabilised insulin, formally, consists of a non-protease stabilised insulin (parent insulin) wherein at least two hydrophobic amino acids have been substituted with hydrophilic amino acids, and wherein said substitutions are within or in close proximity to two or more protease cleavage sites of the non-protease stabilised insulin (parent insulin) and wherein such protease stabilised insulin optionally further comprises one or more additional mutations with the proviso that there is only one lysine residue in the stabilized insulin, and wherein the acyl moiety is attached to the lysine residue or to a N-terminal position in the protease stabilized insulin.
4. An acylated insulin according any of the preceding clauses wherein the protease stabilised insulin has increased solubility relative to the acylated parent insulin.
5. An acylated insulin according to any one of the preceding clauses to the extent possible wherein the B-chain of the insulin comprises at least one mutation relative to the parent insulin.
6. An acylated insulin according to the preceding clause to the extent possible wherein the B-chain of the insulin comprises one, two or three but not more mutations relative to the parent insulin.
7. An acylated insulin according to any one of the preceding clauses to the extent possible, wherein the A chain of the protease stabilised insulin is identical with the A chain of human insulin.
8. An acylated insulin according to any one of the preceding clauses to the extend possible wherein the A-chain of the insulin comprises at least one mutation and the B-chain of the insulin comprises at least one mutation relative to the parent insulin.
9. An acylated insulin according to any one of the preceding clauses to the extend possible wherein the A-chain of the insulin comprises at least two mutations and the B-chain of the insulin comprises at least one mutation relative to the parent insulin.
10. An acylated insulin according to any one of the preceding clauses to the extent possible wherein the insulin further comprises at least one amino acid substitution in a protease site of a first modified protease stabilised insulin, wherein said at least one amino acid substitution is such that at least one hydrophobic amino acid has been substituted with at least one hydrophilic amino acid.

11. An acylated protease stabilised insulin according to any of the preceding clauses to the extent possible wherein the amino acid in position A12 is Glu or Asp; and/or the amino acid in position A13 is His, Asn, Glu or Asp; and/or the amino acid in position A14 is Tyr, Asn, Gln, Glu, Arg, Asp, Gly or His; and/or the amino acid in position A15 is Glu or His; and the amino acid in position B24 is His; and/or the amino acid in position B25 is His or Asn; and/or the amino acid in position B26 is His, Gly, Asp or Thr; and/or the amino acid in position B27 is His, Glu, Asp, Gly or Arg; and/or the amino acid in position B28 is His, Gly, Glu or Asp; and which optionally further comprises one or more additional mutations.

12. An acylated protease stabilised insulin according to any of the preceding clauses to the extent possible wherein the amino acid in position A12 is Glu or Asp; and/or the amino acid in position A13 is His, Asn, Glu or Asp; and/or the amino acid in position A14 is Tyr, Asn, Gln, Glu, Arg, Asp, Gly or His; and/or the amino acid in position A15 is Glu or Asp; and/or the amino acid in position B16 is Tyr, His or Glu; and/or the amino acid in position B24 is His; and/or the amino acid in position B25 is His or Asn; and/or the amino acid in position B26 is His, Gly, Asp or Thr; and/or the amino acid in position B27 is His, Glu, Asp, Gly, Lys, Arg or deleted; and/or the amino acid in position B28 is His, Gly, Glu, Asp, or absent (deleted); and/or the amino acid in position B29 is Lys, Arg, or absent (deleted); and which optionally further comprises one or more additional mutations and, preferably, acylated protease stabilised insulins wherein the amino acid in position A12 is Glu or Asp; and/or the amino acid in position A13 is His, Asn, Glu or Asp; and/or the amino acid in position A14 is Tyr, Asn, Gln, Glu, Arg, Asp, Gly or His; and/or the amino acid in position A15 is Glu or Asp; and the amino acid in position B24 is His; and/or the amino acid in position B25 is His or Asn; and/or the amino acid in position B26 is His, Gly, Asp or Thr; and/or the amino acid in position B27 is His, Glu, Asp, Gly or Arg; and/or the amino acid in position B28 is His, Gly, Glu, or Asp; and which optionally further comprises one or more additional mutations.

13. An acylated protease stabilised insulin according to any of the preceding clauses to the extent possible wherein the amino acid in position A14 is Glu, Asp or His, the amino acid in position B25 is His or Asn and which optionally further comprises one or more additional mutations.

14. An acylated protease stabilised insulin according to any of the preceding clauses to the extent possible wherein the amino acid in position A14 is Glu, Asp or His, the amino acid in position B25 is His or Asn and the amino acid in position B30 is deleted.

15. An acylated protease stabilised insulin according to any of the preceding clauses to the extent possible wherein the amino acid in position A14 is Glu, Asp or His, the amino acid in position B16 is His or Glu, the amino acid in position B25 is His and the amino acid in position B30 is deleted.

16. An acylated protease stabilised insulin according to any of the preceding clauses to the extent possible wherein the amino acid in position A14 is Glu, Asp or His and the amino acid in position B25 is His and the amino acid in position B30 is deleted.

17. An acylated protease stabilised insulin according to any of the preceding clauses to the extent possible wherein the amino acid in position A14 is Glu or Asp and the amino acid in position B28 is Glu or Asp, and, optionally, there is no amino acid residue in the B30 position.

18. An acylated protease stabilised insulin according to any of the preceding clauses to the extent possible wherein the one or more additional mutations is selected from a group consisting of: A8His, A18Gln, A21Gln, A21Gly, B1Glu, B1Gln, B3Gln, B10Pro, B14Thr, B16Glu, B17Ser, B26Asp, B27Glu, B27Asp, B28Asp, B28Glu, and desB30.

19. An acylated protease stabilised insulin according to any of the preceding clauses to the extent possible wherein the additional mutation is desB30.

20. An acylated protease stabilised insulin according to any of the preceding clauses to the extent possible wherein A14 is Glu.

21. An acylated protease stabilised insulin according to any of the preceding clauses to the extent possible wherein B25 is Asn.

22. An acylated protease stabilised insulin according to any of the preceding clauses to the extent possible wherein B25 is His.

23. An acylated protease stabilised insulin according to any of the preceding clauses to the extent possible wherein B25 is Asn and B27 is Glu or Asp.

24. An acylated protease stabilised insulin according to any of the preceding clauses to the extent possible wherein B25 is Asn and B27 is Glu.

25. An acylated protease stabilised insulin according to any of the preceding clauses to the extent possible which shows increased stability towards one or more protease enzymes relative to the parent protein.

26. An acylated protease stabilised insulin according to any of the preceding clauses to the extent possible which shows increased stability towards two or more protease enzymes relative to the parent protein.

27. An acylated protease stabilised insulin according to any of the preceding clauses to the extent possible wherein the parent insulin is selected from a group consisting of a) human insulin; b) an insulin analogue of human insulin wherein the amino acid residue in position B28 is Pro, Asp, Lys, Leu, Val or Ala and the amino acid residue in position B29 is Lys or Pro and optionally the amino acid residue in position B30 is deleted; c) des(B26-B30) human insulin, des(B27-B30) human insulin, des(B28-B30) human insulin, des(B29-B30) human insulin, des (B27) human insulin or des(B30) human insulin; d) an insulin analogue of human insulin wherein the amino acid residue in position B3 is Lys and the amino acid residue in position B29 is Glu or Asp; e) an insulin analogue of human insulin wherein the amino acid residue in position A21 is Gly and wherein the insulin analogue is further extended in the C-terminal with two Arg residues; f) an insulin derivative wherein the amino acid residue in position B30 is substituted with a threonine methyl ester; and g) an insulin derivative wherein to the Nε position of lysine in the position B29 of des(B30) human insulin a tetradecanoyl chain is attached.

28. An acylated protease stabilised insulin according to any of the preceding clauses to the extent possible wherein the one or more additional mutations are selected to enhance chemical stability of insulin.

29. An acylated protease stabilised insulin according to the preceding clause to the extent possible wherein the one or more additional mutations are selected from a group consisting of A18Gln, A21Gln, A21Gly and B3Gln.

30. An acylated protease stabilised insulin according to any of the preceding clauses to the extent possible comprising an A-chain amino acid sequence of formula 1, i.e.: $Xaa_{A(-2)}$-$Xaa_{A(-1)}$-$Xaa_{A0}$-Gly-Ile-Val-Glu-Gln-Cys-Cys- Xaa$_{A8}$-Ser-Ile-Cys-Xaa$_{A12}$-Xaa$_{A13}$-Xaa$_{A14}$-Xaa$_{A15}$-Leu-Glu-Xaa$_{A18}$-Tyr-Cys-Xaa$_{A21}$ (SEQ ID No:1), and a B-chain amino acid sequence of formula 2, i.e.: Xaa$_{B(-2)}$-Xaa$_{B(-1)}$-Xaa$_{B0}$-Xaa$_{B1}$-Xaa$_{B2}$-Xaa$_{B3}$-Xaa$_{B4}$-His-Leu-Cys-Gly-Ser-Xaa$_{B10}$-Leu-Val-Glu-Ala-Leu-Xaa$_{B16}$-Leu-Val-Cys-Gly-Glu-Arg-Gly-Xaa$_{B24}$-Xaa$_{B25}$-Xaa$_{B26}$-Xaa$_{B27}$-Xaa$_{B28}$-Xaa$_{B29}$-Xaa$_{B30}$-Xaa$_{B31}$-Xaa$_{B32}$ (SEQ ID No:2), wherein Xaa$_{A(-2)}$ is absent or Gly; Xaa$_{A(-1)}$ is absent or Pro; Xaa$_{A0}$ is absent or Pro; Xaa$_{A8}$ is independently selected from Thr and His; Xaa$_{A12}$ is independently selected from Ser, Asp and Glu; Xaa$_{A13}$ is independently selected from Leu, Thr, Asn, Asp, Gln, His, Lys, Gly, Arg, Pro, Ser and Glu; Xaa$_{A14}$ is independently selected from Tyr, Thr, Asn, Asp, Gln, His, Lys, Gly, Arg, Pro, Ser and Glu; Xaa$_{A18}$ is independently selected from Gln, Asp and Glu; Xaa$_{A18}$ is independently selected from Asn, Lys and Gln; Xaa$_{A21}$ is independently selected from Asn and Gln; Xaa$_{B(-2)}$ is absent or Gly; Xaa$_{B(-1)}$ is absent or Pro; Xaa$_{B0}$ is absent or Pro; Xaa$_{B1}$ is absent or independently selected from Phe and Glu; Xaa$_{B2}$ is absent or Val; Xaa$_{B3}$ is absent or independently selected from Asn and Gln; Xaa$_{B4}$ is independently selected from Gln and Glu; Xaa$_{B10}$ is independently selected from His, Asp, Pro and Glu; Xaa$_{B16}$ is independently selected from Tyr, Asp, Gln, His, Arg, and Glu; Xaa$_{B24}$ is independently selected from Phe and His; Xaa$_{B25}$ is independently selected from Phe, Asn and His; Xaa$_{B26}$ is absent or independently selected from Tyr, His, Thr, Gly and Asp; Xaa$_{B27}$ is absent or independently selected from Thr, Asn, Asp, Gln, His, Gly, Arg, Pro, Ser and Glu; Xaa$_{B28}$ is absent or independently selected from Pro, His, Gly and Asp; Xaa$_{B29}$ is absent or independently selected from Lys and Gln; Xaa$_{B30}$ is absent or Thr; Xaa$_{B31}$ is absent or Leu; Xaa$_{B32}$ is absent or Glu; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge; wherein optionally the N-terminal A-chain amino acid sequence is connected to the C-terminal B-chain amino acid sequence by an amino acid sequence comprising 3-7 amino acids to form a single chain insulin molecule, wherein optionally the N-terminal of the B-chain is extended with 1-10 amino acids; wherein if $Xaa_{A8}$ is Thr and $Xaa_{A12}$ is Ser and $Xaa_{A13}$ is Leu and $Xaa_{A14}$ is Tyr then $Xaa_{A15}$ is Glu or Asp; and wherein if $Xaa_{B24}$ is Phe and $Xaa_{B25}$ is Phe and $Xaa_{B26}$ is Tyr and $Xaa_{B27}$ is Thr and $Xaa_{B28}$ is Pro then $Xaa_{B29}$Gln.

31. An acylated protease stabilised insulin according to any of the preceding clauses to the extent possible comprising an A-chain amino acid sequence of formula 3, i.e.: Gly-Ile-Val-Glu-Gln-Cys-Cys-$Xaa_{A8}$-Ser-Ile-Cys-$Xaa_{A12}$-$Xaa_{A13}$-$Xaa_{A14}$-$Xaa_{A15}$-Leu-Glu-$Xaa_{A18}$-Tyr-Cys-$Xaa_{A21}$ (SEQ ID No:3), and a B-chain amino acid sequence of formula 4, i.e.: $Xaa_{B1}$-Val-$Xaa_{B3}$-$Xaa_{B4}$-His-Leu-Cys-Gly-Ser-$Xaa_{B10}$-Leu-Val-Glu-Ala-Leu-$Xaa_{B16}$-Leu-Val-Cys-Gly-Glu-Arg-Gly-$Xaa_{B24}$-His-$Xaa_{B26}$-$Xaa_{B27}$-$Xaa_{B28}$-$Xaa_{B29}$-$Xaa_{B30}$ (SEQ ID No:4), wherein $Xaa_{A8}$ is independently selected from Thr and His; $Xaa_{A12}$ is independently selected from Ser, Asp and Glu; $Xaa_{A13}$ is independently selected from Leu, Thr, Asn, Asp, Gln, His, Lys, Gly, Arg, Pro, Ser and Glu; $Xaa_{A14}$ is independently selected from Tyr, Thr, Asn, Asp, Gln, His, Lys, Gly, Arg, Pro, Ser and Glu; $Xaa_{A15}$ is independently selected from Gln, Asp and Glu; $Xaa_{A18}$ is independently selected from Asn, Lys and Gln; $Xaa_{A21}$ is independently selected from Asn, and Gln; $Xaa_{B1}$ is independently selected from Phe and Glu; $Xaa_{B3}$ is independently selected from Asn and Gln; $Xaa_{B4}$ is independently selected from Gln and Glu; $Xaa_{B10}$ is independently selected from His, Asp, Pro and Glu; $Xaa_{B16}$ is independently selected from Tyr, Asp, Gln, His, Arg, and Glu; $Xaa_{B24}$ is independently selected from Phe and His; $Xaa_{B25}$ is independently selected from Phe, Asn and His; $Xaa_{B26}$ is absent or independently selected from Tyr, His, Thr, Gly and Asp; $Xaa_{B27}$ is absent or independently selected from Thr, Asn, Asp, Gln, His, Gly, Arg, Pro, Ser and Glu; $Xaa_{B28}$ is absent or independently selected from Pro, His, Gly and Asp; $Xaa_{B29}$ is absent or independently selected from Lys and Gln; $Xaa_{B30}$ is absent or Thr; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

32. An acylated protease stabilised insulin according to the preceding clause to the extent possible, wherein $Xaa_{A8}$ is independently selected from Thr and His; $Xaa_{A12}$ is independently selected from Ser and Glu; $Xaa_{A13}$ is independently selected from Leu, Thr, Asn, Asp, Gln, His, Lys, Gly, Arg, Pro, Ser and Glu; $Xaa_{A14}$ is independently selected from Tyr, Asp, His, and Glu; $Xaa_{A15}$ is independently selected from Gln and Glu; $Xaa_{A18}$ is independently selected from Asn, Lys and Gln; $Xaa_{A21}$ is independently selected from Asn, and Gln; $Xaa_{B1}$ is independently selected from Phe and Glu; $Xaa_{B3}$ is independently selected from Asn and Gln; $Xaa_{B4}$ is independently selected from Gln and Glu; $Xaa_{B10}$ is independently selected from His, Asp, Pro and Glu; $Xaa_{B16}$ is independently selected from Tyr, Asp, Gln, His, Arg, and Glu; $Xaa_{B24}$ is independently selected from Phe and His; $Xaa_{B25}$ is independently selected from Phe, Asn and His; $Xaa_{B26}$ is independently selected from Tyr, Thr, Gly and Asp; $Xaa_{B27}$ is independently selected from Thr, Asn, Asp, Gln, His, Lys, Gly, Arg, and Glu; $Xaa_{B28}$ is independently selected from Pro, Gly and Asp; $Xaa_{B29}$ is independently selected from Lys and Gln; $Xaa_{B30}$ is absent or Thr; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge.

33. An acylated protease stabilised insulin wherein, in the protease stabilised insulin, the amino acid in position A14 is Glu or His (i.e., E or H, according to the one letter code), the amino acid in position B25 is His and which optionally further comprises one or more additional mutations, and wherein the acyl moiety is attached to the E amino group in the lysine residue in position B29.

34. An acylated protease stabilised insulin wherein, in the protease stabilised insulin, the amino acid in position B25 is His or Asn, the amino acid in position B27 is Glu or Asp, and which optionally further comprises one or more of the following additional mutations: A8H, A14E/D, B1E/D, B28E/D, and desB30 and wherein the acyl moiety is attached to the ε amino group in the lysine residue in position B29.
35. An acylated protease stabilised insulin wherein, in the protease stabilised insulin, the amino acid in position A14 is Tyr, Glu or His (i.e., Y, E or H, according to the one letter code), the amino acid in position B25 is Asn, the amino acid in position B27 is Glu or Asp and which optionally further comprises one or more additional mutations, and wherein the acyl moiety is attached to the ε amino group in the lysine residue in position B29.
36. An acylated protease stabilised insulin according to any one of the preceding clauses to the extent possible wherein the protease stabilised insulin comprises the A14E mutation.
37. An acylated protease stabilised insulin according to any one of the preceding clauses to the extent possible wherein, in the protease stabilised insulin, apart from the mutation in position B25, there is only the mutation in position A14 mentioned in the preceding clause.
38. An acylated protease stabilised insulin according to any one of the preceding clauses to the extent possible wherein the protease stabilised insulin comprises the A14H mutation.
39. An acylated protease stabilised insulin according to any one of the preceding clauses to the extent possible wherein the protease stabilised insulin analogue comprises the desB30 mutation.
40. An acylated protease stabilised insulin according to any of the preceding clauses to the extent possible wherein the one or more additional mutations within the protease stabilised insulin is selected from a group consisting of: A(−1)P, A(0)P, A8H, A21G, B(−1)P, B(0)P, B1E, B1Q, B16E, B26D, B27E, B28D, desB30, B31L and B32E.
41. An acylated protease stabilised insulin according to the preceding clause to the extent possible, wherein the protease stabilised insulin, apart from the mutations in positions A14 and B25, has only one of the mutations mentioned in the previous clauses.
42. An acylated protease stabilised insulin according to any one of the preceding clauses but the last one (i.e., except clause 41) to the extent possible, wherein the protease stabilised insulin, apart from the mutations in positions A14 and B25, has exactly two of the mutations mentioned in the preceding clause but two (i.e., mentioned in clause 40).
43. An acylated protease stabilised insulin according to any one of the preceding clauses but the last two (i.e. except clauses 41 and 42) to the extent possible, wherein the protease stabilised insulin, apart from the mutations in positions A14 and B25, has exactly three of the mutations mentioned in the preceding clause but two (i.e., mentioned in clause 40).
44. An acylated protease stabilised insulin according to any one of the preceding clauses but the last two (i.e. except clauses 41 and 42) to the extent possible wherein, apart from the mutations in positions A14 and B25, the only additional mutation is desB30.
45. An acylated protease stabilised insulin according to any one of the preceding clauses to the extent possible wherein the C terminal amino acid residue in the A chain of the protease stabilized insulin is the A21 amino acid residue.
46. An acylated protease stabilised insulin according to any one of the preceding clauses to the extent possible wherein the protease stabilized insulin is selected from the group consisting of A8H, B25N, B27E, desB30 human insulin; A14E, A18L, B25H, desB30 human insulin; A14E, A21G, B25H, desB27, desB30 human insulin; A14E, B1E, B25H, B27E, B28E, desB30 human insulin; A14E, B1E, B25H, B28E, desB30 human insulin; A14E, B1E, B27E, B28E, desB30 human insulin; A14E, B1E, B28E, desB30 human insulin; A14E, B16H, B25H, desB30 human insulin; A14E, B25H, desB30 human insulin; A14E, B25H, B26G, B27G, B28G, desB30 human insulin; A14E, B25H, B27E, desB30 human insulin; A14E, B25H, desB27, desB30 human insulin; A14E, B25H, B29R, desB30 human insulin; A14E, B28D, desB30 human insulin; A14E, B28E, desB30 human insulin; B25N, B27E, desB30 human insulin; B25H, desB30 human insulin; A14E, B25H, B26G, B27G, B28G, B29R, desB30 human insulin; A14E, B25H, B29R, desB30 human insulin; A14E, A21G, B25H, desB27, desB30 human insulin; A14E, A21G, B25H, desB30 human insulin; A14E, B16H, B25H, desB30 human insulin; A14E, B25H, B16H, desB30 human insulin; A14E, B25H, B26G, B27G, B28G, desB30 human insulin; A14E, B25H, desB27, desB30 human insulin; A14E, B25H, B27K, desB28, desB29, desB30 human insulin; A14E, B25H, desB30 human insulin; A14E, desB30 human insulin and A21G, B25H, desB30 human insulin.
47. An acylated protease stabilised insulin according to any one of the preceding clauses to the extent possible wherein the acyl moiety attached to the protease stabilised insulin has the general formula Acy-AA1$_n$-AA2$_m$-AA3$_p$- (I), wherein Acy, AA1, AA2, AA3, n, m and p are as defined above.
48. An acylated protease stabilised insulin according to the preceding clause to the extent possible wherein Acy is a fatty acid, preferably myristic acid or steric acid, more preferred myristic acid.
49. An acylated protease stabilised insulin according to any one of the preceding clauses except the last one, wherein Acy is a fatty diacid, preferably a fatty (α,ω) diacid, more preferred heptadecanedioic acid, hexadecanedioic acid, octadecanedioic acid, nonadecanedioic acid, docosanedioic acid, eicosanedioic acid.
50. An acylated protease stabilised insulin according to any one of the preceding clauses except the last one, wherein Acy is a ω-(tetrazol-5-yl)-fatty acid, preferably 15-(1H-tetrazol-5-yl)penta-decanoic acid, 16-(1H-tetrazol-5-yl) hexadecanoic acid, 17-(1H-tetrazol-5-yl)heptadecanoic acid, 18-(1H-tetrazol-5-yl)octadecanoic acid, or 19-(1H-tetrazol-5-yl)nonadecanoic acid.
51. An acylated protease stabilised insulin according to any one of the preceding clauses to the extent possible wherein AA1 is tranexamic acid or glycine.
52. An acylated protease stabilised insulin according to any one of the preceding clauses to the extent possible wherein AA1 is tranexamic acid.
53. An acylated protease stabilised insulin according to any one of the preceding clauses to the extent possible wherein n is 0 or 1.
54. An acylated protease stabilised insulin according to any one of the preceding clauses to the extent possible wherein n is 0.
55. An acylated protease stabilised insulin according to any one of the preceding clauses to the extent possible wherein n is 1.
56. An acylated protease stabilised insulin according to any one of the preceding clauses to the extent possible wherein AA2 is γGlu, αGlu, βAsp, αAsp, γ-D-Glu, α-D-Asp, or an amino acid of the following formula:

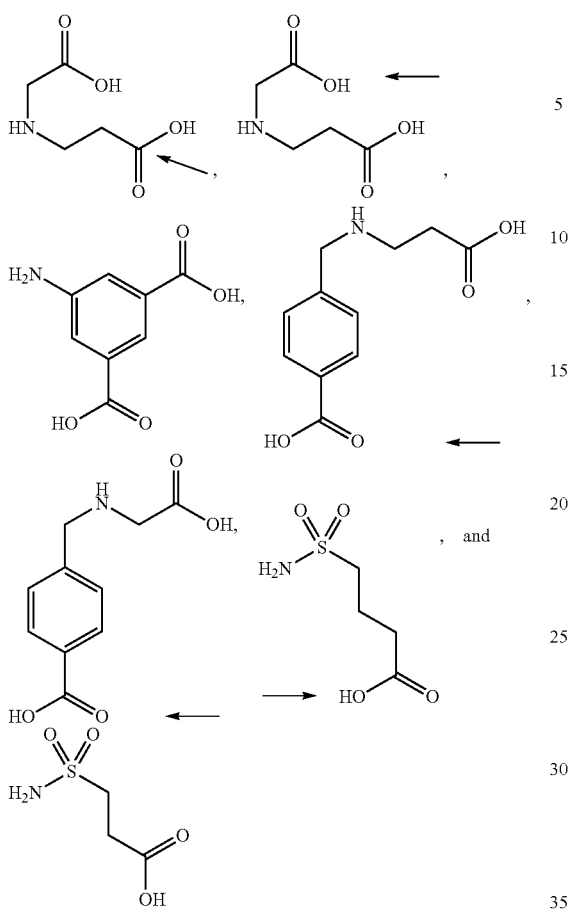

wherein the arrows indicate the attachment point to the amino group of AA1, AA2, AA3 or to the ε-amino group of the B29 lysine residue or to a N-terminal position of the protease stabilised insulin 57. An acylated protease stabilised insulin according to any one of the preceding clauses to the extent possible wherein AA2 is γGlu, βAsp, γ-D-Glu, β-D-Asp, or an amino acid of the following formula:

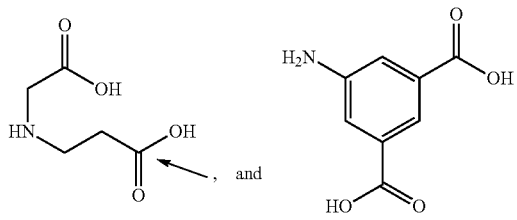

wherein the arrow indicate the attachment point to the amino group of AA1, AA2, AA3 or to the ε-amino group of the B29 lysine residue or to a N-terminal position of the protease stabilised insulin 58. An acylated protease stabilised insulin according to any one of the preceding clauses to the extent possible wherein AA2 is γGlu, γ-D-Glu, or an amino acid of the following formula:

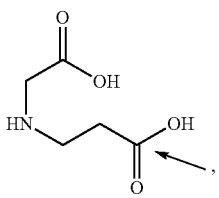

wherein the arrow indicate the attachment point to the amino group of AA1, AA2, AA3 or to the ε-amino group of the B29 lysine residue or to a N-terminal position of the protease stabilised insulin 59. An acylated protease stabilised insulin according to any one of the preceding clauses to the extent possible wherein m is 0, 1, 2, 3, 4, 5, or 6.

60. An acylated protease stabilised insulin according to any one of the preceding clauses to the extent possible wherein m is 0, 1, 2, 3, or 4.

61. An acylated protease stabilised insulin according to any one of the preceding clauses to the extent possible wherein m is 4.

62. An acylated protease stabilised insulin according to any one of the preceding clauses to the extent possible wherein m is 3.

63. An acylated protease stabilised insulin according to any one of the preceding clauses to the extent possible wherein m is 2.

64. An acylated protease stabilised insulin according to any one of the preceding clauses to the extent possible wherein m is 1.

65. An acylated protease stabilised insulin according to any one of the preceding clauses to the extent possible wherein m is 0.

66. An acylated protease stabilised insulin, according to any one of the preceding clauses to the extent possible, wherein AA3 is selected from any of the following:

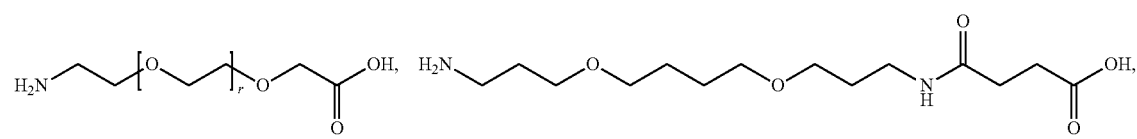

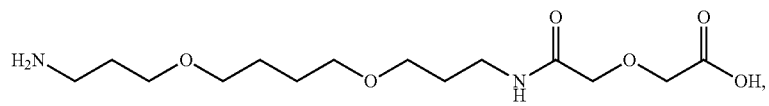

-continued

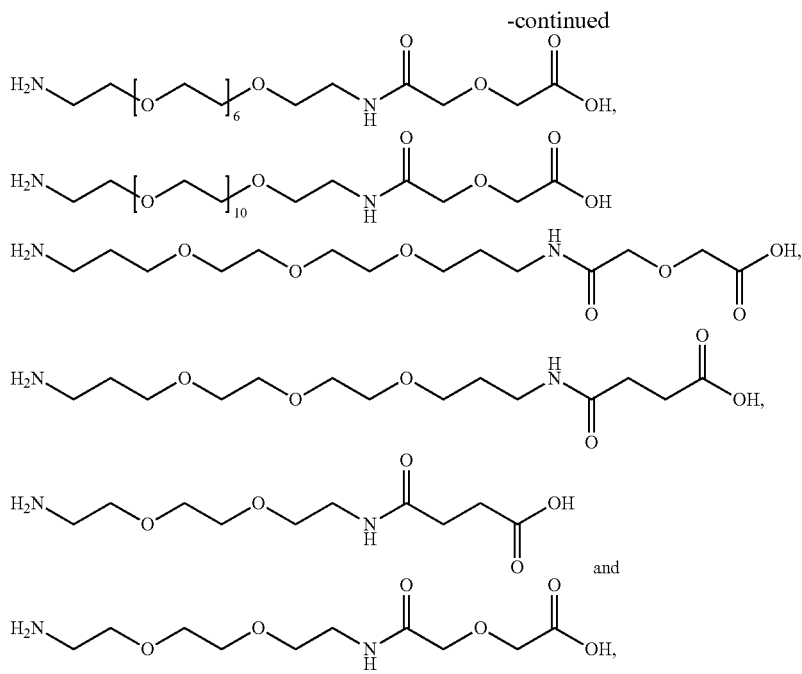

wherein r is 1, 2, 3, 5, 7, 11, 23 or 27.
67. An acylated protease stabilised insulin, according to the preceding clause, wherein r is 1, 3, 5, or 7.
68. An acylated protease stabilised insulin, according to the preceding clause, wherein r is 1.
69. An acylated protease stabilised insulin, according to the preceding clause but one, wherein r is 3.
70. An acylated protease stabilised insulin, according to the preceding clause but two, wherein r is 5.
71. An acylated protease stabilised insulin, according to the preceding clause but three, wherein r is 7.
72. An acylated protease stabilised insulin according to any one of the preceding clauses to the extent possible wherein p is 0, 1, 2, 3, 4, 5, 6, 7, 8, 9, or 10
73. An acylated protease stabilised insulin according to any one of the preceding clauses wherein p is 0, 1, 2, 3 or 4.
74. An acylated protease stabilised insulin according to any one of the preceding clauses wherein p is 0, 1 or 2.
75. An acylated protease stabilised insulin according to any one of the preceding clauses wherein p is 0 or 2.
76. An acylated protease stabilised insulin according to any one of the preceding clauses wherein p is 0.
77. An acylated protease stabilised insulin according to any one of the preceding clauses wherein p is 1.
78. An acylated protease stabilised insulin according to any one of the preceding clauses wherein p is 2.
79. A compound according to any one of the preceding product clauses, which is any one of the compounds mentioned specifically in this specification such as in the specific examples, especially any one of the examples 1 et seq. below
80. A compound according to any one of the preceding product clauses, which is any one of the specific examples of the acyl moieties mentioned specifically in this specification attached to any of the protease stabilised insulins mentioned specifically in this specification.
81. The use of a compound according to any one of the preceding product clauses for the preparation of a pharmaceutical composition for the treatment of diabetes.
82. The use of a compound according to any one of the preceding product clauses for the preparation of a pharmaceutical composition which can be administered pulmonary for the treatment of diabetes.
83. The use of a compound according to any one of the preceding product clauses for the preparation of a pharmaceutical composition which can be administered pulmonary for the treatment of diabetes and which gives a long acting effect.
84. The use of a compound according to any one of the preceding product clauses for the preparation of a powder pharmaceutical composition which can be administered pulmonary for the treatment of diabetes.
85. The use of a compound according to any one of the preceding product clauses for the preparation of a liquid pharmaceutical composition which can be administered pulmonary for the treatment of diabetes.
86. The use of a compound according to any one of the preceding product clauses for the preparation of a pharmaceutical composition which can be administered orally for the treatment of diabetes.
87. A method of treatment of diabetes, the method comprising administering to a subject in need thereof a therapeutically effective amount of a compound according to any one of the preceding product clauses.
88. A composition containing human insulin as well as an acylated protease stabilised insulin according to any one of the preceding clauses.
89. A composition containing insulin as part as well as an acylated protease stabilised insulin according to any one of the preceding clauses.
90. A composition containing insulin Lispro as well as an acylated protease stabilised insulin according to any one of the preceding clauses.
91. A composition containing insulin Glulisine as well as an acylated protease stabilised insulin according to any one of the preceding clauses.
92. A pharmaceutical composition comprising a biologically active amount of the protease stabilised insulin according to any one of the above clauses relating to insulin analogs and a pharmaceutically acceptable carrier.
93. A method for the treatment, prevention or alleviation of hyperglycemia, type 2 diabetes, impaired glucose tolerance, type 1 diabetes, obesity, syndrome X or dyslipidemia in a subject comprising administering to a subject an protease stabilised insulin according to any one of the above clauses relating to insulin analogs or a pharmaceutical composition according to any one of the above clauses.

94. Use of a therapeutically effective amount of an protease stabilised insulin according to any one of the above clauses relating to insulin analogs for the preparation of a pharmaceutical formulation for the treatment or prevention of hyperglycemia, type 2 diabetes, impaired glucose tolerance, type 1 diabetes, obesity, syndrome X or dyslipidemia.

95. A method of treatment of diabetes, the method comprising administering to a subject in need thereof a therapeutically effective amount of an acylated insulin according to any one of the preceding product clauses.

Combining one or more of the clauses described herein, optionally also with one or more of the claims below, results in further clauses and the present invention relates to all possible combinations of said clauses and claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

EXAMPLES

The following examples are offered by way of illustration, not by limitation.

The abbreviations used herein are the following: βAla is beta-alanyl, Aoc is 8-aminooctanoic acid, tBu is tert-butyl, DCM is dichloromethane, DIC is diisopropylcarbodiimide, DIPEA=DIEA is N,N-disopropylethylamine, DMF is N,N-dmethylformamide, DMSO is dimethyl sulphoxide, EtOAc is ethyl acetate, Fmoc is 9-fluorenylmethyloxycarbonyl, γGlu is gamma L-glutamyl, HCl is hydrochloric acid, HOBt is 1-hydroxybenzotriazole, NMP is N-methylpyrrolidone, MeCN is acetonitrile, OEG is [2-(2-aminoethoxy)ethoxy] ethylcarbonyl, Su is succinimidyl-1-yl=2,5-dioxo-pyrrolidin-1-yl, OSu is succinimidyl-1-yloxy=2,5-dioxo-pyrrolidin-1-yloxy, RPC is reverse phase chromatography, RT is room temperature, TFA is trifluoroacetic acid, THF is tetrahydrofuran, TNBS is 2,4,6-trinitrobenzenesulfonic acid, TRIS is tris(hydroxymethyl)aminomethane and TSTU is O—(N-succinimidyl)-1,1,3,3-tetramethyluronium tetrafluoroborate.

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The compounds of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

After acidic HPLC or desalting, the compounds are isolated by lyophilisation of the pure fractions. After neutral HPLC or anion exchange chromatography, the compounds are desalted, precipitated at isoelectrical pH, or purified by acidic HPLC.

Typical Purification Procedures:

The HPLC system is a Gilson system consisting of the following: Model 215 Liquid handler, Model 322-H2 Pump and a Model 155 UV Dector. Detection is typically at 210 nm and 280 nm. The Åkta Purifier FPLC system (Amersham Biosciences) consists of the following: Model P-900 Pump, Model UV-900 UV detector, Model pH/C-900 pH and conductivity detector, Model Frac-950 Fraction collector. UV detection is typically at 214 nm, 254 nm and 276 nm.

Acidic HPLC:
Column: Macherey-Nagel SP 250/21 Nucleusil 300-7 C4
Flow: 8 ml/min
Buffer A: 0.1% TFA in acetonitrile
Buffer B: 0.1% TFA in water.
Gradient: 0.0-5.0 min: 10% A
5.00-30.0 min: 10% A to 90% A
30.0-35.0 min: 90% A
35.0-40.0 min: 100% A
Neutral HPLC:
Column: Phenomenex, Jupiter, C4 5 µm 250×10.00 mm, 300 Å
Flow: 6 ml/min
Buffer A: 5 mM TRIS, 7.5 mM $(NH_4)_2SO_4$, pH=7.3, 20% $CH_3CN$
Buffer B: 60% CH3CN, 40% water
Gradient: 0-5 min: 10% B
5-35 min: 10-60% B
35-39 min: 60% B
39-40 min: 70% B
40-43.5 min: 70% B
Anion Exchange Chromatography:
Column: RessourceQ, 1 ml
Flow: 6 ml/min Buffer A: 0.09% NH$_4$HCO$_3$, 0.25% NH$_4$OAc, 42.5% ethanol pH 8.4
Buffer B: 0.09% NH$_4$HCO$_3$, 2.5% NH$_4$OAc, 42.5% ethanol pH 8.4
Gradient: 100% A to 100% B during 30 column volumes
Desalting:
Column: HiPrep 26/10
Flow: 10 ml/min, 6 column volumes
Buffer: 10 mM NH$_4$HCO$_3$
General Procedure for the Solid Phase Synthesis of Acylation Reagents of the General Formula (II):

$$\text{Acy-AA1}_n\text{-AA2}_m\text{-AA3}_p\text{-Act,} \qquad (II):$$

wherein Acy, AA1, AA2, AA3, n, m, and p are as defined above and Act is the leaving group of an active ester, such as N-hydroxysuccinimide (OSu), or 1-hydroxybenzotriazole, and wherein carboxylic acids within the Acy and AA2 moieties of the acyl moiety are protected as tert-butyl esters.

Compounds of the general formula (II) according to the invention can be synthesised on solid support using procedures well known to skilled persons in the art of solid phase peptide synthesis. This procedure comprises attachment of a Fmoc protected amino acid to a polystyrene 2-chlorotritylchloride resin. The attachment can, e.g., be accomplished using the free N-protected amino acid in the presence of a tertiary amine, like triethyl amine or N,N-diisopropylethylamine (see references below). The C-terminal end (which is attached to the resin) of this amino acid is at the end of the synthetic sequence being coupled to the parent insulins of the invention. After attachment of the Fmoc amino acid to the resin, the Fmoc group is deprotected using, e.g., secondary amines, like piperidine or diethyl amine, followed by coupling of another (or the same) Fmoc protected amino acid and deprotection. The synthetic sequence is terminated by coupling of mono-tert-butyl protected fatty (α,ω) diacids, like hexadecanedioic, heptadecanedioic, octadecanedioic or eicosanedioic acid mono-tert-butyl esters. Cleavage of the compounds from the resin is accomplished using diluted acid like 0.5-5% TFA/DCM (trifluoroacetic acid in dichloromethane), acetic acid (e.g., 10% in DCM, or HOAc/triflouroethanol/DCM 1:1:8), or hecafluoroisopropanol in DCM (See, e.g., "Organic Synthesis on Solid Phase", F. Z. Dörwald, Wiley-VCH, 2000. ISBN 3-527-29950-5, "Peptides: Chemistry and Biology", N. Sewald & H.-D. Jakubke, Wiley-VCH, 2002, ISBN 3-527-30405-3 or "The Combinatorial Chemistry Catalog" 1999, Novabiochem AG, and references cited therein). This ensures that tert-butyl esters present in the compounds as carboxylic acid protecting groups are not deprotected. Finally, the C-terminal carboxy group (liberated from the resin) is activated, e.g., as the N-hydroxysuccinimide ester (OSu) and used either directly or after purification as coupling reagent in attachment to parent insulins of the invention. This procedure is illustrated in example 9.

Alternatively, the acylation reagents of the general formula (II) above can be prepared by solution phase synthesis as described below.

Mono-tert-butyl protected fatty diacids, such as hexadecanedioic, heptadecanedioic, octadecanedioic or eicosanedioic acid mono-tert-butyl esters are activated, e.g., as OSu-esters as described below or as any other activated ester known to those skilled in the art, such as HOBt- or HOAt- esters. This active ester is coupled with one of the amino acids AA1, mono-tert-butyl protected AA2, or AA3 in a suitable solvent such as THF, DMF, NMP (or a solvent mixture) in the presence of a suitable base, such as DIPEA or triethylamine. The intermediate is isolated, e.g., by extractive procedures or by chromatographic procedures. The resulting intermediate is again subjected to activation (as described above) and to coupling with one of the amino acids AA1, mono-tert-butyl protected AA2, or AA3 as described above. This procedure is repeated until the desired protected intermediate Acy-AA1$_n$-AA2$_m$-AA3$_p$-OH is obtained. This is in turn activated to afford the acylation reagents of the general formula (II) Acy-AA1$_n$-AA2$_m$-AA3$_p$-Act. This procedure is illustrated in example 21.

The acylation reagents prepared by any of the above methods can be (tert-butyl) de-protected after activation as OSu esters. This can be done by TFA treatment of the OSu-activated tert-butyl protected acylation reagent. After acylation of any protease stabilised insulin, the resulting unprotected acylated protease stabilised insulin of the invention is obtained. This is illustrated eg. in example 16 below.

If the reagents prepared by any of the above methods are not (tert-butyl) de-protected after activation as OSu esters, acylation of any protease stabilised insulin affords the corresponding tert-butyl protected acylated protease stabilised insulin of the invention. In order to obtain the unprotected acylated protease stabilised insulin of the invention, the protected insulin is to be de-protected. This can be done by TFA treatment to afford the unprotected acylated protease stabilised insulin of the invention. This is illustrated, e.g., in examples 1 and 2 below.

If acylation of a lysine residue (in the epsilon position) of an insulin is desired, acylation is performed at alkaline pH (eg. at pH 10, 10.5, or 11). This is, e.g., illustrated in examples 1 and 2 below.

If acylation of the A-chain N-terminal position (A1) of an insulin is desired, acylation is performed at neutral pH (eg. at pH 7, 7.5, 8, or 8.5). This is, e.g., illustrated in examples 38, and 44 below.

General Procedure (A) for Preparation of Acylated, Protease Stabilised Insulins of this Invention The general procedure (A) is illustrated in the first example.

Example 1, General Procedure (A)

A14E, B25H, B29K(N$^\varepsilon$-Hexadecandioyl), desB30 Human Insulin

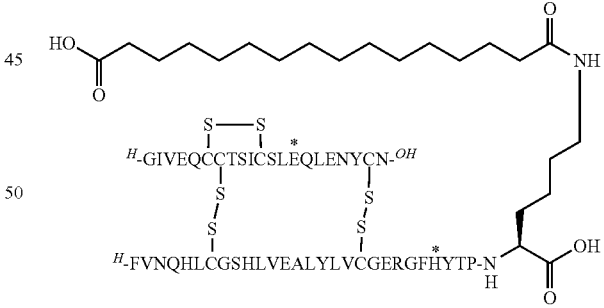

A14E, B25H, desB30 human insulin (500 mg) was dissolved in 100 mM aqueous Na$_2$CO$_3$ (5 mL), and pH adjusted to 10.5 with 1 N NaOH. Hexadecanedioic acid tert-butyl ester N-hydroxysuccinimide ester was dissolved in acetonitrile (10 W/V %) and added to the insulin solution and heated gently under warm tap, to avoid precipitation and left at room temperature for 30 minutes. The mixture was lyophilised. The solid was dissolved in ice-cold 95% trifluoroacetic acid (containing 5% water) and kept on ice for 30 minutes. The mixture was concentrated in vacuo and re-evaporated from dichloromethane. The residue was dissolved in water, and pH was adjusted to neutral (6-7) and the mixture was lyophilised.

The resulting insulin was purified by ion exchange chromatography on a Source 15Q 21 ml column, several runs, eluting with a gradient of 15 to 300 mM ammonium acetate in 15 mM Tris, 50 v/v % ethanol, pH 7.5 (acetic acid). Final desalting of pure fractions were performed on a RPC 3 mL column eluting isocraticlly with 0.1 v/v % TFA, 50 v/v % ethanol. The resulting pure insulin was lyophilised.

LC-MS (electrospray): m/z=1483.2 (M+4)/4. Calcd: 1483.5

Example 2, General Procedure (A)

A14E, B25H, B29K(N^εOctadecandioyl-γGlu), desB30 Human Insulin

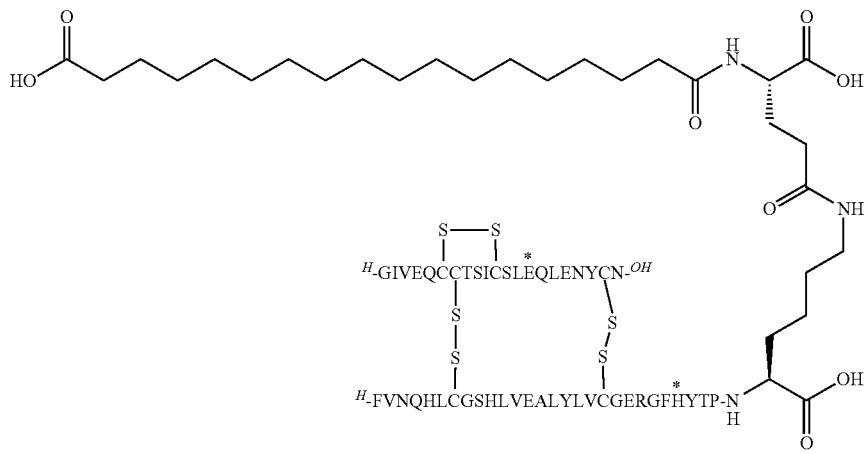

A14E, B25H, desB30 human insulin (2 g) was dissolved in 100 mM aqueous Na$_2$CO$_3$ (10 mL), and DMSO (4 mL) was added. pH was adjusted to 10.5 with 1 N NaOH. tert-Butyl octadecanedioyl-L-Glu(OSu)-OtBu (prepared as described in WO 2005/012347). More 100 mM aqueous Na$_2$CO$_3$ (20 mL) was added followed by THF (20 mL). After 1.5 h was a few drops methylamine added and the mixture was subsequently acidified with acetic acid. The mixture was purified by preparative HPLC and lyophilised to afford the title insulin as di-tert-butyl ester. This was dissolved in dichloromethane and trifluoroacetic acid 1:1 (50 mL). The mixture was left for 2 hours and concentrated in vacuo. After addition of a little water and acetonitrile, the mixture was purified by preparative HPLC. Pure fractions were lyophilised. This afforded 313 mg of the title insulin.

MALDI-TOF MS: m/z=6089 (M+1). Calcd: 6089.

Example 3, General Procedure (A)

A14E, B25H, B29K(N^εEicosanedioyl-γGlu), desB30 Human Insulin

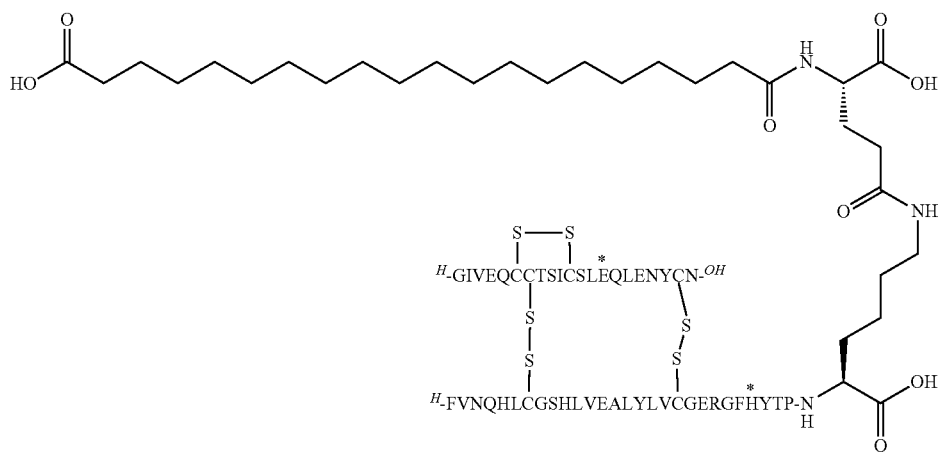

This insulin was prepared similarly as described above starting form eicosanedioic acid via eicosanedioic acid mono-tert-butyl ester and tert-butyl icosanedioyl-L-Glu (OSu)-OtBu.

MALDI-TOF MS: m/z=6120 (M+1). Calcd: 6117.

Example 4, General Procedure (A)

A14E, B25H, B29K($N^\varepsilon$3-Carboxy-5-octadecane-dioylaminobenzoyl), desB30 Human Insulin

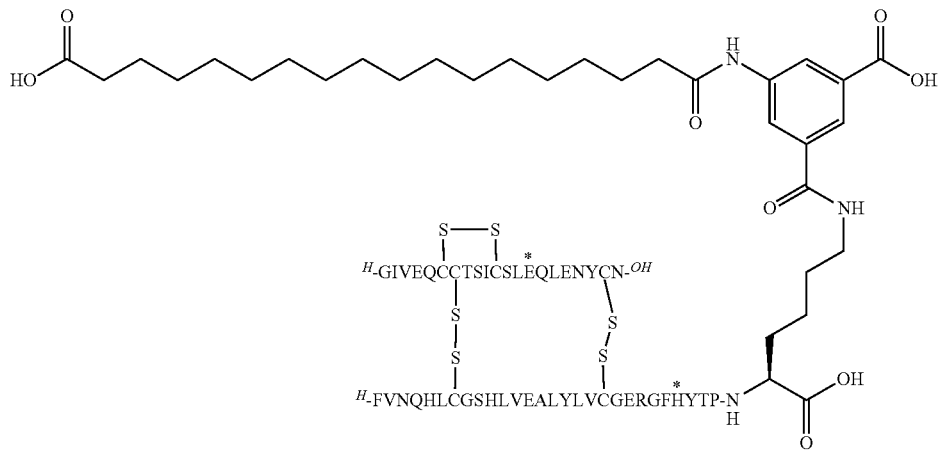

This insulin was prepared similarly as described above starting from 5-(17-tert-butoxycarbonylheptadecanoy-lamino)isophthalic acid mono-(2,5-dioxopyrrolidin-1-yl) ester (prepared as described in WO 2006/082204).

LC-MS: 1531 (M+4), Mw 6124 (deconvoluted). Calc.: 1531 (M+4), 6122.

Example 5, General Procedure (A)

A14E, B25H, B29K($N^\varepsilon$—N-octadecandioyl-N-(2-carboxyethyl)glycyl), desB30 Human Insulin

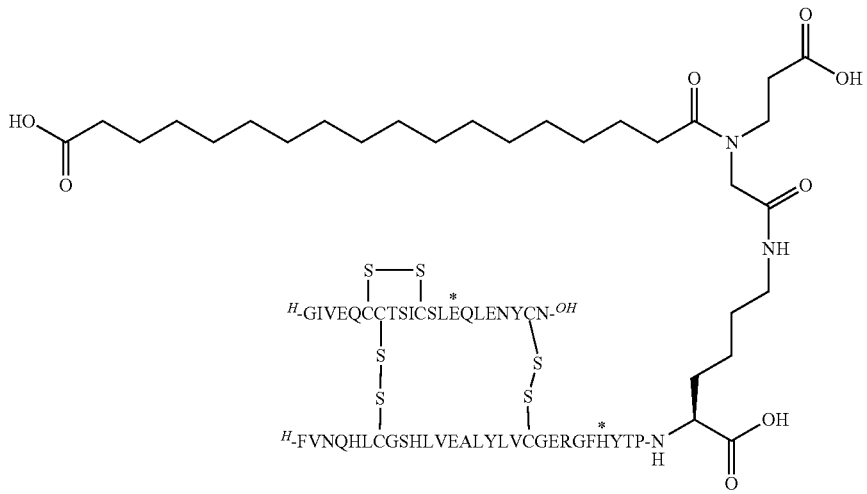

This insulin was prepared similarly as described above starting from tert-butyl octadecandioyl-N-(2-(tert-butoxycarbonyl)ethyl)-Gly-OSu (prepared as described in WO 2005/012347).

LC-MS (electrospray): m/z: 1522.52 (M+4). Calcd.: 1523.

Example 6, General Procedure (A)

A14E, B25H, B29K(N$^\varepsilon$(N-Octadecandioyl-N-carboxymethyl)-beta-alanyl), desB30 Human Insulin

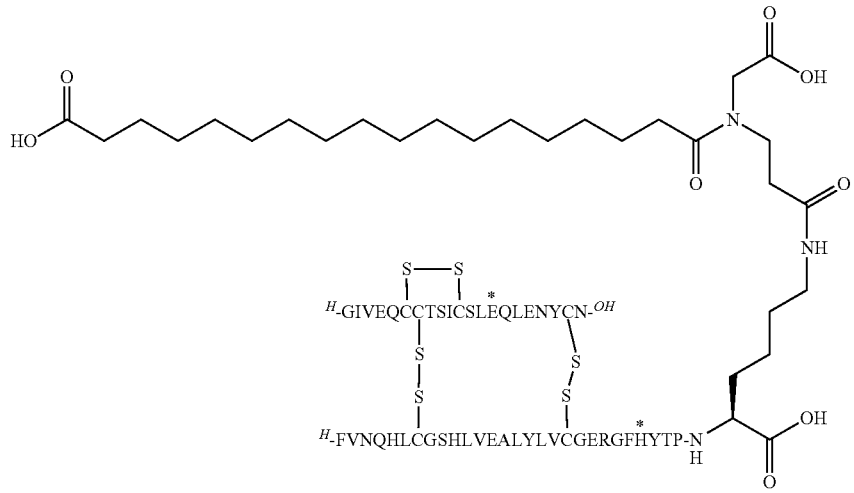

This insulin was prepared similarly as described above starting from tert-butyl octadecandioyl-N-(tert-butoxycarbonylmethyl)-βAla-OSu (prepared as described in WO 2005/012347).

MALDI-TOF MS: m/z=6088 (M+1). Calcd: 6089.

Example 7, General Procedure (A)

A14E, B25H, B29K(N$^\varepsilon$4-([4-({19-Carboxynonadecanoylamino}methyl)trans-cyclohexanecarbonyl]-γGlu), desB30 Human Insulin

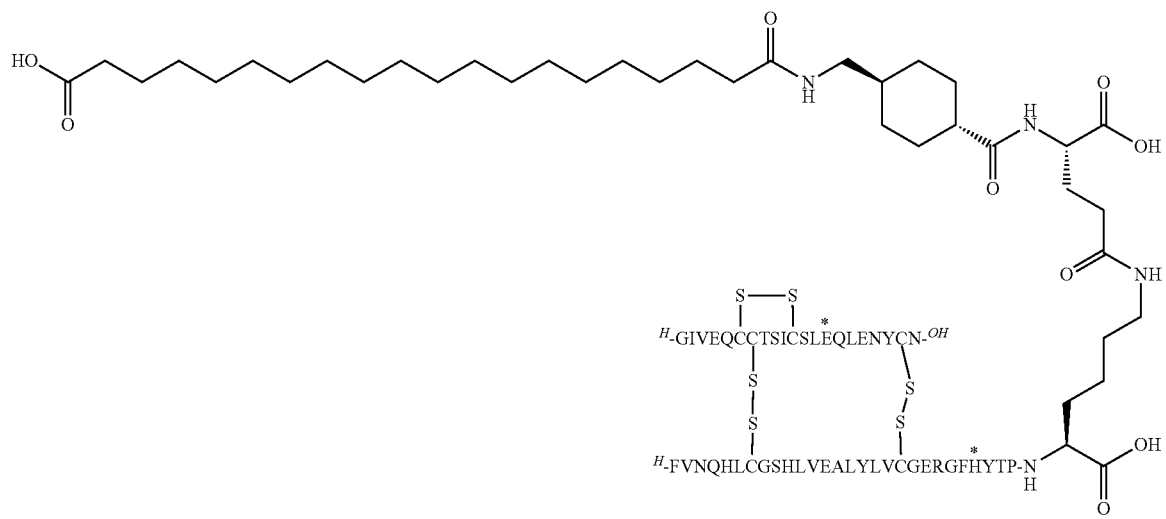

This insulin was prepared similarly as described above starting from 2-({4-[(19-tert-butoxycarbonylnonadecanoylamino)methyl]cyclohexanecarbonyl}amino)pentanedioic acid 1-tert-butyl ester 5-(2,5-dioxopyrrolidin-1-yl) ester LC-MS (electrospray): m/z: 6260. Calcd.: 6255.

Preparation of 2-({4-[(19-tert-butoxycarbonylnonadecanoylamino)methyl]cyclohexanecarbonyl}amino)-pentanedioic acid 1-tert-butyl ester 5-(2,5-dioxopyrrolidin-1-yl) ester 1. OSu Activation of Tert-Butyl Eicosanedioic Acid tert-Butyl icosanedioic acid (5.0 g) was dissolved in THF (50 ml) and DMF (30 ml). TSTU (4.53 g) and DIPEA (2.65 ml) were added. The mixture was stirred for 3 days and then concentrated in vacuo. The solid residue was recrystallized from acetonitrile to give icosanedioic acid tert-butyl ester N-hydroxysuccinimide ester as a white crystalline compound (5.52 g, 89%).

LC-MS (electrospray): m/z: 440 [M−56 (=tert-Bu)]

2. Coupling of Tranexamic Acid

To a solution of icosanedioic acid tert-butyl ester N-hydroxysuccinimide ester (5.52 g) in THF (100 ml) was added tranexamic acid (1.75 g). A precipitate was obtained. Attempts to get a solution by adding DMF (75 ml), water (25 ml) and DMSO (50 ml) and a few drops of DI PEA were not successful. The suspension was stirred over night. The mixture was concentrated in vacuo. To the solid residue was added THF and the precipitate was filtered off. The filtrate was concentrated and the solid residue was recrystallized in acetonitrile to give 4-[(19-tert-butoxycarbonylnonadecanoylamino)methyl]cyclohexanecarboxylic acid as a white crystalline compound (5.56 g, 93%)

LC-MS (electrospray): m/z: 538 (M+1).

3. OSu activation of 4-[(19-tert-butoxycarbonylnonadecanoylamino)methyl]cyclohexanecarboxylic acid To a solution of 4-[(19-tert-butoxycarbonylnonadecanoylamino)methyl]cyclohexanecarboxylic acid (5.56 g) in THF (100 ml) was added a solution of TSTU (3.42 g) in acetonitrile (25 ml). The mixture was concentrated in vacuo after stirring over night. The solid residue was recrystallized from acetonitrile to give 4-[(19-tert-butoxycarbonylnonadecanoylamino)methyl]cyclohexanecarboxylic acid 2,5-dioxo-pyrrolidin-1-yl ester (5.76 g, 88%).

LC-MS (electrospray): m/z: 635 (M+1).

4. Coupling of H-Glu-OtBu and OSu Activation

To a solution of 4-[(19-tert-butoxycarbonylnonadecanoylamino)methyl]cyclohexanecarboxylic acid 2,5-dioxo-pyrrolidin-1-yl ester in THF (150 ml) was added a solution of H-Glu-OtBu (1.84 g) in water (25 ml) and a few drops of DIPEA. The mixture was stirred over night and then concentrated in vacuo. The residue was dissolved in hot (60° C.) THF and filtered. To the cold filtrate was added THF up to 150 ml and TSTU (2.98 g) dissolved in acetonitrile (25 ml) was added. The mixture was concentrated after stirring for 20 min. The residue was recrystallized from acetonitrile to give an white solid, 2-({4-[(19-tert-butoxycarbonylnonadecanoylamino)methyl]cyclohexanecarbonyl}amino)pentanedioic acid 1-tert-butyl ester 5-(2,5-dioxopyrrolidin-1-yl) ester (6.8 g, 92%).

LC-MS (electrospray): m/z: 820 (M+1).

Example 8, General Procedure (A)

A14E, B25H, B29K(N$^\varepsilon$Heptadecanedioyl-γGlu), desB30 Human Insulin

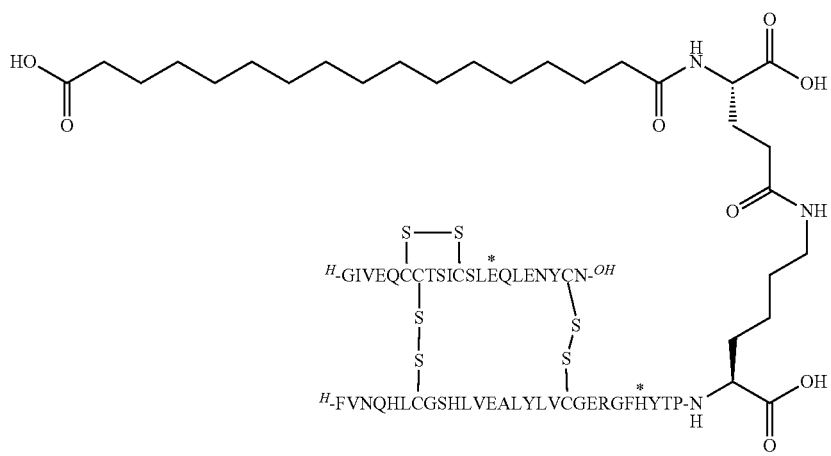

This insulin was prepared similarly as described above starting form heptadecanedioic acid via heptadecanedioic acid mono-tert-butyl ester and tert-butyl heptdecanedioyl-L-Glu(OSu)-OtBu (prepared as described in WO 2006/082204).

LC-MS (electrospray): m/z: 1519 (M+4). Calcd.: 1519.

Example 9, General Procedure (A)

A14E, B25H, B29K(N$^\varepsilon$Octadecanedioyl-γGlu-OEG-OEG), desB30 Human Insulin

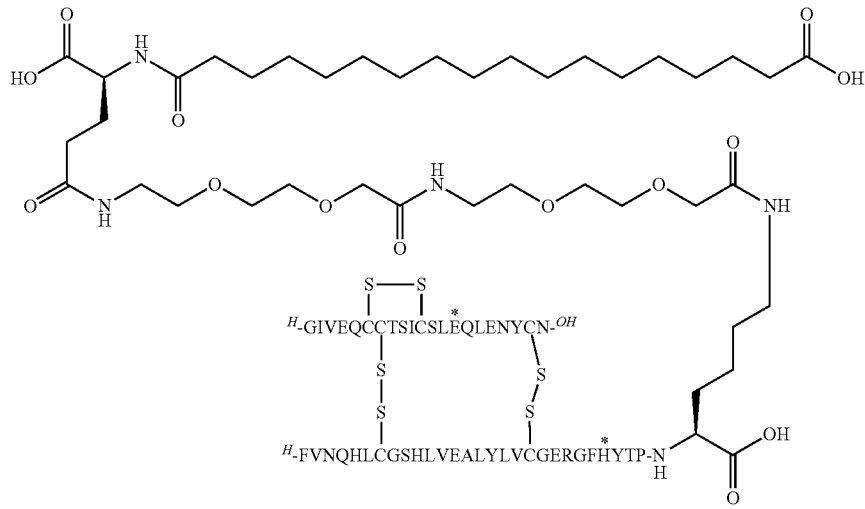

Figure 2A:
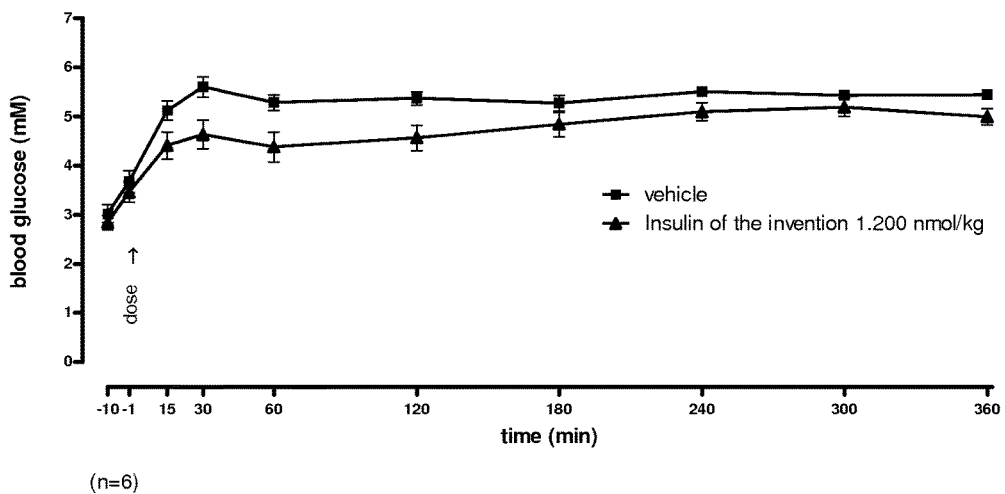
FIGS. 2a and 2b show the oral effect of the compound of Example 9 on overnight fasted male Wistar rats.
Figure 2B:
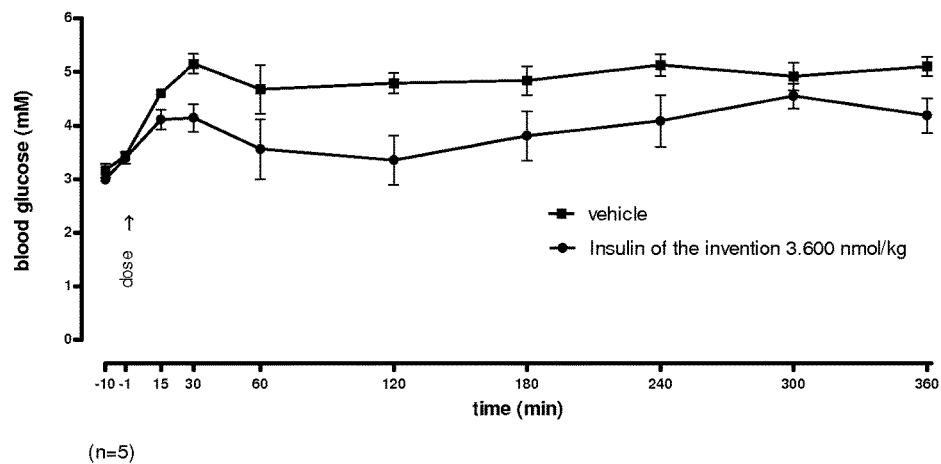

The oral effect of this compound on overnight fasted male Wistar rats is given in FIG. 2a and FIG. 2b below.

This insulin was prepared similarly as described above starting form 17-((S)-1-tert-butoxycarbonyl-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl)heptadecanoic acid tert-butyl ester (alternative name: tert-Butyl octadecandioyl-Glu (OEG-OEG-OSu)-OtBU)

LC-MS (electrospray): m/z: 1596 (M+4). Calcd.: 1596.

The building block for preparation of this insulin was prepared as described in the following:

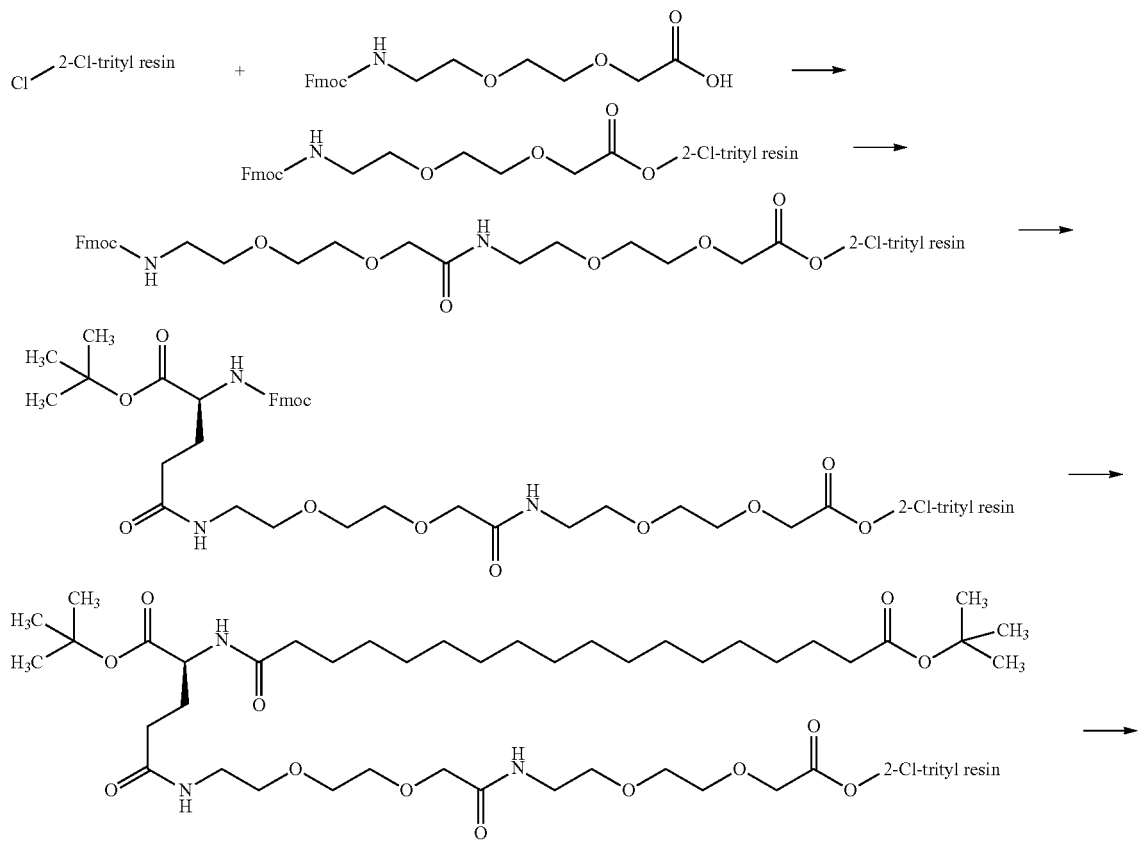

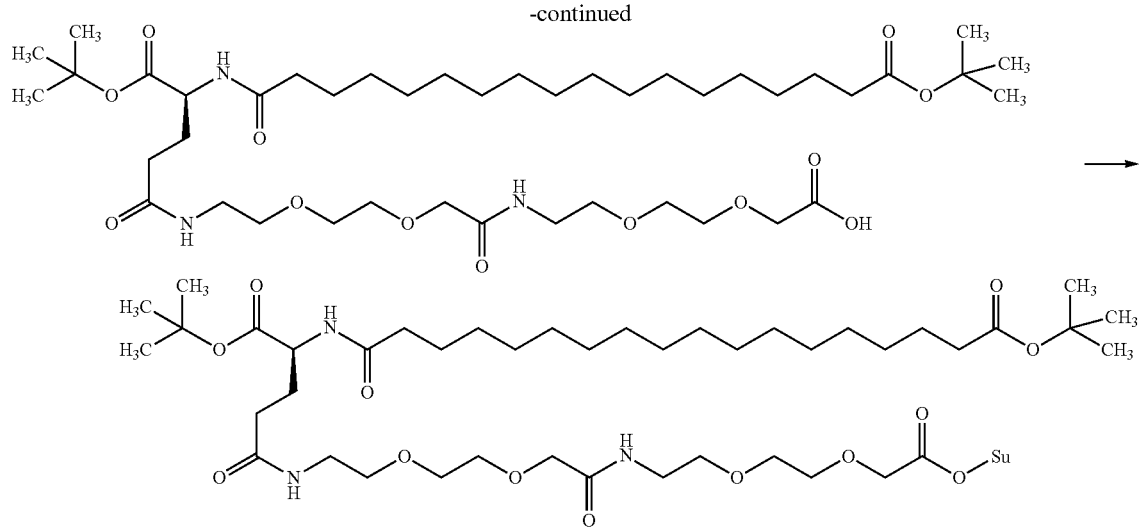

-continued

Starting resin: 2-Chlorotrityl resin, 1.60 mmol/g
1.0 g of the resin was swelled for 30 min in DCM (10 ml).

1. Acylation with Fmoc-8-amino-3,6-dioxaoctanoic acid 0.39 g (0.63 eq, 1.0 mmol) of Fmoc-8-amino-3,6-dioxaoctanoic acid (Fmoc-OEG-OH) was dissolved in DCM (15 ml) and was added to the resin. N,N-Diisopropylethylamine (DIEA) (0.44 ml, 2.5 mmol) was added dropwise. The reaction mixture was vortexed for 30 min. and then methanol (2 ml) was added and the mixture was vortexed for additional 15 min. The resin was filtered and washed with NMP (2×8 ml) and DCM (8×8 ml).

20% piperidine/NMP (8 ml) was added, standing 10 min. repeated once. Filtered and washed with NMP (2×8 ml), DCM (3×8 ml), and NMP (5×8 ml). A positive TNBS test gave red-coloured resins.

2. Acylation with Fmoc-8-amino-3,6-dioxaoctanoic acid 0.78 g (2 eq, 2.0 mmol) of Fmoc-8-amino-3,6-dioxaoctanoic acid was dissolved in NMP/DCM 1:1 (10 ml). 0.28 g (2.2 eq, 2.4 mmol) of HOSu was added followed by addition of 0.37 ml (2.2 eq, 2.4 mmol) of DIC. The reaction mixture was allowed to stand for 1 hour and was then added to the resin and finally 0.407 ml (2.2 eq) of DI EA was added. The mixture was vortexed for 16 hours, filtered and washed with NMP (2×8 ml), DCM (3×8 ml), and NMP (5×8 ml). A positive TNBS test gave colourless resins.

20% piperidine/NMP (10 ml) was added, standing 10 min. repeated once. Filtered and washed with NMP (2×8 ml), DCM (3×8 ml), and NMP (5×8 ml). A positive TNBS test gave red-coloured resins.

Acylation with Fmoc-Glu-OtBu:

0.86 g (2 eq, 2.0 mmol) of Fmoc-Glu-OtBu was dissolved in NMP/DCM 1:1 (10 ml). 0.32 g (2.2 eq, 2.4 mmol) of HOBT was added followed by addition of 0.37 ml (2.2 eq, 2.4 mmol) of DIC. The reaction mixture was allowed to stand for 20 min and was then transferred to the resin and finally 0.407 ml (2.2 eq) of DIEA was added. The mixture was vortexed for 16 hours, filtered and washed with NMP (2×8 ml), DCM (3×8 ml), and NMP (5×8 ml). A positive TNBS test gave colourless resins.

20% piperidine/NMP (10 ml) was added, standing 10 min. repeated once. Filtered and washed with NMP (2×8 ml), DCM (3×8 ml), and NMP (5×8 ml). A positive TNBS test gave red-coloured resins.

Acylation with Octadecanedioic Acid Mono Tert-Butyl Ester:

0.75 g (2 eq, 2.0 mmol) Octadecanedioic acid mono tert-butyl ester was dissolved NMP/DCM 1:1 (10 ml). 0.32 g (2.2 eq, 2.4 mmol) HOBT was added followed by addition of 0.37 ml (2.2 eq, 2.4 mmol) of DIC. The reaction mixture was allowed to stand for 20 min and was then transferred to the resin and finally 0.41 ml (2.2 eq) of DIEA was added. The mixture was vortexed for 16 hours, filtered and washed with NMP (2×8 ml), DCM (3×8 ml), and NMP (5×8 ml).

Cleavage with TFA:

8 ml of 5% TFA/DCM was added to the resin and the reaction mixture was vortexed for 2 hours, filtered and the filtrate was collected. More 5% TFA/DCM (8 ml) was added to the resin, and the mixture was vortexed for 10 min, filtered and the resin was washed with DCM (2×10 ml). The combined filtrates and washings were pH adjusted to basic using about 800 ul of DIEA. The mixture was evaporated in vacuo affording an oil (3.5 g). Diethylether (30 ml) was added and the not dissolved oil was separated by decantation and evaporated in vacuo. This afforded 1.1 g of 17-{(S)-1-tert-butoxycarbonyl-3-[2-(2-{[2-(2-carboxymethoxy-ethoxy)ethylcarbamoyl]methoxy}ethoxy)ethylcarbamoyl] propylcarbamoyl}heptadecanoic acid tert-butyl ester (alternative name: tert-butyl octadecandioyl-Glu(OEG-OEG-OH)-OTBU) as an oil.

LC-MS (Sciex100 API): m/z=846.6 (M+1)+.

OSu-Activation:

The above tert-butyl octadecandioyl-Glu(OEG-OEG-OH)-OtBU (0.63 g) was dissolved in THF (35 ml). DIEA (0.255 ml, 2 eq.) was added followed by TSTU (0.45 g, 2 eq.), and the mixture was stirred at room temperature for 16 hours. The mixture was partitioned between ethyl acetate (250 ml) and aqueous NaHSO4 (3×100 ml). The organic phase was dried (MgSO4) and concentrated in vacuo to afford 0.65 g of 17-((S)-1-tert-butoxycarbonyl-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl)heptadecanoic acid tert-butyl ester (alternative name: tert-butyl octadecandioyl-Glu(OEG-OEG-OSu)-OtBu) as an oil.

LC-MS: m/z=943.4 (M+1).

Example 10, General Procedure (A)

A14E, B25H, B29K(N$^\varepsilon$Myristyl), desB30 Human Insulin

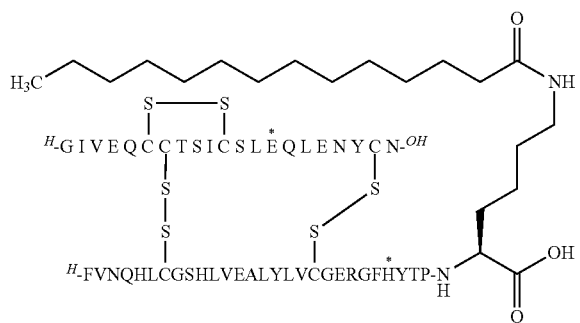

This insulin was prepared similarly as described above starting form 1-tetradecanoyl-pyrrolidine-2,5-dione.

MALDI-TOF MS: m/z=5873.6. Calcd: 5872.9.

Example 11, General Procedure (A)

A14E, B25H, B29K(N$^\varepsilon$Eicosanedioyl-γGlu-γGlu), desB30 Human Insulin This insulin was prepared similarly as described above starting from (S)-2-[4-tert-butoxycarbonyl-4-(19-tert-butoxycarbonylnonadecanoylamino)butyrylamino]pentanedioic acid 5-tert-butyl ester 1-(2,5-dioxo-pyrrolidin-1-yl) ester.

MALDI-TOF MS: m/z=6242.5. Calcd: 6245.2.

Preparation of (S)-2-[4-tert-butoxycarbonyl-4-(19-tert-butoxycarbonylnonadecanoylamino)butyrylamino]pentanedioic acid 5-tert-butyl ester 1-(2,5-dioxopyrrolidin-1-yl) ester 1. (S)-2-[4-tert-Butoxycarbonyl-4-(19-tert-butoxycarbonylnonadecanoylamino)butyrylamino]-pentanedioic acid 1-tert-butyl ester To a solution of (S)-2-(19-tert-butoxycarbonylnonadecanoylamino)pentanedioic acid 1-tert-butyl ester 5-(2,5-dioxopyrrolidin-1-yl) ester (prepared similarly as described in WO 2005/012347) (4.1 g) in THF (100 ml) was added a solution of H-Glu-OtBu (1.47 g) in water (20 ml). pH was adjusted to 8 with DIPEA. The mixture was concentrated after stirring for 1.5 h. The residue was recrystallized from DCM to give the title compound as a white solid (2.81 g, 61%).

LC-MS: m/z=769 (M+1).

(S)-2-[4-tert-Butoxycarbonyl-4-(19-tert-butoxycarbonylnonadecanoylamino)butyrylamino]pentanedioic acid 5-tert-butyl ester 1-(2,5-dioxopyrrolidin-1-yl) ester To a solution of (S)-2-[4-tert-butoxycarbonyl-4-(19-tert-butoxycarbonylnonadecanoylamino)butyrylamino]pentanedioic acid 1-tert-butyl ester (2.81 g) in acetonitrile (80 ml) was added a solution of TSTU (1.32 g) in acetonitrile (20 ml). pH was adjusted to 8 with DIPEA. After stirring for 1.5 h the mixture was concentrated. The residue was recrystallized from acetonitrile to give the title compound (1.7 g, 54%).

LC-MS: m/z=866.4 (M+1).

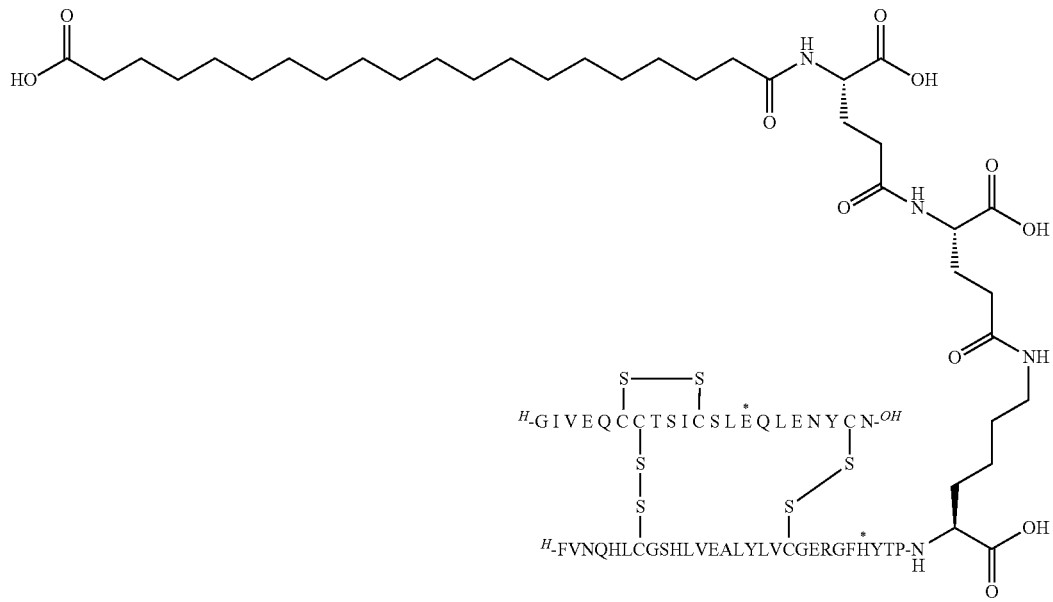

Example 12, General Procedure (A)

A14E, B25H, B29K(Nᵉ4-([4-({19-Carboxynonadecanoylamino}methyl)trans-cyclo-hexane-carbonyl-]-γGlu-γGlu), desB30 Human Insulin

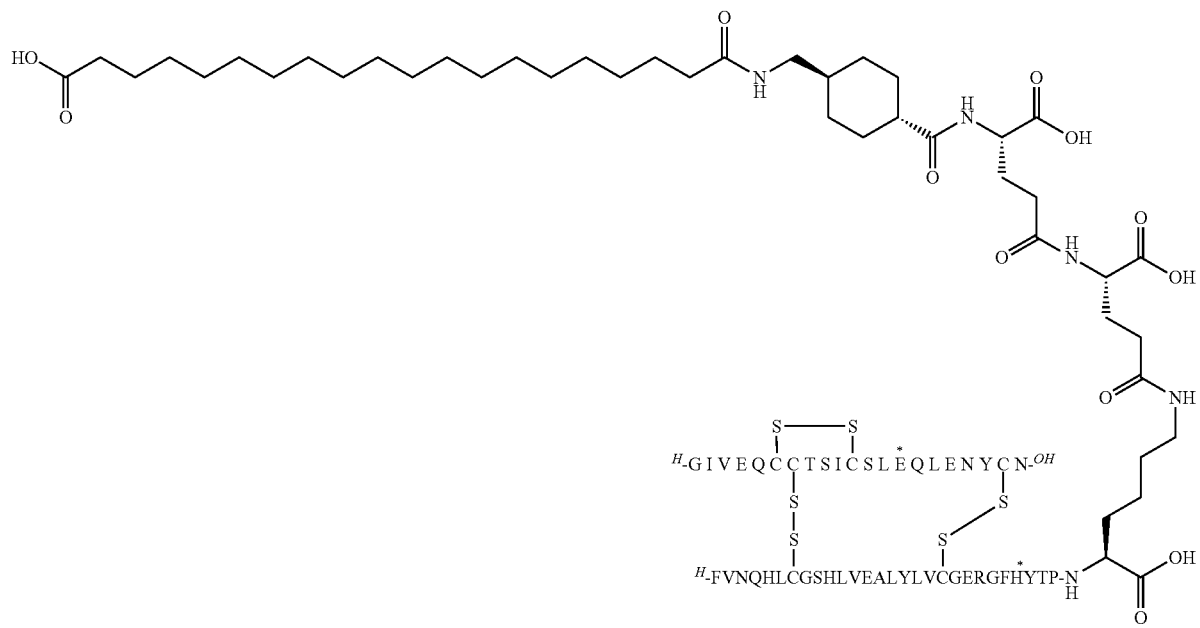

This insulin was prepared similarly as described above starting from 2-[4-tert-butoxycarbonyl-4-({4-[(19-tert-butoxycarbonylnonadecanoylamino)methyl]cyclohexanecarbonyl}amino)butyrylamino]-pentanedioic acid 1-tert-butyl ester 5-(2,5-dioxopyrrolidin-1-yl) ester LC-MS (electrospray): m/z: 6386 (M+1). Calcd.: 6384.

Preparation of 2-[4-tert-butoxycarbonyl-4-({4-[(19-tert-butoxycarbonylnonadecanoylamino)methyl]-cyclohexanecarbonyl}amino)butyrylamino]pentanedioic acid 1-tert-butyl ester 5-(2,5-dioxopyrrolidin-1-yl) ester

1. 2-[4-tert-Butoxycarbonyl-4-({4-[(19-tert-butoxycarbonylnonadecanoylamino)methyl]cyclohexanecarbonyl}amino)butyrylamino]pentanedioic acid 1-tert-butyl ester To a solution of 2-({4-[(19-tert-butoxycarbonylnonadecanoylamino)methyl]cyclohexanecarbonyl}-amino)pentanedioic acid 1-tert-butyl ester 5-(2,5-dioxopyrrolidin-1-yl) ester (5.0 g) in THF (100 ml) was added a solution of H-Glu-OtBu (1.36 g) in water (25 ml). After stirring over night the mixture was concentrated in vacuo. The residue was precipitated from water and filtered off and dried in vacuo to give the title compound (4.63 g, 84%).

LC-MS: m/z=740 (M−3×56, loss of 3×t-Bu).

2-[4-tert-Butoxycarbonyl-4-({4-[(19-tert-butoxycarbonylnonadecanoylamino)methyl]cyclohexanecarbonyl}amino)butyrylamino]pentanedioic acid 1-tert-butyl ester 5-(2,5-dioxopyrrolidin-1-yl) ester To a solution of 2-[4-tert-butoxycarbonyl-4-({4-[(19-tert-butoxycarbonylnonadecanoylamino)methyl]-cyclohexanecarbonyl}amino)butyrylamino]pentanedioic acid 1-tert-butyl ester (4.6 g) in THF (150 ml) was added TSTU (1.68 g). DIPEA (0.97 ml) was added. After stirring over night the mixture was concentrated in vacuo. The residue was crystallized from acetonitrile to afford the title compound as a solid id (4.4 g, 87%)

LC-MS: m/z=837 (M−3×56, loss of 3×t-Bu).

Figure 7:
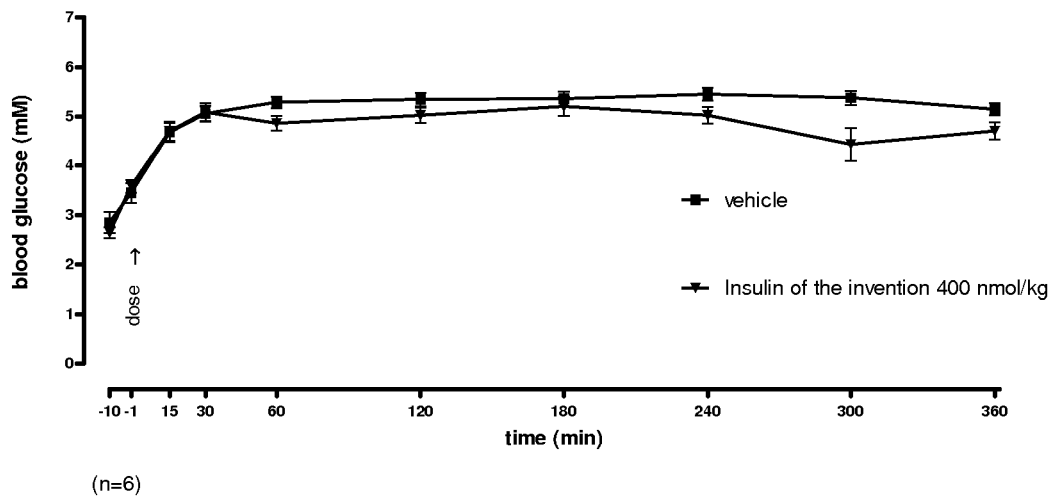
FIG. 7 shows the oral effect of the compound of Example 13 on overnight fasted male Wistar rats.

Example 13, General Procedure (A)
A14E, B25H, B29K(NᵉOctadecanedioyl-γGlu-γGlu), desB30 Human Insulin
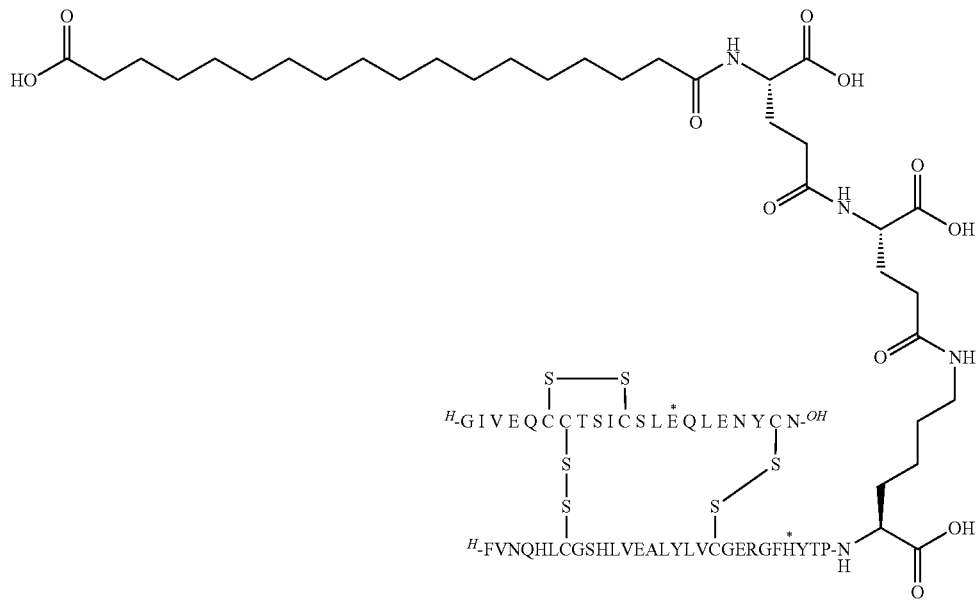
The oral effect of this compound on overnight fasted male Wistar rats is given in FIG. 7 below.
LC-MS: m/z=1555 (M+4)/4.
Example 14, General Procedure (A)
A14E, B28D, B29K(Nᵉoctadecandioyl-γGlu), desB30 Human Insulin
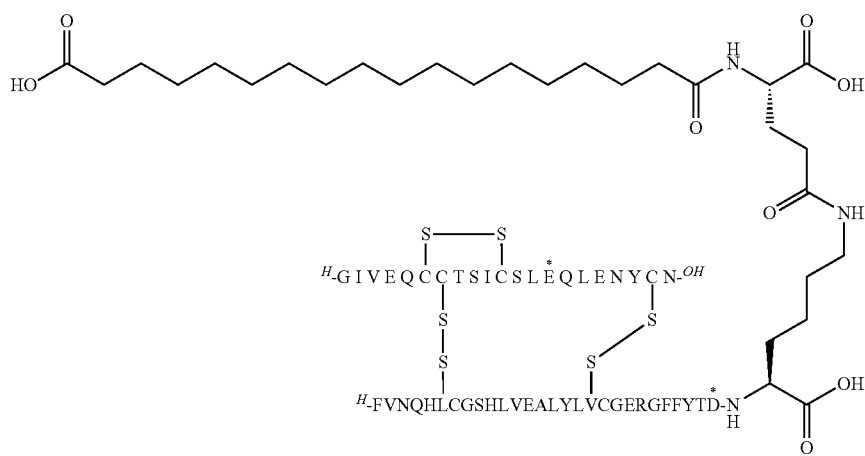
MALDI-TOF MS: m/z = 6118

Example 15, General Procedure (A)

A14E, B25H, B29K(N^ε octadecandioyl-γGlu-PEG7), desB30 Human Insulin

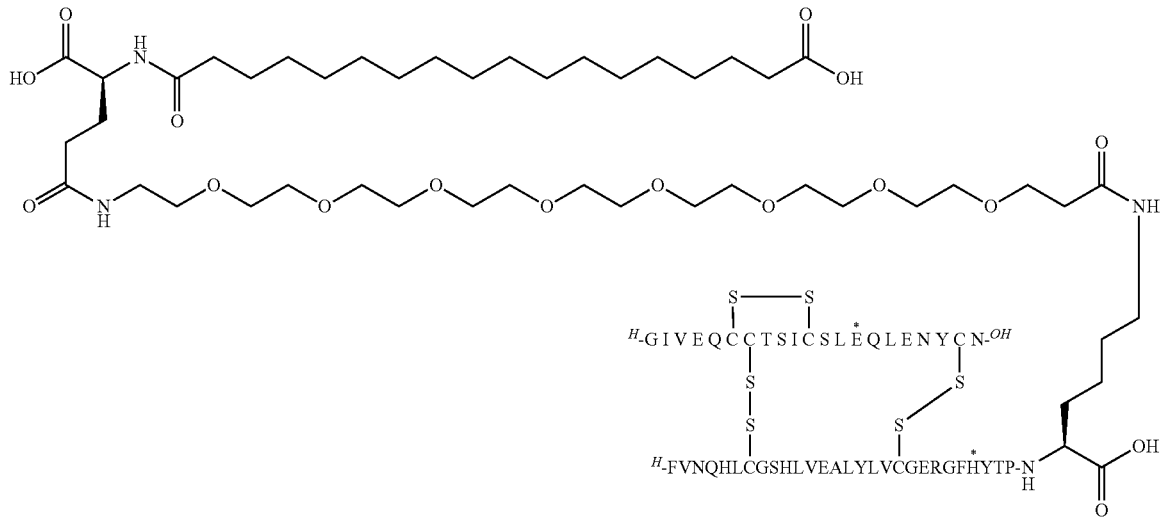

MALDI-TOF MS: m/z = 6510

Example 16, General Procedure (A)

A14E, B25H, B29K(N^ε eicosanedioyl-γGlu-OEG-OEG), desB30 Human Insulin

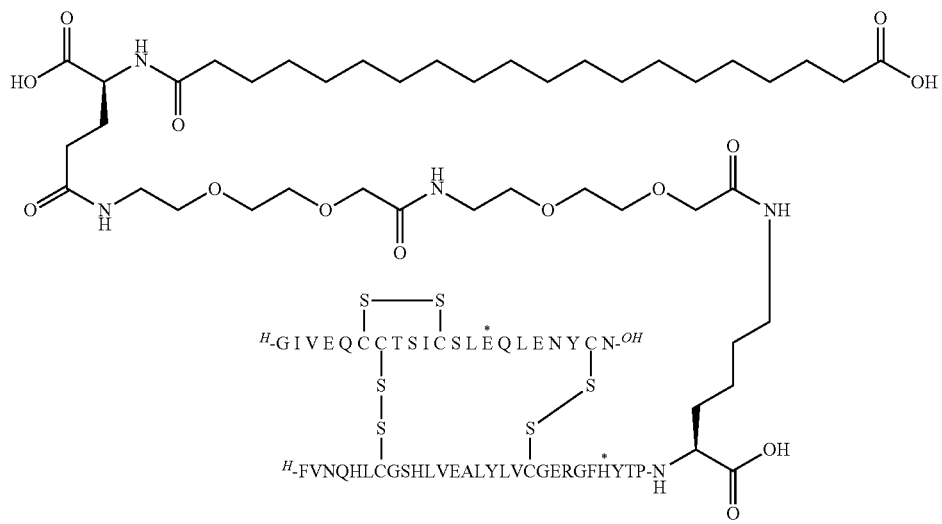

Figure 3:
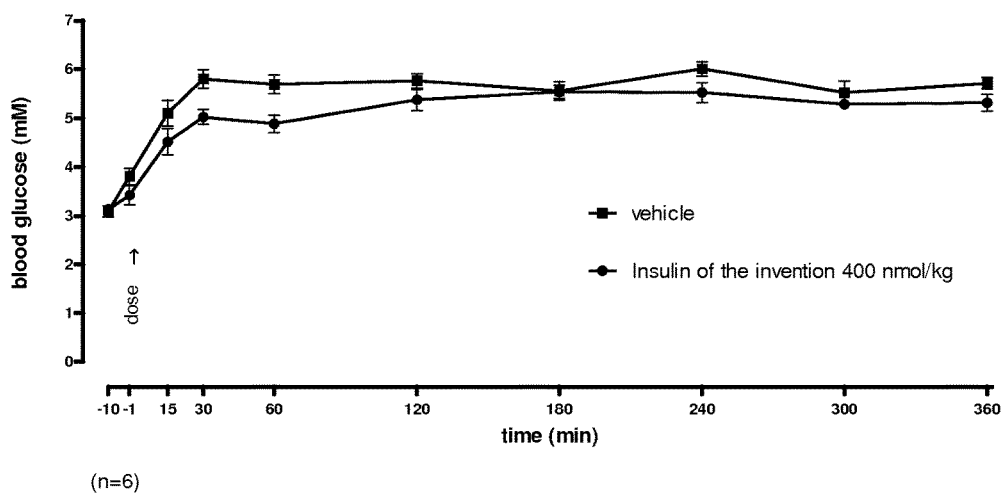
FIG. 3 shows the oral effect of the compound of Example 16 on overnight fasted male Wistar rats.

The oral effect of this compound on overnight fasted male Wistar rats is given in FIG. 3 below.

MALDI-TOF MS: m/z=6407

The intermediate acylation reagent for this example was prepared as described in the following:

Step 1: 19-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-nonadecanoic acid tert-butyl ester

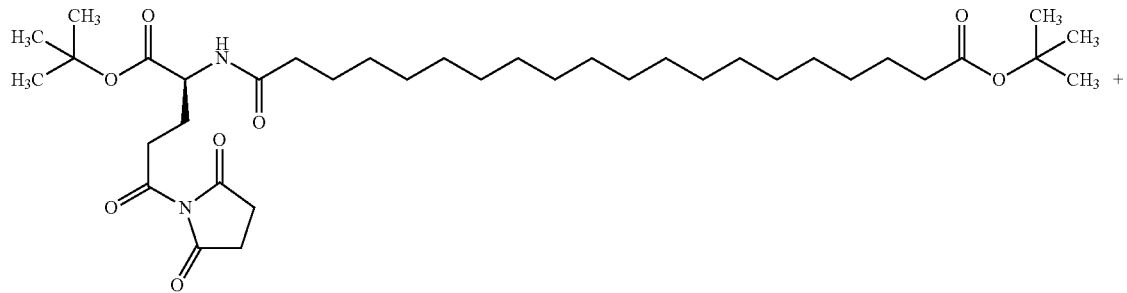

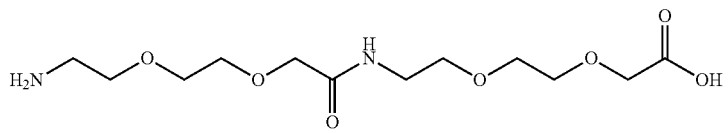

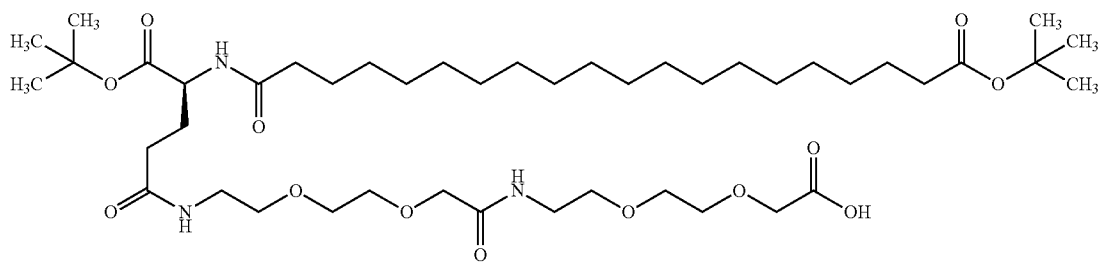

To a solution of 2-(19-tert-Butoxycarbonylnonadecanoylamino)pentanedioic acid 1-tert-butyl ester 5-(2,5-dioxopyrrolidin-1-yl) ester (2.50 g, (prepared similarly as described in WO 2005/012347) and [2-(2-{2-[2-(2-Aminoethoxy)ethoxy]acetylamino}ethoxy)ethoxy]acetic acid (1.47 g, alternative name: 8-amino-3,6-dioxaoctanoic acid dimer, IRIS Biotech GmbH, Cat. No. PEG1221) in ethanol (40 ml) was added DI PEA (1.26 ml). The mixture was stirred at room temperature over night and then concentrated in vacuo. To the residue was added aqueous 0.1 N HCl (150 ml) and ethyl acetate (200 ml). The layers were separated and the aqueous layer was extracted with ethyl acetate (100 ml). The combined organic layers were washed with water and brine, dried (magnesium sulphate) and concentrated in vacuo to give an oil, which crystalised on standing. Yield 96% (3.1 g). LC-MS (electrospray): m/z=874.49.

Step 2: 19-((S)-1-tert-Butoxycarbonyl-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl)nonadecanoic acid tert-butyl ester

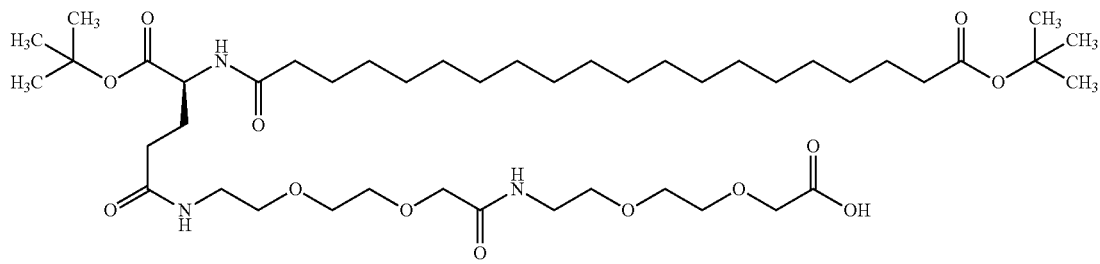

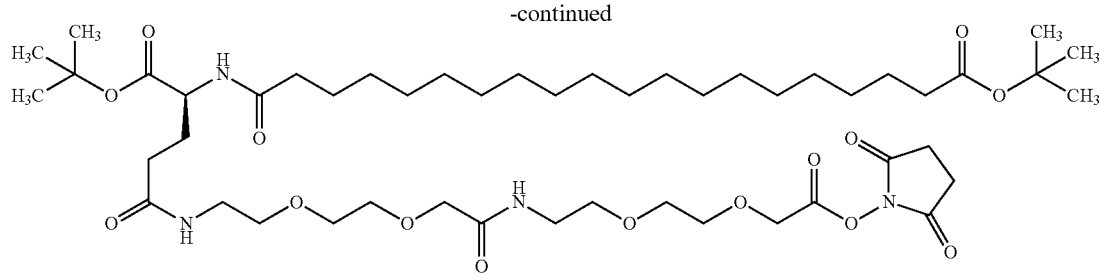

To a solution of 19-{(S)-1-tert-Butoxycarbonyl-3-[2-(2-{[2-(2-carboxymethoxyethoxy)ethylcarbamoyl]-methoxy}ethoxy)ethylcarbamoyl]propylcarbamoyl}nonadecanoic acid tert-butyl ester (3.1 g) in acetonitrile (50 ml) was added TSTU (1.39 g) and DIPEA (0.91 ml). The mixture was stirred at room temperature over night and then concentrated in vacuo. To the residue was added aqueous 0.1 N HCl (100 ml) and ethyl acetate (200 ml). The layers were separated and the aqueous layer was extracted with ethyl acetate (50 ml). The combined organic layers were washed with water and brine, dried (magnesium sulphate) and concentrated in vacuo to give an oil. Yield 99% (3.4 g). LC-MS (electrospray): m/z: 971.8.

Step 3: 19-((S)-1-Carboxy-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl)nonadecanoic acid

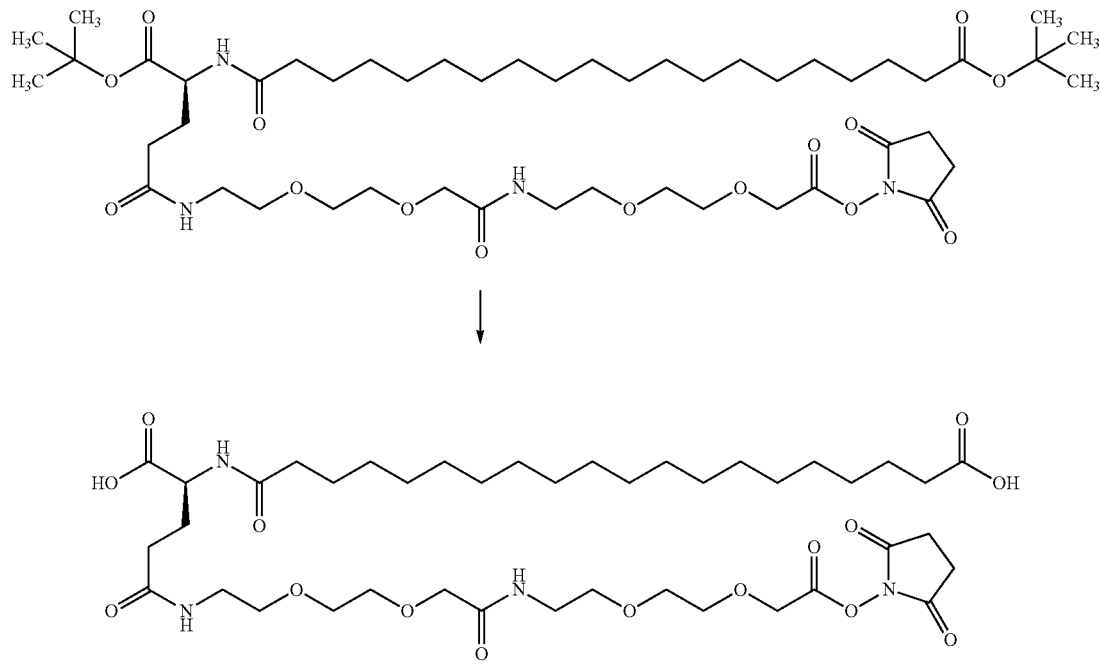

19-((S)-1-tert-Butoxycarbonyl-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl) nonadecanoic acid tert-butyl ester (3.4 g) was stirred in TFA (75 ml) for 45 min and then concentrated in vacuo. The residue was concentrated with toluene 3 times to give a solid. The residue was crystallised in 2-propanol and filtered to give a white crystalline compound. Yield 80% (2.4 g). LC-MS (electrospray): m/z: 859.44.

The similar acylation reagent with the octadecanedioic acid fragment (eg used in example 26 and other examples) can be prepared similarly.

Example 17, General Procedure (A)
A14E, B25H, B29K(Nᵉeicosanedioyl-γGlu-(3-(2-
{2-[2-(2-aminoethoxy)ethoxy]ethoxy}ethoxy)pro-
pionyl-γGlu), desB30 Human Insulin
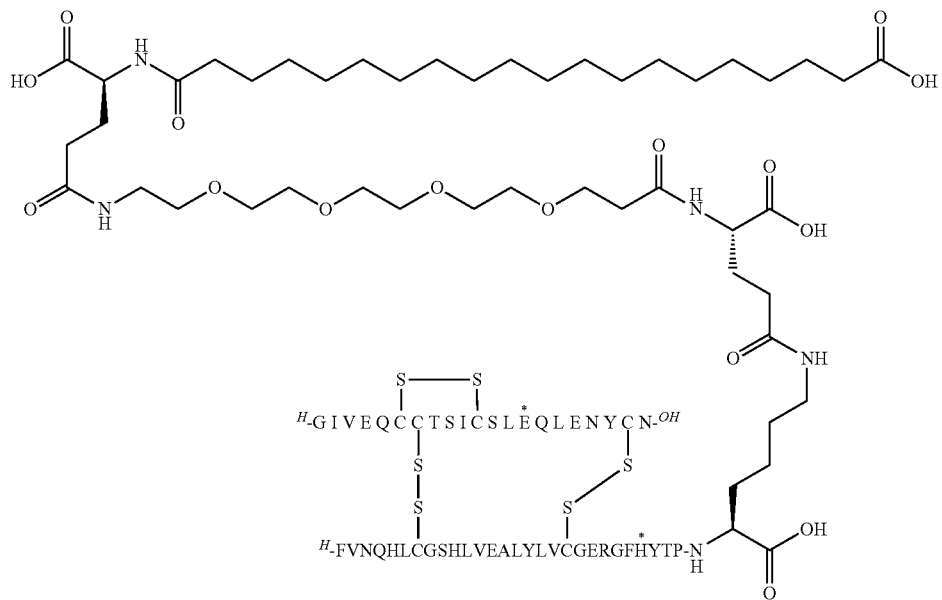
ES-MS: m/z=1626 (M+4)
Example 18, General Procedure (A)
A14E, B25H, B29K(NᵉHexadecanedioyl-γGlu-
OEG-OEG), desB30 Human Insulin
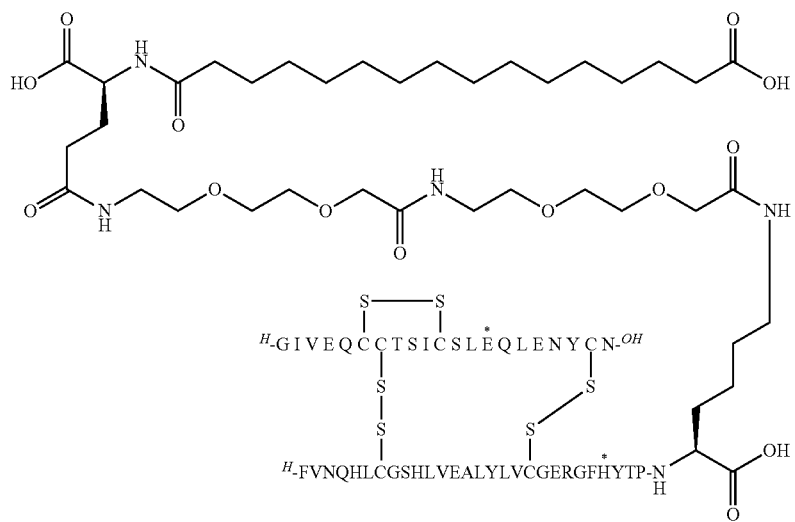
MALDI-TOF MS: m/z=6348

Example 19, General Procedure (A)
A14E, B25H, B29K(N^eHexadecanedioyl-γGlu), desB30 Human Insulin
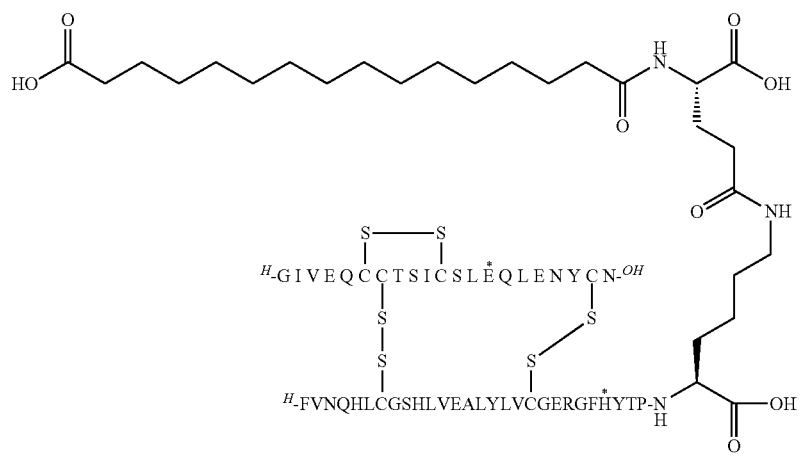
MALDI-TOF MS: m/z=6062
Example 20, General Procedure (A)
A14E, B25H, B29K(N^eheptadecanedioyl-γGlu-OEG-OEG), desB30 Human Insulin
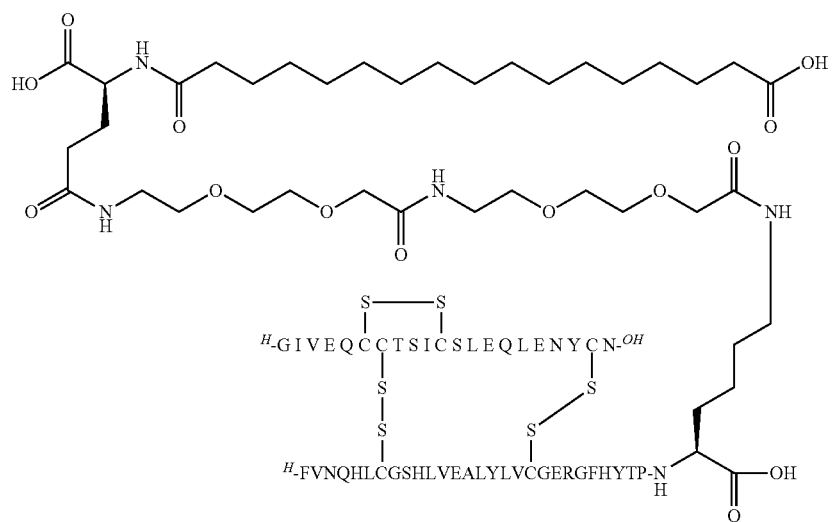
ES-MS: m/z=1592 (M+4)

Example 21, General Procedure (A)

A14E, B25H, B29K(Nᵉoctadecanedioyl-γGlu-γGlu-γGlu-γGlu), desB30 Human Insulin

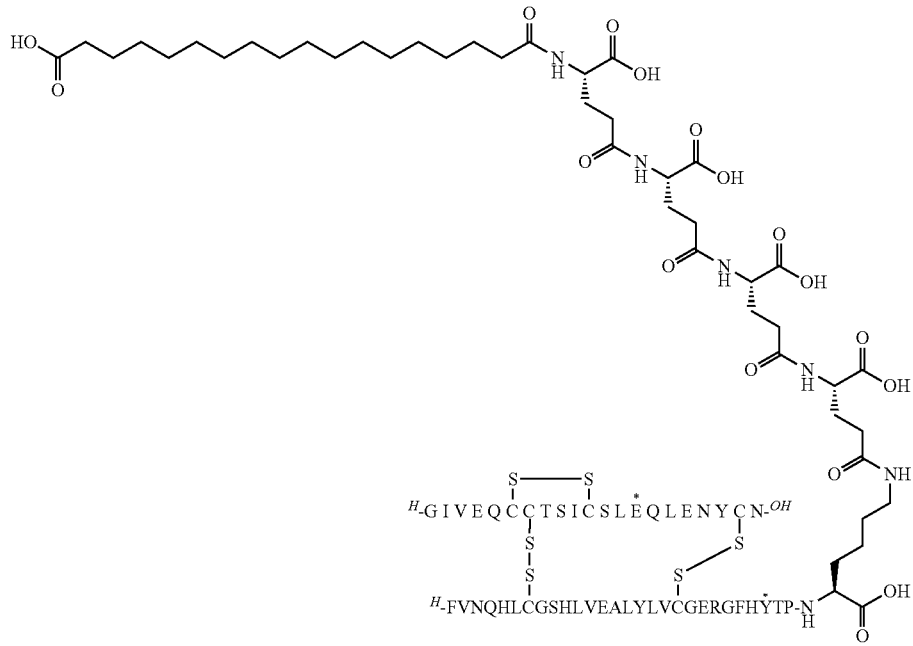

ES-MS: m/z=1620 (M+4)

The intermediate acylation reagent octadecanedioyl-γGlu-γGlu-γGlu-γGlu-OSu (with tert-butyl esters as protection groups on remaining carboxylic acids) was prepared as described below:

Octadecanedioic acid tert-butyl ester 2,5-dioxopyrrolidin-1-yl ester

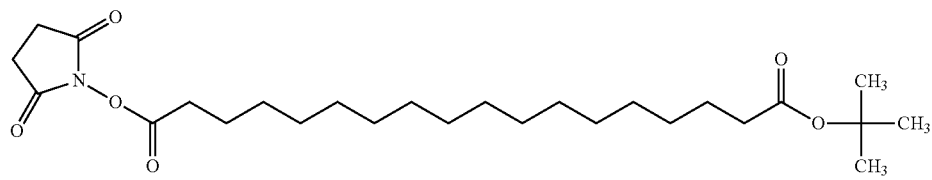 [SMILES: CC(C)(C)OC(=O)CCCCCCCCCCCCCCCCC(=O)ON1C(=O)CCC1=O]

Octadecanedioic acid mono-tert-butyl ester (4.2 g, 0.011 mol) was dissolved in THF (20 mL), TSTU (4 g, 0.013 mol) in acetonitrile (20 mL) was added and pH of the solution was adjusted to 8 with dropwise addition of DIPEA. The mixture was stirred at RT for 4 h, then acidified with HCl (2M) to pH 3 and evaporated in vacuo. The residual oil was subsequently partitioned between ethyl acetate and HCl (0.1 M). The organic layer was dried (MgSO₄), filtered and evaporated to dryness in vacuo. This afforded 5.2 g of octadecanedioic acid tert-butyl ester 2,5-dioxopyrrolidin-1-yl ester as an oil, which could be used in the next step without further purification. LC-MS (electrospray): m/z=468 (M+1) and 412 (M+1-ᵗBu).

(S)-2-(17-tert-Butoxarbonylheptadecanoylamino)-pentanedioic acid 1-tert-butyl ester

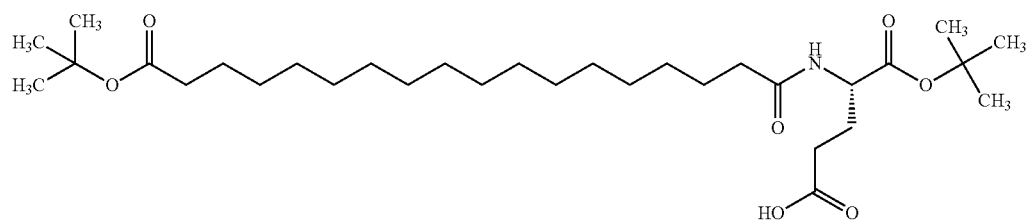 [SMILES: CC(C)(C)OC(=O)CCCCCCCCCCCCCCCCC(=O)N[C@@H](CCC(=O)O)C(=O)OC(C)(C)C]

Octadecanedioic acid tert-butyl ester 2,5-dioxopyrrolidin-1-yl ester (7 g, 0.015 mol) was dissolved in THF (80 mL) and added to a solution of H-Glu-O'Bu (3.7 g, 0.0165 mol) in Na$_2$CO$_3$ (0.1 M, 40 mL). The mixture was stirred at RT overnight, then acidified with HCl (2M) to pH 3 and evaporated in vacuo. The residue was partitioned between ethyl acetate and HCl (0.1 M). The organic layer was dried (MgSO$_4$), filtered and evaporated to dryness in vacuo. Addition of acetonitrile (30 mL) caused the formation of a white precipitate, which was isolated by filtration to and dried to afford 3.75 g of (S)-2-(17-tert-butoxarbonylheptadecanoylamino)pentanedioic acid 1-tert-butyl ester. LC-MS (electrospray): m/z=556 (M+1).

On evaporation of the acetonitrile filtrate further 2.6 g of product was isolated.

(S)-2-(17-tert-Butoxycarbonylheptadecanoylamino)pentanedioic acid 1-tert-butyl ester 5-(2,5-dioxopyrrolidin-1-yl) ester

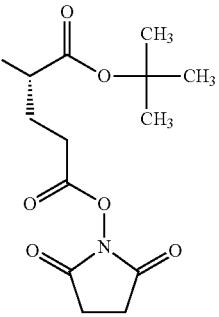

(S)-2-(17-tert-Butoxarbonylheptadecanoylamino)pentanedioic acid 1-tert-butyl ester (3 g, 0.005 mol) was dissolved in THF (100 mL) and added to a solution of TSTU (1.78 g, 0.006 mol) in acetonitrile (30 mL). pH was adjusted to 8 by dropwise addition of DIPEA. The mixture was stirred at RT for 1 h, then acidified with HCl (2M) to pH 3 and evaporated in vacuo. The residual oil was subsequently partitioned between ethyl acetate and HCl (0.1 M). The organic layer was dried (MgSO$_4$), filtered and evaporated in vacuo to dryness. This afforded a white solid (2.75 g) of (S)-2-(17-tert-butoxycarbonylheptadecanoylamino)-pentanedioic acid 1-tert-butyl ester 5-(2,5-dioxopyrrolidin-1-yl) ester. LCMS (electrospray): m/z=653 (M+1).

(S)-2-[(S)-4-tert-Butoxycarbonyl-4-(17-tert-butoxycarbonylheptadecanoylamino)butyrylamino]-pentanedioic acid 1-tert-butyl ester

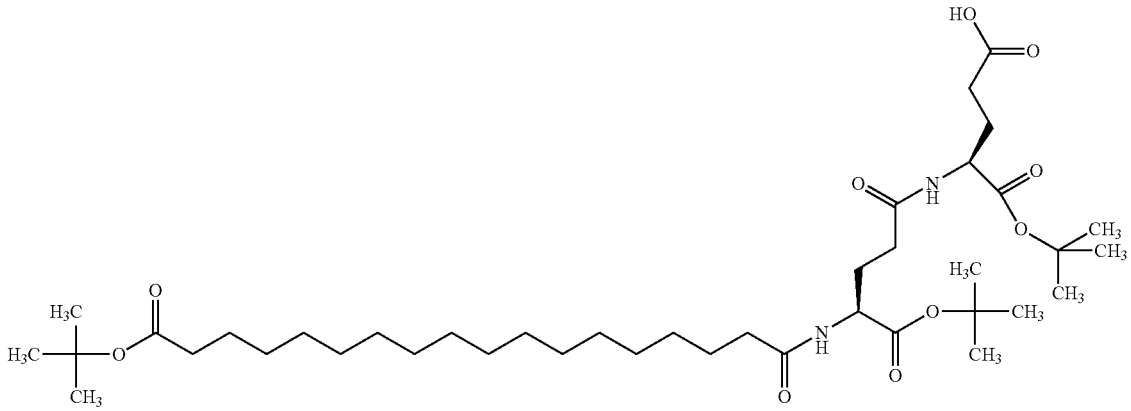 [SMILES: CC(C)(C)OC(=O)CCCCCCCCCCCCCCCCC(=O)N[C@@H](CCC(=O)N[C@@H](CCC(=O)O)C(=O)OC(C)(C)C)C(=O)OC(C)(C)C]

(S)-2-(17-tert-Butoxycarbonylheptadecanoylamino)pentanedioic acid 1-tert-butyl ester 5-(2,5-dioxo-pyrrolidin-1-yl) ester (0.5 g, 0.766 mmol) was dissolved in acetonitrile (20 mL). This solution was added to a solution of H-Glu-OtBu (0.171 g, 0.84 mmol) in water (30 mL) pH was adjusted to 10 with DIPEA. The mixture was stirred at RT for 15 min, then acidified to pH 7 with HCl (2M) and evaporated in vacuo. The residue was partitioned between ethyl acetate and HCl (0.1 M). The organic layer was dried (MgSO₄), filtered, and evaporated in vacuo to dryness. This afforded (S)-2-[(S)-4-tert-butoxycarbonyl-4-(17-tert-butoxycarbonylheptadecanoylamino)butyrylamino]pentanedioic acid 1-tert-butyl ester as an oil. LC-MS (electrospray): m/z=741 (M+1).

(S)-2-[(S)-4-tert-Butoxycarbonyl-4-(17-tert-butoxycarbonylheptadecanoylamino)butyrylamino]-pentanedioic acid 5-tert-butyl ester 1-(2,5-dioxopyrrolidin-1-yl) ester

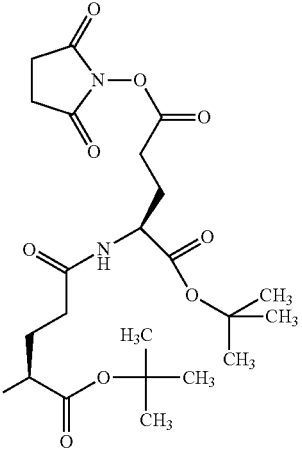
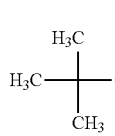

(S)-2-[(S)-4-tert-Butoxycarbonyl-4-(17-tert-butoxycarbonylheptadecanoylamino)butyrylamino]-pentanedioic acid 1-tert-butyl ester (8 g, 10.79 mmol) was dissolved in acetonitrile (40 mL) and a solution of TSTU (3.89 g, 12.95 mmol) in acetonitrile (40 mL) was added. pH was adjusted to 8 by dropwise addition of DIPEA. The mixture was stirred at RT for 1 h, then acidified with HCl (2M) to pH 3 and evaporated in vacuo. This afforded an oil, which was subsequently partitioned between ethyl acetate and HCl (0.1 M). The organic layer was dried (MgSO₄), filtered and evaporated to dryness in vacuo. This afforded 8.2 g of (S)-2-[(S)-4-tert-butoxycarbonyl-4-(17-tert-butoxycarbonylheptadecanoylamino)butyrylamino]pentanedioic acid 5-tert-butyl ester 1-(2,5-dioxopyrrolidin-1-yl) ester as a solid.

(S)-2-{(S)-4-tert-Butoxycarbonyl-4-[(S)-4-tert-butoxycarbonyl-4-(17-tert-butoxycarbonylheptadecanoylamino)butyrylamino]butyrylamino}pentanedioic acid 1-tert-butyl ester

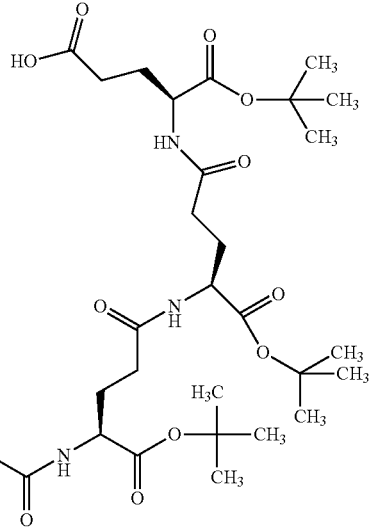
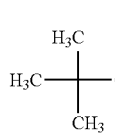

(S)-2-[(S)-4-tert-Butoxycarbonyl-4-(17-tert-butoxycarbonylheptadecanoylamino)butyrylamino]-pentanedioic acid 5-tert-butyl ester 1-(2,5-dioxopyrrolidin-1-yl) ester (4 g, 4.77 mmol) was dissolved in acetonitrile (30 mL) and added to a solution of of H-Glu-OtBu (1.07 g, 5.25 mmol) in Na$_2$CO$_3$ (0.1 M, 20 mL). The mixture was stirred at RT for 1 h, then neutralised with HCl (2M) to pH 7 and evaporated in vacuo. The residual oil was subsequently partitioned between ethyl acetate and HCl (0.1 M). The organic layer was dried (MgSO$_4$), filtered and evaporated to dryness in vacuo. The residue (4 g) was dissolved in acetonitrile and treated with active carbon. After filtration and evaporation to dryness followed by drying overnight in vacuo, 2.8 g of (S)-2-{(S)-4-tert-Butoxycarbonyl-4-[(S)-4-tert-butoxycarbonyl-4-(17-tert-butoxycarbonylheptadecanoylamino)butyrylamino]butyrylamino}pentanedioic acid 1-tert-butyl ester was obtained as a crystalline solid. LC-MS (electrospray): m/z=927 (M+1).

(S)-2-((S)-4-tert-Butoxycarbonyl-4-{(S)-4-tert-butoxycarbonyl-4-[(S)-4-tert-butoxycarbonyl-4-(17-tert-butoxycarbonylheptadecanoylamino)butyrylamino]butyrylamino}butyrylamino)pentanedioic acid 1-tert-butyl ester

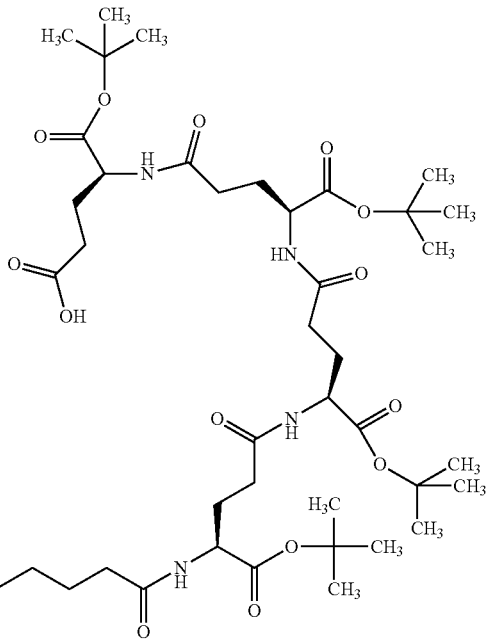

(S)-2-{(S)-4-tert-Butoxycarbonyl-4-[(S)-4-tert-butoxycarbonyl-4-(17-tert-butoxycarbonylheptadecanoylamino)butyrylamino]butyrylamino}pentanedioic acid 1-tert-butyl ester (2.8 g, 3.02 mmol) was activated with TSTU (1.0 g, 3.325 mmol) using the same method as described above, giving crude (S)-2-{(S)-4-tert-butoxycarbonyl-4-[(S)-4-tert-butoxycarbonyl-4-(17-tert-butoxycarbonylheptadecanoylamino)-butyrylamino]butyrylamino}-pentanedioic acid 1-tert-butyl ester 5-(2,5-dioxopyrrolidin-1-yl) ester. LC-MS (electrospray): m/z=1024 (M+1).

1.3 g of this compound was dissolved in acetonitrile (40 mL) and added to a solution of of H-Glu-O$^t$Bu (0.28 g, 1.39 mmol) in water (30 mL), pH was adjusted to 9.3 with DIPEA. The mixture was stirred at RT for 2 h, then neutralised to pH 7 with HCl (2M) and then evaporated in vacuo to almost dryness. The residue was treated with water giving a white precipitate, which was filtered off. After drying in vacuo overnight, 1.1 g of (S)-2-((S)-4-tert-butoxycarbonyl-4-{(S)-4-tert-butoxycarbonyl-4-[(S)-4-tert-butoxycarbonyl-4-(17-tert-butoxycarbonylheptadecanoylamino)butyrylamino]butyrylamino}butyrylamino)pentanedioic acid 1-tert-butyl ester was isolated, containing minor amounts of starting material.

LC-MS (electrospray): m/z=1111.9 (M+1).

(S)-2-((S)-4-tert-Butoxycarbonyl-4-{(S)-4-tert-bu-toxycarbonyl-4-[(S)-4-tert-butoxycarbonyl-4-(17-tert-butoxycarbonylheptadecanoylamino)butyry-lamino]butyrylamino}butyrylamino)-pentanedioic acid 1-tert-butylester-5-(2,5-dioxopyrrolidin-1-yl) ester

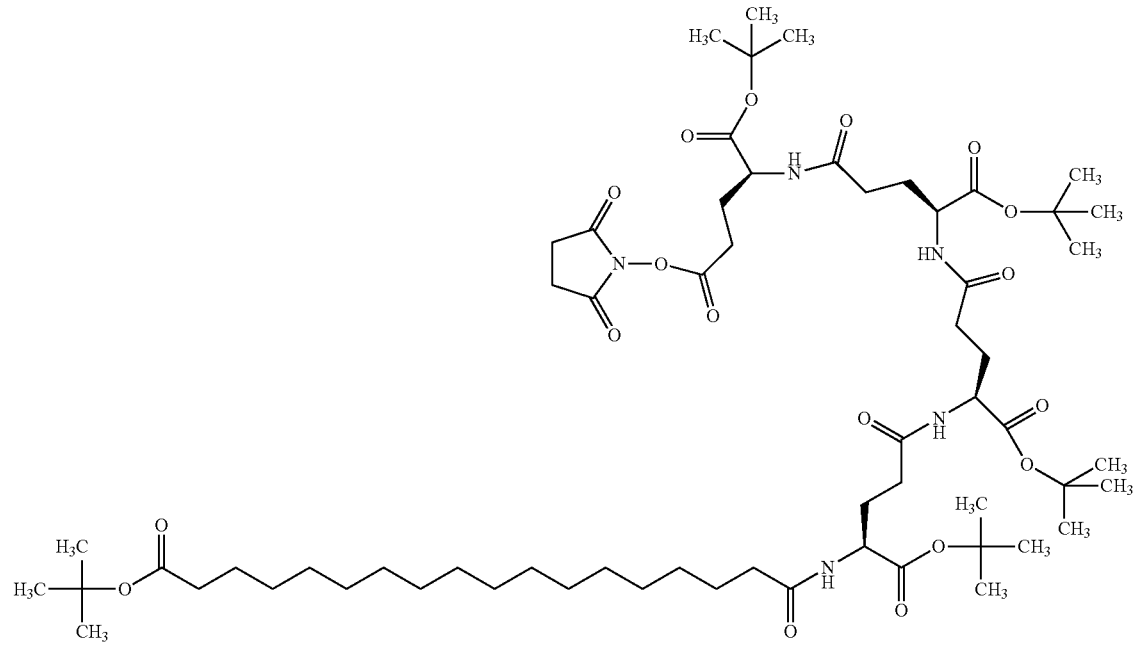 [SMILES: CC(C)(C)OC(=O)CCCCCCCCCCCCCCCCC(=O)N[C@@H](CCC(=O)N[C@@H](CCC(=O)N[C@@H](CCC(=O)N[C@@H](CCC(=O)ON1C(=O)CCC1=O)C(=O)OC(C)(C)C)C(=O)OC(C)(C)C)C(=O)OC(C)(C)C)C(=O)OC(C)(C)C]

(S)-2-((S)-4-tert-Butoxycarbonyl-4-{(S)-4-tert-butoxy-carbonyl-4-[(S)-4-tert-butoxycarbonyl-4-(17-tert-butoxy-carbonylheptadecanoylamino)butyrylamino] butyrylamino}butyrylamino)pentanedioic acid 1-tert-butyl ester (0.1 g, 0.09 mmol) was activated with TSTU (29.8 mg, 0.099 mmol) in acetonitrile solution at RT for 1 h using the same method for activation and work up as described above. This afforded 100 mg crude activated product which could be used as such for insulin acylation without further purification. LC-MS (electrospray): m/z=1208 (M+1).

Example 22, General Procedure (A)

A14E, B25H, B29K(N$^\varepsilon$Eicosanedioyl-γGlu-γGlu-γGlu), desB30 Human Insulin

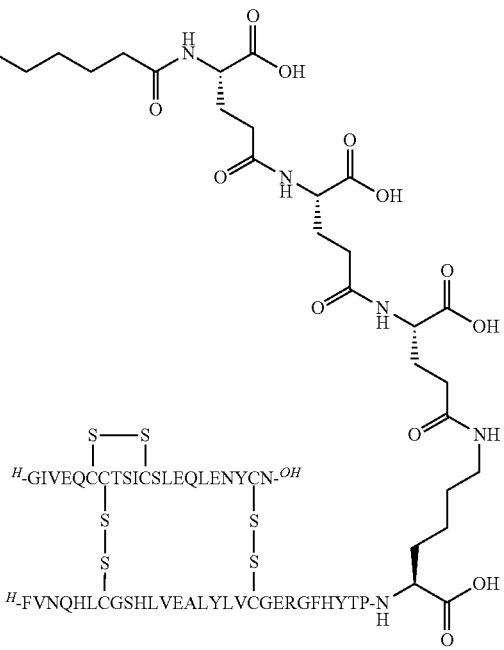

MALDI-TOF MS: m/z=6373

Figure 6:
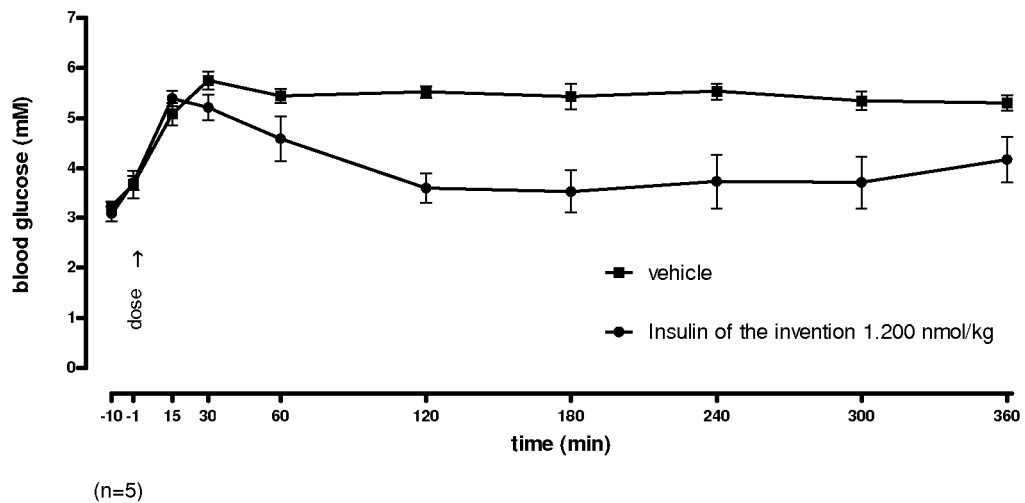
FIG. 6 shows the oral effect of the compound of Example 24 on overnight fasted male Wistar rats.

Example 23, General Procedure (A)
A14E, B25H, B27E, B29K(Nᵋ Octadecanedioyl-γGlu-OEG-OEG), desB30 Human Insulin
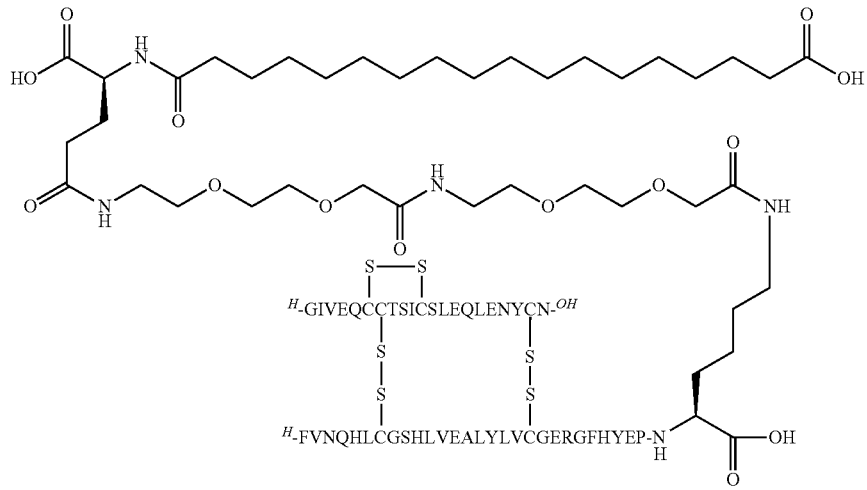
MALDI-TOF MS: m/z=6407
Example 24, General Procedure (A)
A14E, B25H, B26G, B27G, B28G, B29K (Nᵋ Octadecanedioyl-γGlu-OEG-OEG), desB30 Human Insulin
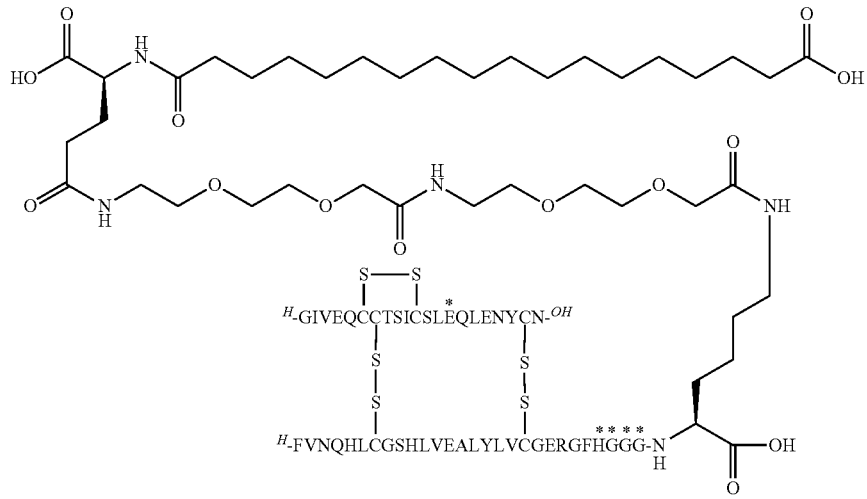
The oral effect of this compound on overnight fasted male Wistar rats is given in FIG. 6 below.
MALDI-TOF MS: m/z=6188

Figure 4:
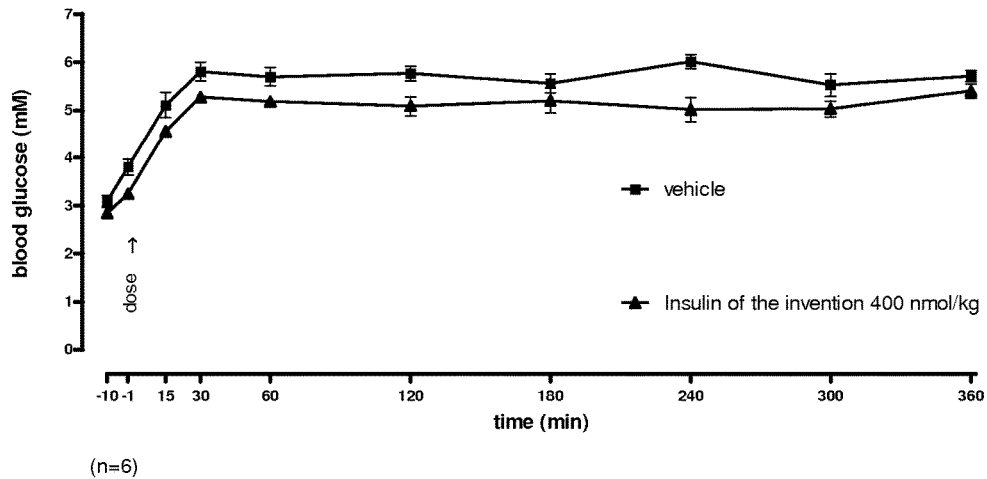
FIG. 4 shows the oral effect of the compound of Example 25 on overnight fasted male Wistar rats.

Example 25, General Procedure (A)
A14E, B16H, B25H, B29K(N^εOctadecanedioyl-γGlu-OEG-OEG), desB30 Human Insulin
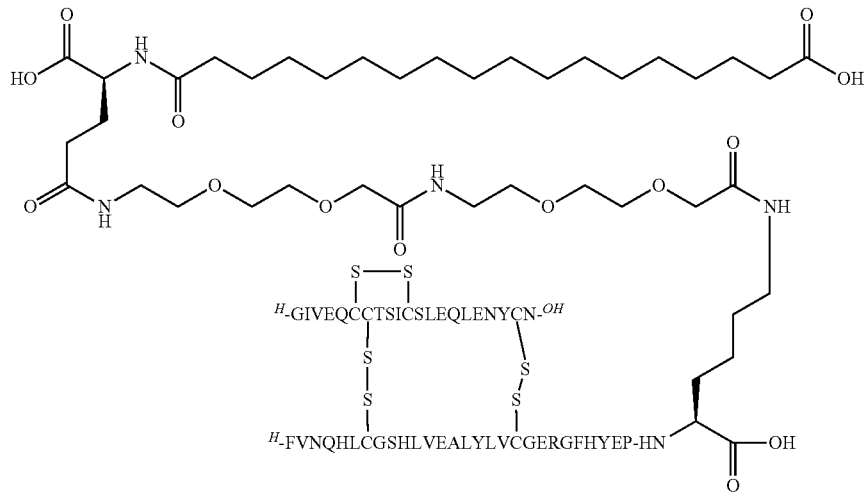
The oral effect of this compound on overnight fasted male Wistar rats is given in FIG. 4 below.
MALDI-TOF MS: m/z=6352
Example 26, General Procedure (A)
A14E, B16E, B25H, B29K(N^εOctadecanedioyl-γGlu-OEG-OEG), desB30 Human Insulin
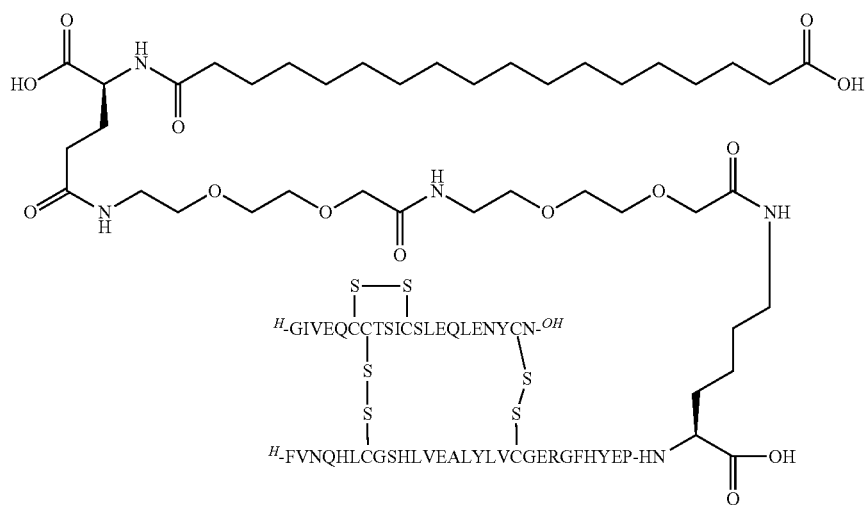
MALDI-TOF MS: m/z=6345

Figure 5:
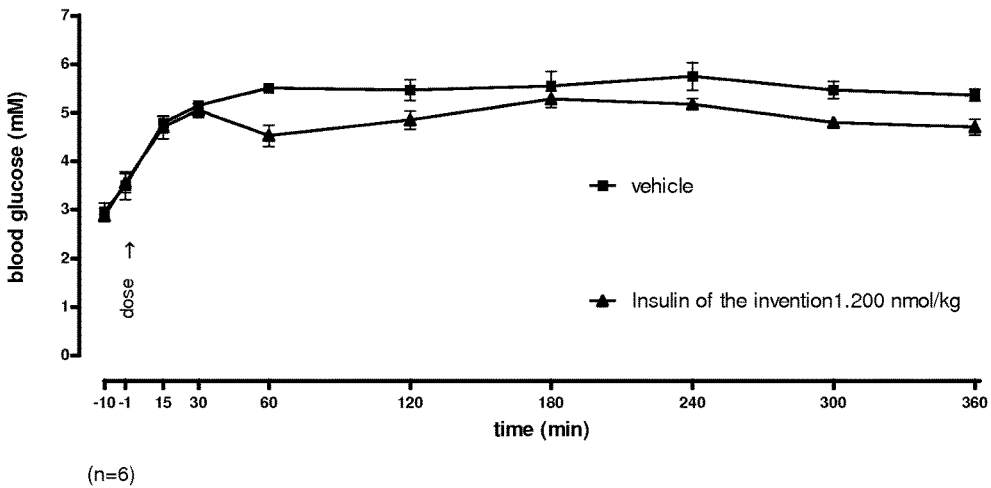
FIG. 5 shows the oral effect of the compound of Example 27 on overnight fasted male Wistar rats.

Example 27, General Procedure (A)
A14E, B16H, B25H, B29K(NᵋHexadecanedioyl-γGlu), desB30 Human Insulin
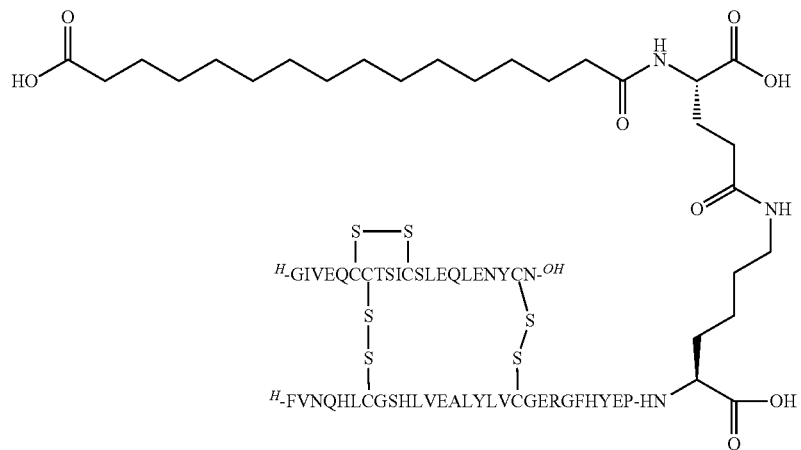
The oral effect of this compound on overnight fasted male Wistar rats is given in FIG. 5 below.
MALDI-TOF MS: m/z=6041
Example 28, General Procedure (A)
A14E, B25H, B29K(NᵋEicosanedioyl-γGlu-OEG-γGlu), desB30 Human Insulin
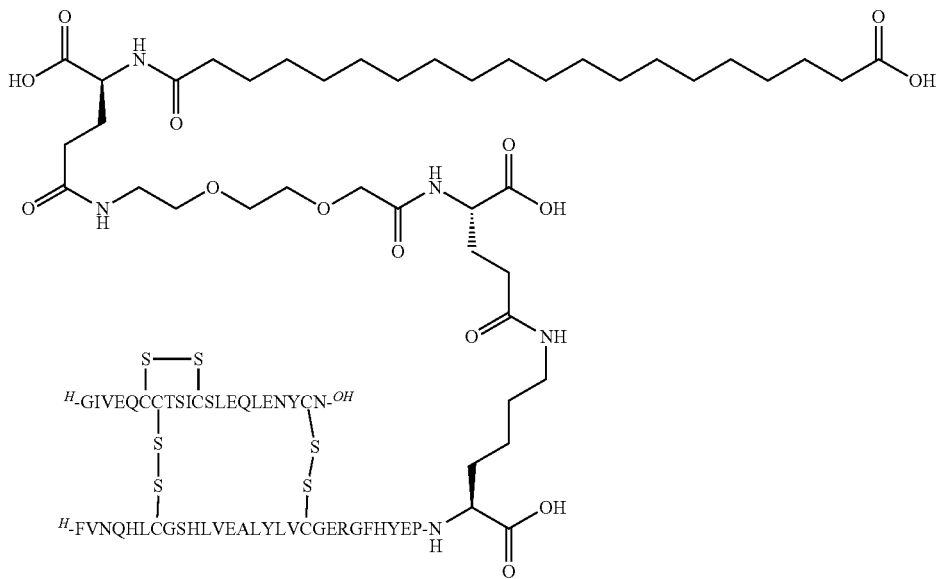
ES-MS: m/z=1598 (M+4)

Example 29, General Procedure (A)
A14E, B16E, B25H, B29K(NᵋHexadecandioyl-γGlu), desB30 Human Insulin
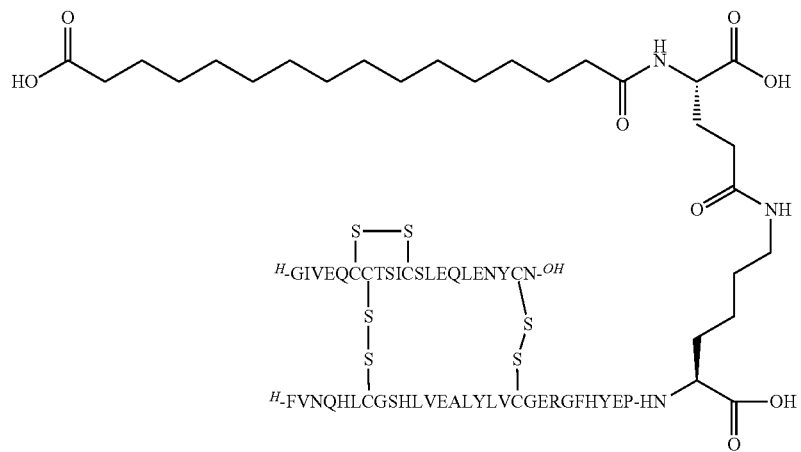
MALDI-TOF MS: m/z=6028
Example 30, General Procedure (A)
A14E, B16H, B25H, B29K(NᵋOctadecanedioyl-γGlu-γGlu-γGlu), desB30 Human Insulin
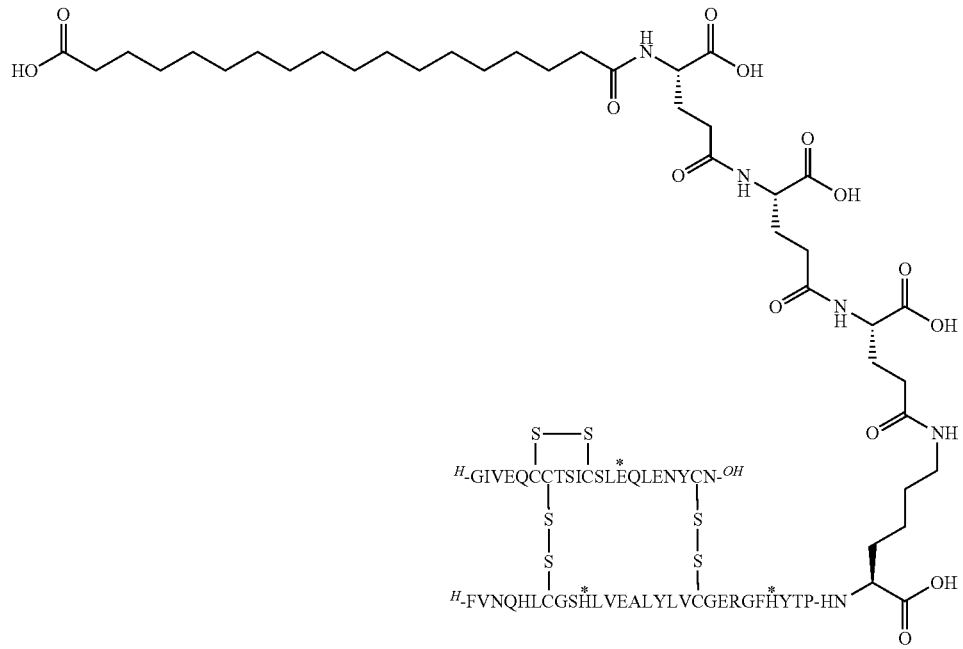
ES-MS: m/z=1581 (M+4)

Example 31, General Procedure (A)
A14E, B25H, B26G, B27G, B28G, B29K(NᵋHexadecandioyl-γGlu), desB30 Human Insulin
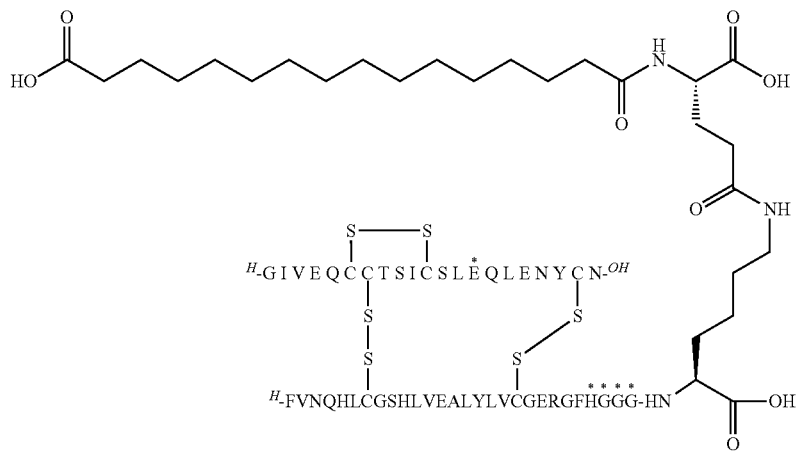
ES-MS: m/z=1484 (M+4)
Example 32, General Procedure (A)
A14E, B16H, B25H, B29K(NᵋOctadecanedioyl-γGlu-γGlu), desB30 Human Insulin
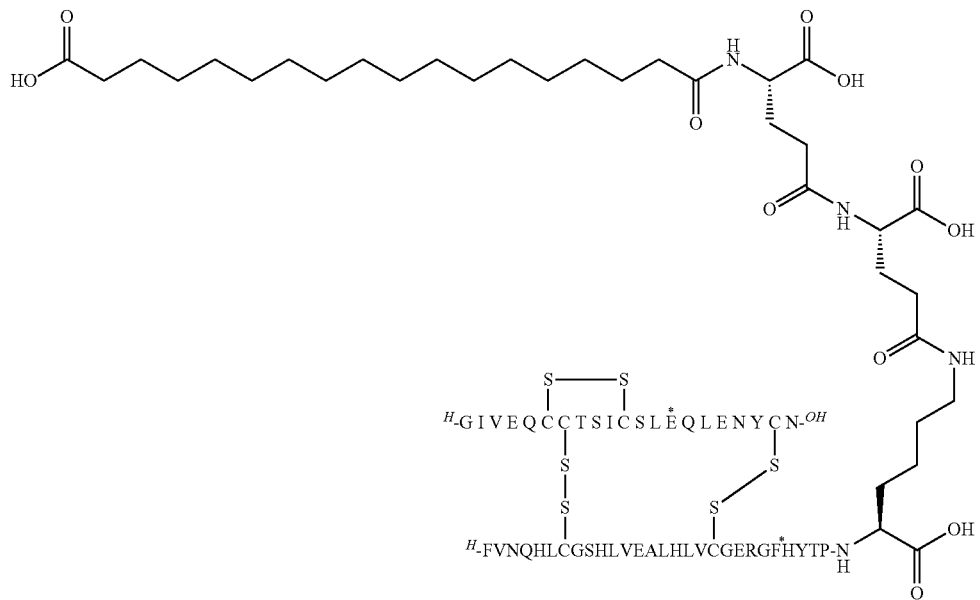
ES-MS: m/z=1548 (M+4)

Example 33, General Procedure (A)
A14E, B16H, B25H, B29K(N(eps)Eicosanedioyl-γGlu-OEG-OEG), desB30 Human Insulin
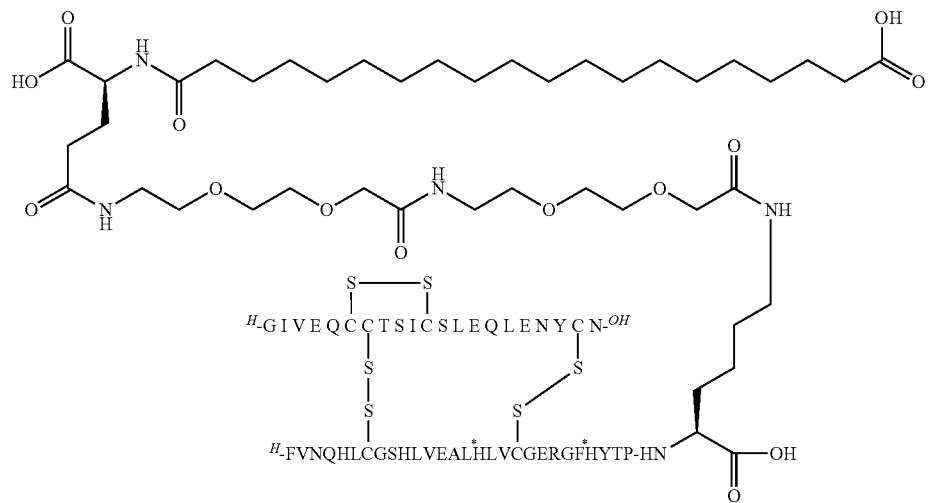
ES-MS: m/z=1596 (M+4)
Example 34, General Procedure (A)
A14E, B25H, B29K(N^εOctadecanedioyl-OEG-γGlu-γGlu), desB30 Human Insulin
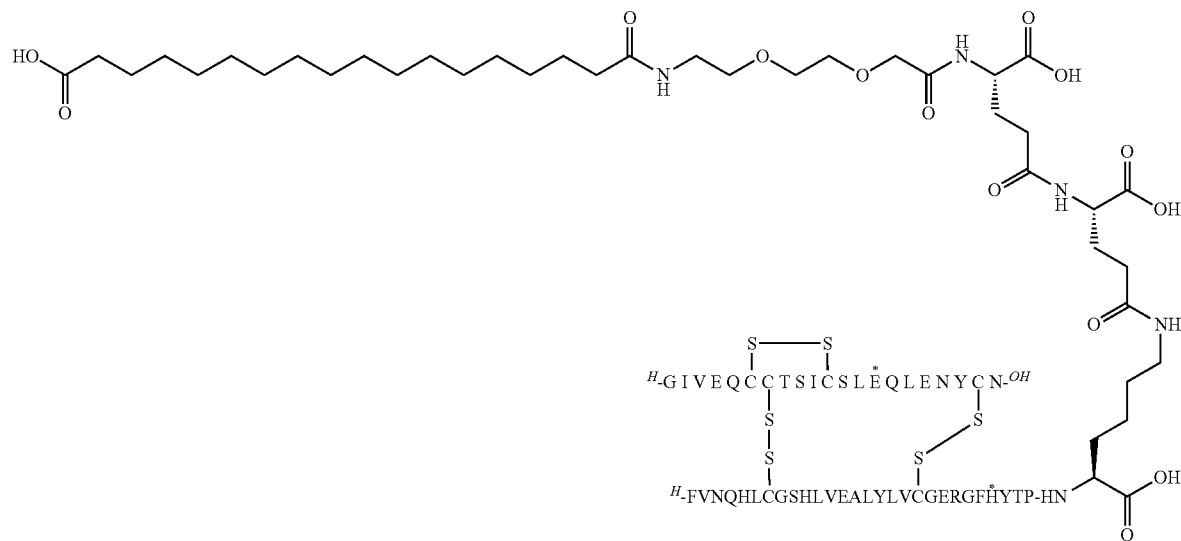
ES-MS: m/z=1592 (M+4)

Example 35, General Procedure (A)
A14E, A18L, B25H, B29K(N$^\varepsilon$Eicosanedioyl-γGlu-OEG-OEG), desB30 Human Insulin
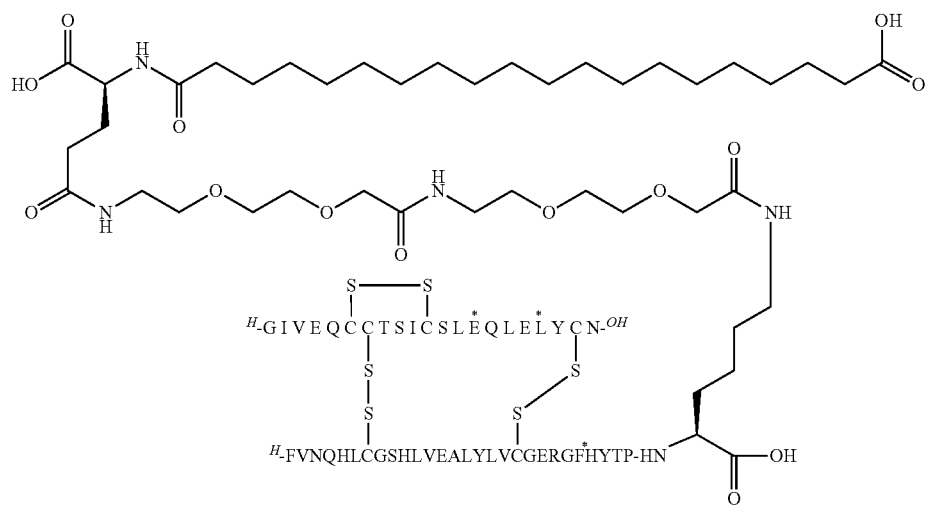
MALDI-TOF MS: m/z=6405
Example 36, General Procedure (A)
A14E, A18L, B25H, B29K(N$^\varepsilon$Octadecanedioyl-γGlu-OEG-OEG), desB30 Human Insulin
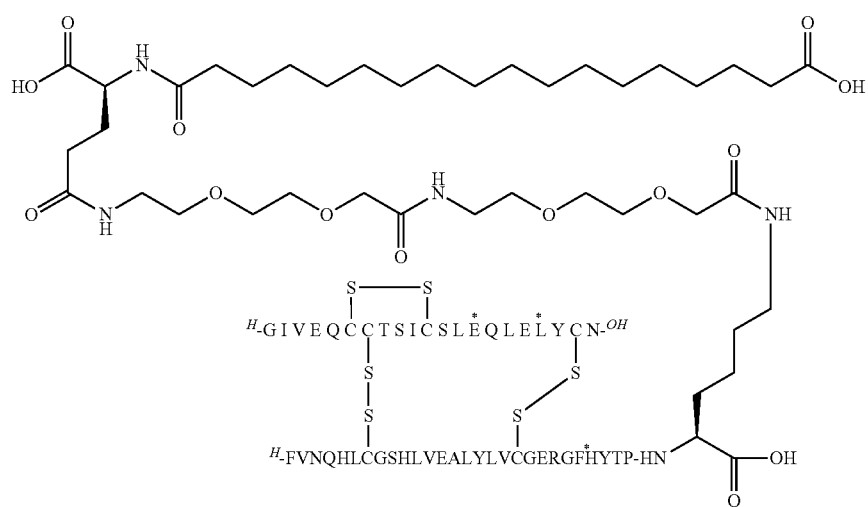
MALDI-TOF MS: m/z=6377

Example 37, General Procedure (A)

A14E, B25H, B27E, B29K(N^εEicosanedioyl-γGlu-OEG-OEG), desB30 Human Insulin

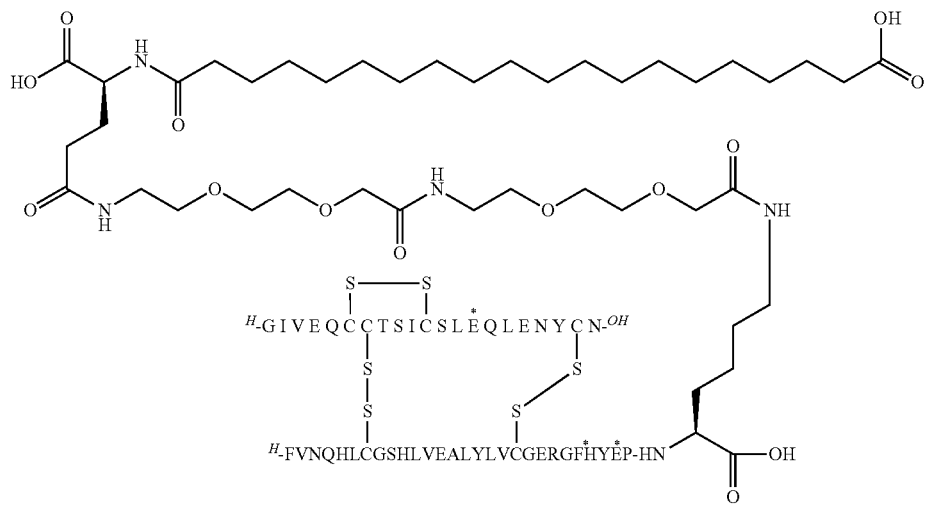

MALDI-TOF MS: m/z=6433

Example 38, General Procedure (A)

A1G(N^αOctadecandioyl-γGlu-OEG-OEG), A14E, B25H, B29R, desB30 Human Insulin

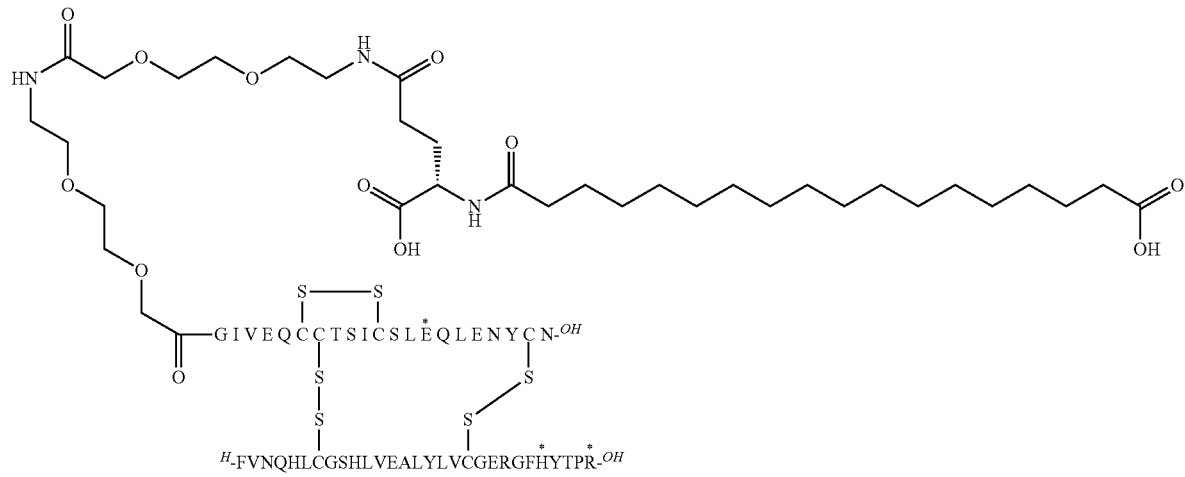

A14E, B25H, B29R, desB30 insulin (500 mg, 88 μmol) was dissolved in 0.1 M NaHCO$_3$, pH 8 (5 mL). ω-carboxy-heptadecanoyl-γ-L-glutamyl-OEG-OEG-OSu (65 mg, 88 μmol) was dissolved in THF/MeCN 1:1 (5 mL) and added to the insulin solution. After 30 minutes, the reaction was quenched by addition of 2 M aqueous methylamine (0.5 mL). The solvent was evaporated in vacuo and the solid was redissolved in the minimal amount of water/MeCN. The main product peak was isolated by use of RP-HPLC on C18 column, buffer A: 0.1% TFA in water, buffer B: 0.1% TFA in MeCN, gradient 30-55% buffer B over 45 mins. The product fractions were partially evaporated in vacuo and freeze-dried to provide 59 mg product (10%). LC-MS analysis: M$^{4+}$=1602.7, calculated 1602.6. Two steps of standard amino acid sequence analysis showed F-V, confirming the acylation at A1.

Example 39, General Procedure (A)

A14E, B1F(N$^\alpha$Octadecandioyl-γGlu-OEG-OEG), B25H, B29R, desB30 Human Insulin

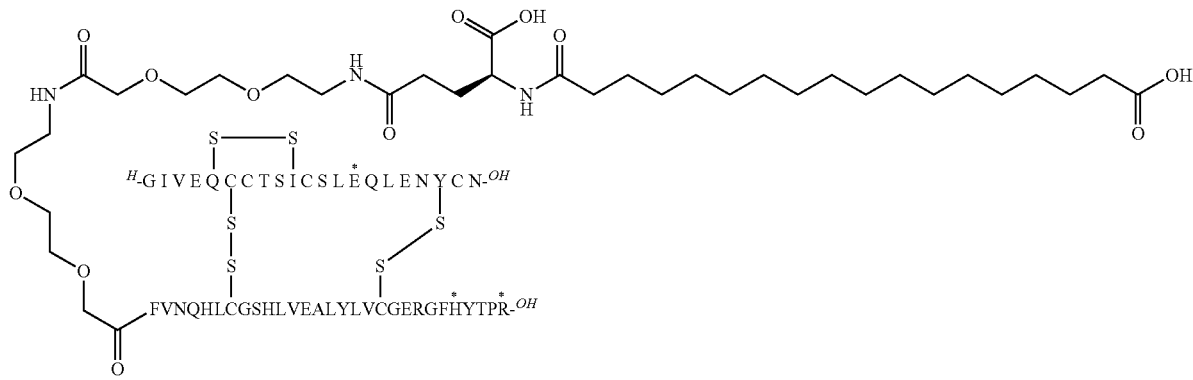

This compound was isolated as a byproduct from the example above (example 38). LCMS analysis: $M^{4+}$=1602.5, calculated 1602.6. Two steps of standard amino acid sequence analysis showed G-I, confirming the acylation at B1.

Example 40, General Procedure (A)

A1G(N$^\alpha$Hexadecandioyl-γGlu), A14E, B25H, B29R, desB30 Human Insulin

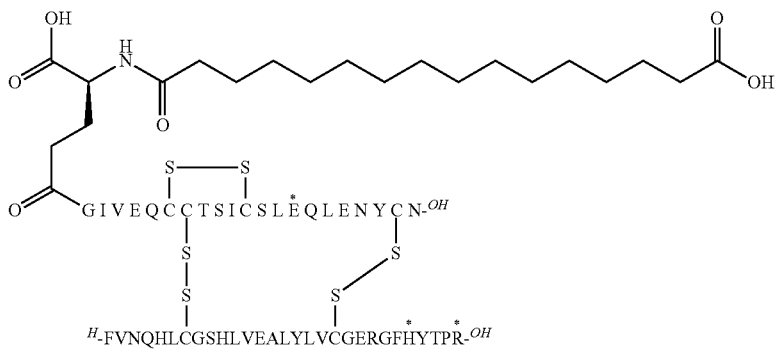

ES-MS: m/z=1523 (M+4)

This compound was prepared similarly to the A1-acylation described above (example 38), using ω-carboxypentadecanoyl-γ-L-glutamyl(OSu) as acylation reagent. The product showed LCMS: $M^{4+}$=1523.2, calculated 1523.0. Two steps of standard amino acid sequence analysis showed F-V, confirming the acylation at A1.

Example 41, General Procedure (A)

A14E, B25H, B29K(NᵋOctadecanedioyl-γGlu-Abu-Abu-Abu-Abu), desB30 Human Insulin

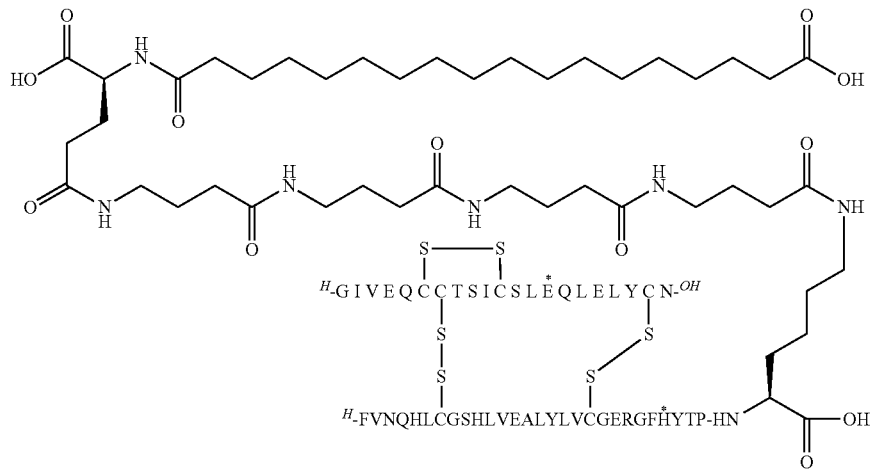

ES-MS: m/z=1286 (M+5)

The acylation reagent for this example was prepared in analogy with the reagent prepared in example 9, starting with attachment of Fmoc protected 4-aminobutyric acid to 2-chlorotrityl resin, followed by deprotection and sequential attachment 3 more units of 3 Fmoc protected 4-aminobutyric acid, and as described in example 9, Fmoc-Glu-OtBu and octadecanedioic acid mono-tert-butul ester.

Example 42, General Procedure (A)

A14E, B25H, B29K(N^αEicosanedioyl), desB30 Human Insulin

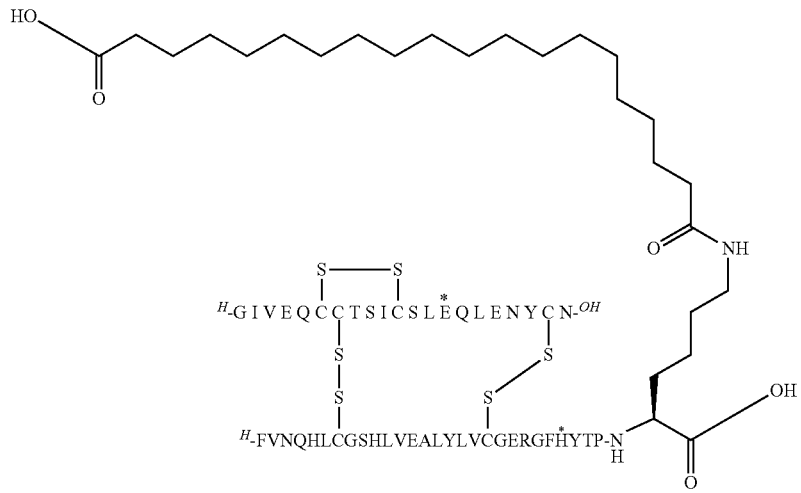

MALDI-TOF-MS: m/z=5987

Example 43, General Procedure (A)

A14E, B25H, B29K(N$^\alpha$4-[16-(1H-Tetrazol-5-yl)hexadecanoylsulfamoyl]butanoyl), desB30 Human Insulin

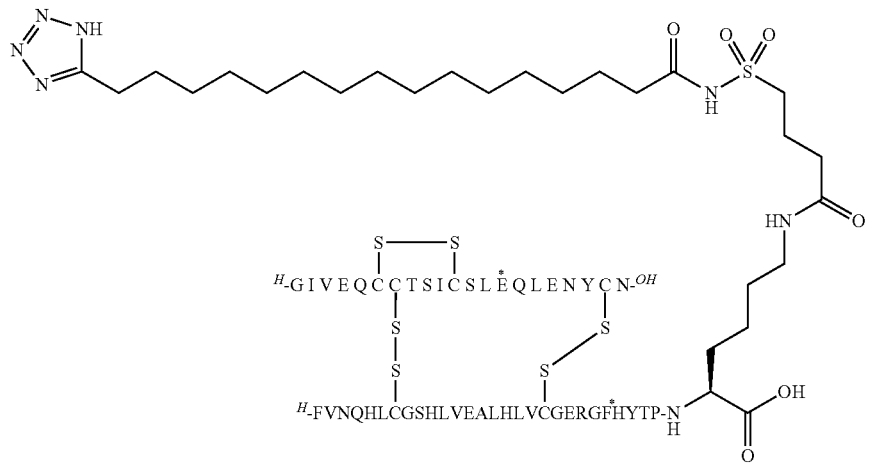

ES-MS: m/z=1530 (M+4)

Preparation of the Intermediateacylation Reagent

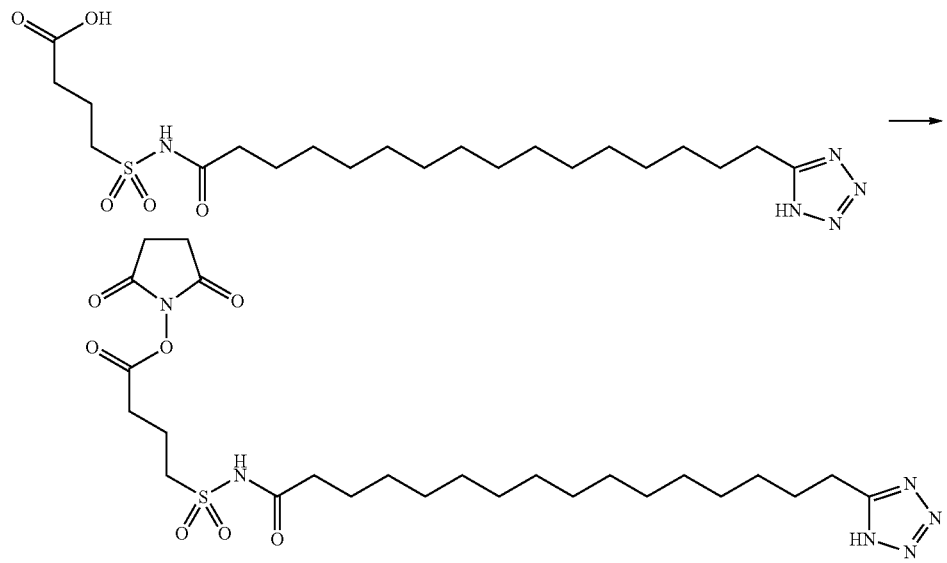

4-[16-(1H-Tetrazol-5-yl)hexadecanoylsulfamoyl]butanoic acid (500 mg, prepared as described in WO 2006/005667) was dissolved in ethanol (20 ml), and TSTU (381 mg), and DIPEA (542 µl) were added and the resulting mixture was stirred at room temperature for 16 hours. The mixture was concentrated in vacuo, and the residue was stirred with 0.25M HCl. The solid was isolated by filtration, washed with water and dried in vacuo to afford 580 mg (91%) of the acylation reagent.

Acylation Reaction:

A14E, B25H, desB30 human insulin (500 mg) was dissolved in 0.1 M aqueous sodium carbonate (10 mL) and ethanol (4 mL). pH was adjusted to 10.8 with 1N NaOH. The above acylation reagent (101 mg) dissolved in THF (2 mL) and ethanol (2 mL) was added in two portions with 10 minutes interval.

The resulting mixture was stirred slowly for 1 hour and diluted with water (50 mL). The resulting insulin was precipitated by addition of 1N HCl to pH 5.5. The precipitate was isolated by centrifugation and purified by HPLC. Pure fractions were pooled and lyophilised.

Example 44, General Procedure (A)
A1G(N$^\alpha$Octadecandioyl-γGlu-OEG-OEG), A14E, A21G, B25H, desB30 Human Insulin
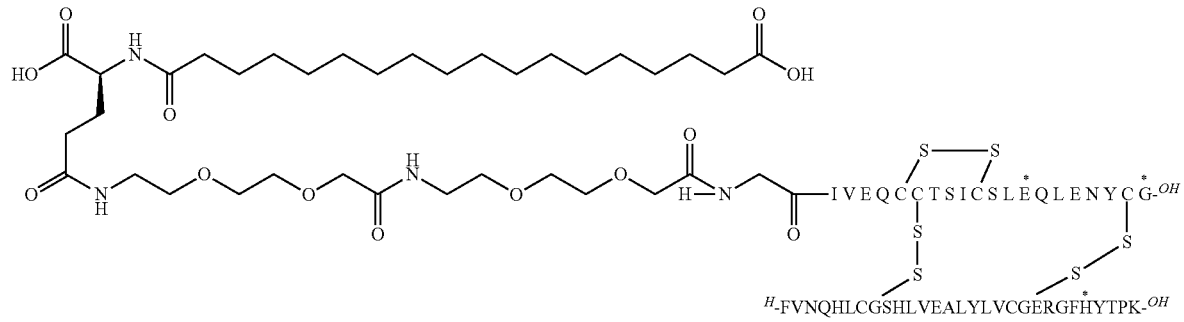
MALDI-TOF-MS: m/z=6321
Example 45, General Procedure (A)
A14E, B25H, B29K(N$^\epsilon$Eicosanedioyl-OEG), desB30 Human Insulin
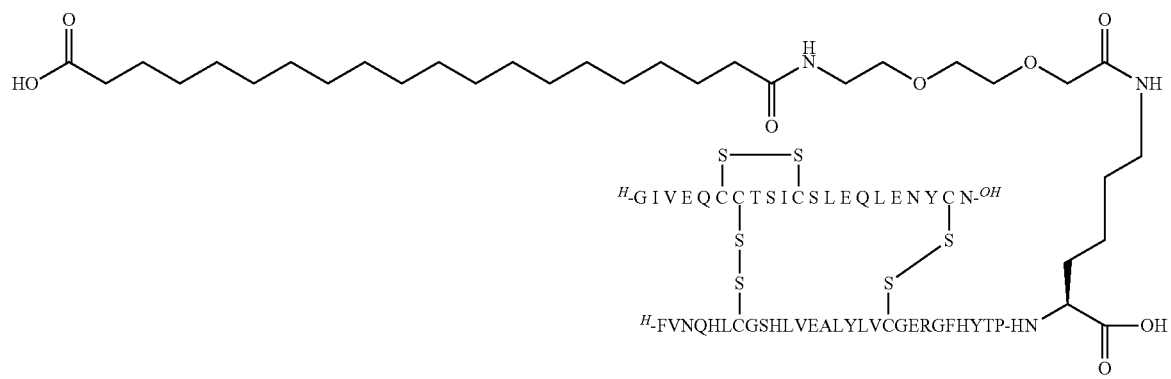
MALDI-TOF-MS: m/z=6130
Example 46, General Procedure (A)
A14E, B25H, B27K(N$^\epsilon$Octadecanedioyl-γGlu-OEG-OEG), desB28, desB29, desB30 Human Insulin
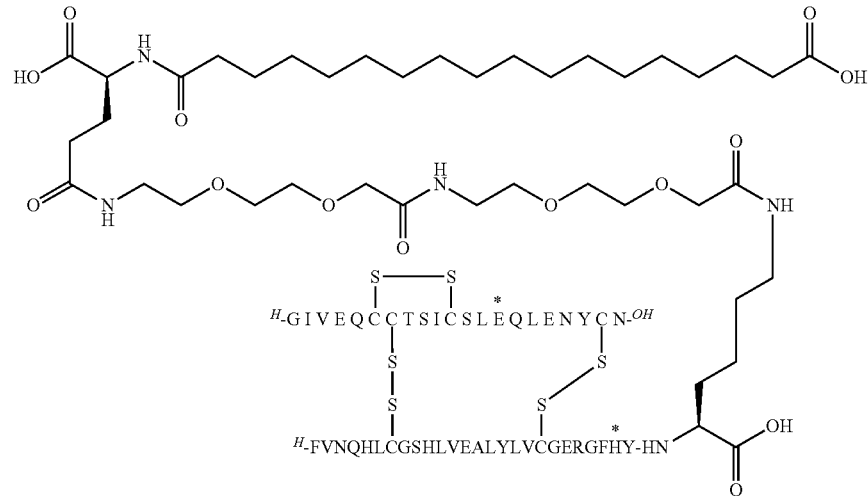
MALDI-TOF-MS: m/z=6181

Example 47, General Procedure (A)
A14E, B25H, B29K(Nᵉ(5-Eicosanedioylamin-oisophthalic acid)), desB30 Human Insulin
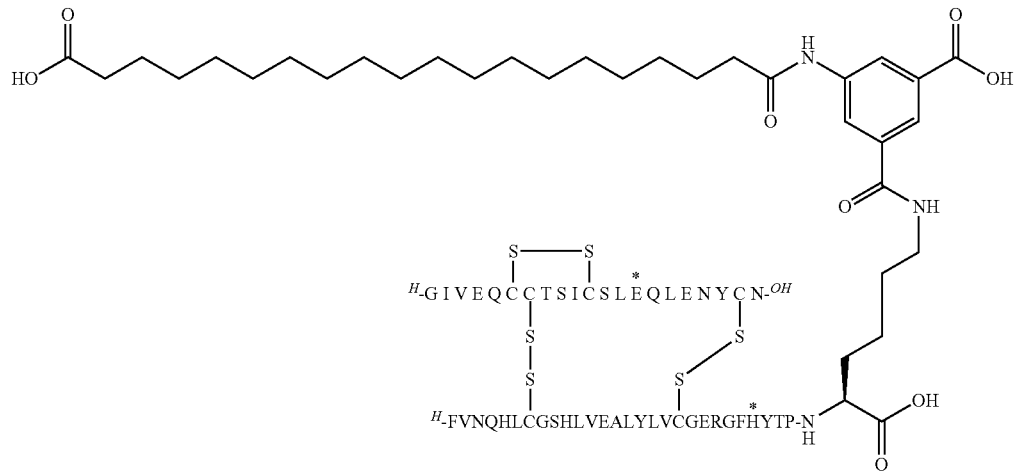
MALDI-TOF-MS: m/z=6150
Example 48, General Procedure (A)
A14E, B25H, B29K(NᵉOctadecanedioyl), desB30 Human Insulin
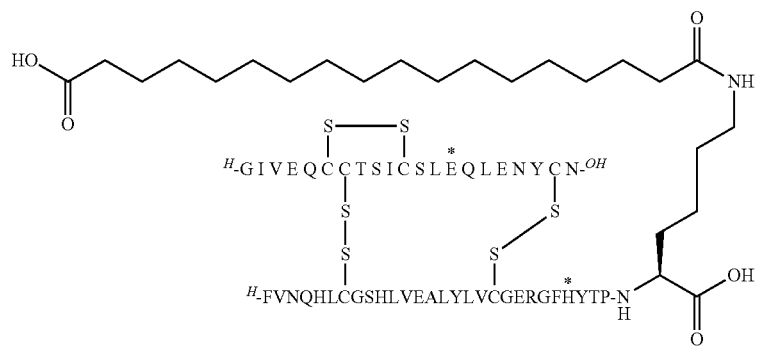
MALDI-TOF-MS: m/z=5959

Example 49, General Procedure (A)
A14E, B29K(NᵋOctadecanedioyl-γGlu-OEG-OEG), desB30 Human Insulin
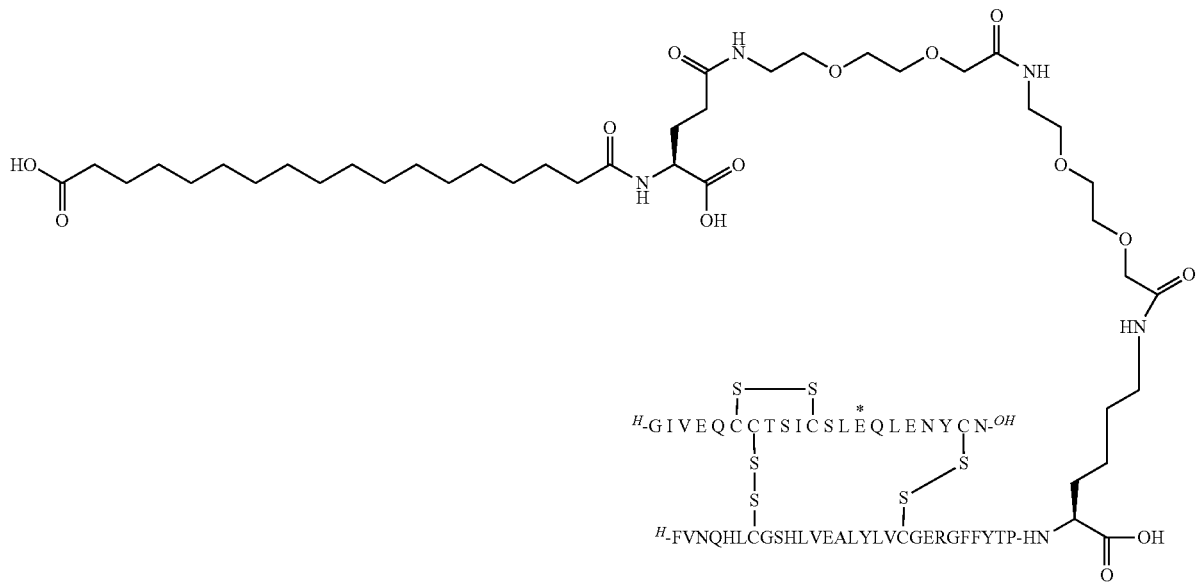
ES-MS: m/z=1598 (M+4)
Example 50, General Procedure (A)
A14E, B25H, B26G, B27G, B28G, B29K (NᵋEicosanedioyl-γGlu-OEG-OEG), desB30 Human Insulin
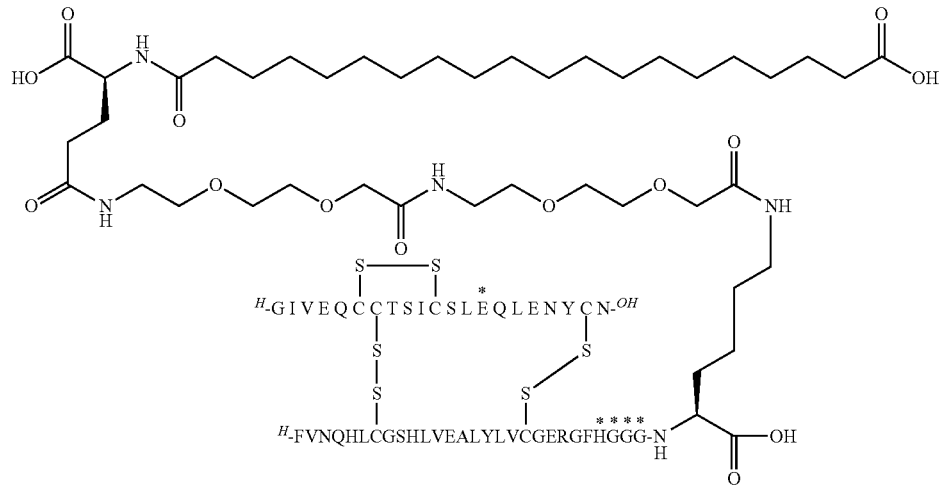
MALDI-TOF-MS: m/z=6216

Example 51, General Procedure (A)
A14E, B25H, B29K(NεOctadecanedioyl-γGlu-OEG), desB30 Human Insulin
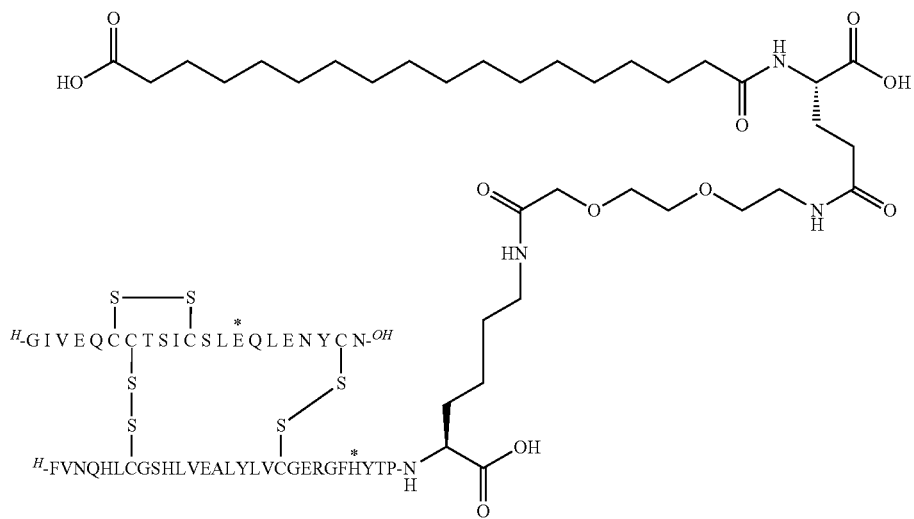
ES-MS: m/z=1559 (M+4)
Example 52, General Procedure (A)
A14E, B25H, B29K(NεEicosanedioyl-OEG-OEG), desB30 Human Insulin
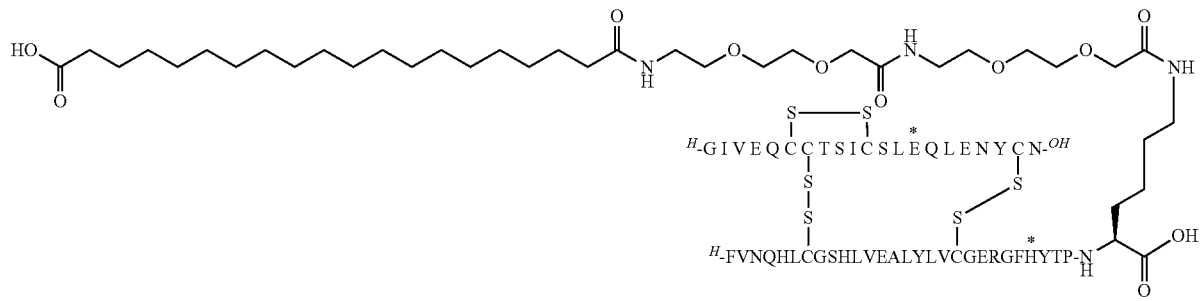
MALDI-TOF-MS: m/z=6278

Example 53, General Procedure (A)
A14E, B25H, B29K(N^εEicosanedioyl-Aoc), desB30 Human Insulin
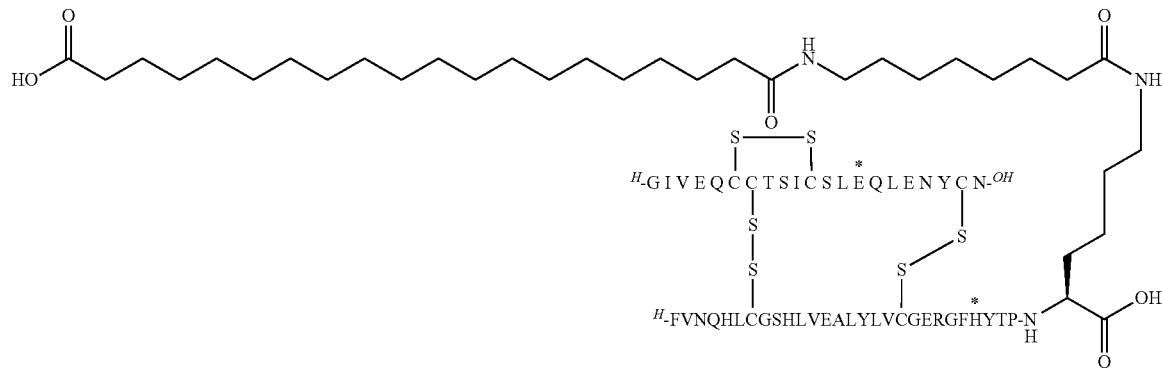
MALDI-TOF-MS: m/z=6126
Example 54, General Procedure (A)
A14E, B25H, B26G, B27G, B28G, B29K (N^εEicosanedioyl-γGlu-γGlu), desB30 Human Insulin
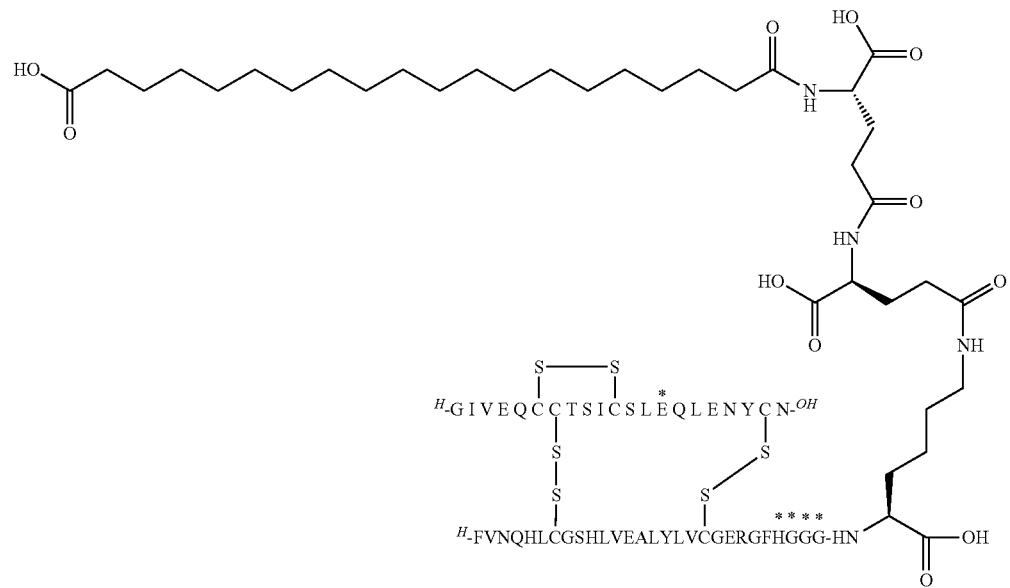
ES-MS: m/z=6055 (deconvoluted)

Example 55, General Procedure (A)
A14E, B25H, B26G, B27G, B28G, B29K (N$^\varepsilon$Eicosanedioyl-γGlu-γGlu), desB30 Human Insulin
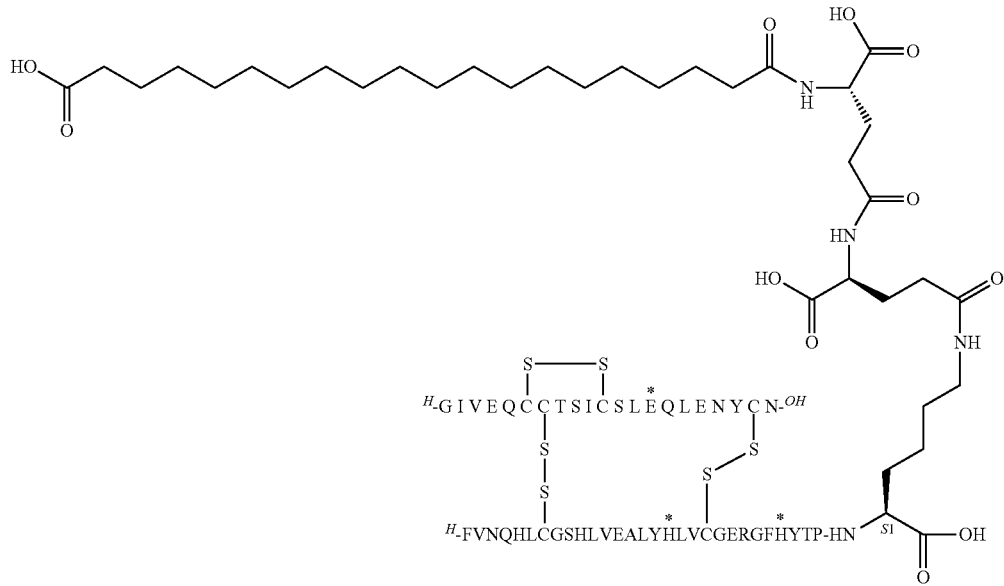
ES-MS: m/z=6220 (deconvoluted)
Example 56, General Procedure (A)
A14E, B25H, B29K(N$^\varepsilon$Octadecanedioyl-OEG), desB30 Human Insulin
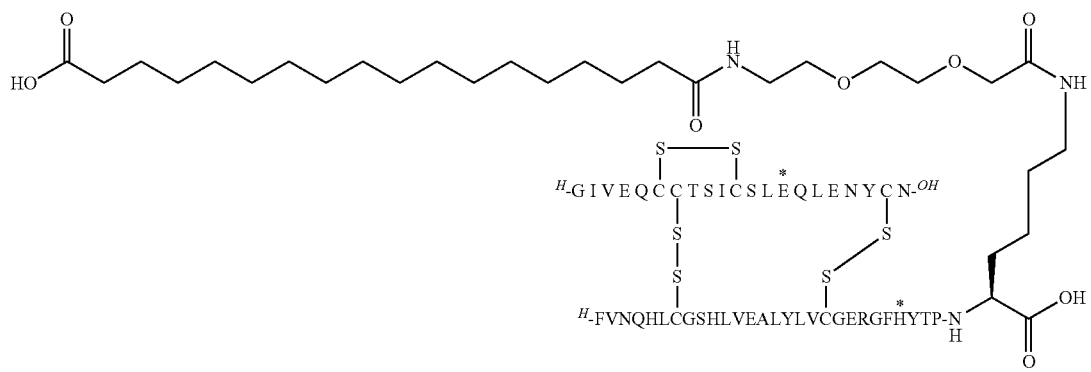
MALDI-TOF-MS: m/z=6101

Example 57, General Procedure (A)
A14E, B25H, desB27, B29K(N$^\varepsilon$Octadecanedioyl-γGlu-OEG-OEG), desB30 Human Insulin
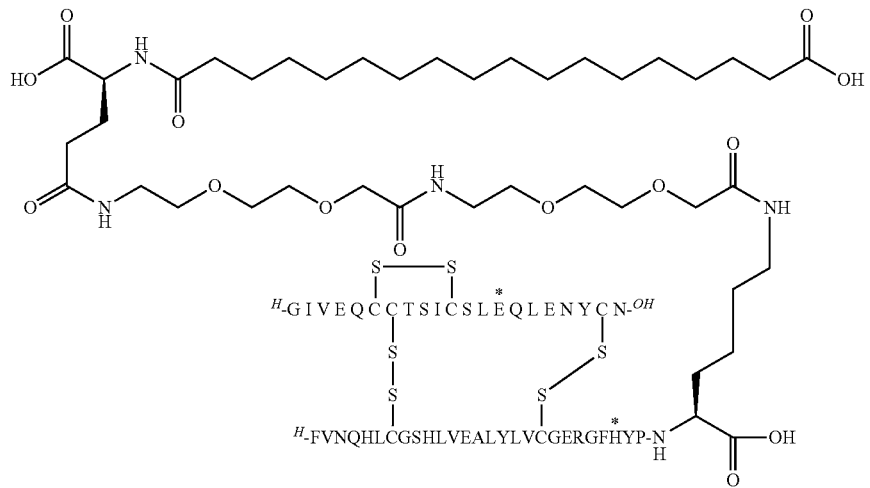
MALDI-TOF-MS: m/z=6277
Example 58, General Procedure (A)
A14E, B25H, B16H, B29K(N$^\varepsilon$Octadecanedioyl-γGlu), desB30 Human Insulin
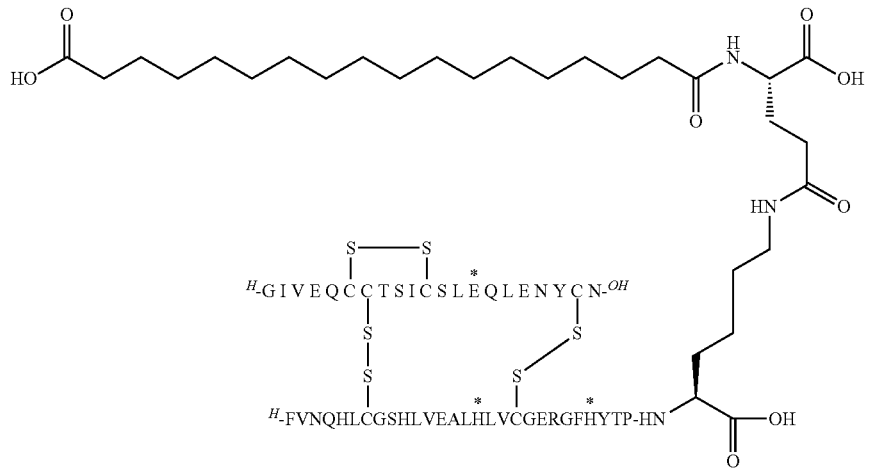
ES-MS: m/z=1516 (M+4)

Example 59, General Procedure (A)
A1G(N$^\alpha$Octadecanedioyl), A14E, B25H, B29R, desB30 Human Insulin
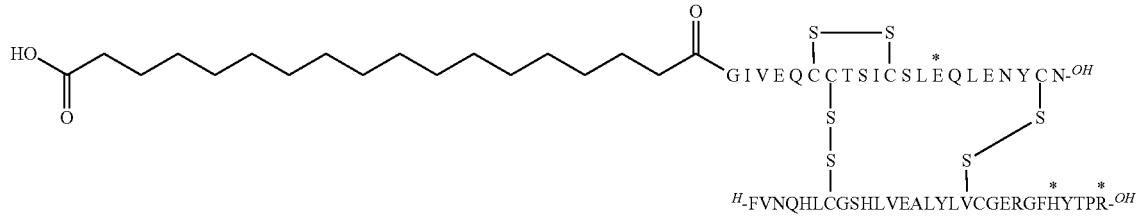
ES-MS: m/z=1498 (M+4)
Example 60, General Procedure (A)
A14E, B16H, B25H, B29K(N$^\epsilon$Eicosanedioyl-γGlu), desB30 Human Insulin
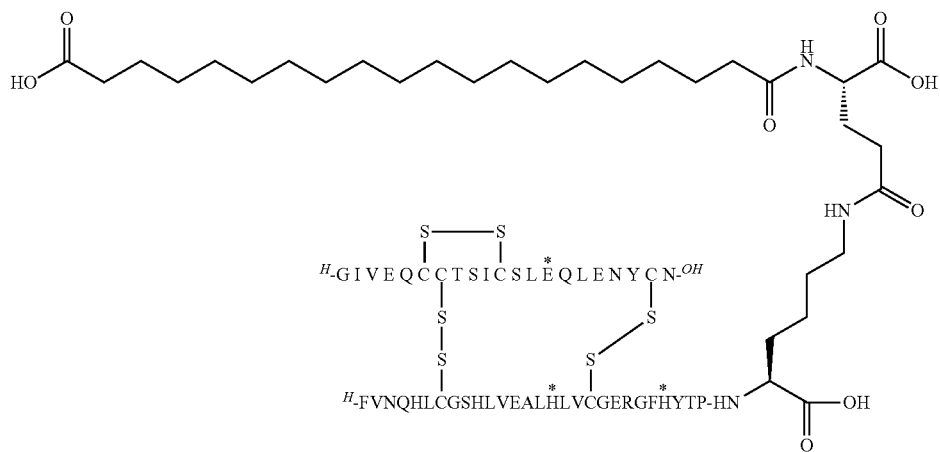
ES-MS: m/z=1523 (M+4)
Example 61, General Procedure (A)
A14E, B25H, B27K(N$^\epsilon$Eicosanedioyl-γGlu), desB28, desB29, desB30 Human Insulin
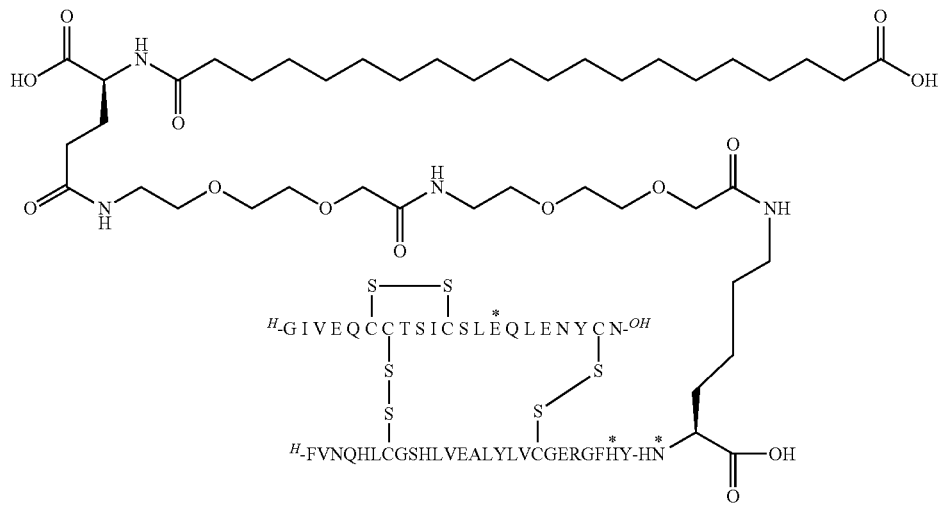
MALDI-TOF MS: m/z=6208

Example 62, General Procedure (A)
A14E, B25H, B29K(Nᵋოctadecanedioyl-γGlu-γGlu-γGlu), desB30 Human Insulin
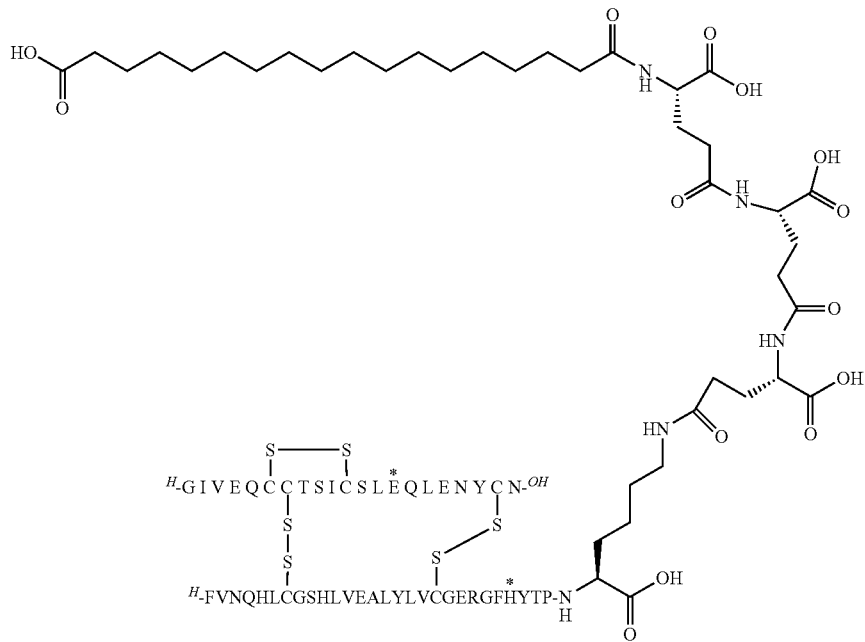
ES-MS: m/z=1587 (M+4)
The acylated insulins of the invention in following examples may be prepared similarly:
Example 63, General Procedure (A)
A14E, B25H, B26G, B27G, B28G, B29K(Nᵋოctadecandioyl-γGlu), desB30 Human Insulin
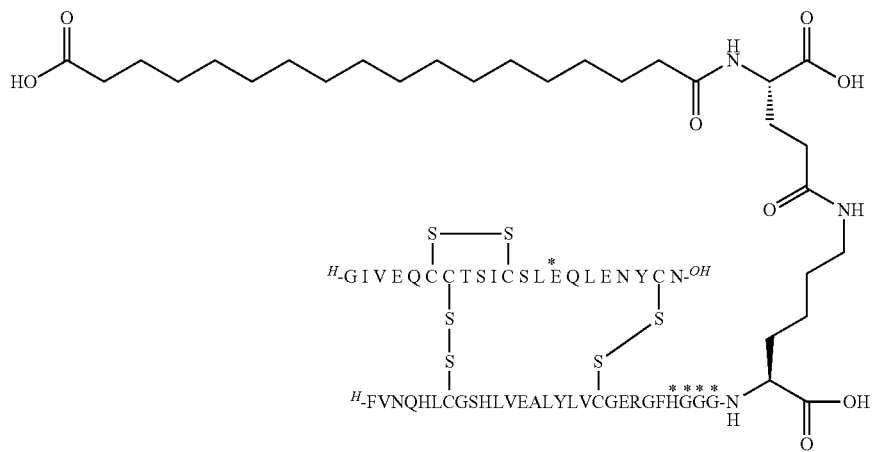

Example 64, General Procedure (A)
A14E, B25H, B26G, B27G, B28G, B29K(N$^\varepsilon$Eicosanedioyl-γGlu), desB30 Human Insulin
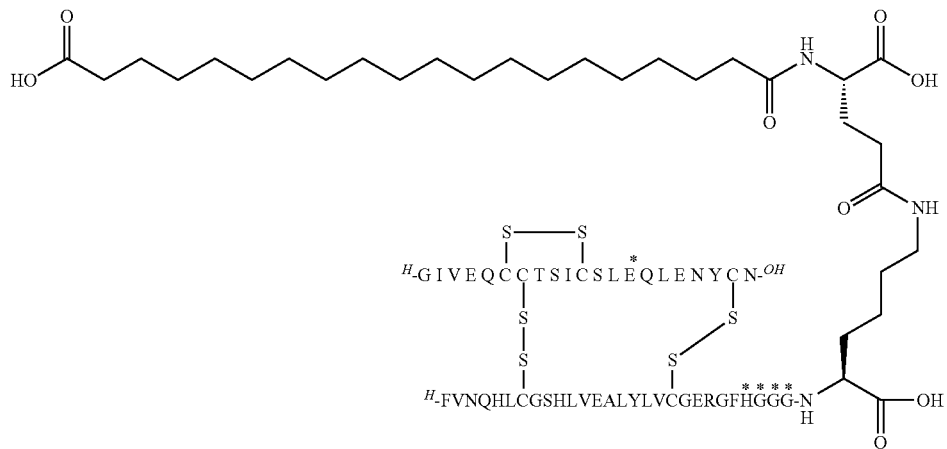
Example 65, General Procedure (A)
A14E, B25H, B26G, B27G, B28G, B29K(N$^\varepsilon$Octadecandioyl), desB30 Human Insulin
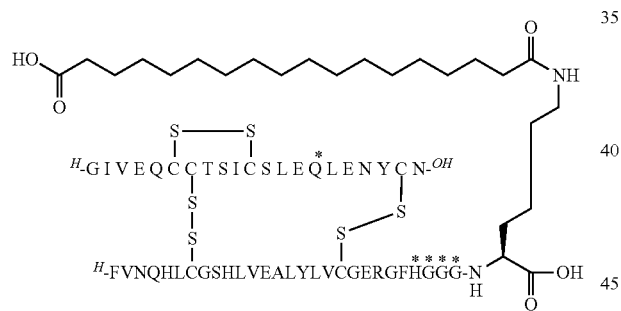
Example 66, General Procedure (A)
A14E, B25H, B26G, B27G, B28G, B29K(N$^\varepsilon$Eicosanedioyl), desB30 Human Insulin
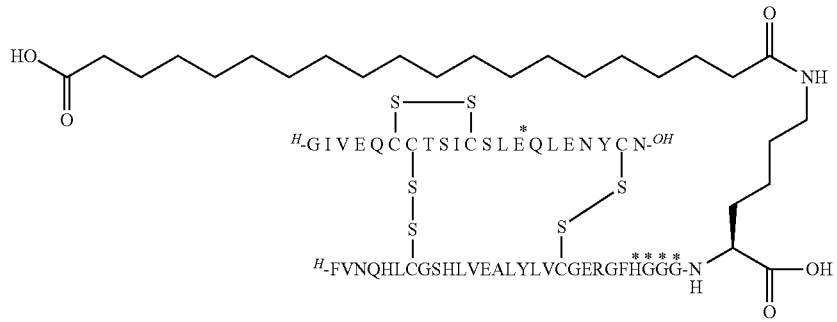

Example 67, General Procedure (A)
A14E, B25H, B29K(Nᵉ Docosanedioyl-γGlu), desB30 Human Insulin
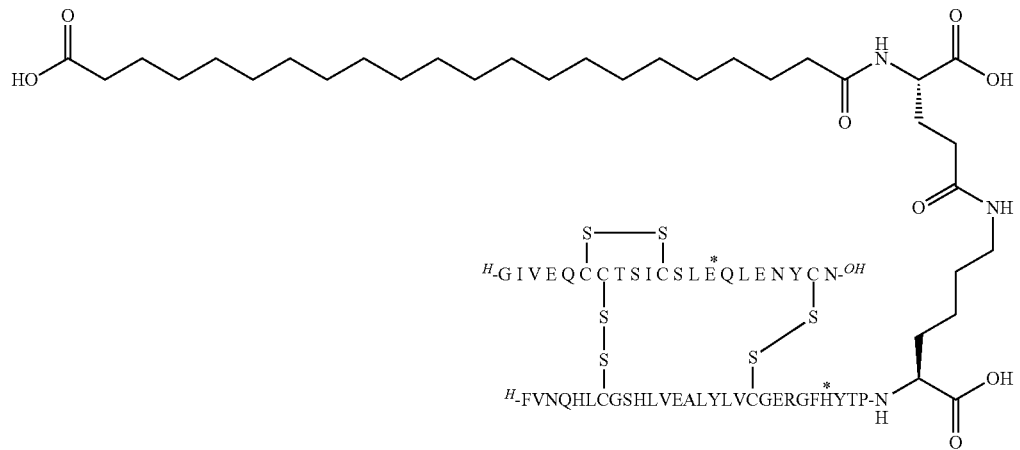
Example 68, General Procedure (A)
A14E, B25H, B29K(Nᵉ Docosanedioyl-γGlu-γGlu), desB30 Human Insulin
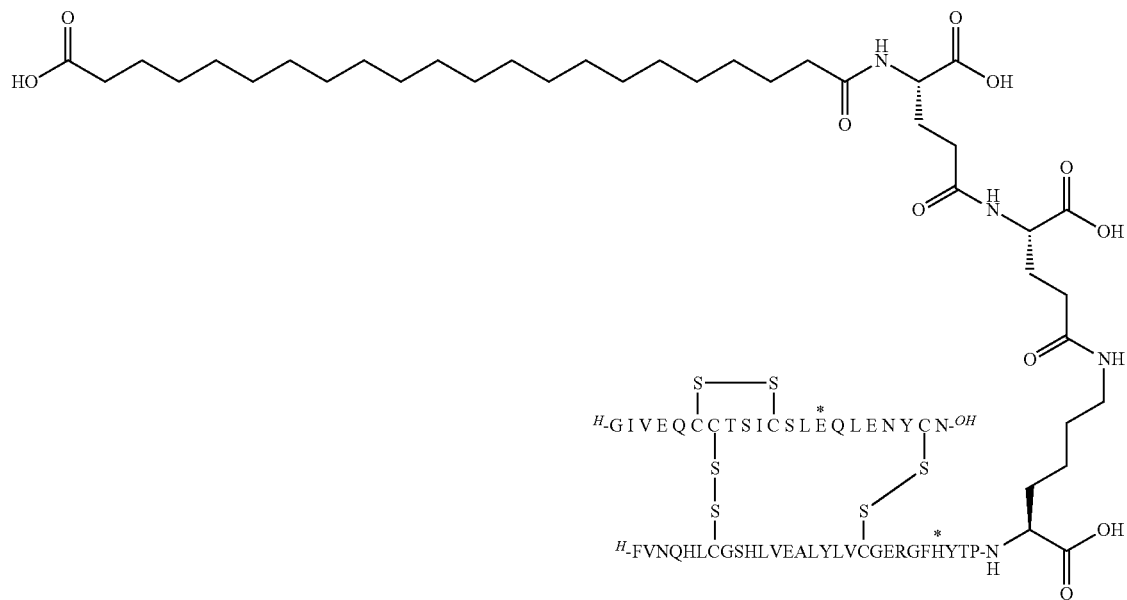

Example 69, General Procedure (A)
A14E, B25H, B29K(Nᵉ Icosanedioyl-γGlu-OEG-OEG-γGlu), desB30 Human Insulin
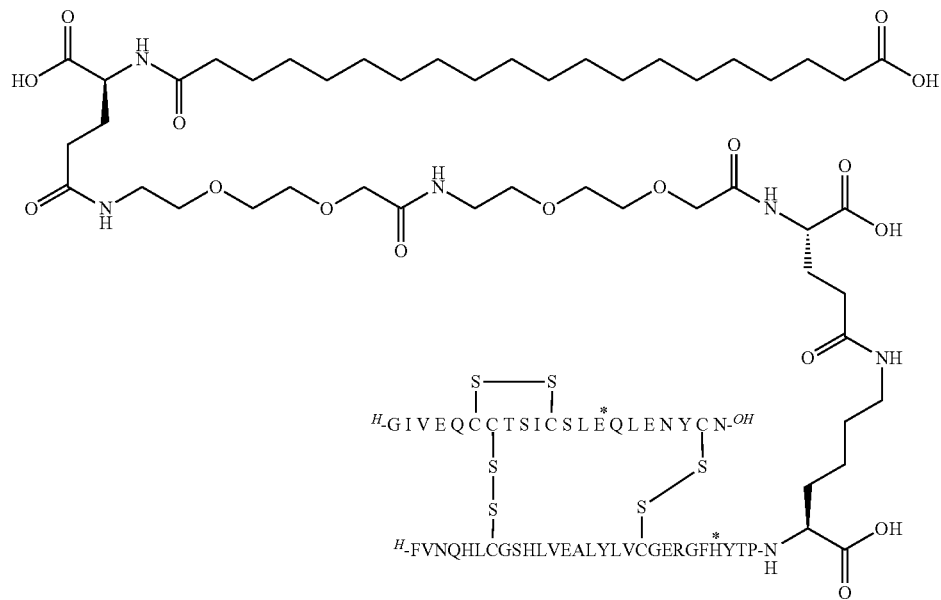
Example 70, General Procedure (A)
A14E, B25H, B29K(Nᵉ Octadecanedioyl-γGlu-OEG-OEG-γGlu), desB30 Human Insulin
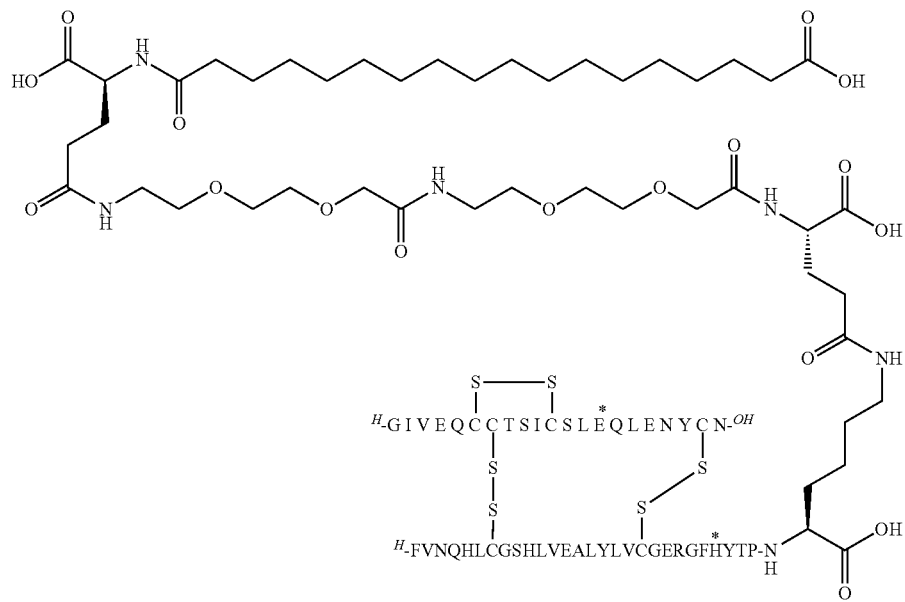

Example 71, General Procedure (A)

A14E, B25H, B29K(N$^\varepsilon$ (N-Icosanedioyl-N-carboxymethyl)-βAla), desB30 Human Insulin

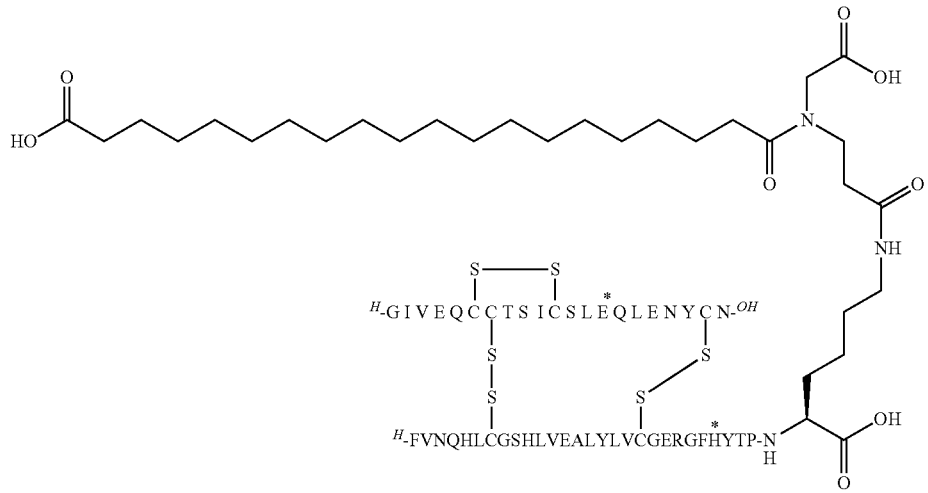

Example 72, General Procedure (A)

A14E, B25H, B29K(N$^\varepsilon$3-[2-(2-{2-[2-(17-Carboxyheptadecanoylamino)ethoxy]ethoxy}ethoxy)-ethoxy] propionyl-γGlu), desB30 Human Insulin

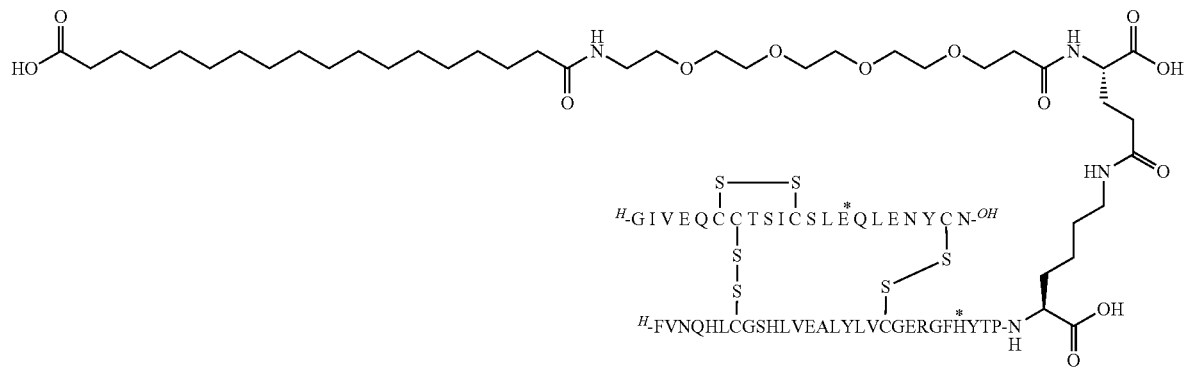

Example 73, General Procedure (A)

A14E, B25H, B29K(N$^\varepsilon$3-[2-(2-{2-[2-(19-Carboxynonadecanoylamino)ethoxy]ethoxy}ethoxy) ethoxy]propionyl-γGlu), desB30 Human Insulin

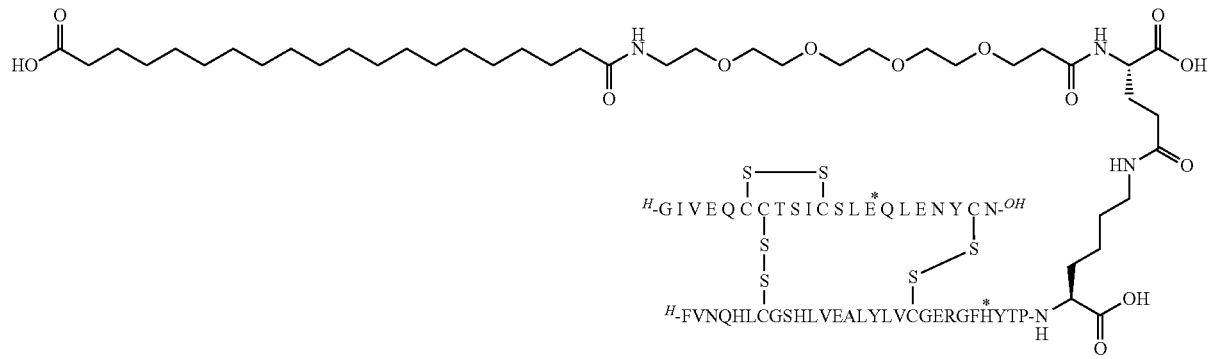

Example 74, General Procedure (A)
A14E, B25H, B29K(N$^\varepsilon$Octadecandioyl-γGlu-(3-(2-{2-[2-(2-aminoethoxy)ethoxy]ethoxy}ethoxy)-propionyl), desB30 Human Insulin
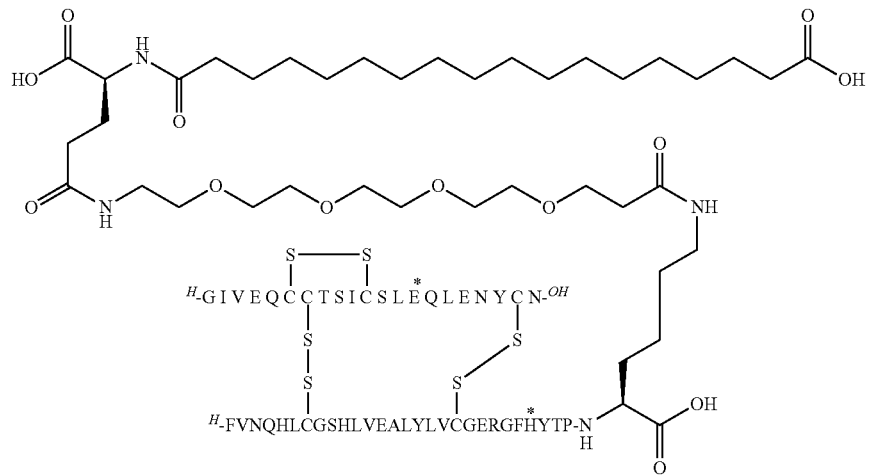
Example 75, General Procedure (A)
A14E, B25H, B29K(N$^\varepsilon$Octadecandioyl-γGlu-(3-(2-{2-[2-(2-aminoethoxy)ethoxy]ethoxy}ethoxy)propionyl-γGlu), desB30 Human Insulin
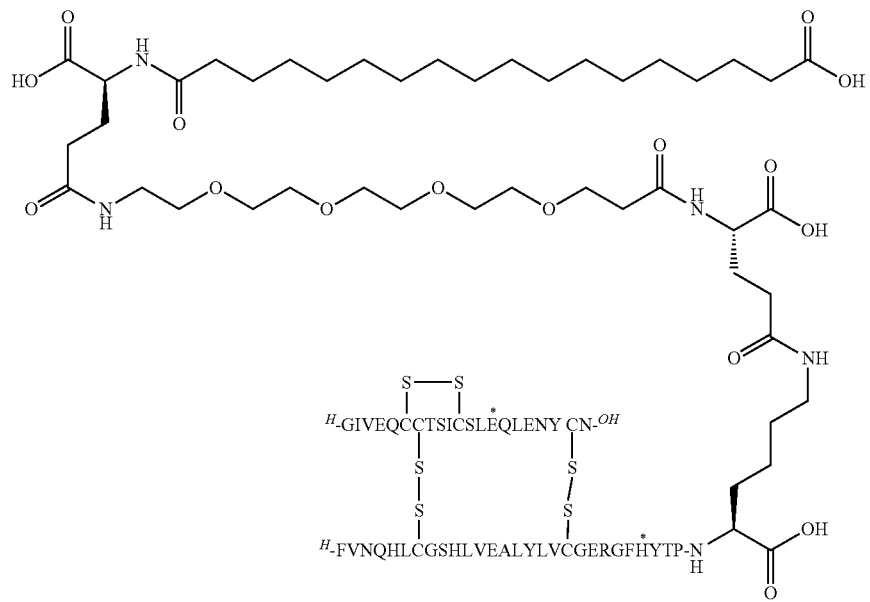

Example 76, General Procedure (A)
A14E, B25H, B29K(N^εIcosanedioyl-γGlu-(3-(2-{2-[2-(2-aminoethoxy)ethoxy]ethoxy}ethoxy)-propionyl), desB30 Human Insulin
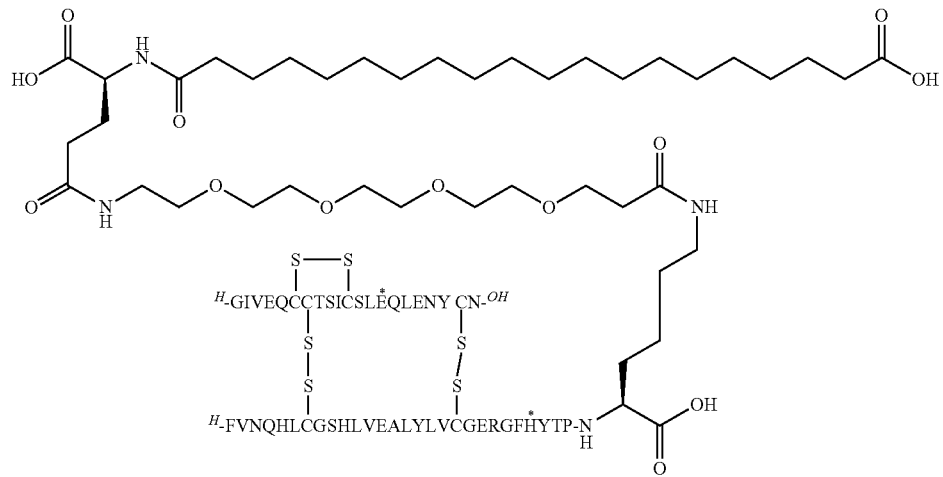
Example 77, General Procedure (A)
A14E, B25H, B29K(N^ε4-([4-({17-Carboxynonadecanoylamino}methyl)trans-cyclohexane-carbonyl]-γGlu), desB30 Human Insulin
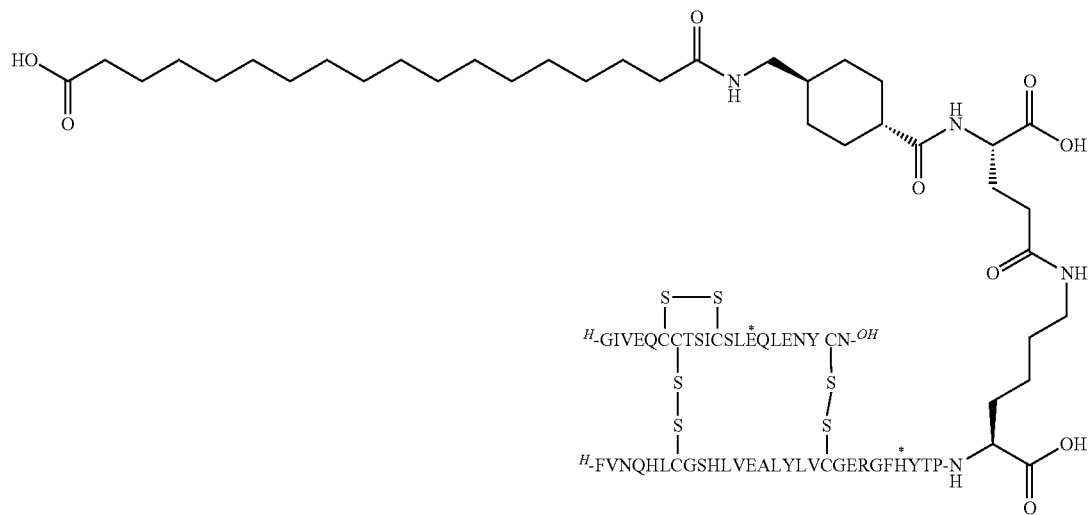

Example 78, General Procedure (A)
A14E, B25H, B29K(Nᵋ4-([4-({17-Carboxyheptadecanoylamino}methyl)trans-cyclo-hexane-carbonyl]-γGlu-γGlu), desB30 Human Insulin
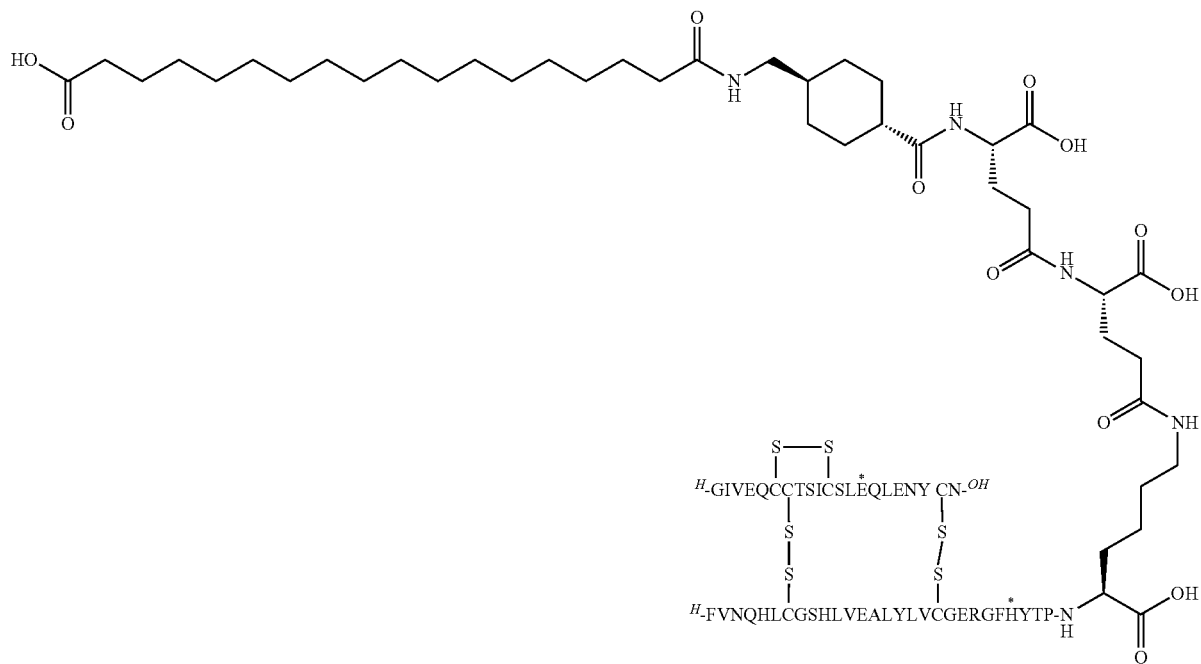
Example 79, General Procedure (A)
A14E, B28D, B29K(Nᵋhexadecandioyl-γGlu), desB30 Human Insulin
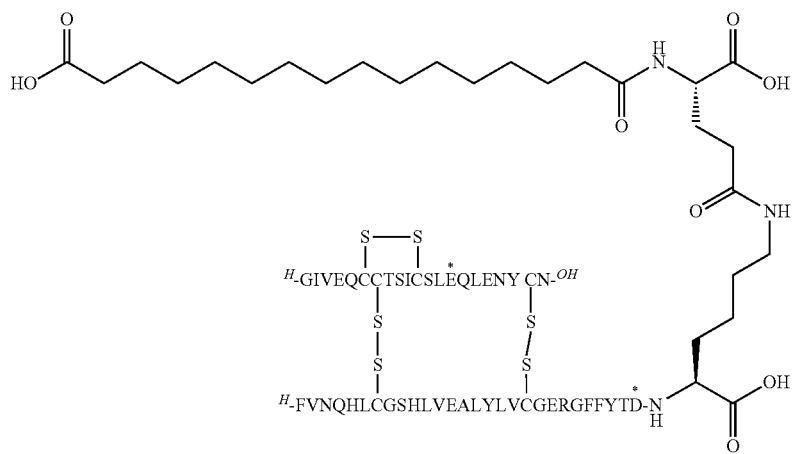

Example 80, General Procedure (A)
A14E, B28D, B29K(N$^\varepsilon$Eicosanedioyl-γGlu), desB30 Human Insulin
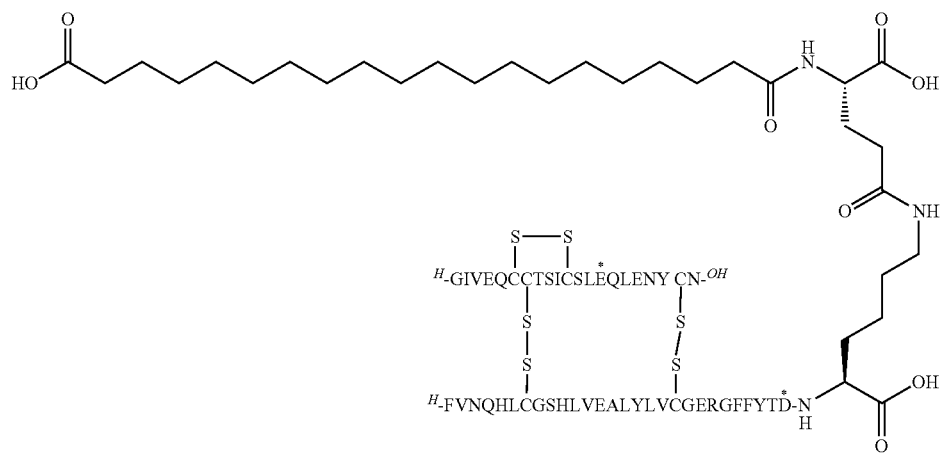
Example 81, General Procedure (A)
A14E, B28D, B29K(N$^\varepsilon$Octadecandioyl-γGlu-OEG-OEG), desB30 Human Insulin
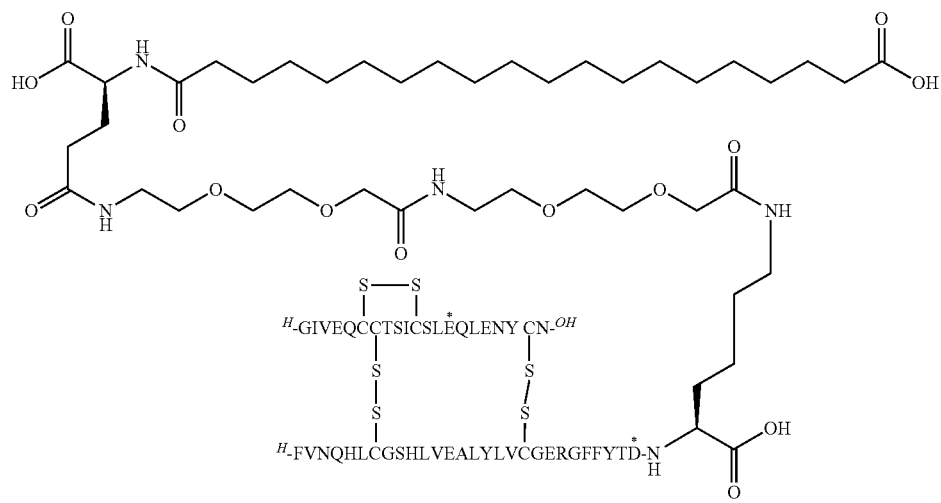

Example 82, General Procedure (A)
A14E, B28D, B29K(N$^\varepsilon$Eicosanedioyl-γGlu-OEG-OEG), desB30 Human Insulin
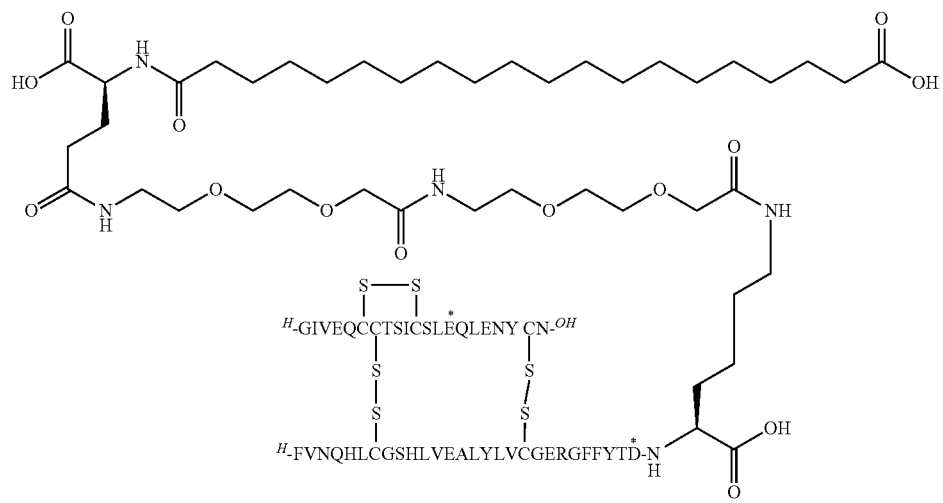
Example 83, General Procedure (A)
A14E, B28E, B29K(N$^\varepsilon$Hexadecandioyl-γGlu), desB30 Human Insulin
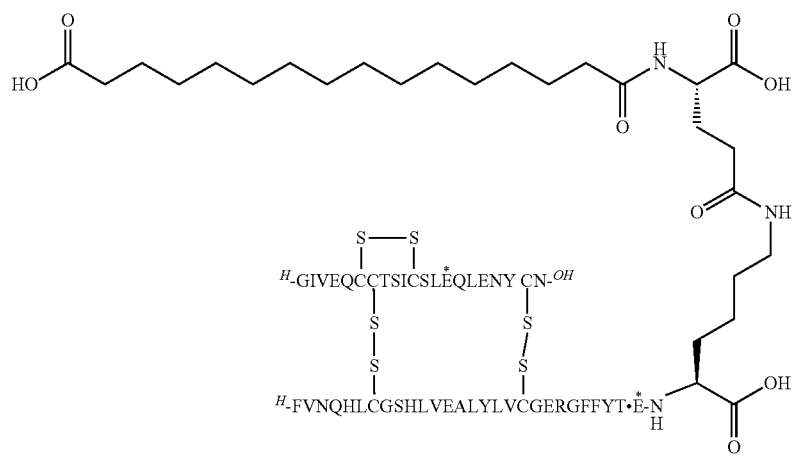

Example 84, General Procedure (A)
A14E, B28E, B29K(N^εOctadecandioyl-γGlu), desB30 Human Insulin
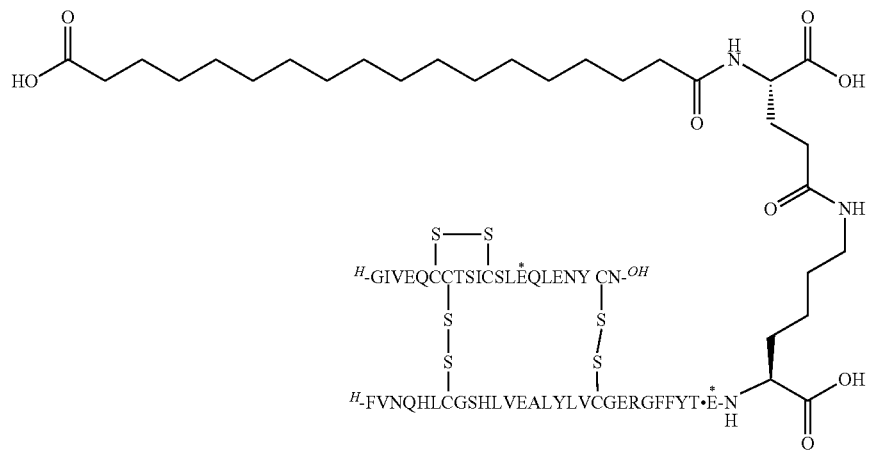
Example 85, General Procedure (A)
A14E, B28E, B29K(N^εEicosanedioyl-γGlu), desB30 Human Insulin
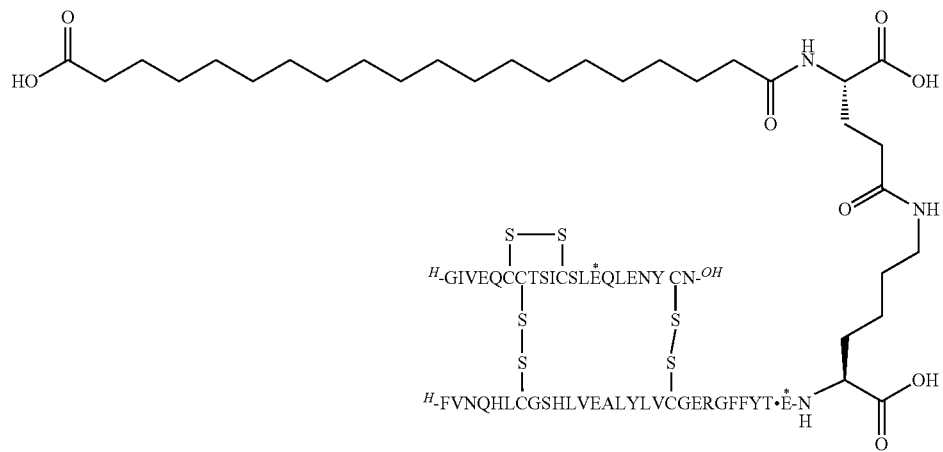

Example 86, General Procedure (A)
A14E, B28E, B29K(N^εOctadecandioyl-γGlu-OEG-OEG), desB30 Human Insulin
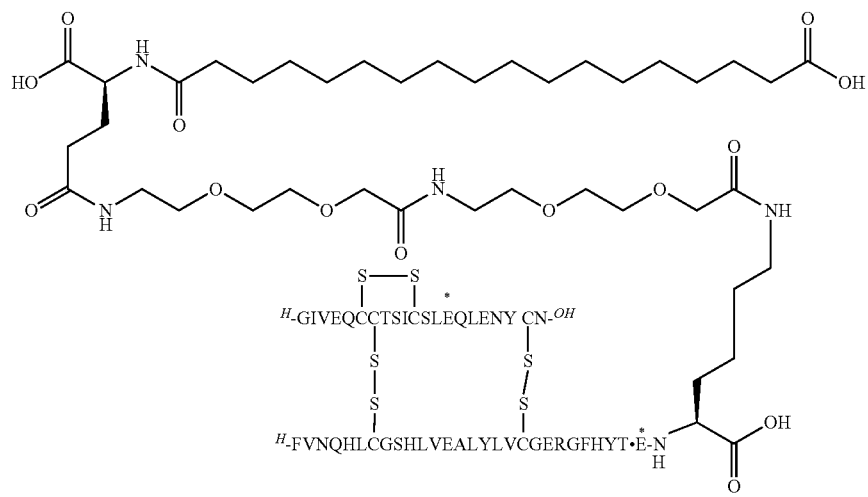
Example 87, General Procedure (A)
A14E, B28E, B29K(N^εEicosanedioyl-γGlu-OEG-OEG), desB30 Human Insulin
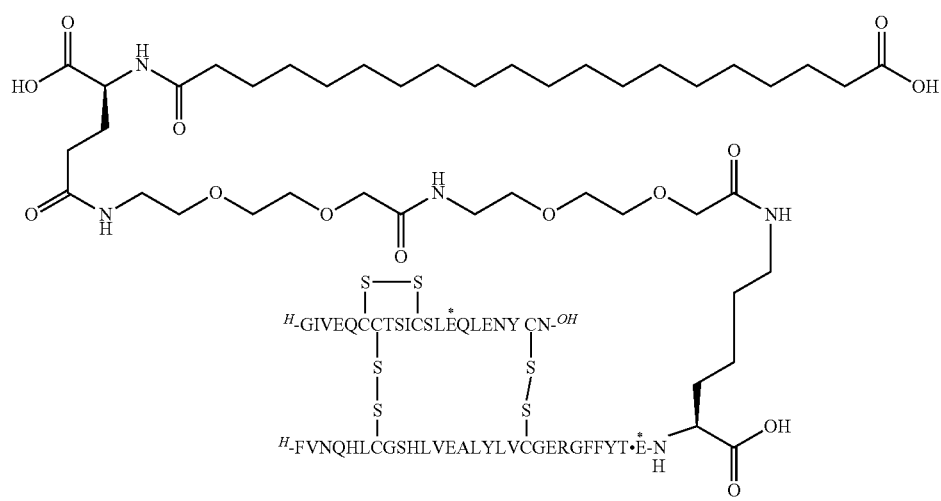

Example 88, General Procedure (A)
5
A14E, B1E, B28E, B29K(NᵋHexadecandioyl-γGlu), desB30 Human Insulin
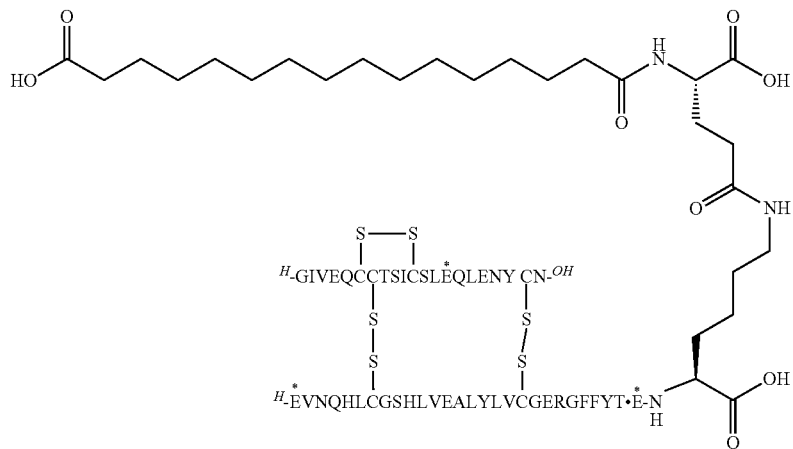
Example 89, General Procedure (A)
40
A14E, B1E, B28E, B29K(NᵋOctadecandioyl-γGlu), desB30 Human Insulin
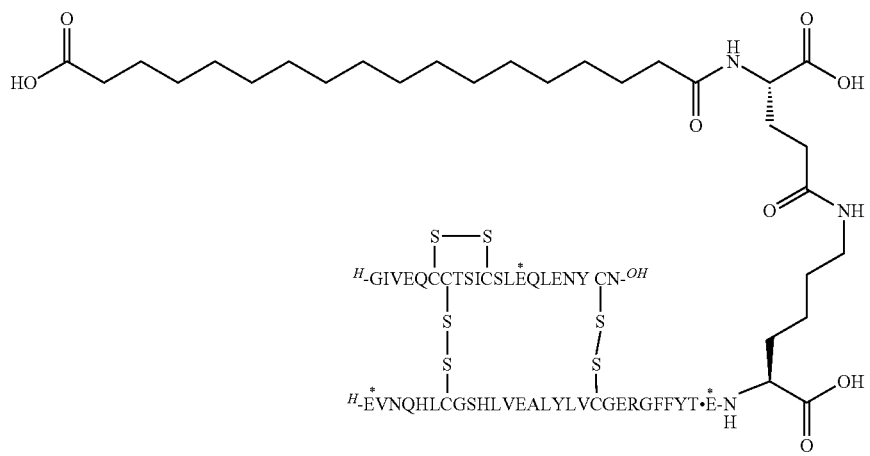

Example 90, General Procedure (A)
A14E, B1E, B28E, B29K(N^εEicosanedioyl-γGlu), desB30 Human Insulin
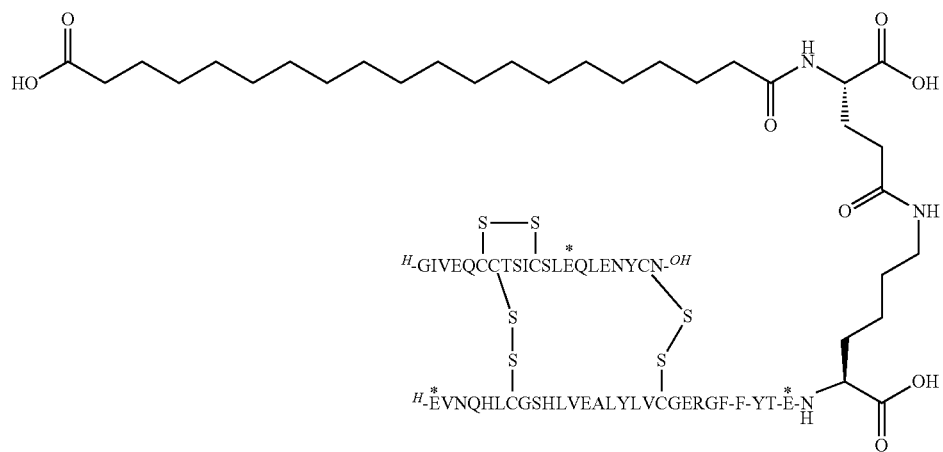
Example 91, General Procedure (A)
A14E, B1E, B28E, B29K(N^εHexadecandioyl-γGlu-OEG-OEG), desB30 Human Insulin
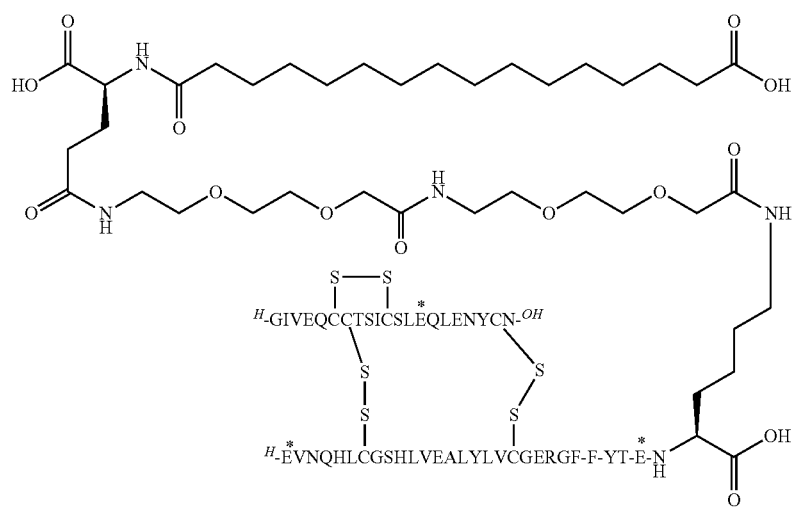

Example 92, General Procedure (A)
A14E, B1E, B28E, B29K(N^εOctadecandioyl-γGlu-OEG-OEG), desB30 Human Insulin
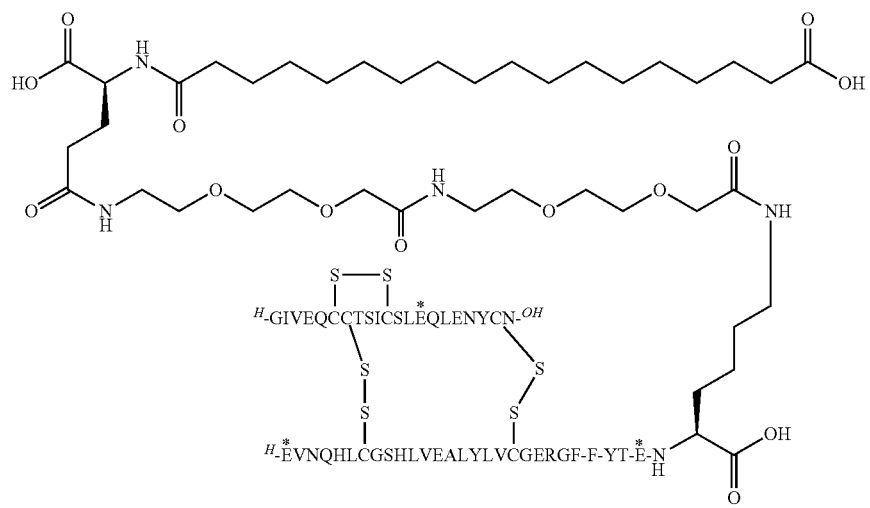
Example 93, General Procedure (A)
A14E, B1E, B28E, B29K(N^εEicosanedioyl-γGlu-OEG-OEG), desB30 Human Insulin
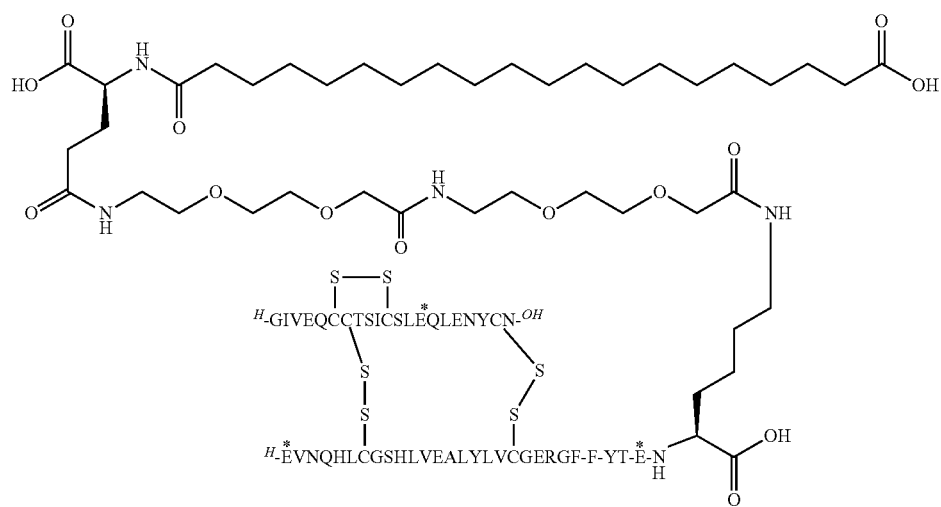

Example 94, General Procedure (A)
A14E, B1E, B27E, B28E,
B29K(NᵋHexadecandioyl-γGlu), desB30 Human Insulin
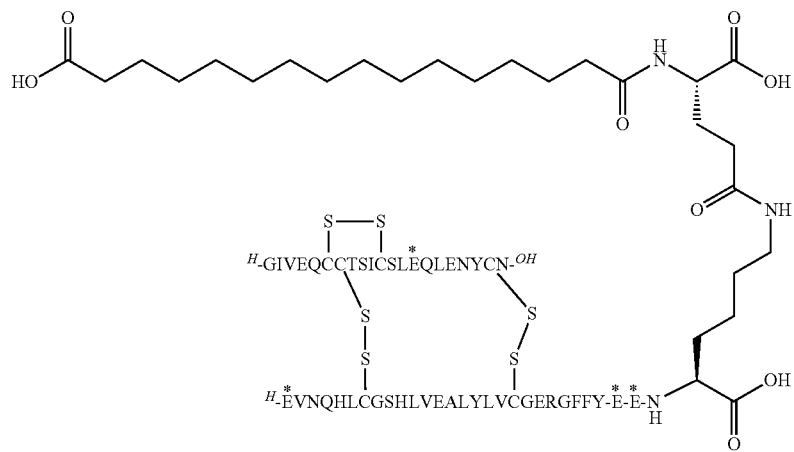
Example 95, General Procedure (A)
A14E, B1E, B27E, B28E,
B29K(NᵋOctadecandioyl-γGlu), desB30 Human Insulin
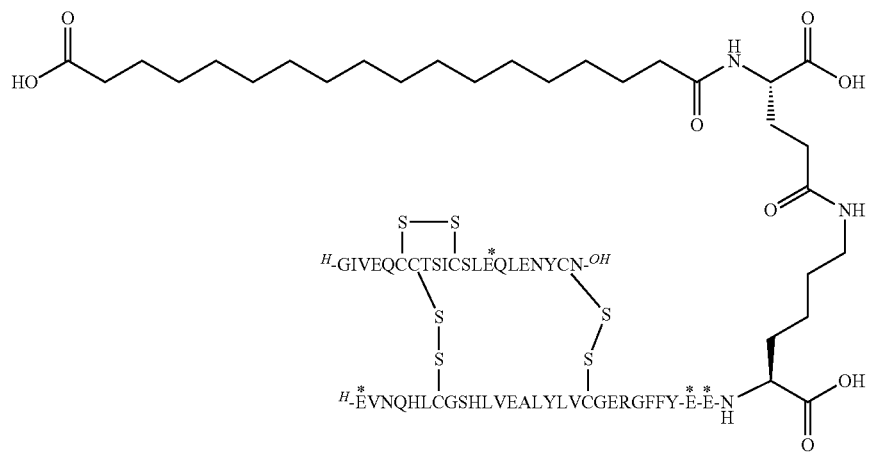

Example 96, General Procedure (A)
A14E, B1E, B27E, B28E, B29K(N$^\varepsilon$Eicosanedioyl-γGlu), desB30 Human Insulin
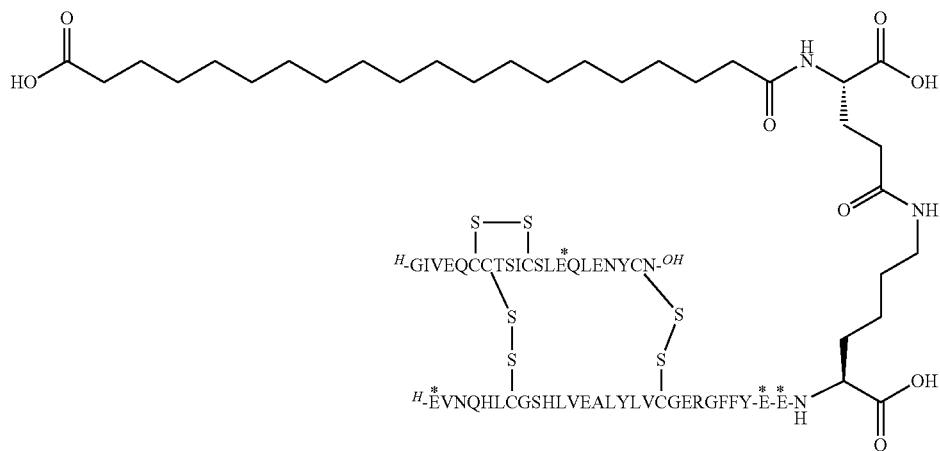
Example 97, General Procedure (A)
A14E, B1E, B27E, B28E, B29K(N$^\varepsilon$Hexadecandioyl-γGlu-OEG-OEG), desB30 Human Insulin
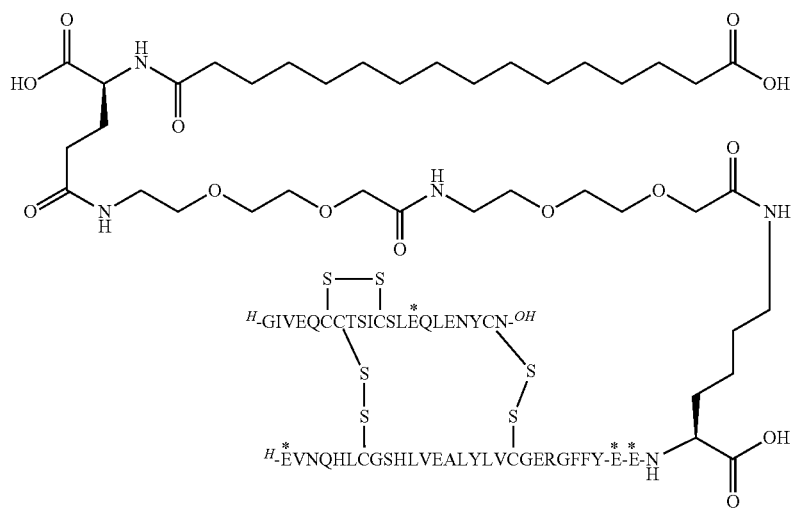

Example 98, General Procedure (A)
A14E, B1E, B27E, B28E, B29K
(N^εOctadecandioyl-γGlu-OEG-OEG), desB30
Human Insulin
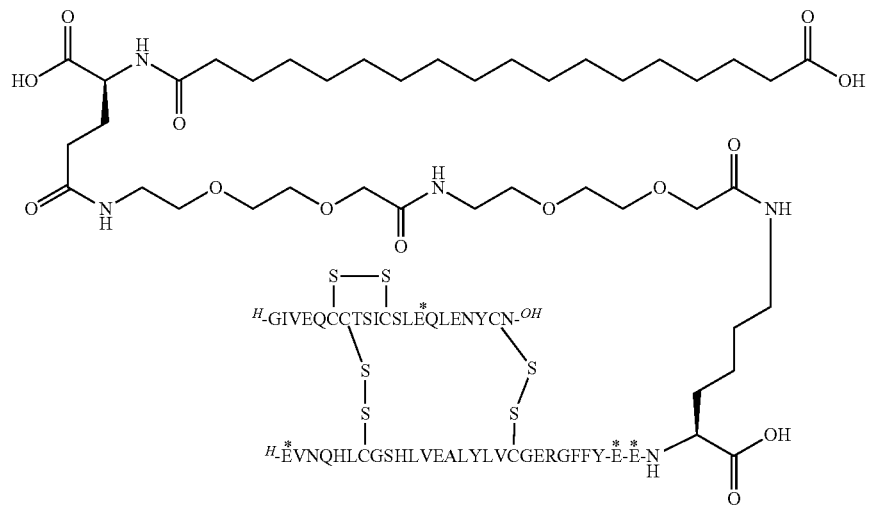
Example 99, General Procedure (A)
A14E, B1E, B27E, B28E, B29K(N^εEicosanedioyl-
γGlu-OEG-OEG), desB30 Human Insulin
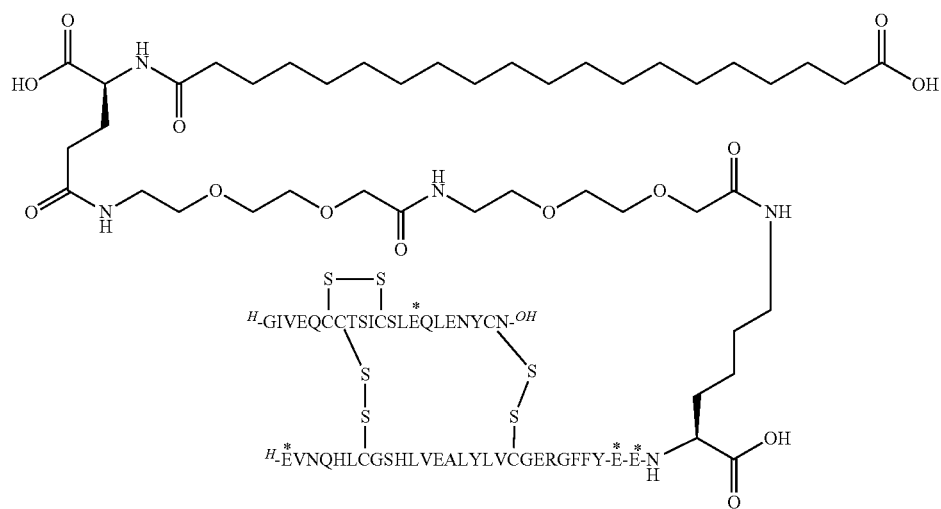

Example 100, General Procedure (A)
A14E, B1E, B25H, B28E, B29K(Nᵋ Hexadecandioyl-γGlu), desB30 Human Insulin
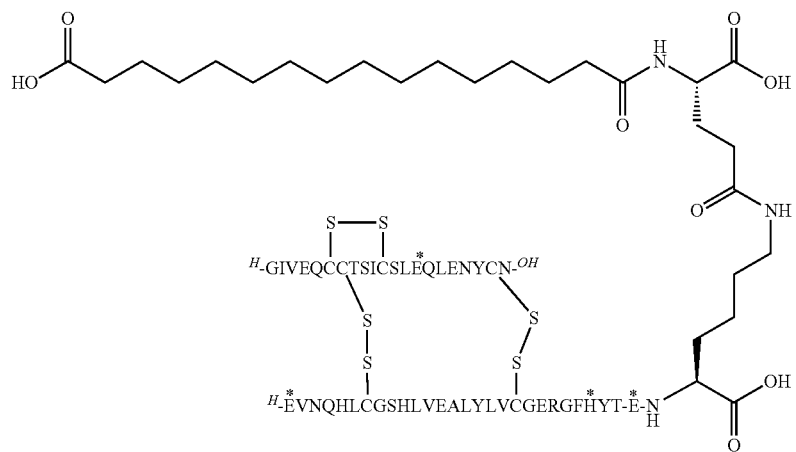
Example 101, General Procedure (A)
A14E, B1E, B25H, B28E, B29K(Nᵋ Octadecandioyl-γGlu), desB30 Human Insulin
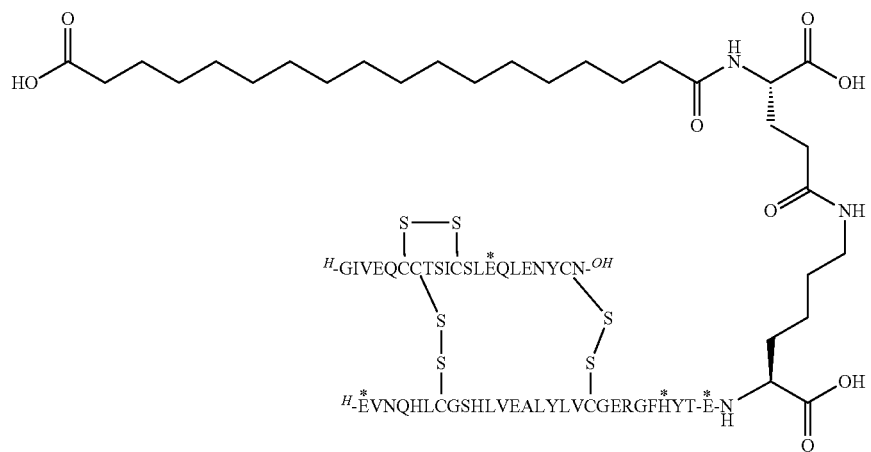

Example 102, General Procedure (A)
A14E, B1E, B25H, B28E, B29K(N^ε Eicosanedioyl-γGlu), desB30 Human Insulin
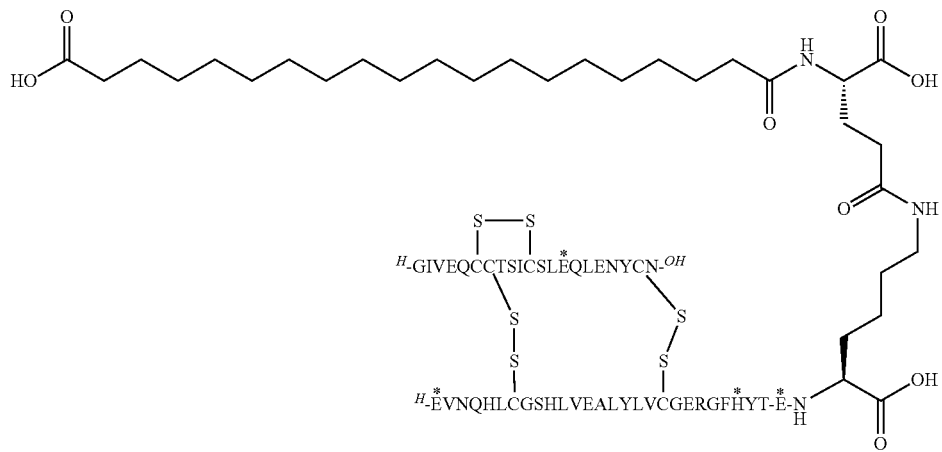
Example 103, General Procedure (A)
A14E, B1E, B25H, B28E, B29K (N^ε Hexadecandioyl-γGlu-OEG-OEG), desB30 Human Insulin
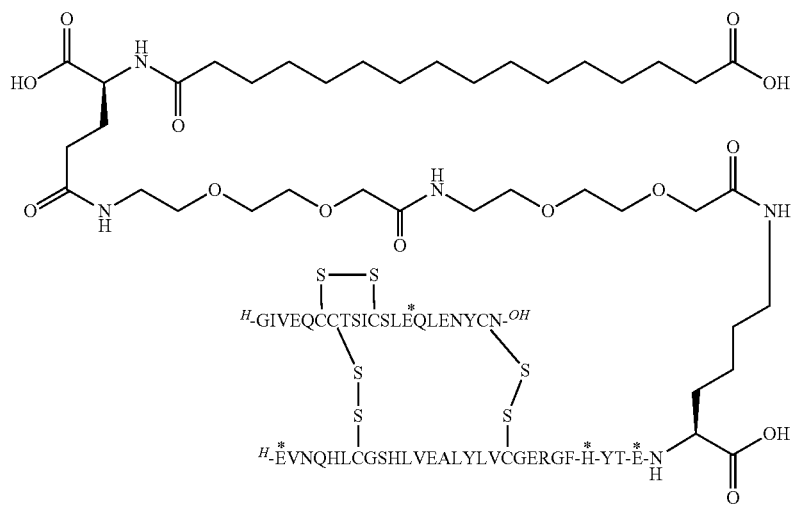

Example 104, General Procedure (A)
A14E, B1E, B25H, B28E, B29K
(N$^\varepsilon$Octadecandioyl-γGlu-OEG-OEG), desB30
Human Insulin
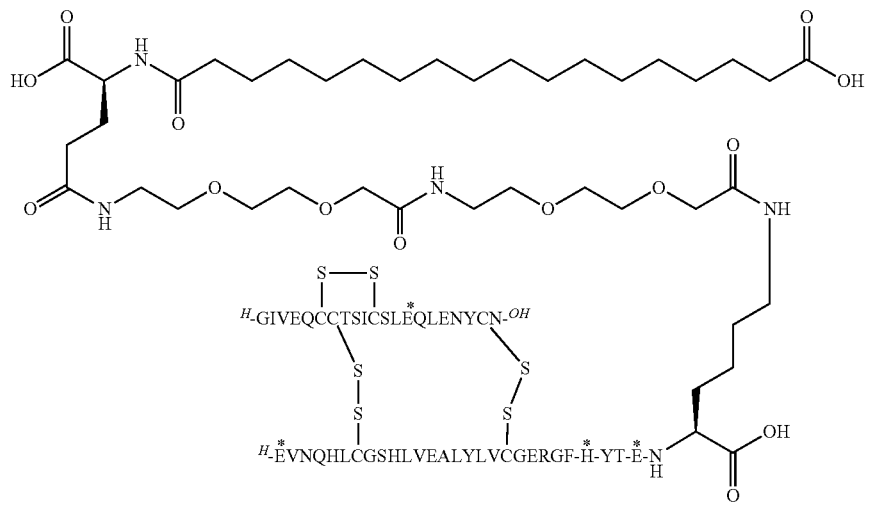
Example 105, General Procedure (A)
A14E, B1E, B25H, B28E, B29K(N$^\varepsilon$Eicosanedioyl-
γGlu-OEG-OEG), desB30 Human Insulin
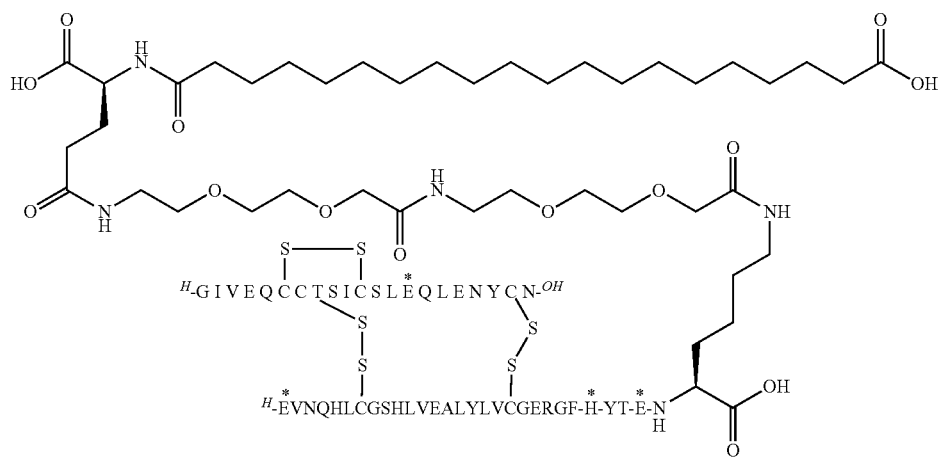

Example 106, General Procedure (A)
A14E, B1E, B25H, B27E, B28E, B29K(NᵋHexadecandioyl-γGlu), desB30 Human Insulin
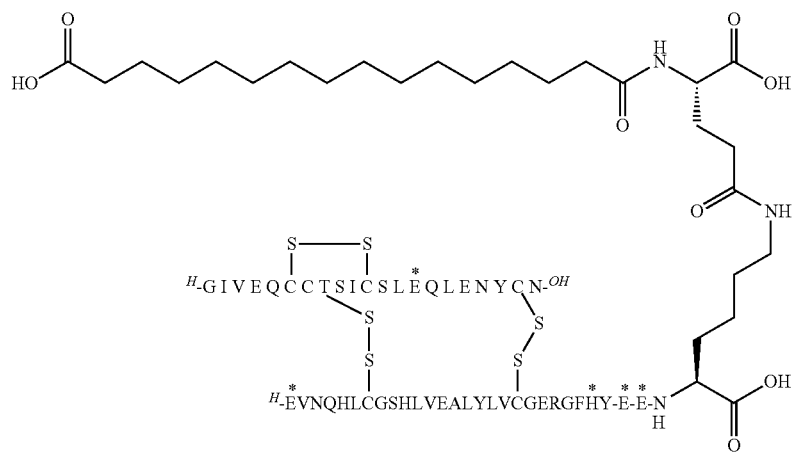
Example 107, General Procedure (A)
A14E, B1E, B25H, B27E, B28E, B29K(NᵋOctadecandioyl-γGlu), desB30 Human Insulin
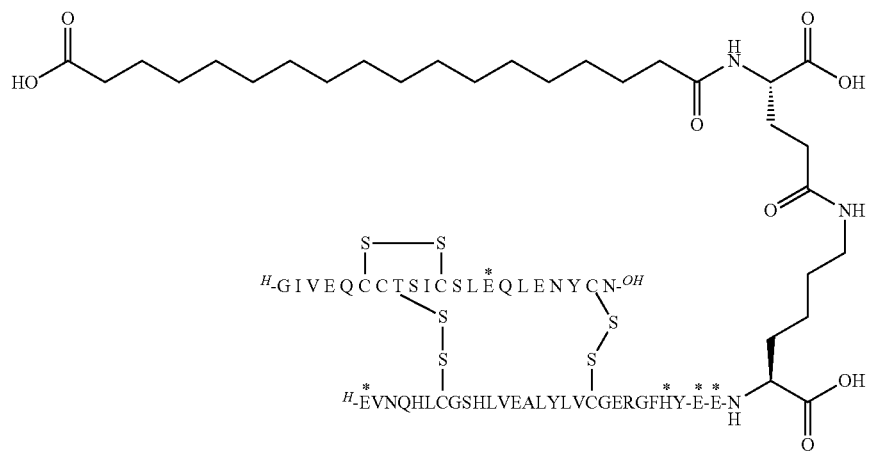

Example 108, General Procedure (A)
A14E, B1E, B25H, B27E, B28E, B29K(N^εEicosanedioyl-γGlu), desB30 Human Insulin
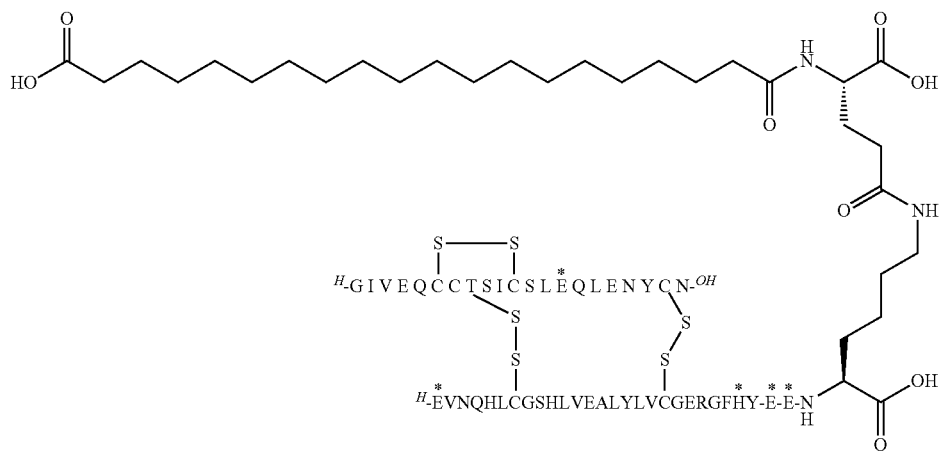
Example 109, General Procedure (A)
A14E, B1E, B25H, B27E, B28E, B29K(N^εHexadecandioyl-γGlu-OEG-OEG), desB30 Human Insulin
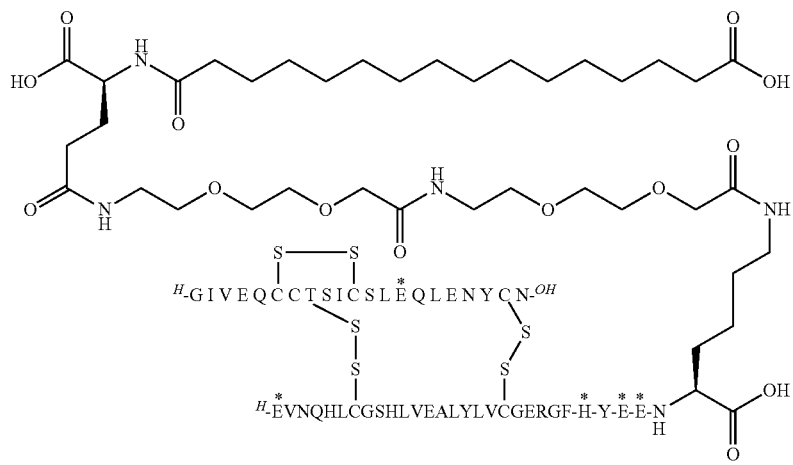

Example 110, General Procedure (A)
A14E, B1E, B25H, B27E, B28E, B29K
(N^εOctadecandioyl-γGlu-OEG-OEG), desB30
Human Insulin
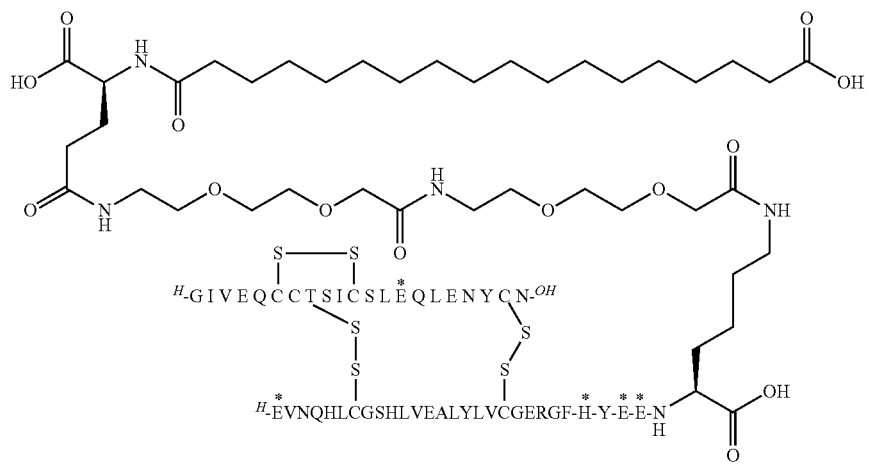
Example 111, General Procedure (A)
A14E, B1E, B25H, B27E, B28E, B29K
(N^εEicosanedioyl-γGlu-OEG-OEG), desB30 Human
Insulin
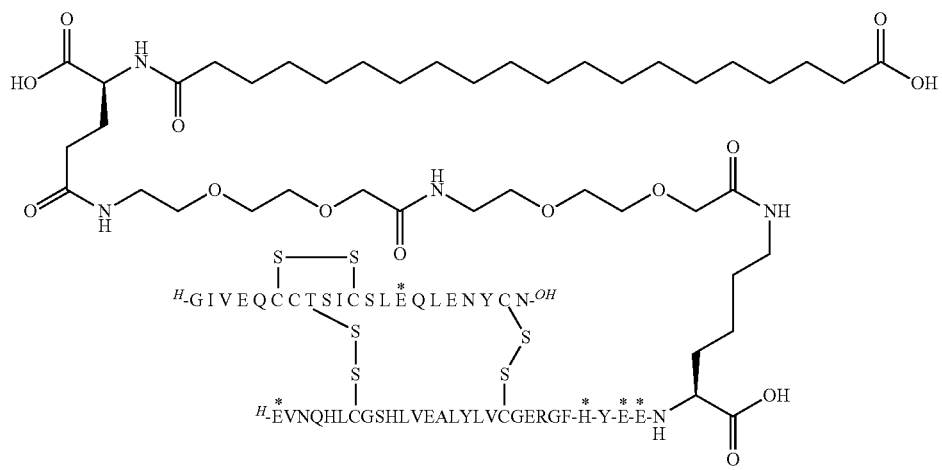

Example 112, General Procedure (A)
A14E, B28D, B29K(NᵉHexadecanedioyl-γGlu-OEG-OEG), desB30 Human Insulin
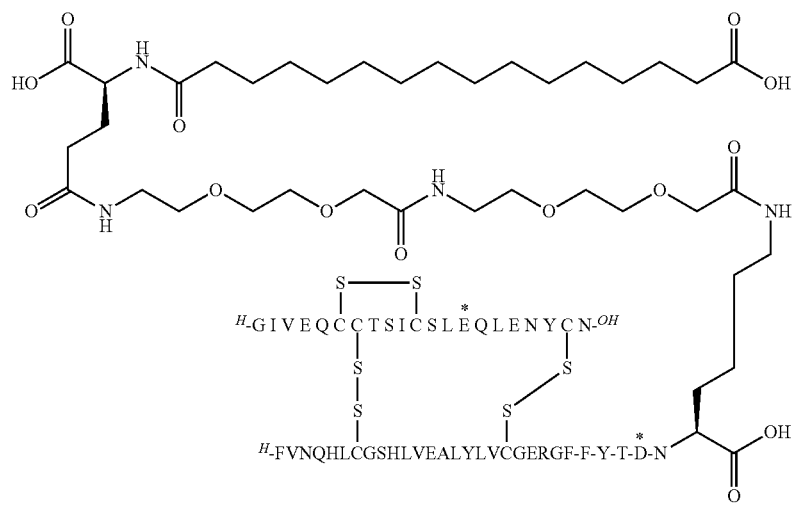
Example 113, General Procedure (A)
A14E, B28E, B29K(NᵉHexadecanedioyl-γGlu-OEG-OEG), desB30 Human Insulin
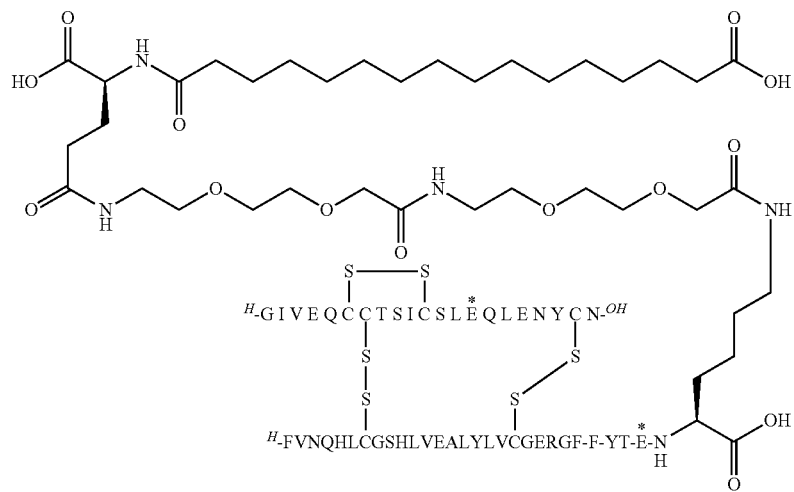

Example 114, General Procedure (A)
B25N, B27E, B29K(N$^\varepsilon$Eicosanedioyl-γGlu-OEG-OEG), desB30 Human Insulin
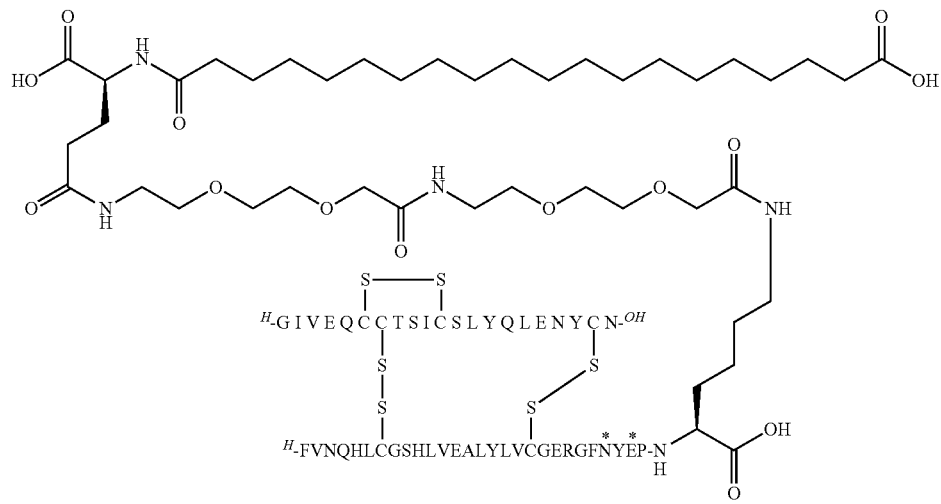
Example 115, General Procedure (A)
B25N, B27E, B29K(N$^\varepsilon$Octadecanedioyl-γGlu-OEG-OEG), desB30 Human Insulin
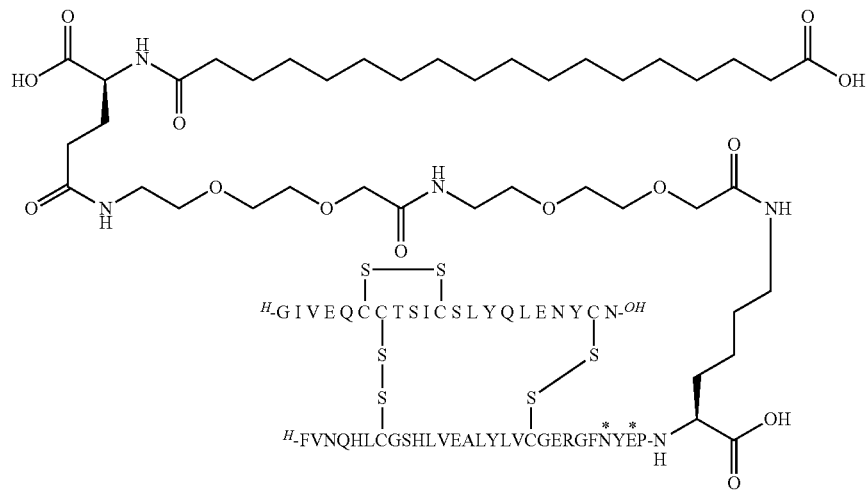

Example 116, General Procedure (A)
B25N, B27E, B29K(NᵋHexadecanedioyl-γGlu-OEG-OEG), desB30 Human Insulin
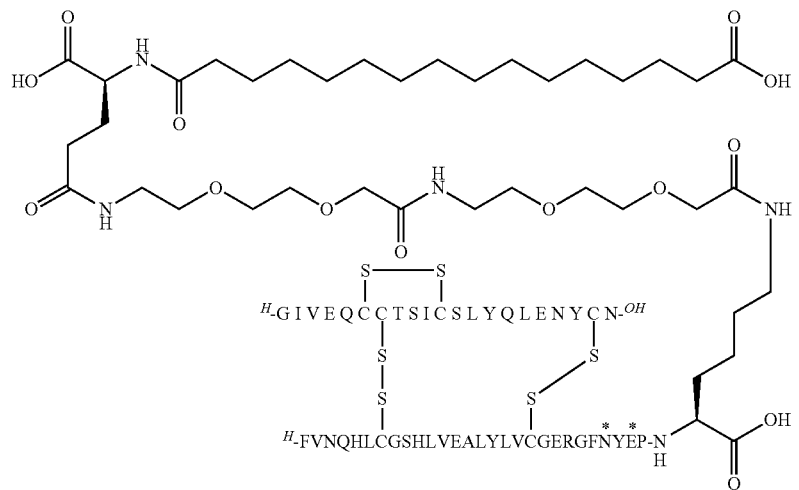
Example 117, General Procedure (A)
B25N, B27E, B29K(NᵋEicosanedioyl-γGlu), desB30 Human Insulin
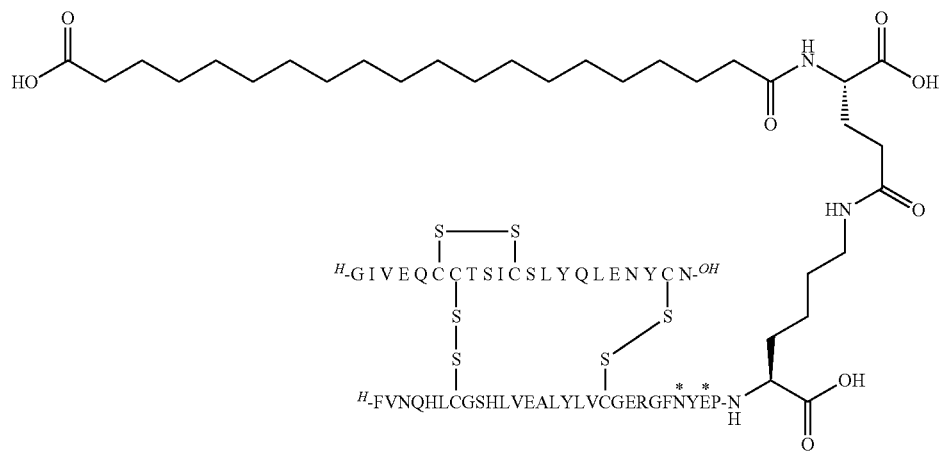

Example 118, General Procedure (A)
5
B25N, B27E, B29K(N^εOctadecanedioyl-γGlu), desB30 Human Insulin
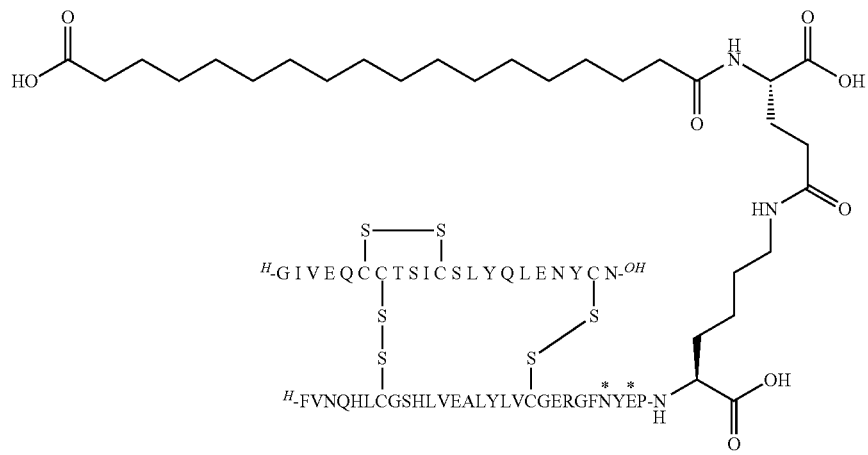
Example 119, General Procedure (A)
40
B25N, B27E, B29K(N^εHexadecanedioyl-γGlu), desB30 Human Insulin
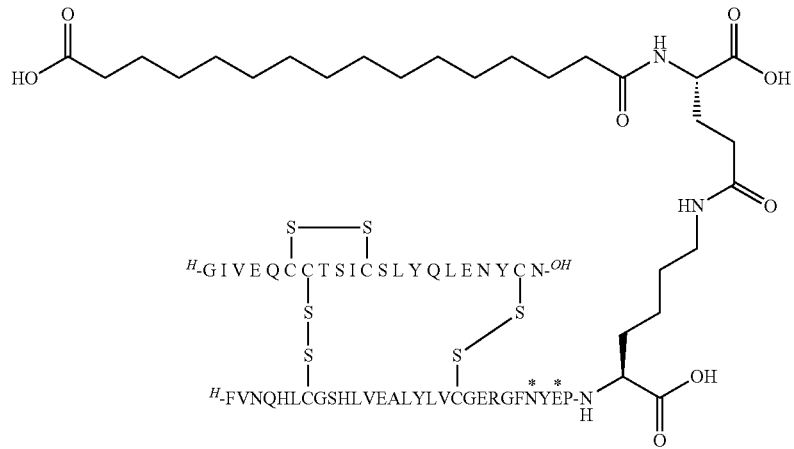

Example 120, General Procedure (A)
A8H, B25N, B27E, B29K(NᵋEicosanedioyl-γGlu-OEG-OEG), desB30 Human Insulin
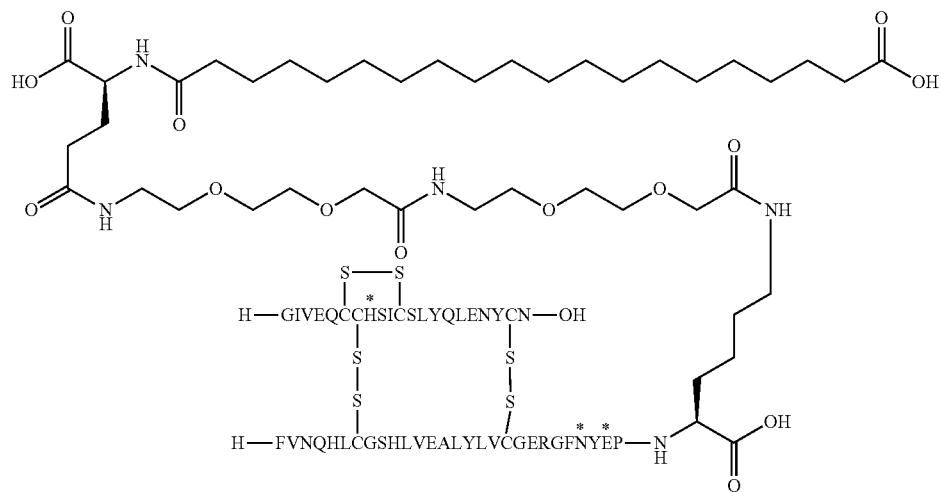
Example 121, General Procedure (A)
A8H, B25N, B27E, B29K(NᵋOctadecanedioyl-γGlu-OEG-OEG), desB30 Human Insulin
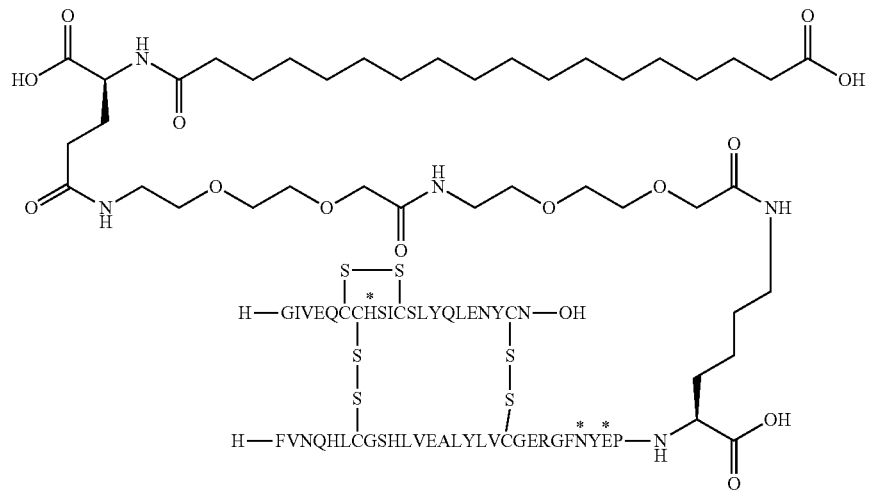

Example 122, General Procedure (A)
5
A8H, B25N, B27E, B29K(N$^\varepsilon$Hexadecanedioyl-
γGlu-OEG-OEG), desB30 Human Insulin
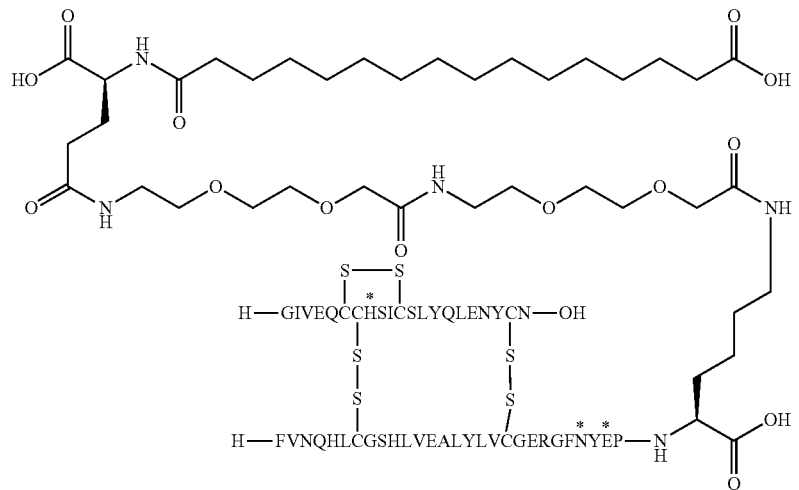
Example 123, General Procedure (A)
40
A8H, B25N, B27E, B29K(N$^\varepsilon$Eicosanedioyl-γGlu),
desB30 Human Insulin
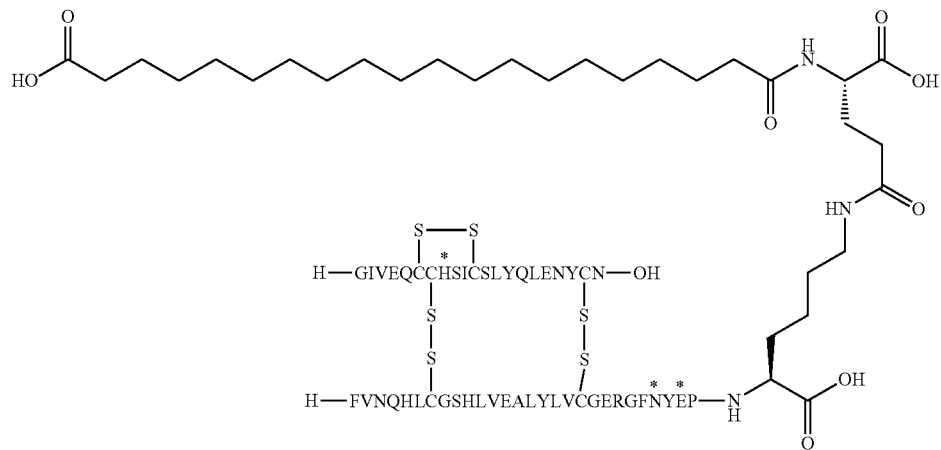

Example 124, General Procedure (A)
A8H, B25N, B27E,
B29K(N$^\varepsilon$Octadecanedioyl-γGlu), desB30 Human Insulin
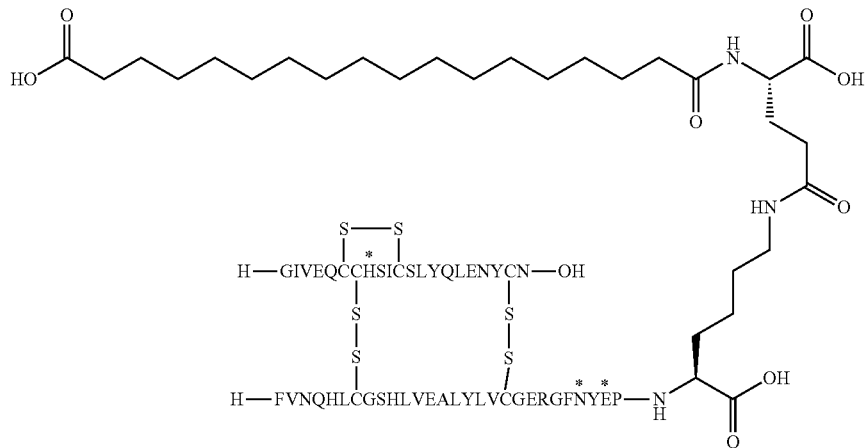
Example 125, General Procedure (A)
A8H, B25N, B27E,
B29K(N$^\varepsilon$Hexadecanedioyl-γGlu), desB30 Human Insulin
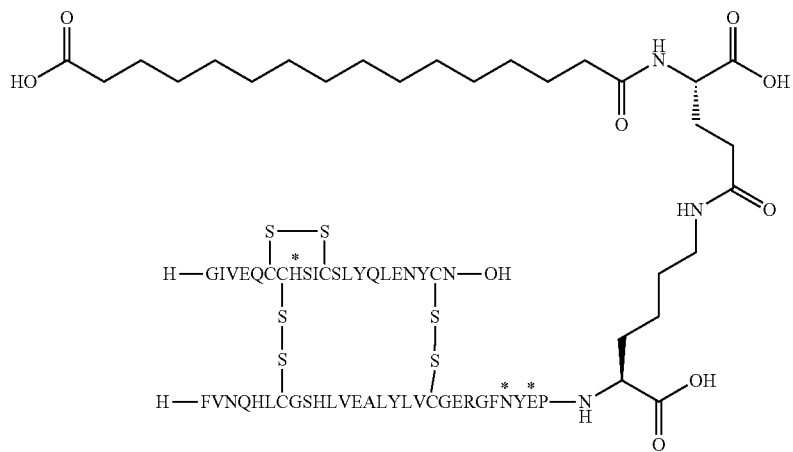

Example 126, General Procedure (A)
A14E, B25H, B29K(N$^{68}$ (N-Icosanedioyl-N-carboxymethyl)-βAla-OEG-OEG), desB30 Human Insulin
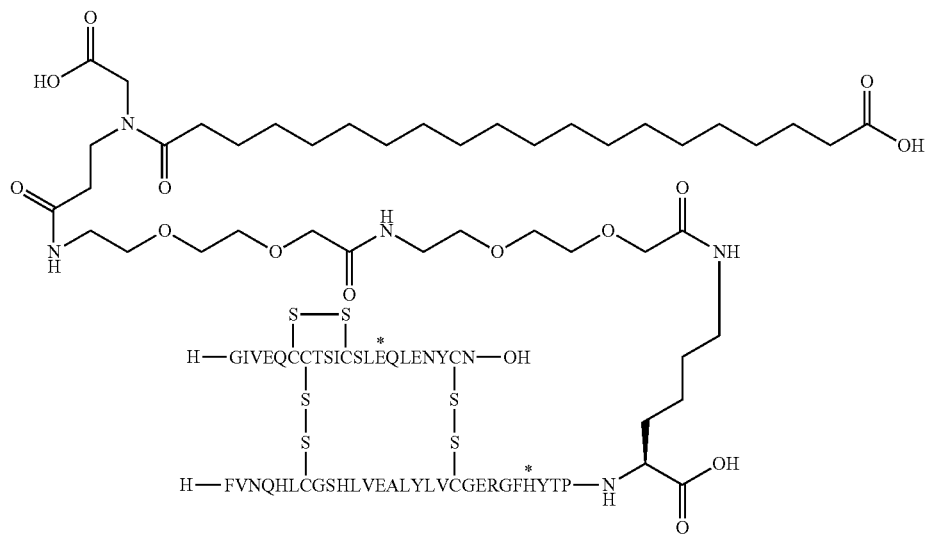
Example 127, General Procedure (A)
A14E, B25H, B29K(N$^{68}$ (N-Octadecanedioyl-N-carboxymethyl)-βAla-OEG-OEG), desB30 human insulin
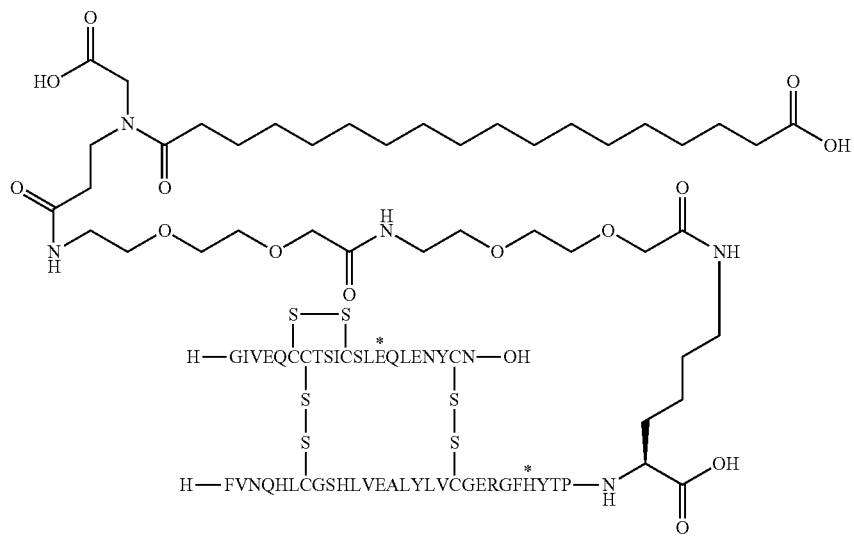

Example 128, General Procedure (A)

A14E, B25H, B29K(N$^{68}$ (N-Hexadecanedioyl-N-carboxymethyl)-βAla-OEG-OEG), desB30 human insulin

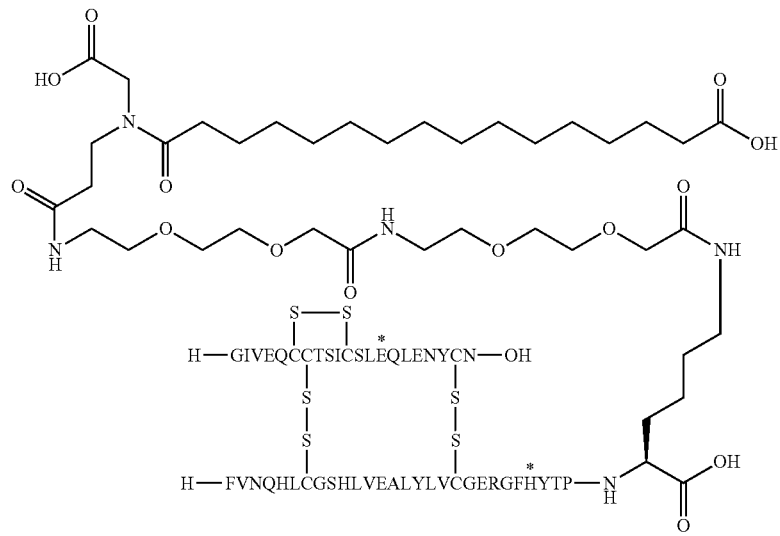

Example 129, General Procedure (A)

A14E, B25H, B29K(N$^\varepsilon$octadecanedioyl-γGlu-2-[(3-{2-[2-(3-aminopropoxy)ethoxy]ethoxy}propylcarbamoyl)methoxy]acetyl), desB30 Human Insulin

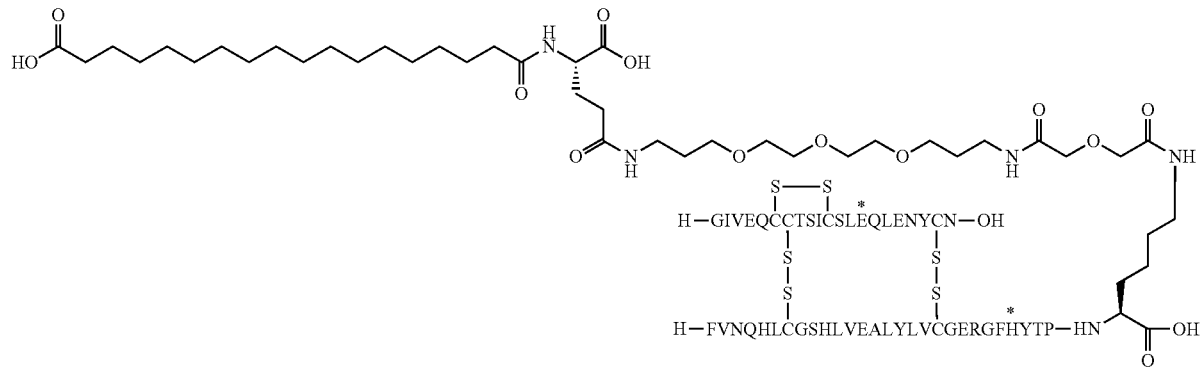

[(3-{2-[2-(3-Aminopropoxy)ethoxy]ethoxy}propylcarbamoyl)methoxy]acetic acid may prepared as described (*Eur. J. Med. Chem.* 2007, 42, 114) and reacted with ω-(tert-butyl-carboxy-heptadecanoyl-γ-L-glutamyl(OSu)-OtBu. The product may be activated using TSTU and coupled to A14E, B25H, desB30 human insulin in 0.1 M Na$_2$CO$_3$ at pH 10.5 to provide the product.

Example 130, General Procedure (A)

A14E, B25H, B29K(Nᵉeicosanedioyl-γGlu-2-[(3-
{2-[2-(3-aminopropoxy)ethoxy]
ethoxy}propylcarbamoyl)methoxy]acetyl), desB30
Human Insulin

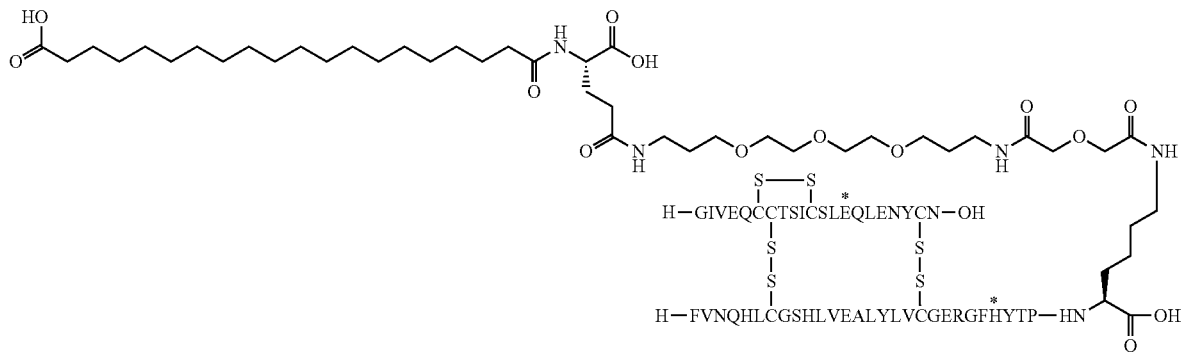

[(3-{2-[2-(3-Aminopropoxy)ethoxy]
ethoxy}propylcarbamoyl)methoxy]acetic acid may be prepared as described (*Eur. J. Med. Chem.* 2007, 42, 114) and reacted with ω-(tert-butyl-carboxy-nonadecanoyl-γ-L-glutamyl(OSu)-OtBu. The product may be activated using TSTU and coupled to A14E, B25H, desB30 human insulin in 0.1 M Na₂CO₃ at pH 10.5 to provide the product.

Example 131, General Procedure (A)

A14E, B16H, B25H, B29K(NᵉOctadecanedioyl-
γGlu-2-[(3-{2-[2-(3-aminopropoxy)ethoxy]
ethoxy}propylcarbamoyl)methoxy]acetyl), desB30
Human Insulin

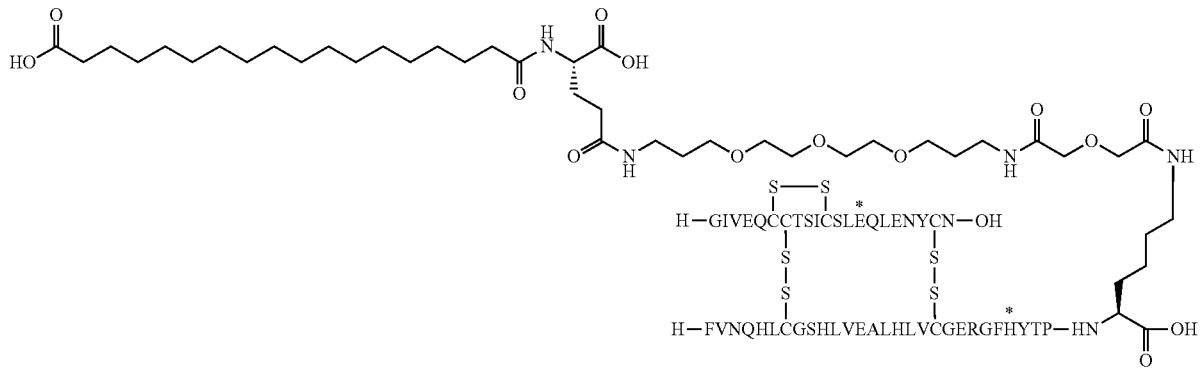

[(3-{2-[2-(3-Aminopropoxy)ethoxy]
ethoxy}propylcarbamoyl)methoxy]acetic acid may prepared as described (*Eur. J. Med. Chem.* 2007, 42, 114) and reacted with ω-(tert-butyl-carboxy-heptadecanoyl-γ-L-glutamyl(OSu)-OtBu. The product may be activated using TSTU and coupled to A14E, B16H, B25H, desB30 human insulin in 0.1 M Na₂CO₃ at pH 10.5 to provide the product.

Example 132, General Procedure (A)

A14E, B16H, B25H, B29K(N^εEicosanedioyl-γGlu-2-[(3-{2-[2-(3-aminopropoxy)ethoxy]ethoxy}propylcarbamoyl)methoxy]acetyl), desB30 Human Insulin

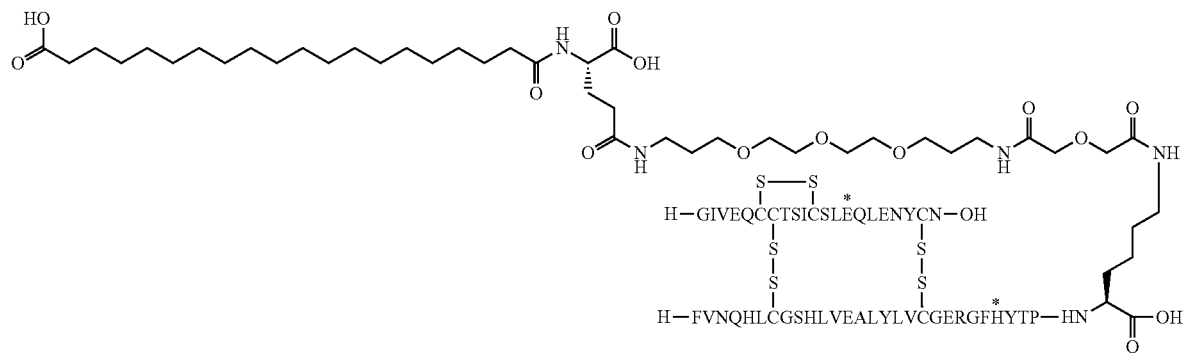

[(3-{2-[2-(3-Aminopropoxy)ethoxy]ethoxy}propylcarbamoyl)methoxy]acetic acid may be prepared as described (*Eur. J. Med. Chem.* 2007, 42, 114) and reacted with ω-(tert-butyl-carboxy-nonadecanoyl-γ-L-glutamyl(OSu)-OtBu. The product may be activated using TSTU and coupled to A14E, B16H, B25H, desB30 human insulin in 0.1 M Na$_2$CO$_3$ at pH 10.5 to provide the product.

Example 133, General Procedure (A)

B25H, B29K(N^εOctadecanedioyl-γGlu-OEG-OEG), desB30 Human Insulin

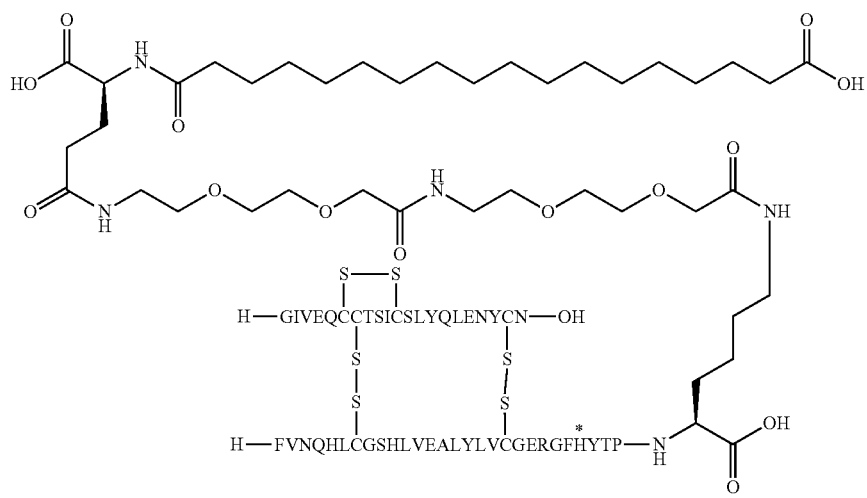

Example 134, General Procedure (A)
B25H, B29K(N^εEicosanedioyl-γGlu-OEG-OEG), desB30 Human Insulin
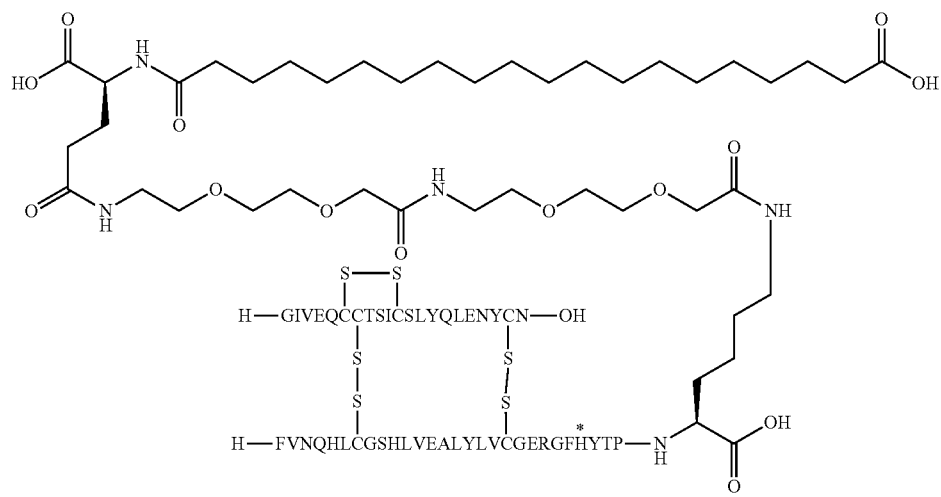
Example 135, General Procedure (A)
B25H, B29K(N^εOctadecanedioyl-γGlu), desB30 Human Insulin
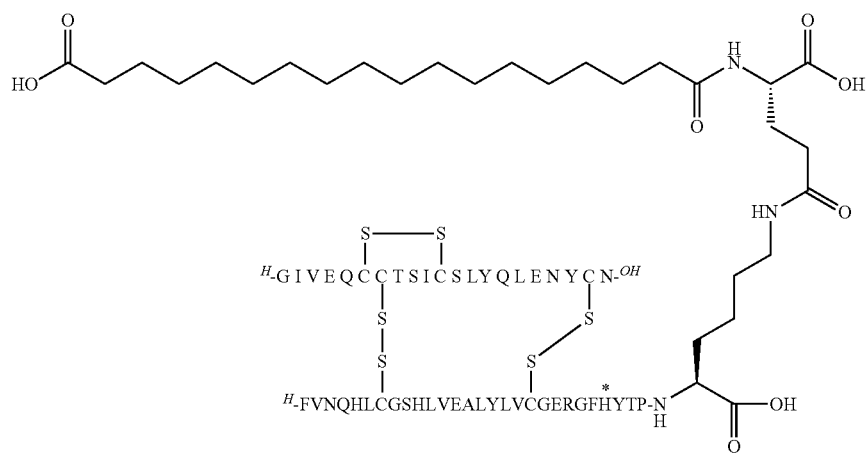

Example 136, General Procedure (A)
B25H, B29K(N^εEicosanedioyl-γGlu), desB30 Human Insulin
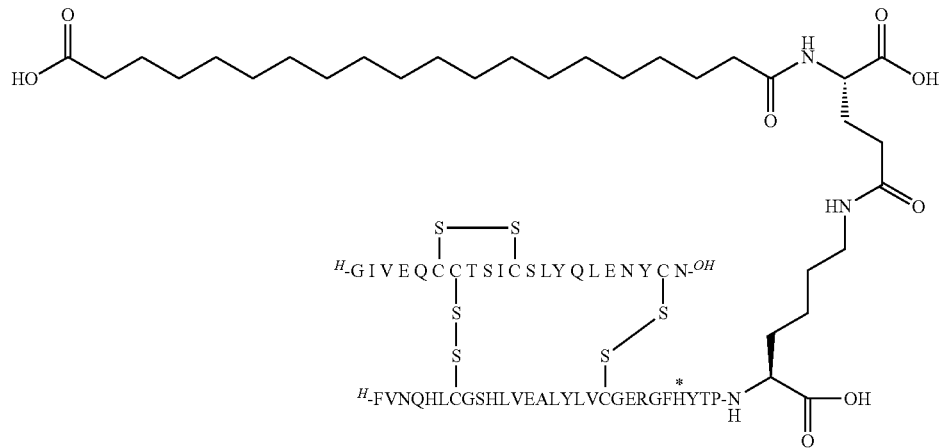
Example 137, General Procedure (A)
B25H, B29K(N^εOctadecanedioyl), desB30 Human Insulin
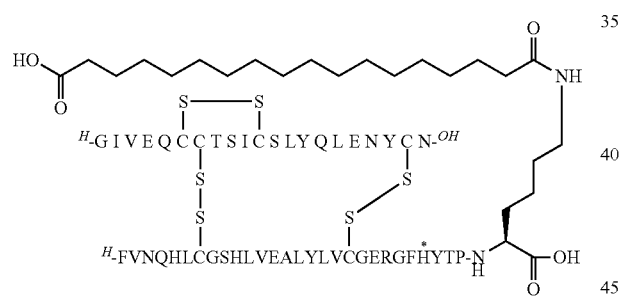
Example 138, General Procedure (A)
B25H, B29K(N^εEicosanedioyl), desB30 Human Insulin
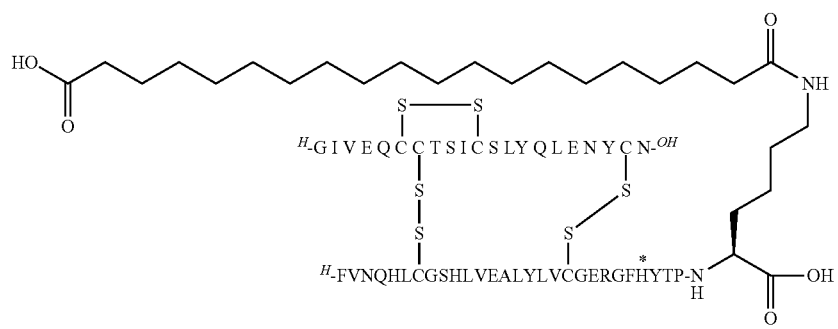

Example 139, General Procedure (A)
B25H, B29K(N⁰Octadecanedioyl-γGlu-OEG-OEG), desB30 Human Insulin
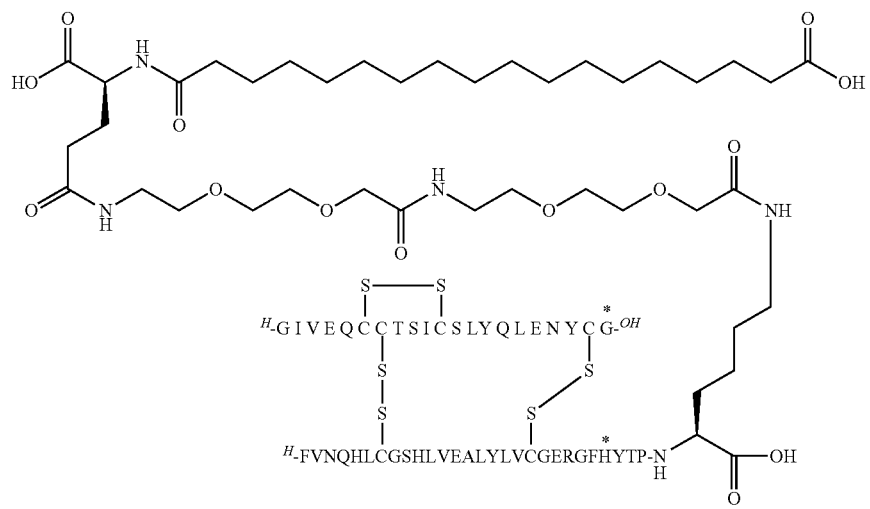
Example 140, General Procedure (A)
B25H, B29K(N⁰Eicosanedioyl-γGlu-OEG-OEG), desB30 Human Insulin
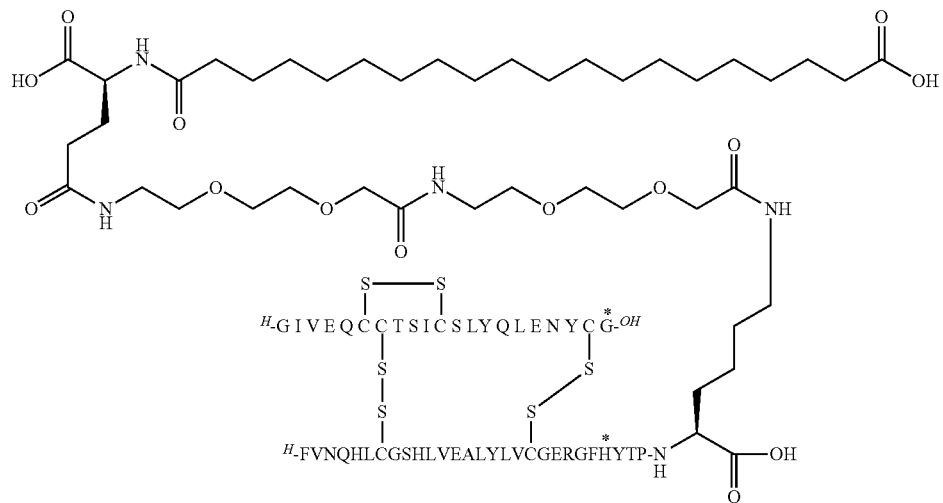

Example 141, General Procedure (A)
B25H, B29K(N^εOctadecanedioyl-γGlu), desB30 Human Insulin
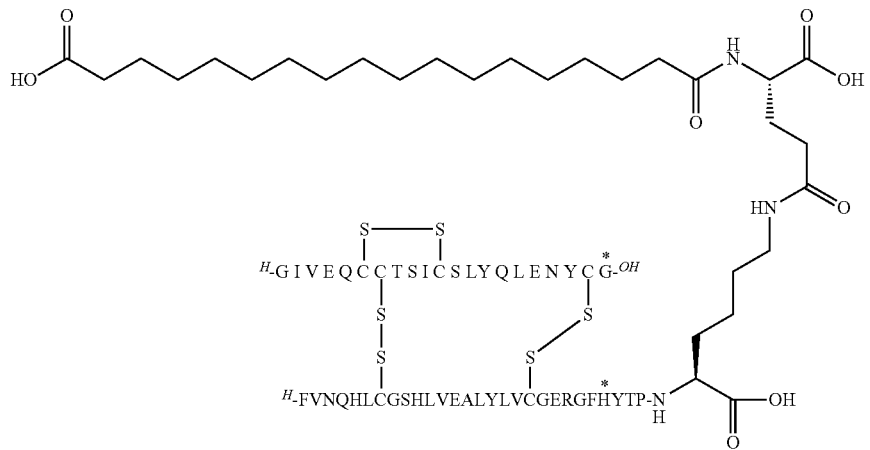
Example 142, General Procedure (A)
B25H, B29K(N^εEicosanedioyl-γGlu), desB30 Human Insulin
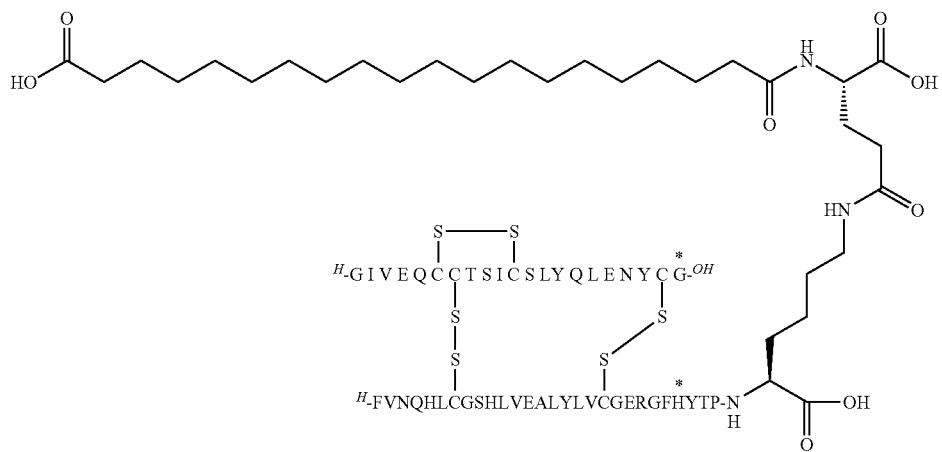

Example 143, General Procedure (A)
A21G, B25H, B29K(N^εOctadecanedioyl), desB30 Human Insulin
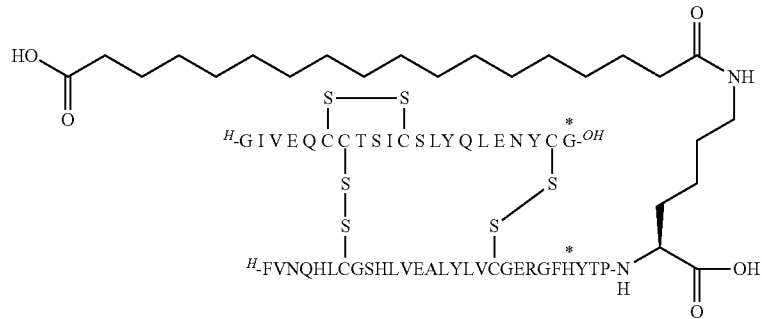
Example 144, General Procedure (A)
A21G, B25H, B29K(N^εEicosanedioyl), desB30 Human Insulin
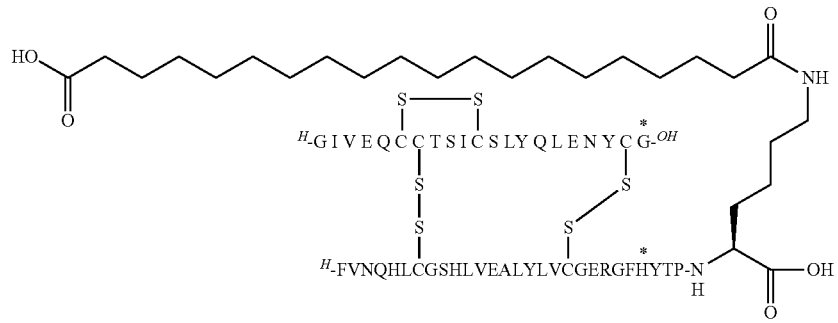
Example 145, General Procedure (A)
A21G, B25H, B29K(N^εOctadecanedioyl-γGlu-OEG-OEG), desB30 Human Insulin
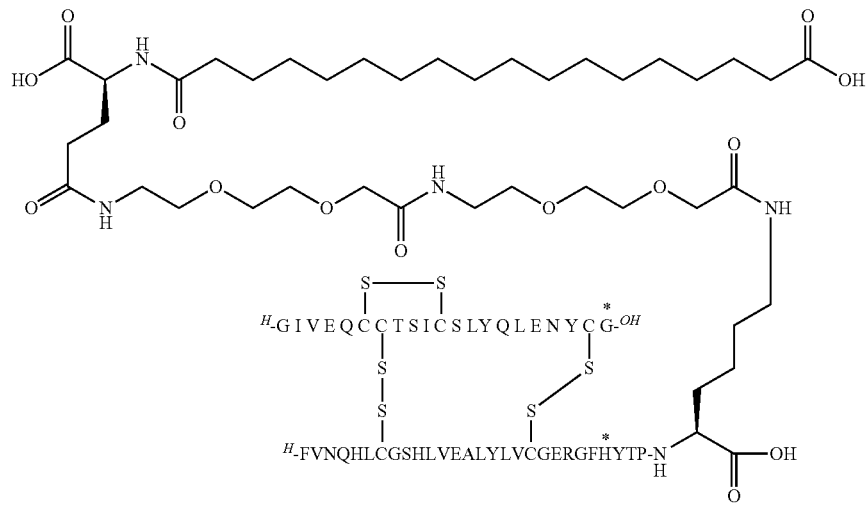

Example 146, General Procedure (A)
A21G, B25H, B29K(NεEicosanedioyl-γGlu-OEG-OEG), desB30 Human Insulin
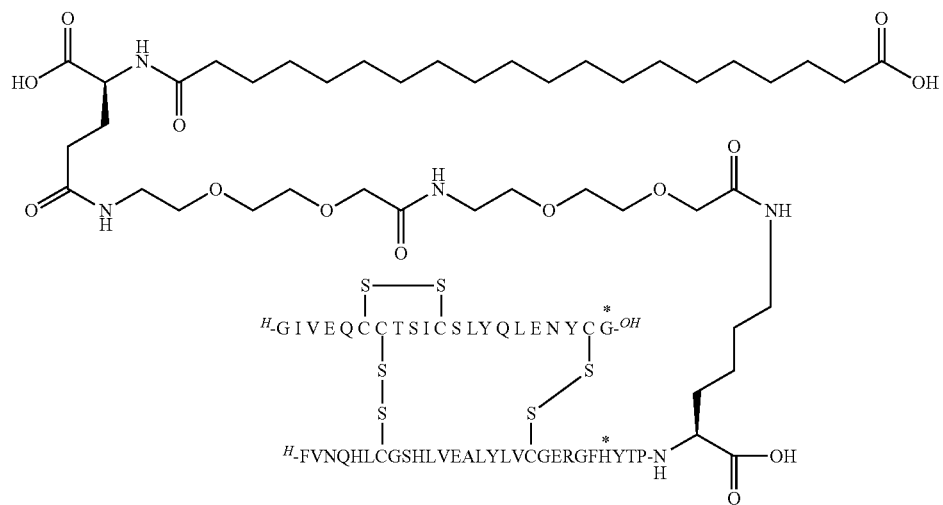
Example 147, General Procedure (A)
A21G, B25H, B29K(NεOctadecanedioyl-γGlu), desB30 Human Insulin
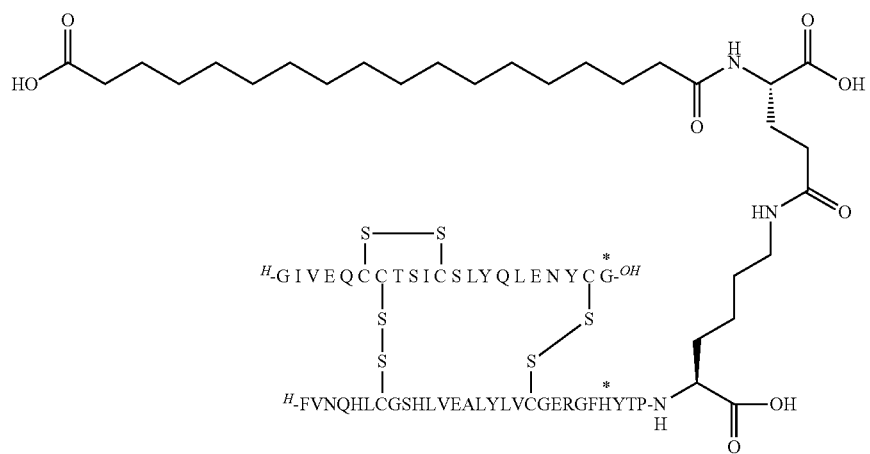

Example 148, General Procedure (A)
A21G, B25H, B29K(N^εEicosanedioyl-γGlu), desB30 Human Insulin
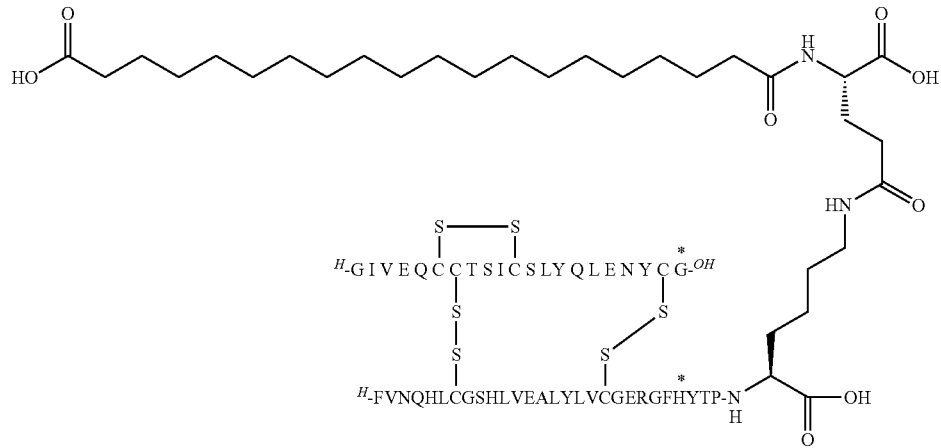
Example 149, General Procedure (A)
A14E, B25H, desB27, B29K(N^εOctadecanedioyl), desB30 Human Insulin
30
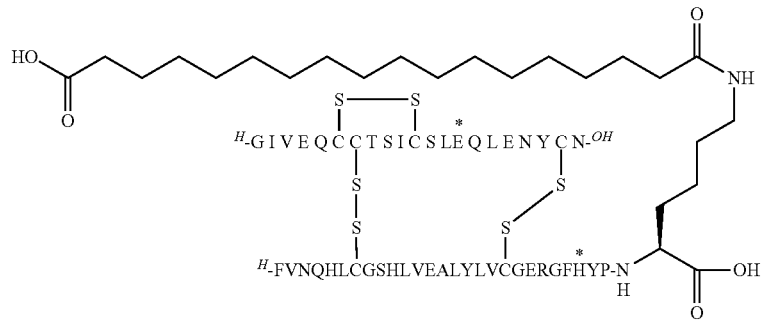
Example 150, General Procedure (A)
A14E, B25H, desB27, B29K(N^εEicosanedioyl), desB30 Human Insulin
50
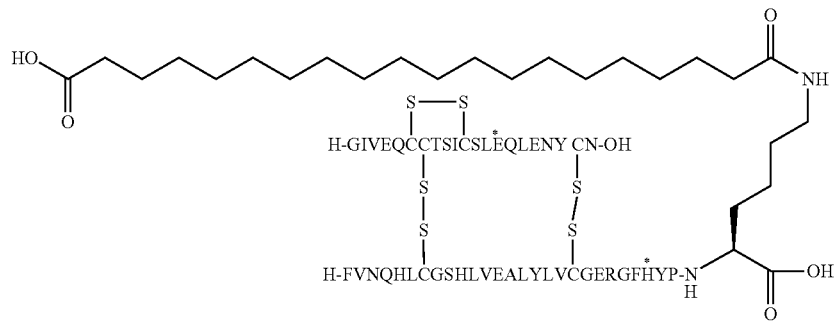

Example 151, General Procedure (A)
A14E, B25H, desB27, B29K(N^εOctadecanedioyl-γGlu), desB30 Human Insulin
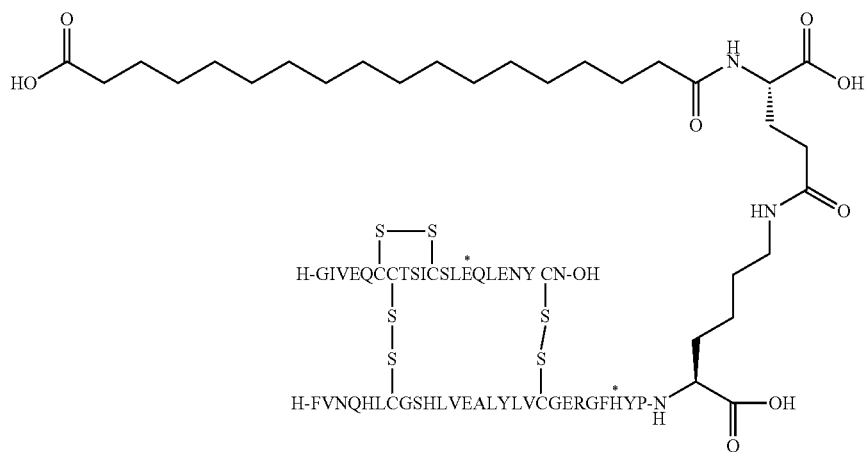
Example 152, General Procedure (A)
A14E, B25H, desB27, B29K(N^εEicosanedioyl-γGlu), desB30 Human Insulin
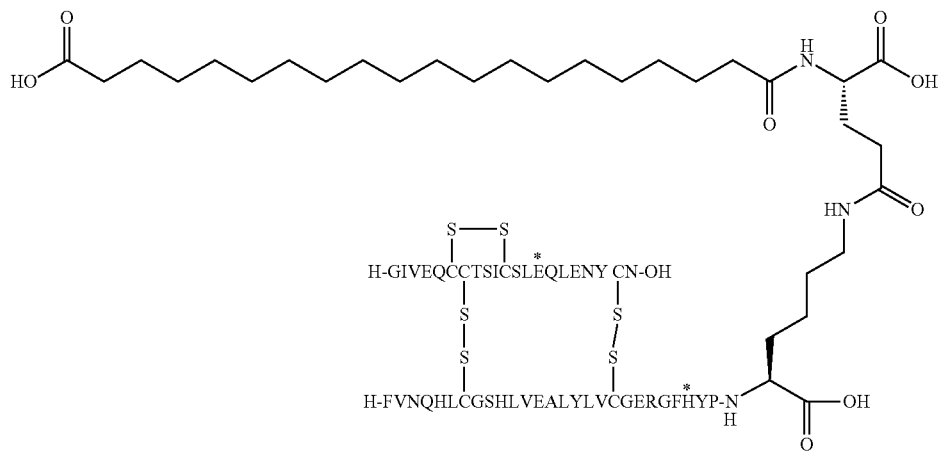

Example 153, General Procedure (A)
A14E, B25H, desB27, B29K(Nᵉ Eicosanedioyl-γGlu-OEG-OEG), desB30 Human Insulin
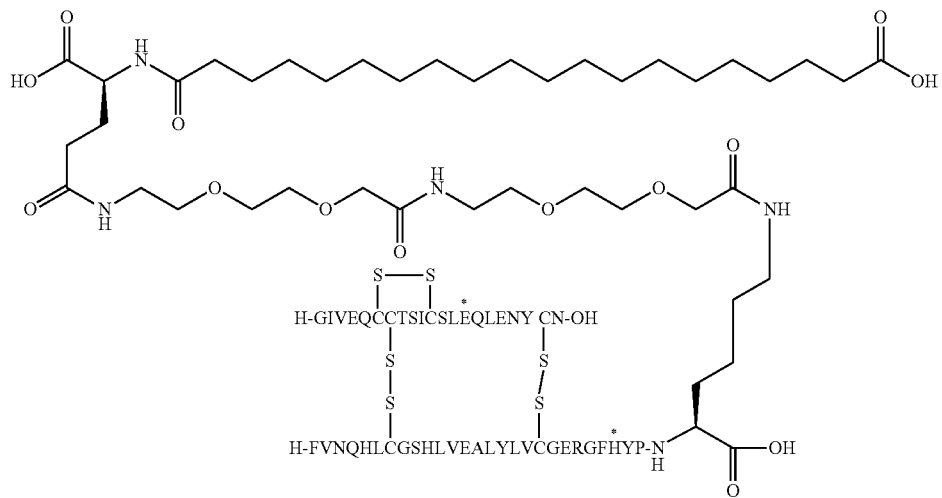
Example 154, General Procedure (A)
A14E, A21G, B25H, desB27, B29K(Nᵉ Octadecanedioyl), desB30 Human Insulin
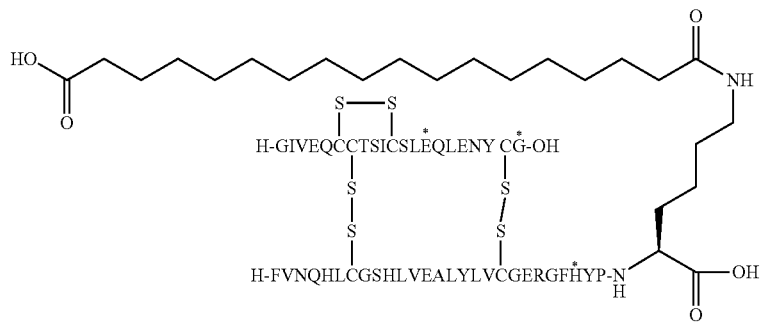

Example 155, General Procedure (A)
A14E, A21G, B25H, desB27, B29K(N^εEicosanedioyl), desB30 Human Insulin
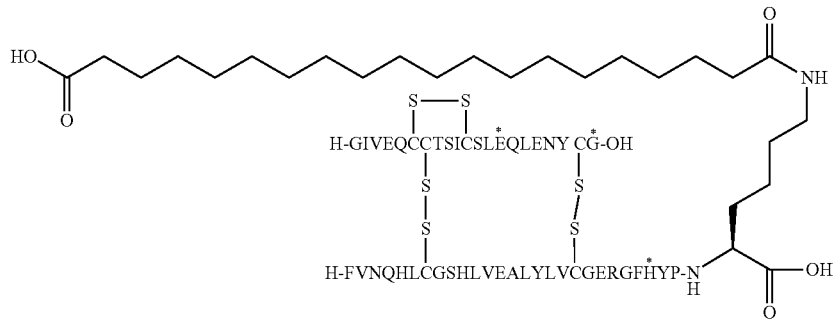
Example 156, General Procedure (A)
A14E, A21G, B25H, desB27, B29K(N^εOctadecanedioyl-γGlu), desB30 Human Insulin
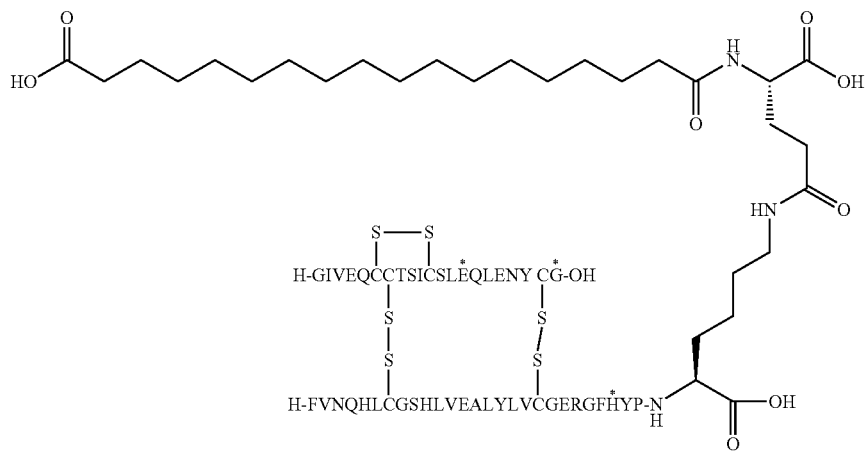
Example 157, General Procedure (A)
A14E, B25H, desB27, B29K(N^εEicosanedioyl-γGlu), desB30 Human Insulin
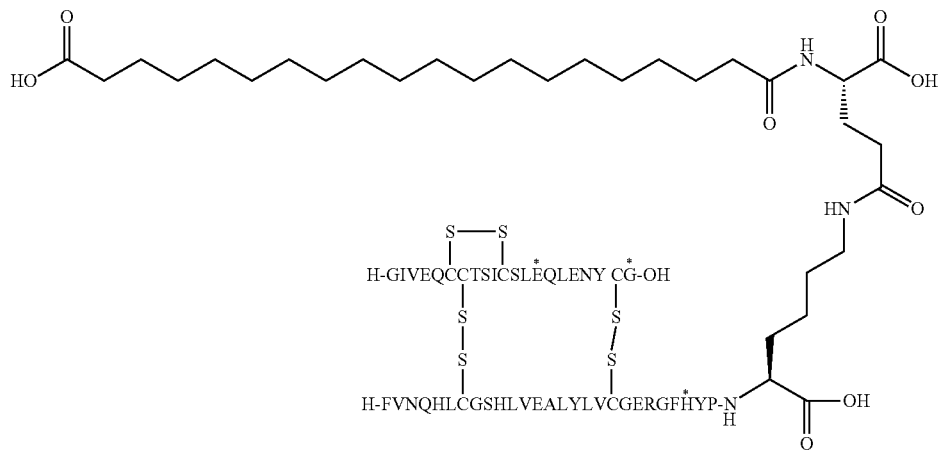

Example 158, General Procedure (A)
A14E, A21G, B25H, desB27, B29K
(N^ε Octadecanedioyl-γGlu-OEG-OEG), desB30
Human Insulin
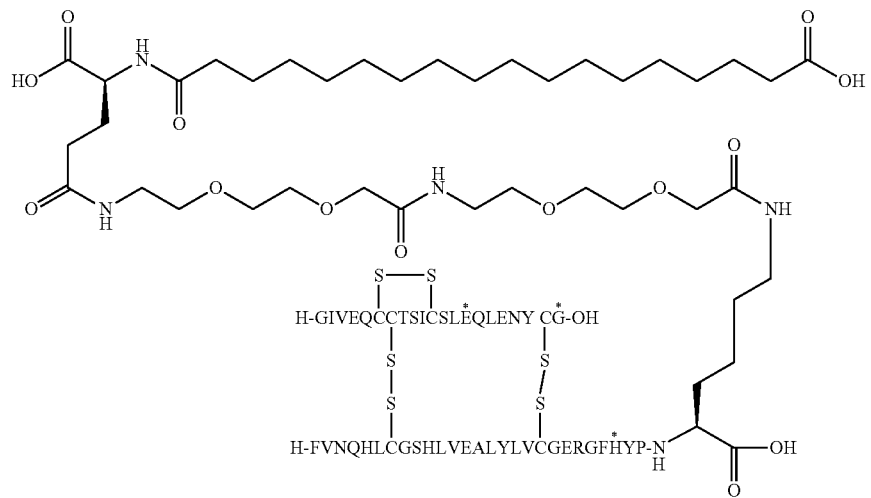
Example 159, General Procedure (A)
A14E, A21G, B25H, desB27, B29K
(N^ε Eicosanedioyl-γGlu-OEG-OEG), desB30 Human
Insulin
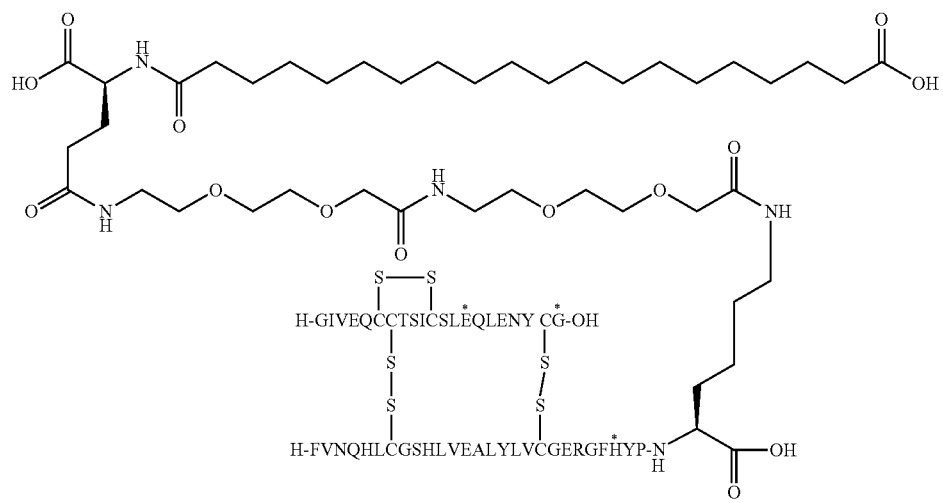

Example 160, General Procedure (A)
A14E, A21G, B25H, B29K(N^εOctadecanedioyl-γGlu-OEG-OEG), desB30 Human Insulin
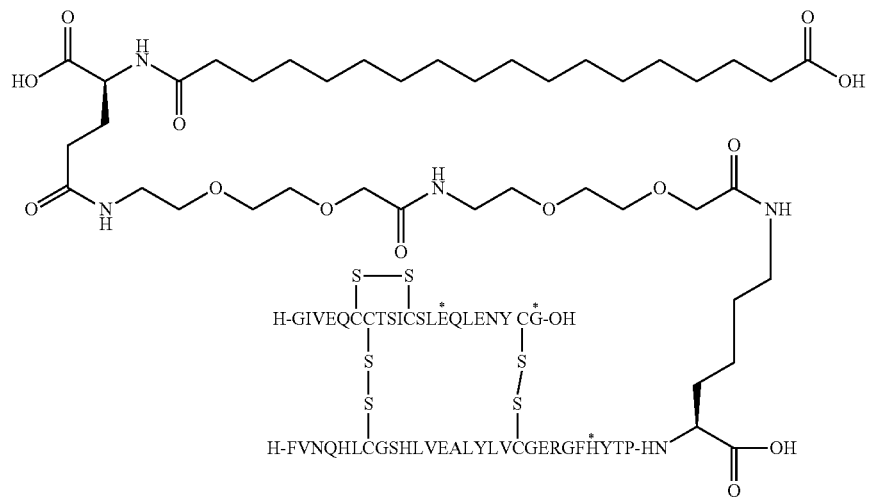
Example 161, General Procedure (A)
A14E, A21G, B25H, B29K(N^εEicosanedioyl-γGlu-OEG-OEG), desB30 Human Insulin
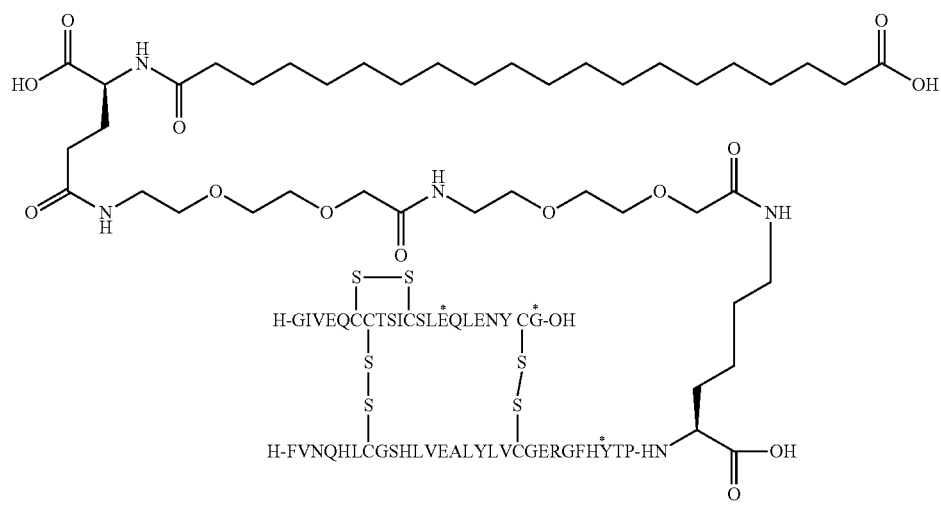

Example 162, General Procedure (A)
A14E, A21G, B25H, B29K(NᵉEicosanedioyl-γGlu), desB30 Human Insulin
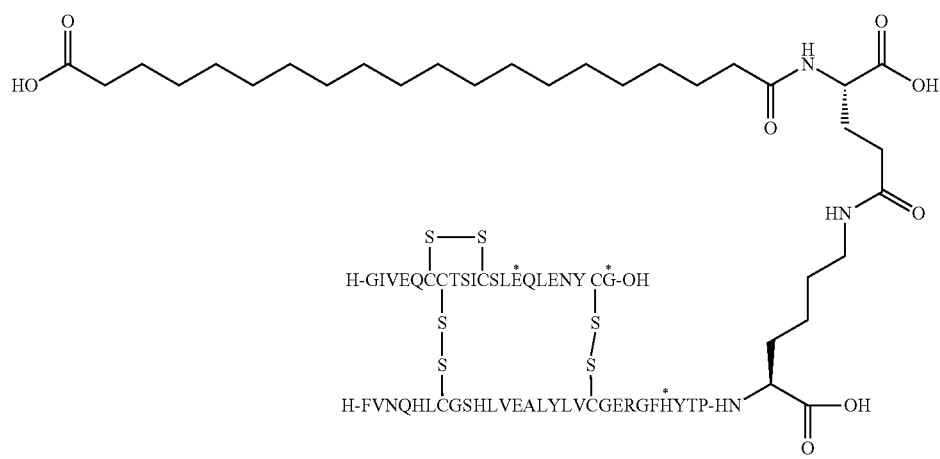
Example 163, General Procedure (A)
A14E, A21G, B25H, B29K(NᵉEicosanedioyl), desB30 Human Insulin
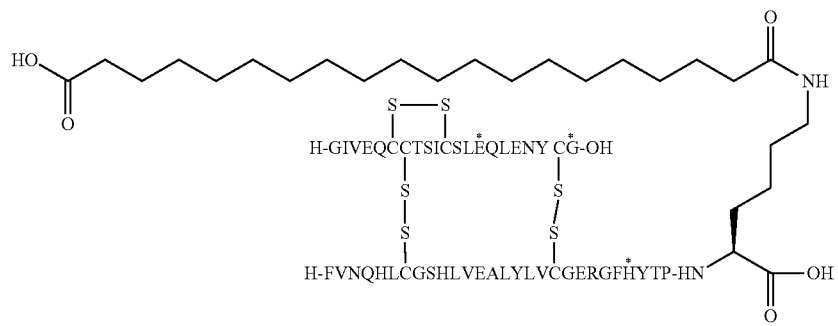

Example 164, General Procedure (A)
A14E, A21G, B25H,
B29K(NᵋOctadecanedioyl-γGlu), desB30 Human Insulin
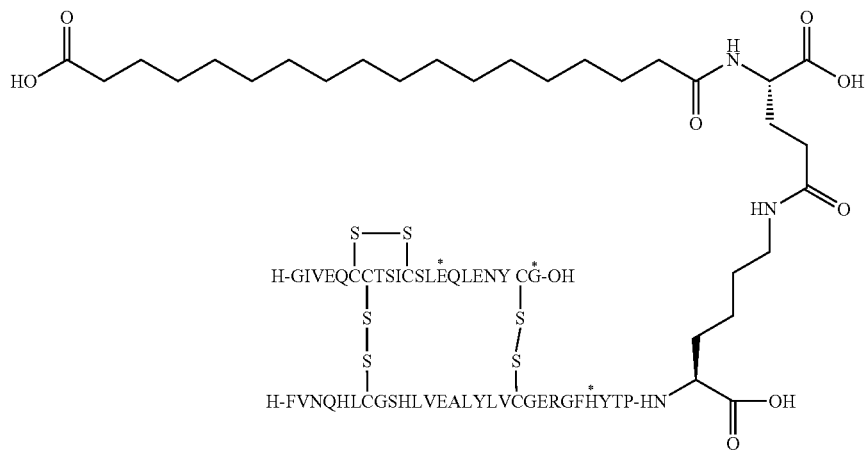
Example 165, General Procedure (A)
A14E, A21G, B25H, B29K(NᵋOctadecanedioyl), desB30 Human Insulin
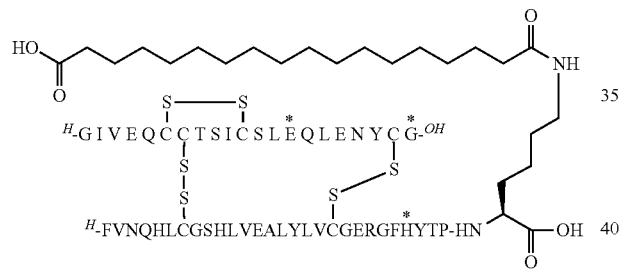
Example 166, General Procedure (A)
A14E, B25H, B26G, B27G, B28G, B29K(NᵋOctadecanedioyl-γGlu), desB30 Human Insulin
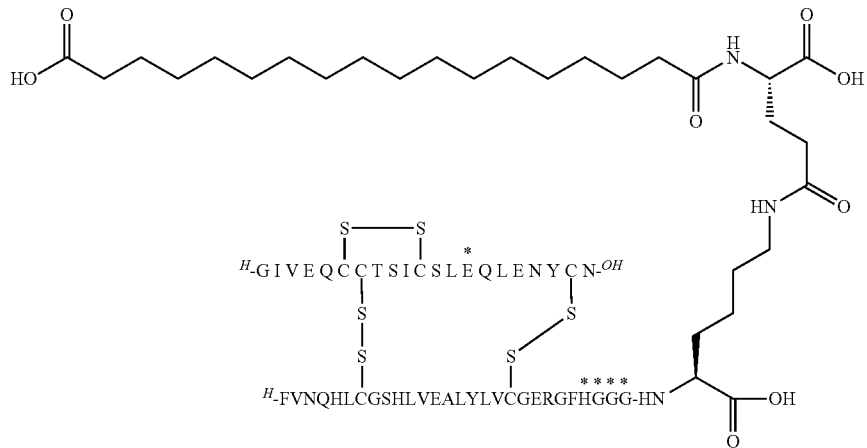

Example 167, General Procedure (A)
A14E, B25H, B26G, B27G, B28G,
B29K(N^εOctadecanedioyl), desB30 Human Insulin
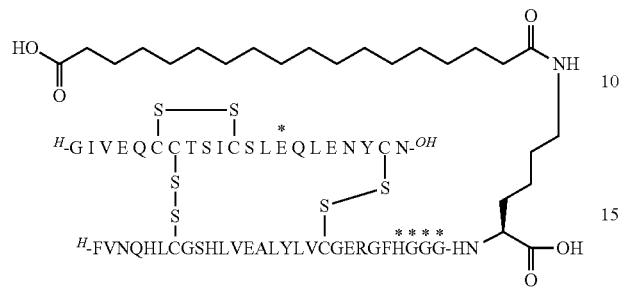
Example 168, General Procedure (A)
A14E, B25H, B26G, B27G, B28G,
B29K(N^εEicosanedioyl-γGlu), desB30 Human Insulin
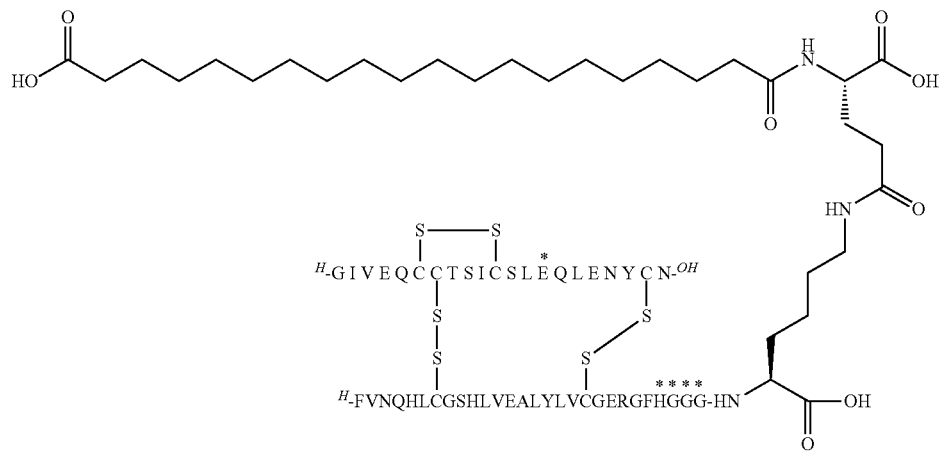
Example 169, General Procedure (A)
A14E, B25H, B26G, B27G, B28G,
B29K(N^εEicosanedioyl), desB30 Human Insulin
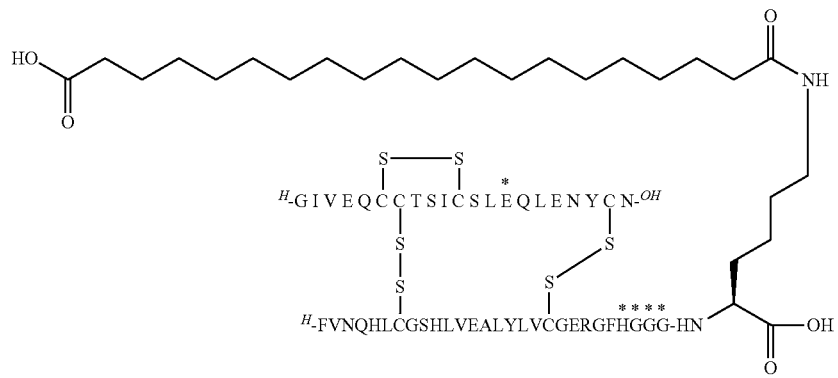

Example 170, General Procedure (A)
A1G(N$^\alpha$Octadecandioyl-γGlu), A14E, B25H, B26G, B27G, B28G, desB30 Human Insulin
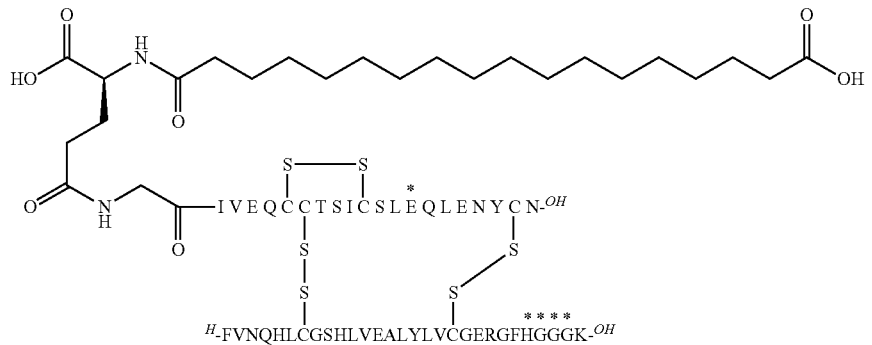
Example 171, General Procedure (A)
A1G(N$^\alpha$Eicosanedioyl-γGlu), A14E, B25H, B26G, B27G, B28G, desB30 Human Insulin
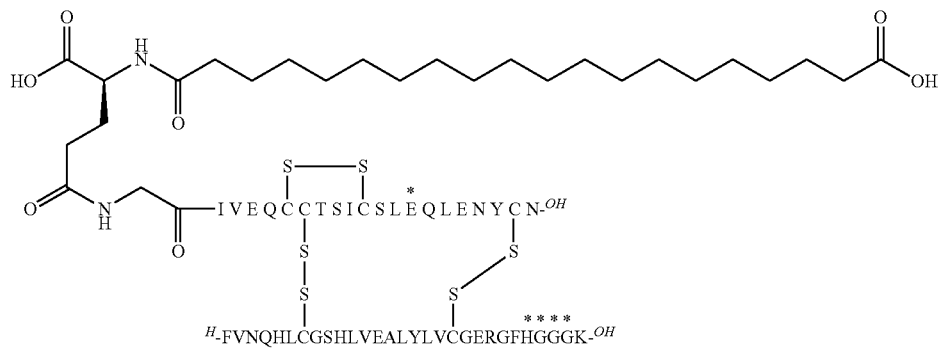
Example 172, General Procedure (A)
A1G(N$^\alpha$Octadecandioyl-γGlu), A14E, B25H, B26G, B27G, B28G, B29R, desB30 Human Insulin
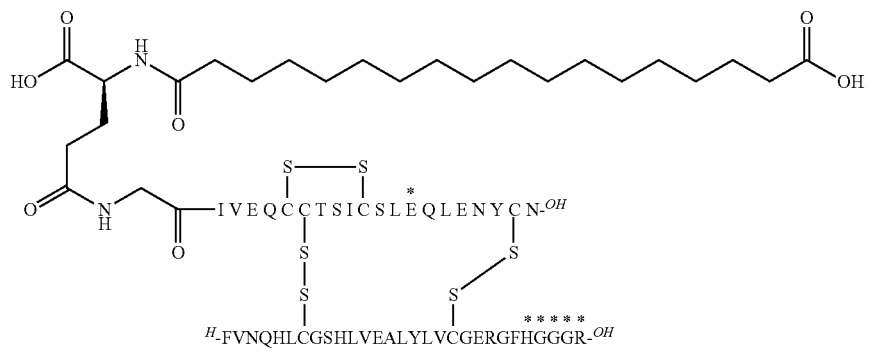

Example 173, General Procedure (A)
A1G(N$^\alpha$Eicosanedioyl-γGlu), A14E, B25H, B26G, B27G, B28G, B29R, desB30 Human Insulin
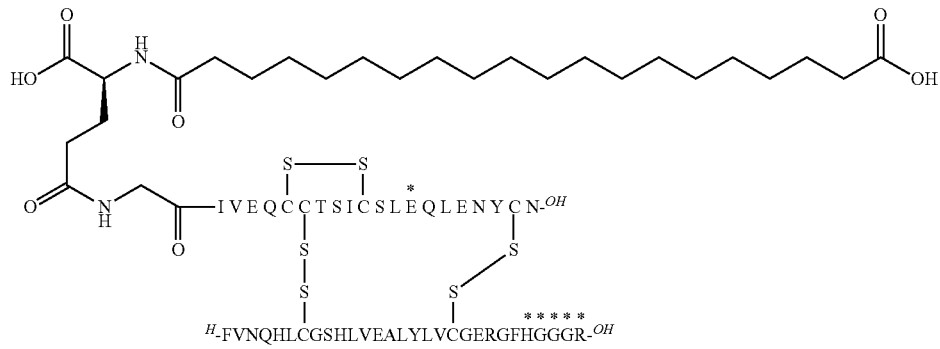
Example 174, General Procedure (A)
A1G(N$^\alpha$Octadecandioyl), A14E, B25H, B26G, B27G, B28G, desB30 Human Insulin
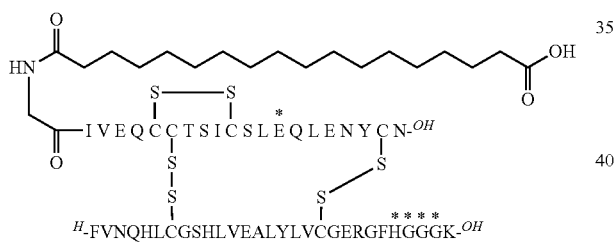
Example 175, General Procedure (A)
A1G(N$^\alpha$Eicosanedioyl), A14E, B25H, B26G, B27G, B28G, desB30 Human Insulin
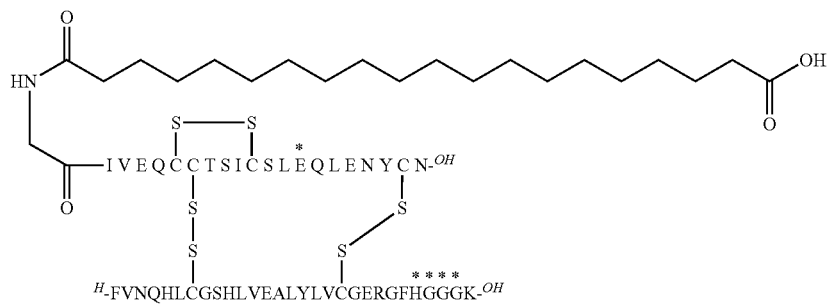

Example 176, General Procedure (A)

A1G(N$^{\alpha}$Octadecandioyl), A14E, B25H, B26G, B27G, B28G, B29R, desB30 Human Insulin

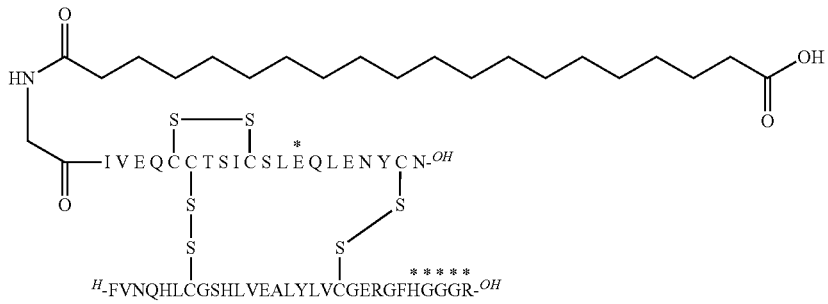

Example 177, General Procedure (A)

A1G(N$^{\alpha}$Eicosanedioyl), A14E, B25H, B26G, B27G, B28G, B29R, desB30 Human Insulin

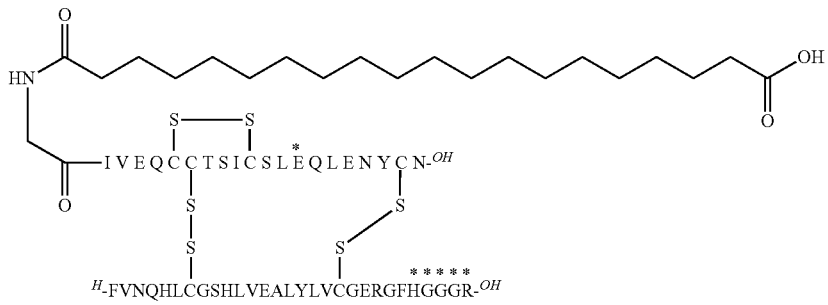

Example 178, Insulin Receptor Affinity of Selected Insulin Derivatives of the Invention The affinity of the acylated insulin analogues of this invention for the human insulin receptor is determined by a SPA assay (Scintillation Proximity Assay) microtiterplate antibody capture assay. SPAP-VT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the GraphPad Prism 2.01 (GraphPad Software, San Diego, Calif.) and affinities are expressed relative (in percentage (%)) to the affinity of human insulin.

A related assay is also used wherein the binding buffer also contains 4.5% HSA in order to mimic physiological conditions Insulin receptor affinities of selected insulins of the invention:

| Example # | Relative IR-A affinity (@ 0% HSA) (%) | Relative IR-A affinity (@ 4.5% HSA) (%) |
| --- | --- | --- |
| 19 | 3.8 | .30 |
| 10 | 9.5 | |
| 1 | 5.0 | .10 |
| 2 | 2.1 | .06 |
| 5 | 2.5 | |
| 4 | 3.4 | |
| 3 | 2.0 | |
| 9 | 1.7 | .20 |
| 6 | 2.6 | .04 |
| 7 | 2.1 | |
| 8 | 2.1 | |
| 12 | 1.7 | |
| 11 | .8 | |
| 17 | .9 | |
| 13 | 1.1 | |
| 15 | 1.9 | |
| 20 | 2.0 | |
| 22 | .7 | |
| 16 | .9 | .23 |

| Example # | Relative IR-A affinity (@ 0% HSA) (%) | Relative IR-A affinity (@ 4.5% HSA) (%) |
|---|---|---|
| 18 | 2.3 | |
| 23 | 1.4 | |
| 24 | 7.9 | 2.23 |
| 25 | .4 | .05 |
| 26 | .0 | .01 |
| 27 | .7 | .06 |
| 28 | .3 | |
| 29 | .2 | .01 |
| 30 | .3 | .02 |
| 31 | 16.2 | 1.11 |
| 32 | .3 | |
| 33 | .5 | 0.06 |
| 21 | .8 | |
| 34 | 1.3 | |
| 35 | 5.8 | |
| 36 | 9.3 | |
| 37 | .8 | |
| 40 | 0.3 | |
| 38 | .6 | .10 |
| 41 | 1.6 | .31 |
| 39 | 11.2 | .67 |
| Prior art 183 | 10 | 1.00 |
| 46 | 1.9 | 0.08 |
| 47 | 1.2 | 0.10 |
| 48 | 1.3 | 0.01 |
| 49 | 6.2 | 0.86 |
| 50 | 4.3 | 1.21 |
| 51 | 1.7 | 0.12 |
| 52 | 2.1 | |
| 53 | 2.3 | 0.03 |
| 54 | 3.9 | 0.91 |
| 55 | 0.3 | 0.03 |
| 56 | 4.4 | 0.03 |
| 57 | 2.5 | |
| 58 | 0.5 | |
| 59 | 0.3 | |

| Example # | Relative hydrophobicity, k'rel$_{deriv}$ |
|---|---|
| 19 | .07 |
| 10 | 14.60 |
| 1 | .33 |
| 2 | .25 |
| 5 | .23 |
| 4 | .48 |
| 3 | .77 |
| 9 | .31 |
| 6 | .19 |
| 7 | 2.78 |
| 8 | .14 |
| 12 | .94 |
| 11 | .19 |
| 17 | .57 |
| 13 | .10 |
| 15 | .43 |
| 20 | .15 |
| 22 | .20 |
| 16 | 1.15 |
| 18 | .10 |
| 23 | .16 |
| 24 | .26 |
| 25 | .22 |
| 26 | .21 |
| 27 | .05 |
| 28 | .42 |
| 29 | .05 |
| 30 | .05 |
| 31 | |
| 32 | .07 |
| 33 | .76 |
| 21 | .04 |
| 34 | |
| 35 | .84 |
| 36 | .24 |
| 37 | .56 |
| 40 | .09 |
| 38 | |
| 41 | |
| 46 | 0.44 |

Example 179, Hydrophobicity of the Insulin Derivatives of the Invention

The hydrophobicity of an insulin derivative is found by reverse phase HPLC run under isocratic conditions. The elution time of the insulin derivative is compared to that of human insulin (herein designated HI) or another derivative with a known hydrophobicity under the same conditions. The hydrophobicity, k'rel, is calculated as: k'rel$_{deriv}$ = $((t_{deriv}-t_0)/(t_{ref}-t_0))*$k'rel$_{ref}$. Using HI as reference: k'rel$_{ref}$=k'rel$_{HI}$=1. The void time of the HPLC system, $t_0$, is determined by injecting 5 µl of 0.1 mM NaNO$_3$. Running conditions:

Column: Lichrosorb RP-C18, 5 µm, 4×250 mm

Buffer A: 0.1 M natrium phosphate pH 7.3, 10 vol % CH$_3$CN

Buffer B: 50 vol % CH$_3$CN

Injection volume: 5 µl

Run time: max 60 minutes

After running an initial gradient, the isocratic level for running the derivative and reference (for example HI) is chosen, and the elution times of the derivative and reference under isocratic conditions are used in the above equation to calculate k'rel$_{deriv}$.

Example 180, Pulmonary Delivery of Insulin Derivatives to Rats

Protocol:

The test substance will be dosed pulmonary by the drop instillation method. In brief, male Wistar rats (app. 250 g) are anaesthetized in app. 60 ml fentanyl/dehydrodenzperidol/-dormicum given as a 6.6 ml/kg sc priming dose and followed by 3 maintenance doses of 3.3 ml/kg sc with an interval of 30 min.

Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 ul air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthetized during the test (blood samples for up to 4 or 8 hrs) and are euthanized after the experiment.

Figure 8:
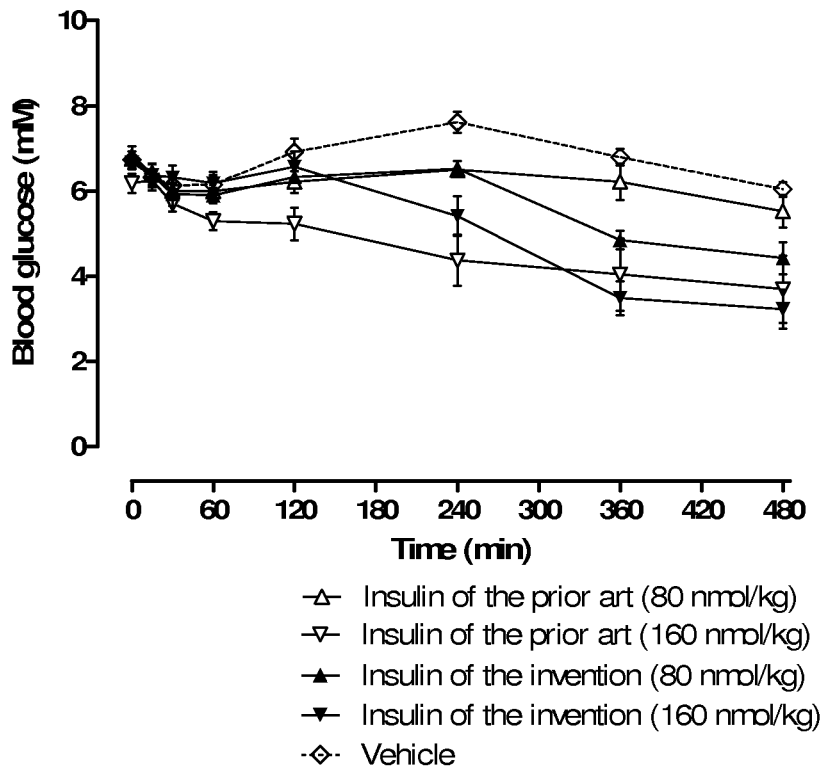
FIG. 8 shows blood glucose lowering effects from intratracheal drop instillation of the compound of Example 9, compared with a similar, but non-protease resistant compound of Example 183.
Figure 9:
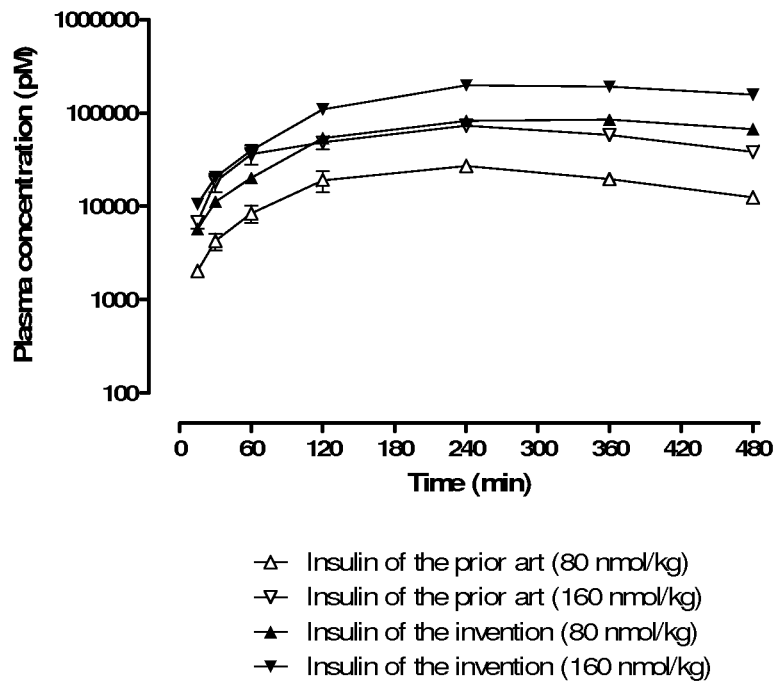
FIG. 9 shows plasma insulin concentrations from intratracheal drop instillation of the compound of Example 9, compared with a similar, but non-protease resistant compound of Example 183.

FIGS. 8 and 9 show blood glucose lowering effects and plasma insulin concentrations, respectively, from intratracheal drop instillation of an insulin of the invention (example 9), compared with a similar, but non-protease resistant insulin of the prior art (example 183).

Example 181, Pulmonary Delivery of Insulin Derivatives to Mini-Pigs

Protocol:

The pigs were instrumented with central venous catheters for intravenous injections and blood sampling. The pigs are fasted prior to the pulmonary experiment, i.e. the day before dosing, the leftovers from the afternoon feeding is removed approximately one hour after feeding and on the day of dosing, the pigs are not fed. The patency of the catheters is checked prior to the experiment with saline added 10 IU/ml heparin.

After pulmonary dosing, a glucose solution should be ready for i.v. injection to prevent hypoglycaemia, i.e. 4-5 syringes (20 ml) are filled with sterile 20% glucose, ready for use. Diagnosis of hypoglycemia is based on clinical symptoms and blood glucose measurements on a glucometer (Glucocard X-meter). Treatment consists of slow i.v. injection 50-100 ml 20% glucose (10-20 g glucose). The glucose is given in fractions over 5-10 minutes until effect.

The pigs are fasted during the first part of the experiment (until 24 h), but with free access to water. After the 16 h blood sample catheters are closed with 5000 IU/ml heparin, placed in the pockets and the pigs are released. After the 24 h blood sample the pigs are fed with double ration of food and apples. Pigs are not fasted from 24 h to 48 h.

Compound and Pulmonary Dosing

Powder for Pulmonary Dosing

The insulin powders are weighed into 8 separate powder chamber of the dry powder device (PennCentury™ Model DP-4, custom made porcine device) the day before the experiment. All chambers are kept protected from light and humidity by keeping them on a desiccating material in a container with aluminumfoil around in a temperature and humidity controlled laboratory until dosing.

Based on the most recent individual animal weight, the delivery device was preloaded with 25 nmol/kg as some powder retention was expected.

Loading dose=(Weight of powder+(weight of device and powder−weight of device))/2.

Anaesthesia

By an i.v. injection of Domitor® Vet inj. (medetomidein 1 mg/ml), 0.15 ml/10 kg=0.4 ml/pig, the pig is sedated.

Immediately after, Rapinovet Vet. inj. (propofol 10 mg/ml) is injected slowly i.v. until sufficient depth of anaesthesia is obtained. In general, 2-3 ml/10 kg is enough, but it may be necessary to supplement with 1-2 ml at a time until intubation is possible. Atropin (1 mg/ml) is injected i.m. at 0.5 ml/pig and allowed to work min. 5 minutes before intubation.

For intubation the pig is placed in ventral position with slightly elevated front, local anesthetics Xylocaine® kutanspray (lidocain 10 mg/dosis) is sprayed onto the epiglottis, and the pigs are intubated using a laryngoscope and a disposable tube size 8.0 mm (ID). The two parts of the tube are pressed tightly together.

Device Position During Pulmonal Dosing

The position of the PennCentury™ device during dosing should be just outside the end of the endotracheal tube and this should be measured on the device before intubation (remember the connecting L-piece when measuring this). During dosing the tip of the PennCentury™ device should positioned in the trachea just below the bronchus that goes to lobus cranialis dexter, which is confirmed with the bronchoscope.

Artificial Respiration

The respiration frequency is set to 10/min and the respiration depth to 250 ml/breath. The respirator is mounted with "baby" bag to optimise timing of dosing. The anaesthesia apparatus is connected to a filter that is connected to the endotracheal tube via a L-piece. The PennCentury™ device is introduced through the L-piece, which will allow control over the respiration depth and frequency during dosing.

Dosing Technique

The PennCentury™ device should be placed as described above. The pigs are dosed (one at a time) with the PennCentury™ device by manual administration during inhalation using the adjustable PennCentury air pump (Model AP-1). Each pig is given 8 air sprays (air pump set to 4 mL) during 8 consecutive respirator-forced inhalations to ensure that the entire dose is given. The chamber is gently tapped between sprays to avoid sticking of the powder to the device. A new delivery tube is used for each pig. The timing in relation to the inhalation is very important, and the air sprays should be given in the very beginning of the inhalation (aim for start at 50 mL inhalation).

To counteract the effect of Domitor, Antisedan® Vet inj. (atipamezol 5 mg/ml) will be injected as an intramuscular injection (0.4 ml/pig) immediately after dosing, and the pigs will be taken back to their pens and allowed to wake up from anaesthesia.

Retention Analysis

The emitted dose should be the entire content of the chamber and after dosing the device is weighed again with any residual powder, and the retained powder is extracted with 9 ml of 0.01 N HCl med 0.05% (w/v) Tween 80 extraction buffer and sent to analysis.

Blood Sampling

After the dosing, blood samples will be taken from a central venous catheter at the following time points:

10, 0, 10, 20, 40, 60, 90, 120, 150, 180, 240 (4 h), 300 (5 h), 360 (6 h), 8 h, 10 h, 12 h, 14 h, 16 h, 24 h, 32 h and 48 h.

Samples are taken with a 3-way stop-cock; waste blood is injected back into the animal. Sample size is: 0.8 ml of blood collected in a tube coated with EDTA. After each blood sample the catheter is flushed with 5 ml of sterile 0.9% NaCl with 10 IU/ml heparin. The tube is tilted gently a minimum of 8 times to ensure sufficient mixing of blood and anticoagulant (EDTA) and after one minute it is placed on wet ice. The tubes are spun for 10 min at 3000 rpm and 4° C. within 1 hour after sampling. The samples are stored on wet ice until pipetting.

Closure of the Catheters after the Experiment

A single intravenous treatment with Ampicillin (10 mg/kg=0.1 ml/kg of a 100 mg/ml solution) dissolved in sterile saline (1 g Ampicillin in 10 ml=100 mg/ml) is given via the catheter that has been used for blood sampling. Both catheters are flushed with 4-5 ml of sterile 0.9% NaCl added heparin to a concentration to 10 IU/ml. The catheters are closed with a new luer-lock with latex injection membrane. 4-5 ml sterile 0.9% NaCl is injected through the membrane. Finally 0.8 ml of heparin, 5000 IU/ml, is injected through the catheter as a lock. Aseptic technique is demanded to avoid bacterial growth in the catheter with increased risk of clotting.

Analysis of Blood Samples

10 µl of plasma is pippetted into 500 µl of EBIO buffer solution for measurements of glucose concentration in plasma in the Biosen autoanalyser.

Plasma samples are also assayed for exogenous insulin by immunoassays to calculate PK parameters.

Figure 10:
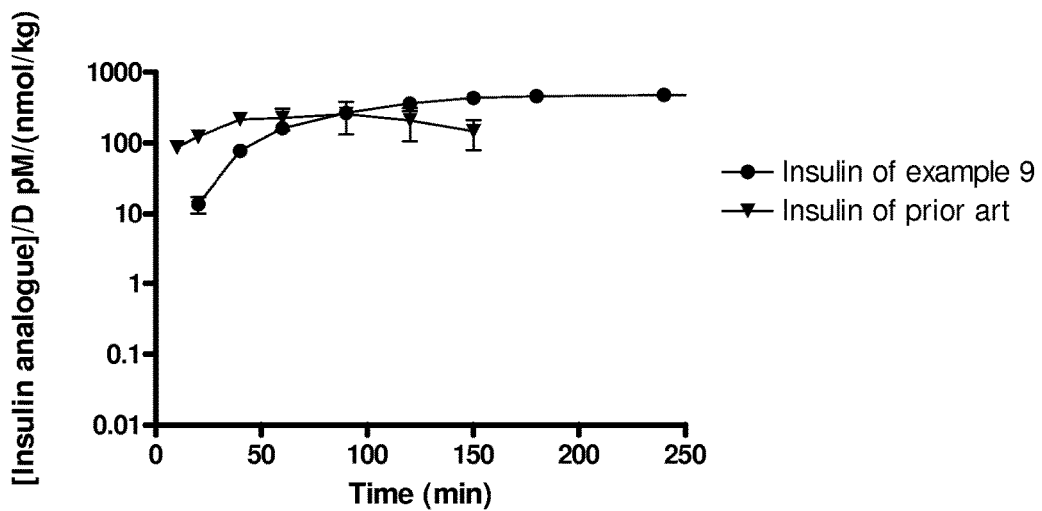
FIGS. 10 and 11 show the pharmacokinetic profile of the compound of Example 9 compared to the same compound but without the protease stabilising A14E and 825H mutations. The data are from the same experiment.
Figure 11:
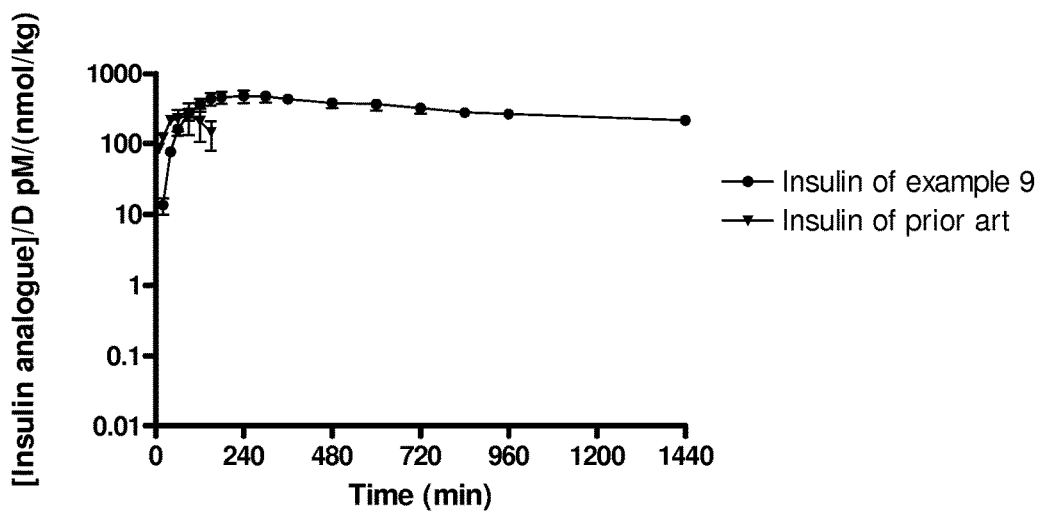

Pulmonary Dosing of the Insulin of Example 9 to Mini-Pigs According to the Protocol Above:

FIGS. 10 and 11 shows the pharmacokinetic profile of the insulin of example 9 compared to the same insulin but without the protease stabilising A14E and B25H mutations (insulin of prior art). The data are from the same experiment, FIG. 10 is shown with the data from the first 250 minutes, and FIG. 11 is shown with the full 24 hour (1440 minutes) time-course.

Pharmacokinetic data for the insulin of example 9 compared to the same insulin but without the protease stabilising A14E and B25H mutations (insulin of prior art). The data are from the same experiment, half-life (T½) and bioavailability ($F_{it}$) relative to intravenous administration:

| Insulin, example # | $T_{1/2}$ (minutes) | $F_{it}$ |
|---|---|---|
| Prior art (see ex. 183) | 211 | 4% |
| 9 | 1127 | 13% |

Example 182, Degradation of Insulin Analogs Using Duodenum Lumen Enzymes

Degradation of insulin analogs using duodenum lumen enzymes (prepared by filtration of duodenum lumen content) from SPD rats. The assay is performed by a robot in a 96 well plate (2 ml) with 16 wells available for insulin analogs and standards. Insulin analogs ~15 µM are incubated with duodenum enzymes in 100 mM Hepes, pH=7.4 at 37° C., samples are taken after 1, 15, 30, 60, 120 and 240 min and reaction quenched by addition of TFA. Intact insulin analogs at each point are determined by RP-HPLC. Degradation half time is determined by exponential fitting of the data and normalized to half time determined for the reference insulins, A14E, B25H, desB30 human insulin or human insulin in each assay. The amount of enzymes added for the degradation is such that the half time for degradation of the reference insulin is between 60 min and 180 min. The result is given as the degradation half time for the insulin analog in rat duodenum divided by the degradation half time of the reference insulin from the same experiment (relative degradation rate).

| Example # | Duodenum degradation. Relative stability vs. A14E, B25H, desB30 human insulin | Duodenum degradation. Relative stability vs. human insulin |
|---|---|---|
| 19 | 1.8 | 21.6 |
| 2 | 1.3 | 15.6 |
| 3 | .7 | 8.4 |
| 9 | .8 | 9.6 |
| 8 | 1.8 | 21.6 |
| 11 | .9 | 10.8 |
| 13 | 1.5 | 18 |
| 22 | .9 | 11 |
| 16 | .5 | 6 |
| 18 | 1.1 | 13.2 |
| 23 | 1.9 | 22.8 |
| 24 | 1.2 | 14.4 |
| 25 | 1.1 | 13.2 |
| 26 | 1.2 | 14.4 |
| 27 | 2.9 | 35 |
| 28 | .7 | 7.2 |
| 29 | 3.1 | 37 |
| 30 | 2.1 | 25.2 |
| 31 | 1.6 | 19.2 |
| 32 | 1.9 | 22.8 |
| 33 | .5 | 6 |
| 21 | 1.1 | 13.2 |
| 34 | 1.0 | 12 |
| 35 | .6 | 7.2 |
| 36 | .9 | 10.8 |
| 37 | .8 | 9.6 |
| 40 | .7 | 8.4 |
| 38 | .5 | 6 |
| 41 | .7 | 8.4 |
| Prior art 183 | 0.1 | 1.2 |
| 46 | 2.0 | 24 |
| 47 | 0.6 | 7 |
| 48 | 0.5 | 6 |
| 49 | 0.1 | 1.2 |
| 50 | 0.5 | 6 |
| 51 | 1.0 | 12 |

Rat Pharmacokinetics:

Intravenous Rat PK:

Anaesthetized rats are dosed intravenously (i.v.) with insulin analogs at various doses and plasma concentrations of the employed compounds are measured using immunoassays or mass spectrometry at specified intervals for 4 hours or more post-dose. Pharmacokinetic parameters are subsequently calculated using WinNonLin Professional (Pharsight Inc., Mountain View, Calif., USA).

Non-fasted male Wistar rats (Taconic) weighing approximately 200 gram are used.

Body weight is measured and rats are subsequently anaesthetized with Hypnorm/Dormicum (each compound is separately diluted 1:1 in sterile water and then mixed; prepared freshly on the experimental day). Aanaesthesia is initiated by 2 ml/kg Hypnorm/Doricum mixture sc followed by two maintenance doses of 1 ml/kg sc at 30 min intervals and two maintenance doses of 1 ml/kg sc with 45 min intervals. If required in order to keep the rats lightly anaesthetised throughout a further dose(s) 1-2 ml/kg sc is supplied. Weighing and initial anaesthesia is performed in the rat holding room in order to avoid stressing the animals by moving them from one room to another.

Peroral Rat PK:

Gavage:

Conscious rats are p.o. dosed with insulin analogs. Plasma concentrations of the employed compounds as well as changes in blood glucose are measured at specified intervals for 4-6 hours post-dosing. Pharmacokinetic parameters are subsequently calculated using WinNonLin Professional (Pharsight Inc., Mountain View, Calif., USA)

Male Sprague-Dawley rats (Taconic), weighing 250-300 g are fasted for ~18 h and p.o. dosed with test compound or vehicle.

The Composition of the Formulation Used for the Oral Gavage Dosing is the Following (in Weight %):

| | |
|---|---|
| 45% Propylene glycol | (Merck) |
| 33% Capmul MCM 010 | (Abitec) |
| 11% Poloxamer 407 | (BASF) |
| 11% Polyethyleneglycol 3350 Ultra | (Fluka) |

The amount of added insulin is subtracted equaly from Capmul MCM C10, Poloxamer 407 and PEG 3350 and not from propylene glycol in order to keep the amount of propylene glycol independent of the drug load constant at 45%.

Neutral insulin (freeze-dried from pH 7.4) is dissolved in propylene glycol at RT under gentle agitation. Depending on the insulin and the amount of insulin it can take a few hours to dissolve in propylene glycol. The resulting solution should be clear. The other additives, Capmul, poloxamer and PEG3350 are mixed and melted together at 58 C and should also result in a clear, slightly yellowish solution. Then the insulin propylene glycol solution is warmed up to 35° C. and the melted additives are added portionwise under magnetic stirring. The resulting mixture should be clear and homogenously at 35° C. and results in a semi solid after storage in the fridge. After preparation the SEDDS composition is cooled down to 5° C. in order to solidify.

Blood samples for the determination of whole blood glucose concentrations are collected in heparinised 10 μl capillary tubes by puncture of the capillary vessels in the tail tip. Blood glucose concentrations are measured after dilution in 500 μl analysis buffer by the glucose oxidase method using a Biosen autoanalyzer (EKF Diagnostic Gmbh, Germany). Mean blood glucose concentration courses (mean±SEM) are made for each compound.

Samples are collected for determination of the plasma insulin concentration. 100 μl blood samples are drawn into chilled tubes containing EDTA. The samples are kept on ice until centrifuged (7000 rpm, 4° C., 5 min), plasma is pipetted into Micronic tubes and then frozen at 20° C. until assay. Plasma concentrations of the insulin analogs are measured in the Assay and Technology dept. using an immunoassay which is considered appropriate or validated for the individual analog.

Blood samples are drawn at t=−10 (for blood glucose only), at t=−1 (just before dosing) and at specified intervals for 4-6 hours post-dosing.

Intraintestinal Injection:

Anaesthetized rats are dosed intraintestinally (into jejunum) with insulin analogs. Plasma concentrations of the employed compounds as well as changes in blood glucose are measured at specified intervals for 4 hours or more post-dosing. Pharmacokinetic parameters are subsequently calculated using WinNonLin Professional (Pharsight Inc., Mountain View, Calif., USA).

Male Sprague-Dawley rats (Taconic), weighing 250-300 g, fasted for ~18 h are anesthetized using Hypnorm-Dormicum s.c. (0.079 mg/ml fentanyl citrate, 2.5 mg/ml fluanisone and 1.25 mg/ml midazolam) 2 ml/kg as a priming dose (to timepoint −60 min prior to test substance dosing), 1 ml/kg after 20 min followed by 1 ml/kg every 40 min.

The insulins to be tested in the intraintestinal injection model are formulated as formulated for the gavage model above.

The anesthetized rat is placed on a homeothermic blanket stabilized at 37° C. A 20 cm polyethylene catheter mounted a 1-ml syringe is filled with insulin formulation or vehicle. A 4-5 cm midline incision is made in the abdominal wall. The catheter is gently inserted into mid-jejunum ~50 cm from the caecum by penetration of the intestinal wall. If intestinal content is present, the application site is moved ±10 cm. The catheter tip is placed approx. 2 cm inside the lumen of the intestinal segment and fixed without the use of ligatures. The intestines are carefully replaced in the abdominal cavity and the abdominal wall and skin are closed with autoclips in each layer. At time 0, the rats are dosed via the catheter, 0.4 ml/kg of test compound or vehicle.

Blood samples for the determination of whole blood glucose concentrations are collected in heparinised 10 μl capillary tubes by puncture of the capillary vessels in the tail tip. Blood glucose concentrations are measured after dilution in 500 μl analysis buffer by the glucose oxidase method using a Biosen autoanalyzer (EKF Diagnostic Gmbh, Germany). Mean blood glucose concentration courses (mean±SEM) are made for each compound.

Samples are collected for determination of the plasma insulin concentration. 100 μl blood samples are drawn into chilled tubes containing EDTA. The samples are kept on ice until centrifuged (7000 rpm, 4° C., 5 min), plasma is pipetted into Micronic tubes and then frozen at 20° C. until assay. Plasma concentrations of the insulin analogs are measured in a immunoassay which is considered appropriate or validated for the individual analog.

Blood samples are drawn at t=−10 (for blood glucose only), at t=−1 (just before dosing) and at specified intervals for 4 hours or more post-dosing.

| Example # | MRT (min) (Mean retention time, gavage) | Fpo, Gavage (%) | Fpo, Intraintestinal injection (%) |
|---|---|---|---|
| 183 (Prior art) | 97 ± 15 | 0.005 ± 0.009 | 0.28 ± 0.14 |
| 2 | 401 ± 82 | 0.05 ± 0.02 | |
| 9 | 345 ± 111 | 0.10 ± 0.09 | 1.9 ± 1.0 |
| 13 | 251 ± 47 | 0.12 ± 0.08 | |
| 16 | 416 ± 37 | 0.06 ± 0.04 | 1.8 ± 1.9 |
| 18 | 149 ± 29 | 0.13 ± 0.07 | |
| 24 | 194 ± 54 | 0.06 ± 0.05 | 1.4 ± 1.1 |
| 25 | 481 ± 108 | 0.20 ± 0.05 | 3.3 ± 1.2 |
| 26 | | | |
| 33 | | | |

Rat Pharmacodynamics:

Blood glucose vs. time profiles following oral administration (as described above) of selected acylated insulins of the invention are shown below:

Example 183

The oral effect of overnight fasted male Wistar rats on an insulin of the prior art, i.e.:

B29K(N^εOctadecanedioyl-γGlu-OEG-OEG), desB30 human insulin is given in FIG. 1 below.

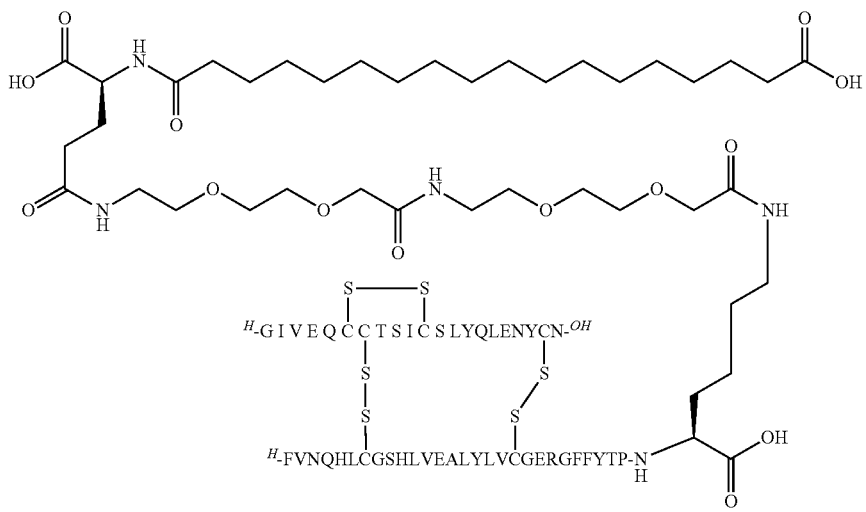

Example 184

Potency of the Acylated Insulin Analogues of this Invention Relative to Human Insulin Sprague Dawley male rats weighing 238-383 g on the experimental day are used for the clamp experiment. The rats have free access to feed under controlled ambient conditions and are fasted overnight (from 3 pm) prior to the clamp experiment.

Experimental Protocol:

The rats are acclimatized in the animal facilities for at least 1 week prior to the surgical procedure. Approximately 1 week prior to the clamp experiment, Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

At 7 am on the experimental day overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and have free access to drinking water. After a 30 min basal period during which plasma glucose levels were measured at 10 min intervals, the insulin derivative to be tested and human insulin (one dose level per rat, n=6-7 per dose level) are infused (i.v.) at a constant rate for 300 min. Optionally a priming bolus infusion of the insulin derivative to be tested is administered in order to reach immediate steady state levels in plasma. The dose of the priming bolus infusion can be calculated based on clearance data obtained from i.v. bolus pharmacokinetics by a pharmacokinetician skilled in the art. Plasma glucose levels are measured at 10 min intervals throughout and infusion of 20% aqueous glucose is adjusted accordingly in order to maintain euglyceamia. Samples of re-suspended erythrocytes are pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides are confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

SEQUENCE LISTS

SEQ ID Nos. 5-11 are the sequences for the A chains present in the compounds of this invention shown in the above specific examples and SEQ ID Nos. 12-29 are the sequences for the B chains present in the compounds of this invention shown in the above specific examples.

The invention claimed is:

1. An acylated protease stabilized insulin, wherein said protease stabilized insulin derived from a non-protease stabilized human insulin or human insulin analogue, wherein at least two hydrophobic amino acids have been substituted with hydrophilic amino acids, and wherein said substitutions are situated one amino acid away from or within two or more protease cleavage sites which are selected from positions B14-15, B24-25, B25-26 and A14-15 of the non-protease stabilized insulin and wherein such protease stabilized insulin optionally further comprises one or more additional mutations, with the proviso that there is only one lysine residue in the stabilized insulin, and wherein the acyl moiety is attached to the lysine residue or to a N-terminal position in the protease stabilized insulin and has the general formula $$\text{Acy-AA1}_n\text{-AA2}_m\text{-AA3}_p\text{-} \qquad (I),$$

wherein n is 0 or an integer in the range from 1 to 3;
m is an integer in the range from 1 to 10;
p is 0 or an integer in the range from 1 to 10;
Acy is a fatty acid or a fatty diacid comprising from about 8 to about 24 carbon atoms;
AA1 is a neutral linear or cyclic amino acid residue;
AA2 is an acidic amino acid residue;
AA3 is a neutral, alkyleneglycol-containing amino acid residue;
the order by which AA1, AA2 and AA3 appears in the formula can be interchanged independently;
AA2 can occur several times along the formula;
AA2 can occur independently several times along the connections between Acy, AA1, AA2 and/or AA3 are amide bonds which, formally, can be obtained by removal of a hydrogen atom or a hydroxyl group from each of Acy, AA1, AA2 and AA3; and
attachment to the protease stabilized insulin can be from the C-terminal end of a AA1, AA2, or AA3 residue in the acyl moiety of the formula (I) or from one of the side chain(s) of an AA2 residue present in the moiety of formula (I).

2. The acylated protease stabilized insulin according to claim 1, wherein the acyl moiety is attached to the lysine residue in the protease stabilized insulin.

3. The acylated protease stabilized insulin according to claim 1, wherein the acyl moiety is attached to the amino group of the A-chain N-terminal residue in the protease stabilized insulin.

4. The acylated protease stabilized insulin according to claim 1, wherein Acy is a fatty diacid, preferably a fatty (α,ω) diacid, more preferred heptadecanedioic acid, hexadecanedioic acid, octadecanedioic acid, nonadecanedioic acid, docosanedioic acid, eicosanedioic acid.

5. The acylated protease stabilized insulin according to claim 1, wherein AA2 is γGlu, αGlu, βAsp, αAsp, γ-D-Glu, α-D-Glu, β-D-Asp, α-D-Asp, or an amino acid of the following formula selected from the group consisting of:

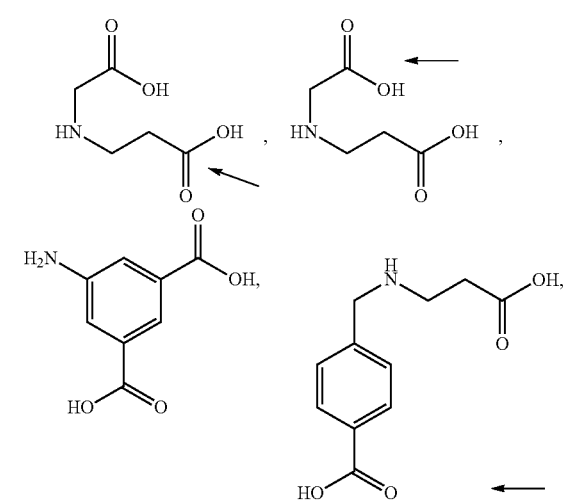

-continued

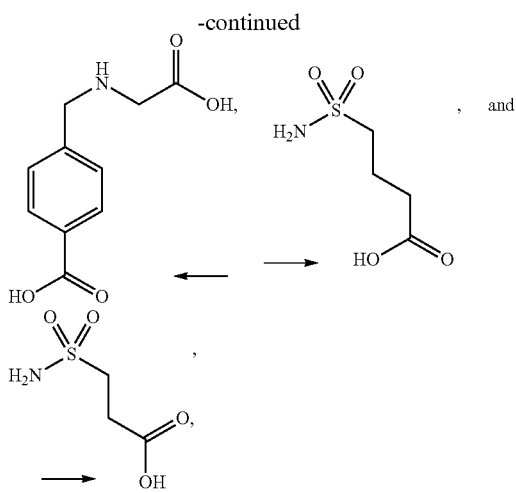

wherein the arrows indicate the attachment point to the amino group of AA1, AA2, AA3 or to the ε-amino group of the B29 lysine residue or to a N-terminal position of the protease stabilised insulin.

6. The acylated protease stabilized insulin according to claim 1, wherein AA3 is selected from the group consisting of:

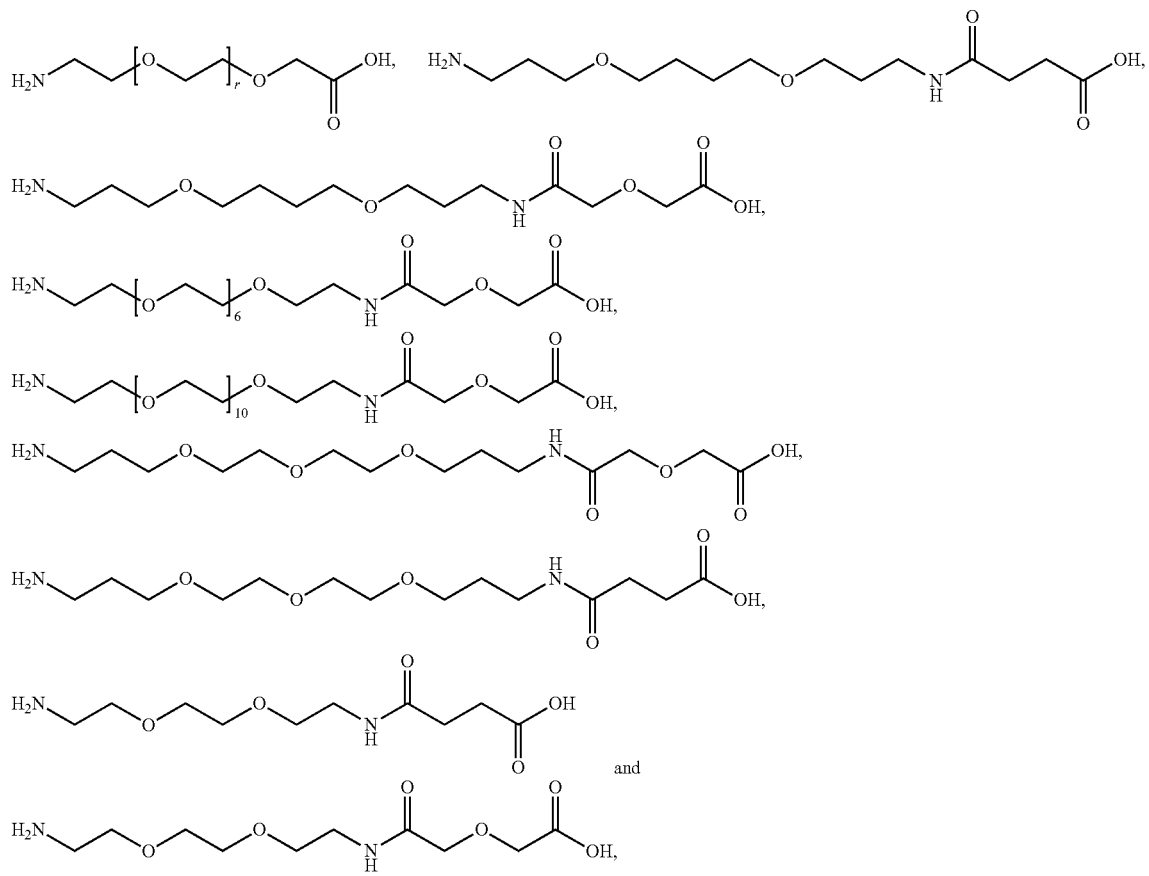

wherein r is 1, 2, 3, 5, 7, 11, 23 or 27.

7. The acylated protease stabilized insulin according to claim 1, wherein the amino acid in position A12 is Glu or Asp; and/or the amino acid in position A13 is His, Asn, Glu or Asp; and/or the amino acid in position A14 is Tyr, Asn, Gln, Glu, Arg, Asp, Gly or His; and/or the amino acid in position A15 is Glu or Asp; and the amino acid in position B24 is His; and/or the amino acid in position B25 is His or Asn; and/or the amino acid in position B26 is His, Gly, Asp or Thr; and/or the amino acid in position B27 is His, Glu, Asp, Gly or Arg; and/or the amino acid in position B28 is His, Gly, Glu or Asp; and which optionally further comprises one or more additional mutations.

8. The acylated protease stabilized insulin according to claim 1, wherein the amino acid in position A14 is Glu, Asp or His and the amino acid in position B25 is His and the amino acid in position B30 is deleted.

9. The acylated protease stabilized insulin according to claim 1, wherein the one or more additional mutations is selected from a group consisting of: A8His, A18Gln, A21Gln, A21Gly, B1Glu, B1Gln, B3Gln, B10Pro, B14Thr, B16Glu, B17Ser, B26Asp, B27Glu, B27Asp, B28Asp, B28Glu, and desB30.

10. The acylated protease stabilized insulin according to claim 1, wherein the additional mutation is desB30.

11. The acylated protease stabilized insulin according to claim 1, wherein A14 is Glu.

12. The acylated protease stabilized insulin according to claim 1, wherein B25 is His.

13. The acylated protease stabilized insulin according to claim 1, wherein the C terminal amino acid residue in the A chain of the protease stabilized insulin is the A21 amino acid residue.

14. The acylated protease stabilized insulin according to claim 1, comprising an A-chain amino acid sequence of formula 1, i.e.: $Xaa_{A(-2)}$-$Xaa_{A(-1)}$-$Xaa_{A0}$-Gly-Ile-Val-Glu-Gln-Cys-Cys-$Xaa_{A8}$-Ser-Ile-Cys-$Xaa_{A12}$-$Xaa_{A13}$-$Xaa_{A14}$-$Xaa_{A15}$-Leu-Glu-$Xaa_{A18}$-Tyr-Cys-$Xaa_{A21}$ (SEQ ID No:1), and a B-chain amino acid sequence of formula 2, i.e.: $Xaa_{B(-2)}$-$Xaa_{B(-1)}$-$Xaa_{B0}$-$Xaa_{B1}$-$Xaa_{B2}$-$Xaa_{B3}$-$Xaa_{B4}$-His-Leu-Cys-Gly-Ser-$Xaa_{B10}$-Leu-Val-Glu-Ala-Leu-$Xaa_{B16}$-Leu-Val-Cys-Gly-Glu-Arg-Gly-$Xaa_{B24}$-$Xaa_{B25}$-$Xaa_{B26}$-$Xaa_{B27}$-$Xaa_{B28}$-$Xaa_{B29}$-$Xaa_{B30}$-$Xaa_{B31}$-$Xaa_{B32}$ (SEQ ID No:2), wherein $Xaa_{A(-2)}$ is absent or Gly; $Xaa_{A(-1)}$ is absent or Pro; $Xaa_{A0}$ is absent or Pro; $Xaa_{A8}$ is independently selected from Thr and His; $Xaa_{A12}$ is independently selected from Ser, Asp and Glu; $Xaa_{A13}$ is independently selected from Leu, Thr, Asn, Asp, Gln, His, Lys, Gly, Arg, Pro, Ser and Glu; $Xaa_{A14}$ is independently selected from Tyr, Thr, Asn, Asp, Gln, His, Lys, Gly, Arg, Pro, Ser and Glu; $Xaa_{A15}$ is independently selected from Gln, Asp and Glu; $Xaa_{A18}$ is independently selected from Asn, Lys and Gln; $Xaa_{A21}$ is independently selected from Asn and Gln; $Xaa_{B(-2)}$ is absent or Gly; $Xaa_{B(-1)}$ is absent or Pro; $Xaa_{B0}$ is absent or Pro; $Xaa_{B1}$ is absent or independently selected from Phe and Glu; $Xaa_{B2}$ is absent or Val; $Xaa_{B3}$ is absent or independently selected from Asn and Gln; $Xaa_{B4}$ is independently selected from Gln and Glu; $Xaa_{B10}$ is independently selected from His, Asp, Pro and Glu; $Xaa_{B16}$ is independently selected from Tyr, Asp, Gln, His, Arg, and Glu; $Xaa_{B24}$ is independently selected from Phe and His; $Xaa_{B25}$ is independently selected from Phe, Asn and His; $Xaa_{B26}$ is absent or independently selected from Tyr, His, Thr, Gly and Asp; $Xaa_{B27}$ is absent or independently selected from Thr, Asn, Asp, Gln, His, Gly, Arg, Pro, Ser and Glu; $Xaa_{B28}$ is absent or independently selected from Pro, His, Gly and Asp; $Xaa_{B29}$ is absent or independently selected from Lys and Gln; $Xaa_{B30}$ is absent or Thr; $Xaa_{B31}$ is absent or Leu; $Xaa_{B32}$ is absent or Glu; the C-terminal may optionally be derivatized as an amide; wherein the A-chain amino acid sequence and the B-chain amino acid sequence are connected by disulphide bridges between the cysteines in position 7 of the A-chain and the cysteine in position 7 of the B-chain, and between the cysteine in position 20 of the A-chain and the cysteine in position 19 of the B-chain and wherein the cysteines in position 6 and 11 of the A-chain are connected by a disulphide bridge; wherein optionally the N-terminal A-chain amino acid sequence is connected to the C-terminal B-chain amino acid sequence by an amino acid sequence comprising 3-7 amino acids to form a single chain insulin molecule, wherein optionally the N-terminal of the B-chain is extended with 1-10 amino acids; wherein if $Xaa_{A8}$ is Thr and $Xaa_{A12}$ is Ser and $Xaa_{A13}$ is Leu and $Xaa_{A14}$ is Tyr then $Xaa_{A15}$ is Glu or Asp; and wherein if $Xaa_{B24}$ is Phe and $Xaa_{B25}$ is Phe and $Xaa_{B26}$ is Tyr and $Xaa_{B27}$ is Thr and $Xaa_{B28}$ is Pro then $Xaa_{B29}$ Gln.

15. A pharmaceutical composition comprising an acylated protease stabilized insulin according to claim 1 and a pharmaceutically acceptable carrier or excipient.

16. A method of treating hyperglycemia, type 2 diabetes, impaired glucose tolerance or type 1 diabetes in a subject in need thereof, comprising administering to said subject a therapeutically effective amount of the pharmaceutical composition of claim 15.

17. An acylated protease stabilized insulin, wherein the protease stabilized insulin is selected from the group consisting of A8H, B25N, B27E, desB30 human insulin; A14E, A18L, B25H, desB30 human insulin; A14E, A21G, B25H, desB27, desB30 human insulin; A14E, B1E, B25H, B27E, B28E, desB30 human insulin; A14E, B1E, B25H, B28E, desB30 human insulin; A14E, B1E, B27E, B28E, desB30 human insulin; A14E, B1E, B28E, desB30 human insulin; A14E, B16H, B25H, desB30 human insulin; A14E, B25H, desB30 human insulin; A14E, B25H, B26G, B27G, B28G, desB30 human insulin; A14E, B25H, B27E, desB30 human insulin; A14E, B25H, desB27, desB30 human insulin; A14E, B25H, B29R, desB30 human insulin; A14E, B28D, desB30 human insulin; A14E, B28E, desB30 human insulin; B25N, B27E, desB30 human insulin; A14E, A21G, B16H, B25H, desB30 human insulin; A14E, A21G, B25H, B26G, B27G, B28G, desB30 human insulin; B25H, desB30 human insulin; A21G, B25H, desB30 human insulin; A14E, A21G, B25H, desB30 human insulin and A14E, A21G, B25H, desB27, desB30 human insulin, and wherein an acyl moiety is attached to the lysine residue or to a N-terminal position in said protease stabilized insulin and has the general formula $$Acy\text{-}AA1_n\text{-}AA2_m\text{-}AA3_p\text{-} \qquad (I),$$

wherein
n is 0 or an integer in the range from 1 to 3;
m is an integer in the range from 1 to 10;
p is 0 or an integer in the range from 1 to 10;
Acy is a fatty acid or a fatty diacid comprising from about 8 to about 24 carbon atoms;
AA1 is a neutral linear or cyclic amino acid residue;
AA2 is an acidic amino acid residue;
AA3 is a neutral, alkyleneglycol-containing amino acid residue;
the order by which AA1, AA2 and AA3 appears in the formula can be interchanged independently;
AA2 can occur several times along the formula;
AA2 can occur independently several times along the connections between Acy, AA1, AA2 and/or AA3 are amide bonds which, formally, can be obtained by removal of a hydrogen atom or a hydroxyl group from each of Acy, AA1, AA2 and AA3; and
attachment to the protease stabilized insulin can be from the C-terminal end of a AA1, AA2, or AA3 residue in the acyl moiety of the formula (I) or from one of the side chain(s) of an AA2 residue present in the moiety of formula (I).

18. An acylated protease stabilized insulin selected from the group consisting of A14E, B25H, B29K($N^\varepsilon$-hexadecandioyl), desB30 human insulin; A14E, B25H, B29K($N^\varepsilon$eicosanedioyl-γGlu), desB30 human insulin; A14E, B25H, B29K($N^\varepsilon$3-carboxy-5-octadecanedioylaminobenzoyl), desB30 human insulin; A14E, B25H, B29K($N^\varepsilon$—N-octadecandioyl-N-(2-carboxyethyl)glycyl), desB30 human insulin; A14E, B25H, B29K($N^\varepsilon$ (N-octadecandioyl-N-carboxymethyl)-beta-alanyl), desB30 human insulin; A14E, B25H, B29K($N^\varepsilon$4-([4-({19-carboxynonadecanoylamino}methyl)trans-cyclohexanecarbonyl]-γGlu), desB30 human insulin; A14E, B25H, B29K($N^\varepsilon$heptadecanedioyl-γGlu), desB30 human insulin; A14E, B25H, B29K($N^\varepsilon$myristyl), desB30 human insulin; A14E, B25H, B29K($N^\varepsilon$eicosanedioyl-γGlu-γGlu), desB30 human insulin; A14E, B25H, B29K($N^\varepsilon$4-([4-({19-carboxynonadecanoylamino}methyl)trans-cyclohexanecarbonyl]-γGlu-γGlu), desB30 human insulin; A14E, B25H, B29K($N^\varepsilon$octadecanedioyl-γGlu-γGlu), desB30 human insulin; A14E, B28D, B29K($N^\varepsilon$octadecandioyl-γGlu), desB30 human insulin; A14E, B25H, B29K($N^\varepsilon$octadecandioyl-γGlu-PEG7), desB30 human insulin; A14E, B25H, B29K ($N^\varepsilon$eicosanedioyl-γGlu-(3-(2-{2-[2-(2-aminoethoxy)ethoxy]ethoxy}ethoxy)propionyl-γGlu), desB30 human insulin; A14E, B25H, B29K($N^\varepsilon$hexadecanedioyl-γGlu), desB30 human insulin; A14E, B25H, B29K (Nᵋoctadecanedioyl-γGlu-γGlu-γGlu-γGlu), desB30 human insulin; A14E, B25H, B29K(Nᵋeicosanedioyl-γGlu-γGlu-γGlu), desB30 human insulin; A14E, B25H, B27E, B29K (Nᵋoctadecandioyl-γGlu-OEG-OEG), desB30 human insulin; A14E, B25H, B26G, B27G, B28G, B29K (Nᵋoctadecandioyl-γGlu-OEG-OEG), desB30 human insulin; A14E, B16E, B25H, B29K(Nᵋoctadecanedioyl-γGlu-OEG-OEG), desB30 human insulin; A14E, B16H, B25H, B29K(Nᵋhexadecandioyl-γGlu), desB30 human insulin; A14E, B16E, B25H, B29K(Nᵋhexadecandioyl-γGlu), desB30 human insulin; A14E, B25H, B26G, B27G, B28G, B29K(Nᵋhexadecandioyl-γGlu), desB30 human insulin; A14E, A18L, B25H, B29K(Nᵋeicosanedioyl-γGlu-OEG-OEG), desB30 human insulin; A14E, A18L, B25H, B29K(Nᵋoctadecandioyl-γGlu-OEG-OEG), desB30 human insulin; A14E, B25H, B27E, B29K (Nᵋeicosanedioyl-γGlu-OEG-OEG), desB30 human insulin; A1G(Nᵅoctadecandioyl-γGlu-OEG-OEG), A14E, B25H, B29R, desB30 human insulin; A14E, B1F (Nᵅoctadecandioyl-γGlu-OEG-OEG), B25H, B29R, desB30 human insulin; A1G(Nᵅhexadecandioyl-γGlu), A14E, B25H, B29R, desB30 human insulin; A14E, B25H, B29K(Nᵋoctadecandioyl-γGlu-Abu-Abu-Abu-Abu), desB30 human insulin; A14E, B25H, B29K (Nᵅeicosanedioyl), desB30 human insulin; A14E, B25H, B29K(Nᵅ4-[16-(1H-tetrazol-5-yl)hexadecanoylsulfamoyl] butanoyl), desB30 human insulin; A14E, B25H, B26G, B27G, B28G, B29K(Nᵋoctadecandioyl-γGlu), desB30 human insulin; A14E, B25H, B26G, B27G, B28G, B29K (Nᵋeicosanedioyl-γGlu), desB30 human insulin; A14E, B25H, B26G, B27G, B28G, B29K(Nᵋoctadecandioyl), desB30 human insulin; A14E, B25H, B26G, B27G, B28G, B29K(Nᵋeicosanedioyl), desB30 human insulin; A14E, B25H, B26G, B27G, B28G, B29K(Nᵋeicosanedioyl-γGlu-OEG-OEG), desB30 human insulin; A14E, B25H, B29K (Nᵋdocosanedioyl-γGlu), desB30 human insulin; A14E, B25H, B29K(Nᵋdocosanedioyl-γGlu-γGlu), desB30 human insulin; A14E, B25H, B29K(Nᵋ (N-icosanedioyl-N-carboxymethyl)-3Ala), desB30 human insulin; A14E, B25H, B29K(Nᵋ3-[2-(2-{2-[2-(17-carboxyheptadecanoylamino) ethoxy]ethoxy}ethoxy)ethoxy]propionyl-γGlu), desB30 human insulin; A14E, B25H, B29K(Nᵋ3-[2-(2-{2-[2-(19-carboxynonadecanoylamino)-ethoxy]}ethoxy)ethoxy]propionyl-γGlu), desB30 human insulin; A14E, B25H, B29K (Nᵋoctadecandioyl-γGlu-(3-(2-{2-[2-(2-aminoethoxy) ethoxy]ethoxy}ethoxy)propionyl), desB30 human insulin; A14E, B25H, B29K(Nᵋoctadecandioyl-γGlu-(3-(2-{2-[2-(2-aminoethoxy)ethoxy]ethoxy}ethoxy)propionyl-γGlu), desB30 human insulin; A14E, B25H, B29K (Nᵋicosanedioyl-γGlu-(3-(2-{2-[2-(2-aminoethoxy)ethoxy] ethoxy}ethoxy)propionyl), desB30 human insulin; A14E, B25H, B29K(Nᵋ4-([4-({17-carboxynonadecanoylamino}methyl)trans-cyclohexanecarbonyl]-γGlu), desB30 human insulin; A14E, B25H, B29K (Nᵋ4-([4-({17-carboxyheptadecanoylamino}methyl)trans-cyclohexanecarbonyl]-γGlu-γGlu), desB30 human insulin; A14E, B28D, B29K(Nᵋhexadecandioyl-γGlu), desB30 human insulin; A14E, B28D, B29K(Nᵋ eicosanedioyl-γGlu), desB30 human insulin; A14E, B28D, B29K(Nᵋ octadecandioyl-γGlu-OEG-OEG), desB30 human insulin; A14E, B28D, B29K(Nᵋeicosanedioyl-γGlu-OEG-OEG), desB30 human insulin; A14E, B28E, B29K(Nᵋhexadecandioyl-γGlu), desB30 human insulin; A14E, B28E, B29K(Nᵋ octadecandioyl-γGlu), desB30 human insulin; A14E, B28E, B29K(Nᵋ eicosanedioyl-γGlu), desB30 human insulin; A14E, B28E, B29K(Nᵋoctadecandioyl-γGlu-OEG-OEG), desB30 human insulin; A14E, B28E, B29K (Nᵋeicosanedioyl-γGlu-OEG-OEG), desB30 human insulin; A14E, B1E, B28E, B29K(Nᵋhexadecandioyl-γGlu), desB30 human insulin; A14E, B1E, B28E, B29K(Nᵋoctadecandioyl-γGlu), desB30 human insulin; A14E, B1E, B28E, B29K (Nᵋeicosanedioyl-γGlu), desB30 human insulin; A14E, B1E, B28E, B29K(Nᵋhexadecandioyl-γGlu-OEG-OEG), desB30 human insulin; A14E, B1E, B28E, B29K(Nᵋoctadecandioyl-γGlu-OEG-OEG), desB30 human insulin; A14E, B1E, B28E, B29K(Nᵋeicosanedioyl-γGlu-OEG-OEG), desB30 human insulin; A14E, B1E, B27E, B28E, B29K (Nᵋhexadecandioyl-γGlu), desB30 human insulin; A14E, B1E, B27E, B28E, B29K(Nᵋoctadecandioyl-γGlu), desB30 human insulin; A14E, B1E, B27E, B28E, B29K (Nᵋeicosanedioyl-γGlu), desB30 human insulin; A14E, B1E, B27E, B28E, B29K(Nᵋhexadecandioyl-γGlu-OEG-OEG), desB30 human insulin; A14E, B1E, B27E, B28E, B29K (Nᵋoctadecandioyl-γGlu-OEG-OEG), desB30 human insulin; A14E, B1E, B27E, B28E, B29K(Nᵋeicosanedioyl-γGlu-OEG-OEG), desB30 human insulin; A14E, B1E, B25H, B28E, B29K(Nᵋhexadecandioyl-γGlu), desB30 human insulin; A14E, B1E, B25H, B28E, B29K(Nᵋoctadecandioyl-γGlu), desB30 human insulin; A14E, B1E, B25H, B28E, B29K(Nᵋeicosanedioyl-γGlu), desB30 human insulin; A14E, B1E, B25H, B28E, B29K(Nᵋhexadecandioyl-γGlu-OEG-OEG), desB30 human insulin; A14E, B1E, B25H, B28E, B29K(Nᵋoctadecandioyl-γGlu-OEG-OEG), desB30 human insulin; A14E, B1E, B25H, B28E, B29K (Nᵋeicosanedioyl-γGlu-OEG-OEG), desB30 human insulin; A14E, B1E, B25H, B27E, B28E, B29K(Nᵋhexadecandioyl-γGlu), desB30 human insulin; A14E, B1E, B25H, B27E, B28E, B29K(Nᵋoctadecandioyl-γGlu), desB30 human insulin; A14E, B1E, B25H, B27E, B28E, B29K (Nᵋeicosanedioyl-γGlu), desB30 human insulin; A14E, B1E, B25H, B27E, B28E, B29K(Nᵋhexadecandioyl-γGlu-OEG-OEG), desB30 human insulin; A14E, B1E, B25H, B27E, B28E, B29K(Nᵋoctadecandioyl-γGlu-OEG-OEG), desB30 human insulin; A14E, B1E, B25H, B27E, B28E, B29K (Nᵋeicosanedioyl-γGlu-OEG-OEG), desB30 human insulin; A14E, B28D, B29K(Nᵋhexadecanedioyl-γGlu-OEG-OEG), desB30 human insulin; A14E, B28E, B29K (Nᵋhexadecanedioyl-γGlu-OEG-OEG), desB30 human insulin; B25N, B27E, B29K(Nᵋeicosanedioyl-γGlu-OEG-OEG), desB30 human insulin; B25N, B27E, B29K (Nᵋoctadecanedioyl-γGlu-OEG-OEG), desB30 human insulin; B25N, B27E, B29K(Nᵋhexadecanedioyl-γGlu-OEG-OEG), desB30 human insulin; B25N, B27E, B29K (Nᵋeicosanedioyl-γGlu), desB30 human insulin; B25N, B27E, B29K(Nᵋoctadecanedioyl-γGlu), desB30 human insulin; B25N, B27E, B29K(Nᵋhexadecanedioyl-γGlu), desB30 human insulin; A8H, B25N, B27E, B29K (Nᵋeicosanedioyl-γGlu-OEG-OEG), desB30 human insulin; A8H, B25N, B27E, B29K(Nᵋoctadecanedioyl-γGlu-OEG-OEG), desB30 human insulin; A8H, B25N, B27E, B29K (Nᵋhexadecanedioyl-γGlu-OEG-OEG), desB30 human insulin; A8H, B25N, B27E, B29K(Nᵋeicosanedioyl-γGlu), desB30 human insulin; A8H, B25N, B27E, B29K (Nᵋoctadecanedioyl-γGlu), desB30 human insulin; A8H, B25N, B27E, B29K(Nᵋhexadecanedioyl-γGlu), desB30 human insulin; A14E, B25H, B29K(Nᵋ (N-icosanedioyl-N-carboxymethyl)-3Ala-OEG-OEG), desB30 human insulin; A14E, B25H, B29K(Nᵋ (N-octadecanedioyl-N-carboxymethyl)-3Ala-OEG-OEG), desB30 human insulin; A14E, B25H, B29K(Nᵋ (N-hexadecanedioyl-N-carboxymethyl)-3Ala-OEG-OEG), desB30 human insulin; A14E, B25H, B29K(Nᵋoctadecanedioyl-γGlu-2-[(3-{2-[2-(3-aminopropoxy)ethoxy]ethoxy}propyl-carbamoyl)methoxy]

acetyl), desB30 human insulin; A14E, B25H, B29K(N$^\varepsilon$eicosanedioyl-γGlu-2-[(3-{2-[2-(3-aminopropoxy)ethoxy]ethoxy}propylcarbamoyl)methoxy]acetyl), desB30 human insulin; A14E, B16H, B25H, B29K(N$^\varepsilon$octadecanedioyl-γGlu-2-[(3-{2-[2-(3-amino-propoxy)ethoxy]ethoxy}propylcarbamoyl)methoxy]acetyl), desB30 human insulin; A14E, B16H, B25H, B29K(N$^\varepsilon$eicosanedioyl-γGlu-2-[(3-{2-[2-(3-aminopropoxy)ethoxy]ethoxy}propyl-carbamoyl)methoxy]acetyl), desB30 human insulin; B25H, B29K(N$^\varepsilon$octadecanedioyl-γGlu-OEG-OEG), desB30 human insulin; B25H, B29K(N$^\varepsilon$eicosanedioyl-γGlu-OEG-OEG), desB30 human insulin; B25H, B29K(N$^\varepsilon$octadecanedioyl-γGlu), desB30 human insulin; B25H, B29K(N$^\varepsilon$eicosanedioyl-γGlu), desB30 human insulin; B25H, B29K(N$^\varepsilon$octadecanedioyl), desB30 human insulin; B25H, B29K(N$^\varepsilon$eicosanedioyl), desB30 human insulin; B25H, B29K(N$^\varepsilon$octadecanedioyl-γGlu-OEG-OEG), desB30 human insulin; B25H, B29K(N$^\varepsilon$eicosanedioyl-γGlu-OEG-OEG), desB30 human insulin; B25H, B29K(N$^\varepsilon$octadecanedioyl-γGlu), desB30 human insulin; B25H, B29K(N$^\varepsilon$eicosanedioyl-γGlu), desB30 human insulin; B25H, B29K(N$^\varepsilon$octadecanedioyl), desB30 human insulin; B25H, B29K(N$^\varepsilon$eicosanedioyl), desB30 human insulin; B25H, B29K(N$^\varepsilon$octadecanedioyl-γGlu-OEG-OEG), desB30 human insulin; B25H, B29K(N$^\varepsilon$eicosanedioyl-γGlu-OEG-OEG), desB30 human insulin; B25H, B29K(N$^\varepsilon$octadecanedioyl-γGlu), desB30 human insulin; B25H, B29K(N$^\varepsilon$eicosanedioyl-γGlu), desB30 human insulin; A14E, B25H, desB27, B29K(N$^\varepsilon$eicosanedioyl-γGlu), desB30 human insulin; A14E, A21G, B25H, desB27, B29K(N$^\varepsilon$octadecanedioyl), desB30 human insulin; A14E, A21G, B25H, desB27, B29K(N$^\varepsilon$eicosanedioyl), desB30 human insulin; A14E, A21G, B25H, desB27, B29K(N$^\varepsilon$octadecanedioyl-γGlu), desB30 human insulin; A14E, B25H, desB27, B29K(N$^\varepsilon$eicosanedioyl-γGlu), desB30 human insulin; A14E, A21G, B25H, desB27, B29K(N$^\varepsilon$octadecanedioyl-γGlu-OEG-OEG), desB30 human insulin; A1G(N$^\alpha$octadecandioyl-γGlu-OEG-OEG), A14E, A21G, B25H, desB30 human insulin; A14E, B25H, B29K(N$^\varepsilon$eicosanedioyl-OEG), desB30 human insulin; A14E, B25H, B27K(N$^\varepsilon$octadecanedioyl-γGlu-OEG-OEG), desB28, desB29, desB30 human insulin; A14E, B25H, B29K(N$^\varepsilon$(5-cicosancdioylaminoisophthalic acid)), desB30 human insulin; A14E, B25H, B29K(N$^\varepsilon$octadecanedioyl), desB30 human insulin; A14E, B29K(N$^\varepsilon$octadecanedioyl-γGlu-OEG-OEG), desB30 human insulin; A14E, B25H, B26G, B27G, B28G, B29K(N$^\varepsilon$eicosanedioyl-γGlu-OEG-OEG), desB30 human insulin; A14E, B25H, B29K(N$^\varepsilon$octadecanedioyl-γGlu-OEG), desB30 human insulin; A14E, B25H, B29K(N$^\varepsilon$eicosanedioyl-OEG-OEG), desB30 human insulin; A14E, B25H, B29K(N$^\varepsilon$eicosanedioyl-Aoc), desB30 human insulin; A14E, B25H, B26G, B27G, B28G, B29K(N$^\varepsilon$eicosanedioyl-γGlu-γGlu), desB30 human insulin; A14E, B25H, B26G, B27G, B28G, B29K(N$^\varepsilon$eicosanedioyl-γGlu-γGlu), desB30 human insulin; A14E, B25H, B29K(N$^\varepsilon$octadecanedioyl-OEG), desB30 human insulin; A14E, B25H, desB27, B29K(N$^\varepsilon$octadecanedioyl-γGlu-OEG-OEG), desB30 human insulin; A1G(N$_\varepsilon$octadecanedioyl), A14E, B25H, B29R, desB30 human insulin; A14E, B25H, B27K(N$^\varepsilon$eicosanedioyl-γGlu), desB28, desB29, desB30 human insulin; A14E, B25H, B29K(N$^\varepsilon$octadecanedioyl-γGlu-γGlu-γGlu), desB30 human insulin; A21G, B25H, B29K(N$^\varepsilon$octadecanedioyl), desB30 human insulin; A14E, A21G, B25H, desB27, B29K(N$^\varepsilon$eicosanedioyl-γGlu-OEG-OEG), desB30 human insulin; A14E, A21G, B25H, B29K(N$^\varepsilon$octadecanedioyl-γGlu-OEG-OEG), desB30 human insulin; A14E, A21G, B25H, B29K(N$^\varepsilon$eicosanedioyl-γGlu-OEG-OEG), desB30 human insulin; A14E, A21G, B25H, B29K(N$^\varepsilon$eicosanedioyl-γGlu), desB30 human insulin; A14E, A21G, B25H, B29K(N$^\varepsilon$eicosanedioyl), desB30 human insulin; A14E, A21G, B25H, B29K(N$^\varepsilon$eicosanedioyl-γGlu), desB30 human insulin; A14E, A21G, B25H, B29K(N$^\varepsilon$octadecanedioyl), desB30 human insulin; A14E, B25H, B26G, B27G, B28G, B29K(N$^\varepsilon$octadecanedioyl-γGlu), desB30 human insulin; A14E, B25H, B26G, B27G, B28G, B29K(N$^\varepsilon$octadecanedioyl), desB30 human insulin; A14E, B25H, B26G, B27G, B28G, B29K(N$^\varepsilon$eicosanedioyl-γGlu), desB30 human insulin; A14E, B25H, B26G, B27G, B28G, B29K(N$^\varepsilon$eicosanedioyl), desB30 human insulin; A1G(N$^\alpha$octadecandioyl-γGlu), A14E, B25H, B26G, B27G, B28G, desB30 human insulin; A1G(N$_\alpha$eicosanedioyl-γGlu), A14E, B25H, B26G, B27G, B28G, desB30 human insulin; A1G(N$^\alpha$octadecandioyl-γGlu), A14E, B25H, B26G, B27G, B28G, B29R, desB30 human insulin; A1G(N$^\alpha$eicosanedioyl-γGlu), A14E, B25H, B26G, B27G, B28G, B29R, desB30 human insulin; A1G(N$^\alpha$octadecandioyl), A14E, B25H, B26G, B27G, B28G, desB30 human insulin; A1G(N$^\alpha$eicosanedioyl), A14E, B25H, B26G, B27G, B28G, desB30 human insulin; A1G(N$^\alpha$octadecandioyl), A14E, B25H, B26G, B27G, B28G, B29R, desB30 human insulin and A1G(N$^\alpha$eicosanedioyl), A14E, B25H, B26G, B27G, B28G, B29R, desB30 human insulin.

\* \* \* \* \*

UNITED STATES PATENT AND TRADEMARK OFFICE
CERTIFICATE OF CORRECTION

PATENT NO. : 10,259,856 B2
APPLICATION NO. : 14/686176
DATED : April 16, 2019
INVENTOR(S) : Peter Madsen et al.

Page 1 of 1

It is certified that error appears in the above-identified patent and that said Letters Patent is hereby corrected as shown below:

In the Claims

Column 305, Claim 17, Line 64, please amend as follows:
"...consisting of A8H, B25N, B27E, desB30 human insulin; A14E,..."

Column 308, Claim 18, Line 61, please amend as follows:
"...carboxyethyl)-βAla-OEG-OEG), desB30 human insulin;..."

Column 308, Claim 18, Line 63, please amend as follows:
"...ethyl)-βAla-OEG-OEG), desB30 human insulin; A14E,..."

Column 308, Claim 18, Line 65, please amend as follows:
"...βAla-OEG-OEG), desB30 human insulin; A14E, B25H,..."

Signed and Sealed this
Sixteenth Day of July, 2019

Andrei Iancu
*Director of the United States Patent and Trademark Office*

SEQUENCE LISTING

```
<160> NUMBER OF SEQ ID NOS: 29

<210> SEQ ID NO 1
<211> LENGTH: 24
<212> TYPE: PRT
<213> ORGANISM: Artificial Sequence
<220> FEATURE:
<223> OTHER INFORMATION: Modified Insulin A chain
```

```
<220> FEATURE:
<221> NAME/KEY: MISC_FEATURE
<222> LOCATION: (1)..(1)
<223> OTHER INFORMATION: Xaa is absent or Gly
<220> FEATURE:
<221> NAME/KEY: MISC_FEATURE
<222> LOCATION: (2)..(2)
<223> OTHER INFORMATION: Xaa is absent or Pro
<220> FEATURE:
<221> NAME/KEY: MISC_FEATURE
<222> LOCATION: (3)..(3)
<223> OTHER INFORMATION: Xaa is absent or Pro
<220> FEATURE:
<221> NAME/KEY: MISC_FEATURE
<222> LOCATION: (11)..(11)
<223> OTHER INFORMATION: Xaa is Thr or His
<220> FEATURE:
<221> NAME/KEY: MISC_FEATURE
<222> LOCATION: (15)..(15)
<223> OTHER INFORMATION: Xaa is Ser, Asp or Glu
<220> FEATURE:
<221> NAME/KEY: MISC_FEATURE
<222> LOCATION: (16)..(16)
<223> OTHER INFORMATION: Xaa is Leu, Thr, Asn, Asp, Gln, His, Lys, Gly,
      Arg, Pro, Ser or Glu
<220> FEATURE:
<221> NAME/KEY: MISC_FEATURE
<222> LOCATION: (17)..(17)
<223> OTHER INFORMATION: Xaa is Tyr, Thr, Asn, Asp, Gln, His, Lys, Gly,
      Arg, Pro, Ser or Glu
<220> FEATURE:
<221> NAME/KEY: MISC_FEATURE
<222> LOCATION: (18)..(18)
<223> OTHER INFORMATION: Xaa is Gln, Asp or Glu
<220> FEATURE:
<221> NAME/KEY: MISC_FEATURE
<222> LOCATION: (21)..(21)
<223> OTHER INFORMATION: Xaa is Asn, Lys or Gln
<220> FEATURE:
<221> NAME/KEY: MISC_FEATURE
<222> LOCATION: (24)..(24)
<223> OTHER INFORMATION: Xaa is Asn or Gln

<400> SEQUENCE: 1

Xaa Xaa Xaa Gly Ile Val Glu Gln Cys Cys Xaa Ser Ile Cys Xaa Xaa
1               5                   10                  15

Xaa Xaa Leu Glu Xaa Tyr Cys Xaa
            20

<210> SEQ ID NO 2
<211> LENGTH: 35
<212> TYPE: PRT
<213> ORGANISM: Artificial Sequence
<220> FEATURE:
<223> OTHER INFORMATION: Modified Insulin B chain
<220> FEATURE:
<221> NAME/KEY: MISC_FEATURE
<222> LOCATION: (1)..(1)
<223> OTHER INFORMATION: Xaa is absent or Gly
<220> FEATURE:
<221> NAME/KEY: MISC_FEATURE
<222> LOCATION: (2)..(2)
<223> OTHER INFORMATION: Xaa is absent or Pro
<220> FEATURE:
<221> NAME/KEY: MISC_FEATURE
<222> LOCATION: (3)..(3)
<223> OTHER INFORMATION: Xaa is absent or Pro
<220> FEATURE:
<221> NAME/KEY: MISC_FEATURE
<222> LOCATION: (4)..(4)
<223> OTHER INFORMATION: Xaa is absent Phe or Glu
<220> FEATURE:
<221> NAME/KEY: MISC_FEATURE
<222> LOCATION: (5)..(5)
<223> OTHER INFORMATION: Xaa is absent or Val
```

```
<220> FEATURE:
<221> NAME/KEY: MISC_FEATURE
<222> LOCATION: (6)..(6)
<223> OTHER INFORMATION: Xaa is absent, Asn or Gln
<220> FEATURE:
<221> NAME/KEY: MISC_FEATURE
<222> LOCATION: (7)..(7)
<223> OTHER INFORMATION: Xaa is Gln or Glu
<220> FEATURE:
<221> NAME/KEY: MISC_FEATURE
<222> LOCATION: (13)..(13)
<223> OTHER INFORMATION: Xaa is His, Asp, Pro or Glu
<220> FEATURE:
<221> NAME/KEY: MISC_FEATURE
<222> LOCATION: (19)..(19)
<223> OTHER INFORMATION: Xaa is Tyr, Asp, Gln, His, Arg or Glu
<220> FEATURE:
<221> NAME/KEY: MISC_FEATURE
<222> LOCATION: (27)..(27)
<223> OTHER INFORMATION: Xaa is Phe or His
<220> FEATURE:
<221> NAME/KEY: MISC_FEATURE
<222> LOCATION: (28)..(28)
<223> OTHER INFORMATION: Xaa is Phe, Asn or His
<220> FEATURE:
<221> NAME/KEY: MISC_FEATURE
<222> LOCATION: (29)..(29)
<223> OTHER INFORMATION: Xaa is absent, Tyr, His, Thr, Gly or Asp
<220> FEATURE:
<221> NAME/KEY: MISC_FEATURE
<222> LOCATION: (30)..(30)
<223> OTHER INFORMATION: Xaa is absent, Thr, Asn, Asp, Gln, His, Lys,
      Gly, Arg, Pro, Ser or Glu
<220> FEATURE:
<221> NAME/KEY: MISC_FEATURE
<222> LOCATION: (31)..(31)
<223> OTHER INFORMATION: Xaa is absent, Pro, His, Gly or Asp
<220> FEATURE:
<221> NAME/KEY: MISC_FEATURE
<222> LOCATION: (32)..(32)
<223> OTHER INFORMATION: Xaa is absent, Lys, Arg or Gln
<220> FEATURE:
<221> NAME/KEY: MISC_FEATURE
<222> LOCATION: (33)..(33)
<223> OTHER INFORMATION: Xaa is absent or Thr
<220> FEATURE:
<221> NAME/KEY: MISC_FEATURE
<222> LOCATION: (34)..(34)
<223> OTHER INFORMATION: Xaa is absent or Leu
<220> FEATURE:
<221> NAME/KEY: MISC_FEATURE
<222> LOCATION: (35)..(35)
<223> OTHER INFORMATION: Xaa is absent or Glu

<400> SEQUENCE: 2

Xaa Xaa Xaa Xaa Xaa Xaa Xaa His Leu Cys Gly Ser Xaa Leu Val Glu
1               5                   10                  15

Ala Leu Xaa Leu Val Cys Gly Glu Arg Gly Xaa Xaa Xaa Xaa Xaa Xaa
            20                  25                  30

Xaa Xaa Xaa
        35

<210> SEQ ID NO 3
<211> LENGTH: 21
<212> TYPE: PRT
<213> ORGANISM: Artificial Sequence
<220> FEATURE:
<223> OTHER INFORMATION: Modified insulin A chain
<220> FEATURE:
<221> NAME/KEY: MISC_FEATURE
<222> LOCATION: (8)..(8)
<223> OTHER INFORMATION: Xaa is Thr or His
```

```
<220> FEATURE:
<221> NAME/KEY: MISC_FEATURE
<222> LOCATION: (12)..(12)
<223> OTHER INFORMATION: Xaa is Ser, Asp or Glu
<220> FEATURE:
<221> NAME/KEY: MISC_FEATURE
<222> LOCATION: (13)..(13)
<223> OTHER INFORMATION: Xaa is Leu, Thr, Asn, Asp, Gln, His, Lys, Gly,
      Arg, Pro, Ser or Glu
<220> FEATURE:
<221> NAME/KEY: MISC_FEATURE
<222> LOCATION: (14)..(14)
<223> OTHER INFORMATION: Xaa is Thr, Asn, Asp, Gln, His, Lys, Gly, Arg,
      Pro, Ser or Glu
<220> FEATURE:
<221> NAME/KEY: MISC_FEATURE
<222> LOCATION: (15)..(15)
<223> OTHER INFORMATION: Xaa is Gln, Asp or Glu
<220> FEATURE:
<221> NAME/KEY: MISC_FEATURE
<222> LOCATION: (18)..(18)
<223> OTHER INFORMATION: Xaa is Asn, Lys or Gln
<220> FEATURE:
<221> NAME/KEY: MISC_FEATURE
<222> LOCATION: (21)..(21)
<223> OTHER INFORMATION: Xaa is Asn or Gln

<400> SEQUENCE: 3

Gly Ile Val Glu Gln Cys Cys Xaa Ser Ile Cys Xaa Xaa Xaa Xaa Leu
1               5                   10                  15

Glu Xaa Tyr Cys Xaa
            20

<210> SEQ ID NO 4
<211> LENGTH: 30
<212> TYPE: PRT
<213> ORGANISM: Artificial Sequence
<220> FEATURE:
<223> OTHER INFORMATION: Modified insulin B chain
<220> FEATURE:
<221> NAME/KEY: MISC_FEATURE
<222> LOCATION: (1)..(1)
<223> OTHER INFORMATION: Xaa is Phe or Glu
<220> FEATURE:
<221> NAME/KEY: MISC_FEATURE
<222> LOCATION: (3)..(3)
<223> OTHER INFORMATION: Xaa is Asn or Gln
<220> FEATURE:
<221> NAME/KEY: MISC_FEATURE
<222> LOCATION: (4)..(4)
<223> OTHER INFORMATION: Xaa is Gln or Glu
<220> FEATURE:
<221> NAME/KEY: MISC_FEATURE
<222> LOCATION: (10)..(10)
<223> OTHER INFORMATION: Xaa is His, Asp, Pro or Glu
<220> FEATURE:
<221> NAME/KEY: MISC_FEATURE
<222> LOCATION: (16)..(16)
<223> OTHER INFORMATION: Xaa is Tyr, Asp, Gln, His, Arg or Glu
<220> FEATURE:
<221> NAME/KEY: MISC_FEATURE
<222> LOCATION: (24)..(24)
<223> OTHER INFORMATION: Xaa is Phe or His
<220> FEATURE:
<221> NAME/KEY: MISC_FEATURE
<222> LOCATION: (26)..(26)
<223> OTHER INFORMATION: Xaa is absent, Tyr, His, Thr, Gly or Asp
<220> FEATURE:
<221> NAME/KEY: MISC_FEATURE
<222> LOCATION: (27)..(27)
<223> OTHER INFORMATION: Xaa is absent, Thr, Asn, Asp, Gln, His, Lys,
      Gly, Arg, Pro, Ser or Glu
<220> FEATURE:
<221> NAME/KEY: MISC_FEATURE
<222> LOCATION: (28)..(28)
<223> OTHER INFORMATION: Xaa is absent, Pro, His, Gly or Asp
```

```
<220> FEATURE:
<221> NAME/KEY: MISC_FEATURE
<222> LOCATION: (29)..(29)
<223> OTHER INFORMATION: Xaa is absent, Lys, Arg or Gln
<220> FEATURE:
<221> NAME/KEY: MISC_FEATURE
<222> LOCATION: (30)..(30)
<223> OTHER INFORMATION: Xaa is absent or Thr

<400> SEQUENCE: 4

Xaa Val Xaa Xaa His Leu Cys Gly Ser Xaa Leu Val Glu Ala Leu Xaa
1               5                   10                  15

Leu Val Cys Gly Glu Arg Gly Xaa His Xaa Xaa Xaa Xaa
            20                  25                  30

<210> SEQ ID NO 5
<211> LENGTH: 21
<212> TYPE: PRT
<213> ORGANISM: Artificial Sequence
<220> FEATURE:
<223> OTHER INFORMATION: A chain

<400> SEQUENCE: 5

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 6
<211> LENGTH: 21
<212> TYPE: PRT
<213> ORGANISM: Artificial Sequence
<220> FEATURE:
<223> OTHER INFORMATION: A chain

<400> SEQUENCE: 6

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 7
<211> LENGTH: 21
<212> TYPE: PRT
<213> ORGANISM: Artificial Sequence
<220> FEATURE:
<223> OTHER INFORMATION: A chain

<400> SEQUENCE: 7

Gly Ile Val Glu Gln Cys Cys His Ser Ile Cys Ser Leu Tyr Gln Leu
1               5                   10                  15

Glu Asn Tyr Cys Asn
            20

<210> SEQ ID NO 8
<211> LENGTH: 21
<212> TYPE: PRT
<213> ORGANISM: Artificial Sequence
<220> FEATURE:
<223> OTHER INFORMATION: A chain
```

-continued

<400> SEQUENCE: 8

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 9
<211> LENGTH: 21
<212> TYPE: PRT
<213> ORGANISM: Artificial Sequence
<220> FEATURE:
<223> OTHER INFORMATION: A chain

<400> SEQUENCE: 9

Gly Ile Val Glu Gln Cys Cys Thr Ser Ile Cys Ser Leu Glu Gln Leu
1               5                   10                  15

Glu Leu Tyr Cys Asn
            20

<210> SEQ ID NO 10
<211> LENGTH: 21
<212> TYPE: PRT
<213> ORGANISM: Artificial Sequence
<220> FEATURE:
<223> OTHER INFORMATION: A chain

<400> SEQUENCE: 10

Gly Ile Val Glu Gln Cys Cys Thr Ser Ile Cys Ser Leu Glu Gln Leu
1               5                   10                  15

Glu Asn Tyr Cys Gly
            20

<210> SEQ ID NO 11
<211> LENGTH: 21
<212> TYPE: PRT
<213> ORGANISM: Artificial Sequence
<220> FEATURE:
<223> OTHER INFORMATION: A chain

<400> SEQUENCE: 11

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 12
<211> LENGTH: 29
<212> TYPE: PRT
<213> ORGANISM: Artificial Sequence
<220> FEATURE:
<223> OTHER INFORMATION: B chain

<400> SEQUENCE: 12

Glu Val Asn Gln His Leu Cys Gly Ser His Leu Val Glu Ala Leu Tyr
1               5                   10                  15

Leu Val Cys Gly Glu Arg Gly Phe Phe Tyr Thr Glu Lys
            20                  25

<210> SEQ ID NO 13
<211> LENGTH: 29
<212> TYPE: PRT
<213> ORGANISM: Artificial Sequence

```
<220> FEATURE:
<223> OTHER INFORMATION: B chain

<400> SEQUENCE: 13

Glu Val Asn Gln His Leu Cys Gly Ser His Leu Val Glu Ala Leu Tyr
1               5                   10                  15

Leu Val Cys Gly Glu Arg Gly Phe Phe Tyr Glu Glu Lys
            20                  25

<210> SEQ ID NO 14
<211> LENGTH: 29
<212> TYPE: PRT
<213> ORGANISM: Artificial Sequence
<220> FEATURE:
<223> OTHER INFORMATION: B chain

<400> SEQUENCE: 14

Glu Val Asn Gln His Leu Cys Gly Ser His Leu Val Glu Ala Leu Tyr
1               5                   10                  15

Leu Val Cys Gly Glu Arg Gly Phe His Tyr Thr Glu Lys
            20                  25

<210> SEQ ID NO 15
<211> LENGTH: 29
<212> TYPE: PRT
<213> ORGANISM: Artificial Sequence
<220> FEATURE:
<223> OTHER INFORMATION: B chain

<400> SEQUENCE: 15

Glu Val Asn Gln His Leu Cys Gly Ser His Leu Val Glu Ala Leu Tyr
1               5                   10                  15

Leu Val Cys Gly Glu Arg Gly Phe His Tyr Glu Glu Lys
            20                  25

<210> SEQ ID NO 16
<211> LENGTH: 29
<212> TYPE: PRT
<213> ORGANISM: Artificial Sequence
<220> FEATURE:
<223> OTHER INFORMATION: B chain

<400> SEQUENCE: 16

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25

<210> SEQ ID NO 17
<211> LENGTH: 29
<212> TYPE: PRT
<213> ORGANISM: Artificial Sequence
<220> FEATURE:
<223> OTHER INFORMATION: B chain

<400> SEQUENCE: 17

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys
            20                  25
```

```
<210> SEQ ID NO 18
<211> LENGTH: 29
<212> TYPE: PRT
<213> ORGANISM: Artificial Sequence
<220> FEATURE:
<223> OTHER INFORMATION: B chain

<400> SEQUENCE: 18

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Lys
            20                  25

<210> SEQ ID NO 19
<211> LENGTH: 29
<212> TYPE: PRT
<213> ORGANISM: Artificial Sequence
<220> FEATURE:
<223> OTHER INFORMATION: B chain

<400> SEQUENCE: 19

Phe Val Asn Gln His Leu Cys Gly Ser His Leu Val Glu Ala Leu Tyr
1               5                   10                  15

Leu Val Cys Gly Glu Arg Gly Phe His Tyr Glu Pro Lys
            20                  25

<210> SEQ ID NO 20
<211> LENGTH: 28
<212> TYPE: PRT
<213> ORGANISM: Artificial Sequence
<220> FEATURE:
<223> OTHER INFORMATION: B chain

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe His Tyr Pro Lys
            20                  25

<210> SEQ ID NO 21
<211> LENGTH: 29
<212> TYPE: PRT
<213> ORGANISM: Artificial Sequence
<220> FEATURE:
<223> OTHER INFORMATION: B chain

<400> SEQUENCE: 21

Phe Val Asn Gln His Leu Cys Gly Ser His Leu Val Glu Ala Leu Tyr
1               5                   10                  15

Leu Val Cys Gly Glu Arg Gly Phe His Gly Gly Gly Arg
            20                  25

<210> SEQ ID NO 22
<211> LENGTH: 29
<212> TYPE: PRT
<213> ORGANISM: Artificial Sequence
<220> FEATURE:
<223> OTHER INFORMATION: B chain

<400> SEQUENCE: 22

Phe Val Asn Gln His Leu Cys Gly Ser His Leu Val Glu Ala Leu Tyr
1               5                   10                  15

Leu Val Cys Gly Glu Arg Gly Phe His Gly Gly Gly Lys
            20                  25
```

```
<210> SEQ ID NO 23
<211> LENGTH: 27
<212> TYPE: PRT
<213> ORGANISM: Artificial Sequence
<220> FEATURE:
<223> OTHER INFORMATION: B chain

<400> SEQUENCE: 23

Phe Val Asn Gln His Leu Cys Gly Ser His Leu Val Glu Ala Leu Tyr
1               5                   10                  15

Leu Val Cys Gly Glu Arg Gly Phe His Tyr Lys
            20                  25

<210> SEQ ID NO 24
<211> LENGTH: 29
<212> TYPE: PRT
<213> ORGANISM: Artificial Sequence
<220> FEATURE:
<223> OTHER INFORMATION: B chain

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Asn Tyr Glu Pro Lys
            20                  25

<210> SEQ ID NO 25
<211> LENGTH: 29
<212> TYPE: PRT
<213> ORGANISM: Artificial Sequence
<220> FEATURE:
<223> OTHER INFORMATION: B chain

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Arg
            20                  25

<210> SEQ ID NO 26
<211> LENGTH: 29
<212> TYPE: PRT
<213> ORGANISM: Artificial Sequence
<220> FEATURE:
<223> OTHER INFORMATION: B chain

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Glu Lys
            20                  25

<210> SEQ ID NO 27
<211> LENGTH: 29
<212> TYPE: PRT
<213> ORGANISM: Artificial Sequence
<220> FEATURE:
<223> OTHER INFORMATION: B chain

<400> SEQUENCE: 27

Phe Val Asn Gln His Leu Cys Gly Ser His Leu Val Glu Ala Leu Tyr
1               5                   10                  15

Leu Val Cys Gly Glu Arg Gly Phe Phe Tyr Thr His Arg
            20                  25
```

```
<210> SEQ ID NO 28
<211> LENGTH: 29
<212> TYPE: PRT
<213> ORGANISM: Artificial Sequence
<220> FEATURE:
<223> OTHER INFORMATION: B chain

<400> SEQUENCE: 28

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys
            20                  25

<210> SEQ ID NO 29
<211> LENGTH: 29
<212> TYPE: PRT
<213> ORGANISM: Artificial Sequence
<220> FEATURE:
<223> OTHER INFORMATION: B chain

<400> SEQUENCE: 29

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```